US006590075B2

(12) United States Patent
Ruben et al.

(10) Patent No.: US 6,590,075 B2
(45) Date of Patent: *Jul. 8, 2003

(54) SECRETED PROTEIN HODAZ50

(75) Inventors: Steven M. Ruben, Olney, MD (US); Craig A. Rosen, Laytonsville, MD (US); Carrie L. Fischer, Burke, VA (US); Daniel R. Soppet, Centreville, VA (US); Kenneth C. Carter, North Potomac, MD (US); Daniel P. Bednarik, Columbia, MD (US); Gregory A. Endress, Potomac, MD (US); Guo-Liang Yu, Berkeley, CA (US); Jian Ni, Rockville, MD (US); Ping Feng, Gaithersburg, MD (US); Paul E. Young, Gaithersburg, MD (US); John M. Greene, Gaithersburg, MD (US); Ann M. Ferrie, Tewksbury, MA (US); Roxanne Duan, Bethesda, MD (US); Jing-Shan Hu, Sunnyvale, CA (US); Kimberly A. Florence, Rockville, MD (US); Henrik S. Olsen, Gaithersburg, MD (US); Reinhard Ebner, Gaithersburg, MD (US); Laurie A. Brewer, St. Paul, MN (US); Yanggu Shi, Gaithersburg, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 42 days.

(21) Appl. No.: 09/148,545

(22) Filed: Sep. 4, 1998

(65) Prior Publication Data

US 2003/0027132 A1 Feb. 6, 2003

Related U.S. Application Data

(60) Provisional application No. 60/040,162, filed on Mar. 7, 1997, provisional application No. 60/040,333, filed on Mar. 7, 1997, provisional application No. 60/038,621, filed on Mar. 7, 1997, provisional application No. 60/040,161, filed on Mar. 7, 1997, provisional application No. 60/040,626, filed on Mar. 7, 1997, provisional application No. 60/040,336, filed on Mar. 7, 1997, provisional application No. 60/040,163, filed on Mar. 7, 1997, provisional application No. 60/047,615, filed on May 23, 1997, provisional application No. 60/047,600, filed on May 23, 1997, provisional application No. 60/047,597, filed on May 23, 1997, provisional application No. 60/047,502, filed on May 23, 1997, provisional application No. 60/047,633, filed on May 23, 1997, provisional application No. 60/047,583, filed on May 23, 1997, provisional application No. 60/047,617, filed on May 23, 1997, provisional application No. 60/047,618, filed on May 23, 1997, provisional application No. 60/047,503, filed on May 23, 1997, provisional application No. 60/047,592, filed on May 23, 1997, provisional application No. 60/047,581, filed on May 23, 1997, provisional application No. 60/047,584, filed on May 23, 1997, provisional application No. 60/047,500, filed on May 23, 1997, provisional application No. 60/047,587, filed on May 23, 1997, provisional application No. 60/047,492, filed on May 23, 1997, provisional application No. 60/047,598, filed on May 23, 1997, provisional application No. 60/047,613, filed on May 23, 1997, provisional application No. 60/047,582, filed on May 23, 1997, provisional application No. 60/047,612, filed on May 23, 1997, provisional application No. 60/047,632, filed on May 23, 1997, provisional application No. 60/047,601, filed on May 23, 1997, provisional application No. 60/043,580, filed on Apr. 11, 1997, provisional application No. 60/040,334, filed on Mar. 7, 1997, provisional application No. 60/047,596, filed on May 23, 1997, provisional application No. 60/043,311, filed on Apr. 11, 1997, provisional application No. 60/056,845, filed on Aug. 22, 1997, provisional application No. 60/056,631, filed on Aug. 22, 1997, provisional application No. 60/043,568, filed on Apr. 11, 1997, provisional application No. 60/043,314, filed on Apr. 11, 1997, provisional application No. 60/043,569, filed on Apr. 11, 1997, provisional application No. 60/043,671, filed on Apr. 11, 1997, provisional application No. 60/043,674, filed on Apr. 11, 1997, provisional application No. 60/043,669, filed on Apr. 11, 1997, provisional application No. 60/043,312, filed on Apr. 11, 1997, provisional application No. 60/043,313, filed on Apr. 11, 1997, provisional application No. 60/043,672, filed on Apr. 11, 1997, provisional application No. 60/043,315, filed on Apr. 11, 1997, provisional application No. 60/048,974, filed on Apr. 6, 1997, provisional application No. 60/056,886, filed on Aug. 22, 1997, provisional application No. 60/056,877, filed on Aug. 22, 1997, provisional application No. 60/056,889, filed on Aug. 22, 1997, provisional application No. 60/056,893, filed on Aug. 22, 1997, provisional application No. 60/056,630, filed on Aug. 22, 1997, provisional application No. 60/056,878, filed on Aug. 22, 1997, provisional application No. 60/056,662, filed on Aug. 22, 1997, provisional application No. 60/056,872, filed on Aug. 22, 1997, provisional application No. 60/056,882, filed on Aug. 22, 1997, provisional application No. 60/056,637, filed on Aug. 22, 1997, provisional application No. 60/056,903, filed on Aug. 22, 1997, provisional application No. 60/056,888, filed on Aug. 22, 1997, provisional application No. 60/056,879, filed on Aug. 22, 1997, provisional application No. 60/056,880, filed on Aug. 22, 1997, provisional application No. 60/056,894, filed on Aug. 22, 1997, provisional application No. 60/056,911, filed on Aug. 22, 1997, provisional application No. 60/056,636, filed on Aug. 22, 1997, provisional application No. 60/056,874, filed on Aug. 22, 1997, provisional application No. 60/056,910, filed on Aug. 22, 1997, provisional application No. 60/056,864, filed on Aug. 22, 1997, provisional application No. 60/056,892, filed on Aug. 22, 1997, provisional application No. 60/047,595, filed on May 23, 1997, provisional application No. 60/057,761, filed on Sep. 5, 1997, provisional application No. 60/047,599, filed on May 23, 1997, provisional application No. 60/047,588, filed on May 23, 1997, provisional application No. 60/047,585, filed on May 23, 1997, provisional application No. 60/047,586, filed on May 23, 1997, provisional application No. 60/047,590, filed on May 23, 1997, provisional application No. 60/047,594, filed on May 23, 1997, provisional application No. 60/047, 589, filed on May 23, 1997, provisional application No. 60/047,593, filed on May 23, 1997, provisional application No. 60/047,614, filed on May 23, 1997, provisional application No. 60/043/578, filed on Apr. 11, 1997, provisional application No. 60/043,576, filed on Apr. 11, 1997, provisional application No. 60/047,501, filed on May 23, 1997, provisional application No. 60/043,670, filed on Apr. 11, 1997, provisional application No. 60/056,632, filed on Aug. 22, 1997, provisional application No. 60/056,664, filed on Aug. 22, 1997, provisional application No. 60/056,876, filed on Aug. 22, 1997, provisional application No. 60/056,881, filed on Aug. 22, 1997, provisional application No. 60/056,909, filed on Aug. 22, 1997, provisional application No. 60/056,875, filed on Aug. 22, 1997, provisional application No. 60/056,862, filed on Aug. 22, 1997, provisional application No. 60/056,887, filed on Aug. 22, 1997, provisional application No. 60/056,908, filed on Aug. 22, 1997, provisional application No. 60/048,964, filed on Jun. 6, 1997, provisional application No. 60/057,650, filed on Sep. 5, 1997, provisional application No. 60/056,884, filed on Aug. 22, 1997.

(51) Int. Cl.[7] .............................................. C07K 1/00

(52) U.S. Cl. .................. 530/350; 530/350; 435/7.1; 435/69.1; 435/6; 536/23.1

(58) Field of Search .................. 435/69.1, 7.1, 435/6; 536/23.1; 530/350

(56) References Cited

U.S. PATENT DOCUMENTS 5,536,637 A    7/1996   Jacobs ..................... 435/6

FOREIGN PATENT DOCUMENTS

| WO | 90/14432 | 11/1990 |
|----|----------|---------|
| WO | 96/17925 | 6/1996 |
| WO | 97/04097 | 2/1997 |
| WO | 97/07198 | 2/1997 |
| WO | WO 98/39446 | 9/1998 |

OTHER PUBLICATIONS

Genbank Accession No. AA234924 (1997).
Genbank Accession No. AA151194 (1996).
Genbank Accession No. W52490 (1996).
Jacobs et al., Journal Of Cellular Biochemistry Supplement 0 (21A), p. 19, abstract No. C1–207 (1995).
Occhiodoro et al., Biochemical and Biophysical Research Communications, 164(1):439–445 (1989).
Genbank Accession No. AA065306 (1996).
Genbank Accession No. AA065307 (1996).

*Primary Examiner*—Karen Cochrane Carlson
*Assistant Examiner*—Hope A. Robinson
(74) *Attorney, Agent, or Firm*—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating disorders related to these novel human secreted proteins.

48 Claims, No Drawings

SECRETED PROTEIN HODAZ50

This application is a continuation in part under 35 U.S.C. §120 of copending U.S. patent application Ser. No: PCT/US98/04482, filed Mar. 6, 1998, which claims benefit under 35 U.S.C. §119(e) based on U.S. Provisional Applications:

|     | Filing Date | Application No |
| --- | --- | --- |
| 1.  | 07-Mar-1997 | 60/040,162 |
| 2.  | 07-Mar-1997 | 60/040,333 |
| 3.  | 07-Mar-1997 | 60/038,621 |
| 4.  | 07-Mar-1997 | 60/040,161 |
| 5.  | 07-Mar-1997 | 60/040,626 |
| 6.  | 07-Mar-1997 | 60/040,334 |
| 7.  | 07-Mar-1997 | 60/040,336 |
| 8.  | 07-Mar-1997 | 60/040,163 |
| 9.  | 23-May-1997 | 60/047,615 |
| 10. | 23-May-1997 | 60/047,600 |
| 11. | 23-May-1997 | 60/047,597 |
| 12. | 23-May-1997 | 60/047,502 |
| 13. | 23-May-1997 | 60/047,633 |
| 14. | 23-May-1997 | 60/047,583 |
| 15. | 23-May-1997 | 60/047,617 |
| 16. | 23-May-1997 | 60/047,618 |
| 17. | 23-May-1997 | 60/047,503 |
| 18. | 23-May-1997 | 60/047,592 |
| 19. | 23-May-1997 | 60/047,581 |
| 20. | 23-May-1997 | 60/047,584 |
| 21. | 23-May-1997 | 60/047,500 |
| 22. | 23-May-1997 | 60/047,587 |
| 23. | 23-May-1997 | 60/047,492 |
| 24. | 23-May-1997 | 60/047,598 |
| 25. | 23-May-1997 | 60/047,613 |
| 26. | 23-May-1997 | 60/047,582 |
| 27. | 23-May-1997 | 60/047,596 |
| 28. | 23-May-1997 | 60/047,612 |
| 29. | 23-May-1997 | 60/047,632 |
| 30. | 23-May-1997 | 60/047,601 |
| 31. | 11-Apr-1997 | 60/043,580 |
| 32. | 11-Apr-1997 | 60/043,568 |
| 33. | 11-Apr-1997 | 60/043,314 |
| 34. | 11-Apr-1997 | 60/043,569 |
| 35. | 11-Apr-1997 | 60/043,311 |
| 36. | 11-Apr-1997 | 60/043,671 |
| 37. | 11-Apr-1997 | 60/043,674 |
| 38. | 11-Apr-1997 | 60/043,669 |
| 39. | 11-Apr-1997 | 60/043,312 |
| 40. | 11-Apr-1997 | 60/043,313 |
| 41. | 11-Apr-1997 | 60/043,672 |
| 42. | 11-Apr-1997 | 60/043,315 |
| 43. | 06-Jun-1997 | 60/048,974 |
| 44. | 22-Aug-1997 | 60/056,886 |
| 45. | 22-Aug-1997 | 60/056,877 |
| 46. | 22-Aug-1997 | 60/056,889 |
| 47. | 22-Aug-1997 | 60/056,893 |
| 48. | 22-Aug-1997 | 60/056,630 |
| 49. | 22-Aug-1997 | 60/056,878 |
| 50. | 22-Aug-1997 | 60/056,662 |
| 51. | 22-Aug-1997 | 60/056,872 |
| 52. | 22-Aug-1997 | 60/056,882 |
| 53. | 22-Aug-1997 | 60/056,637 |
| 54. | 22-Aug-1997 | 60/056,903 |
| 55. | 22-Aug-1997 | 60/056,888 |
| 56. | 22-Aug-1997 | 60/056,879 |
| 57. | 22-Aug-1997 | 60/056,880 |
| 58. | 22-Aug-1997 | 60/056,894 |
| 59. | 22-Aug-1997 | 60/056,911 |
| 60. | 22-Aug-1997 | 60/056,636 |
| 61. | 22-Aug-1997 | 60/056,874 |
| 62. | 22-Aug-1997 | 60/056,910 |
| 63. | 22-Aug-1997 | 60/056,864 |
| 64. | 22-Aug-1997 | 60/056,631 |
| 65. | 22-Aug-1997 | 60/056,845 |
| 66. | 22-Aug-1997 | 60/056,892 |
| 67. | 23-May-1997 | 60/047,595 |
| 68. | 05-Sep-1997 | 60/057,761 |
| 69. | 23-May-1997 | 60/047,599 |

-continued

|     | Filing Date | Application No |
| --- | --- | --- |
| 70. | 23-May-1997 | 60/047,588 |
| 71. | 23-May-1997 | 60/047,585 |
| 72. | 23-May-1997 | 60/047,586 |
| 73. | 23-May-1997 | 60/047,590 |
| 74. | 23-May-1997 | 60/047,594 |
| 75. | 23-May-1997 | 60/047,589 |
| 76. | 23-May-1997 | 60/047,593 |
| 77. | 23-May-1997 | 60/047,614 |
| 78. | 11-Apr-1997 | 60/043,578 |
| 79. | 11-Apr-1997 | 60/043,576 |
| 80. | 23-May-1997 | 60/047,501 |
| 81. | 11-Apr-1997 | 60/043,670 |
| 82. | 22-Aug-1997 | 60/056,632 |
| 83. | 22-Aug-1997 | 60/056,664 |
| 84. | 22-Aug-1997 | 60/056,876 |
| 85. | 22-Aug-1997 | 60/056,881 |
| 86. | 22-Aug-1997 | 60/056,909 |
| 87. | 22-Aug-1997 | 60/056,875 |
| 88. | 22-Aug-1997 | 60/056,862 |
| 89. | 22-Aug-1997 | 60/056,887 |
| 90. | 22-Aug-1997 | 60/056,908 |
| 91. | 06-Jun-1997 | 60/048,964 |
| 92. | 05-Sep-1997 | 60/057,650 |
| 93. | 22-Aug-1997 | 60/056,884 |

FIELD OF THE INVENTION

This invention relates to newly identified polynucleotides and the polypeptides encoded by these polynucleotides, uses of such polynucleobides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organdies.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VW, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical disorders by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant methods for producing the polypeptides and polynucleotides. Also provided are diagnostic methods for detecting disorders related to the polypeptides, and therapeutic methods for treating such disorders. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g. the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE =3M NaCl; 0.2M $NaH_2PO_4$; 0.02M EDTA, pH 7.4), 0.5% SDS, 30% formamide, 100 ug/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g. practically any double-stranded cDNA clone).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamnma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention
Features of Protein Encoded by Gene No: 1

The translation product of Gene NO: 1 shares sequence homology with alpha-L-fucosidase which is thought to be important as a lysosomal enzyme that hydrolyzes fucose from fucoglycoconjugates. (See Accession No. gi/178409.) Lysosome fructosidase is involved in certain lysosome storage diseases. (See Biochem. Biophys. Res. Commun., 164 (1):439–445 (1989).) Fucosidosis, an autosomal recessive lysosomal storage disorder characterized by progressive neurological deterioration and mental retardation. The disease results from deficient activity of alpha-L-fucosidase, a lysosomal enzyme that hydrolyzes fucose from fucoglycoconjugates. This gene likely encodes a novel fucosidase isoenzyme. Based on homology, it is likely that the translated product of this gene is also involved in lysosome catabolism of molecules and that aberrations in the concentration and/or composition of this product may be causative in lysosome storage disorders. Preferred polypeptide fragments comprise the amino acid sequence PGHLLPHK-WENC (SEQ ID NO: 257).

Gene NO: 1 is expressed primarily in stromal cells, and to a lesser extent in human fetal kidney and human tonsils.

Therefore, polynucleotides or polypeptides of the invention are useful as reagents for differential identification of the tissue(s) or cell type(s) present in a biological sample and for diagnosis of diseases and conditions which include, but are not limited to, fucosidosis and other lysosome storage disorders. Similarly, polypeptides and antibodies directed to the polypeptides are useful in providing immunological probes for differential identification of the tissue(s) or cell type(s). For a number of disorders of the above tissues of cells, particularly of the nervous system, expression of this gene at significantly higher or lower levels may routinely be detected in certain tissues and cell types (e.g. stromal cells, kidney, tonsils, and cancerous and wounded tissues) or bodily fluids (e.g. serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology of Gene NO: 1 to alpha-L-fucosidase indicates that polypeptides and polynucleotides corresponding to Gene NO: 1 are useful for the treatment of fucosidosis and general lysosomal disorders.

Preferred epitopes include those comprising a sequence shown in SEQ ID NO: 134 as residues: Met-1 to Leu-6, Thr-32 to Glu-39, Lys-80 to Lys-85, and Met-90 to Pro-96.

Many polynucleotide sequences, such as EST sequences, are publicly available and accessible through sequence databases. Some of these sequences are related to SEQ ID NO: 11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1725 of SEQ ID NO: 11, b is an integer of 15 to 1739, where both a and b correspond to the positions of nucleotide residues shown in SEQ ID NO: 11, and where b is greater than or equal to a+14.

Features of Protein Encoded by Gene No: 2

The translation product of Gene No. 2 shares sequence homology with stromal cell-derived factor-2 (SDF-2) which is a novel secreted factor. See, for example, Gene, 176(1–2):211–214, (1996, October 17.) The amino acid sequence of SDF-2 shows similarity to yeast dolichyl phosphate-D-mannose:protein mannosyltransferases, Pmt1p [Strahl-Bolsinger et al. Proc. Natl. Acad. Sci. USA 90, 8164–8168 (1993)] and Pmt2p [Lussier et al. J. Biol. Chem. 270, 2770–2775 (1995)], whose activities have not been detected in higher eukaryotes. Based on the sequence similarity, the translation product of this gene is expected to share certain biological activities with SDF-2, Pmt1p and Pmt2p.

Gene NO: 2 is expressed primarily in immune system tissue and cancerous tissues, such as liver hepatoma, human B-cell lymphoma, spleen in a patient suffering from chronic lymphocytic leukemia, hemangiopericytoma, pharynx carcinoma, breast cancer, thyroid, bone marrow, osteoblasts and to a lesser extent in a few other tissues such as kidney pyramids.

Therefore, polynucleotides or polypeptides of the invention are useful as reagents for differential identification of the tissue(s) or cell type(s) present in a biological sample and for diagnosis of the diseases and conditions which include, but are not limited to, disorders in kidney, liver, and immune organs, particularly cancers. Similarly, polypeptides and antibodies directed to these polypeptides are useful in providing immunological probes for differential identification of the tissue(s) or cell type(s). For a number of disorders of the above tissues or cells, particularly of the kidney, liver, thyroid, and bone marrow expression of this gene at significantly higher or lower levels may routinely be detected in certain tissues and cell types (e.g. immune, hematopoietic, liver, spleen, B-cells, pharynx, thyroid, mammary tissue, bone marrow, osteoblasts and kidneys, and cancerous and wounded tissues) or bodily fluids (e.g. lymph, serum, plasma, urine, synovial fluid or spinal fluid) or another tissue or cell sample or another tissue or cell sample taken from an individual having such a disorder, relative to the standard gene expression level, i.e., the expression level in healthy tissue or bodily fluid from an individual not having the disorder.

The tissue distribution and homology of Gene NO: 2 to stromal cell-derived factor-2 indicates that polypeptides and polynucleotides corresponding to Gene NO: 2 are useful for diagnosis and therapeutic treatment of disorders in kidney, liver, and immune organs since stromal cells play important role in organ function. Stroma carries the blood supply and provides support for the growth of parenchymal cells and is therefore crucial to the growth of a neoplasm. Nucleic acids of the present invention comprise, but preferably do not consist of, and more preferably do not comprise, SEQ ID NO: 3 from U.S. Pat. No. 5,576,423, incorporated herein by reference, and shown herein as SEQ ID NO: 258).

Preferred epitopes include those comprising a sequence shown in SEQ ID NO: 135 as residues: His-56 to Gly-65, Ala-74 to Ser-80, Ile-84 to Pro-97, Leu-124 to Glu-129, Glu-135 to Asp-143, Gly-175 to Ser-180, and Ala-194 to Thr-199.

Many polynucleotide sequences, such as EST sequences, are publicly available and accessible through sequence databases. Some of these sequences are related to SEQ ID NO: 12 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 830 of SEQ ID NO: 12, b is an integer of 15 to 844, where both a and b correspond to the positions of nucleotide residues shown in SEQ ID NO: 12, and where b is greater than or equal to a+14.

Features of Protein Encoded by Gene No: 3

The translation product of Gene NO: 3 shares sequence homology with LZIP-1, LZIP-2 and other leucine zipper proteins, which are thought to be important in nucleic acid binding. This gene has been reported in Mol. Cell. Biol. 17 (9), 5117–5126 (1997) as "Luman". Luman is a cyclic AMP response element (CRE)-binding protein/activating transcription factor 1 protein of the basic leucine zipper superfamily. It binds CREs in vitro and activates CRE-containing promoters when transfected into COS7 cells. The complete amino acid sequence of Luman reported in Mol. Cell. Biol. 17 (9): 5117–5126 (1997) is:
MELELDAGDQDLLAFLLEESGDLGTAP-
DEAVRAPLDWALPLSEVPSDWEVDDLLCSLLSP
PASLNILSSSNPCLVHHDHTYSL-
PRETVSMDLESESCRKEGTQMTPQH-
MEELAEQEIARLV LTDEEKSLLEKEGLILPETLPLTK-
TEEQILKRVRRKIRNKRSAQESRRKKKVYVGGLESRV
LKYTAQNMELQNKVQLLEEQNLSLLDQL-
RKLQAMVIEISNKTSSSSTCILVLLVSFCLLLV PAM-
YSSDIRGSLPAEHGVLSRQLRALPSED-
PYQLELPALQSEVPKDSTHQWLDGSDCVLQ
APGNTSCLLHYMPQAPSAEPPLEWPFP-
DLSSEPLCRGPILPLQANLTRKGGWLPTGSPSV
ILQDRYSG (SEQ ID N:259).

Gene NO: 3 is expressed primarily in apoptotic T-cells and Soares senescent cells and to a lesser extent in multiple tissues and cell types, including, multiple sclerosis tissue, and hippocampus.

Therefore, polynucleotides or polypeptides of the invention are useful as reagents for differential identification of the tissue(s) or cell type(s) present in a biological sample and for diagnosis of diseases and conditions which include, but are not limited to, immunologically mediated disorders, transplantation, immunodeficiency, and tumor necrosis. Similarly, polypeptides and antibodies directed to these polypeptides are useful in providing immunological probes for differential identification of the tissue(s) or cell type(s). For a number of disorders of the above tissues or cells, particularly of the immune system and transplantation, expression of this gene at significantly higher or lower levels may routinely be detected in certain tissues (e.g.neural, multiple sclerosis tissue, hippocampus, neural, bone marrow and cancerous and wounded tissues) or bodily fluids (e.g.lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology of Gene NO: 3 to leucine zipper nucleic acid binding proteins indicates that polypeptides and polynucleotides corresponding to Gene NO: 3 are useful for diagnosis and treatment of immunologically mediated disorders, transplantation, immunodeficiency, and tumor necrosis. The secreted nucleic acid binding protein in the apoptotic tissues may be involved in the disposal of the DNA released by apoptotic cells. Furthermore, the studies conducted in support of Luman suggest that the translation product of this gene may be used to identify transcriptional regulation elements which in turn are useful in modulation of immune function.

Preferred epitopes include those comprising a sequence shown in SEQ ID NO: 136 as residues: Asn-7 to Ser-12, Tyr-32 to Gly-38, Pro-55 to Tyr-60, Glu-70 to Thr-76, and Pro-104 to Leu-110.

Many polynucleotide sequences, such as EST sequences, are publicly available and accessible through sequence databases. Some of these sequences are related to SEQ ID NO: 13 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 762 of SEQ ID NO: 13, b is an integer of 15 to 776, where both a and b correspond to the positions of nucleotide residues shown in SEQ ID NO: 13, and where b is greater than or equal to a+14.

Features of Protein Encoded by Gene No: 4

The translation product of Gene NO: 4 shares sequence homology with a number of tetraspan transmembrane surface molecules such as human metastasis tumor suppressor gene, CO-029 tumor associated antigen protein, CD53 hematopoietic antigen, human membrane antigen TM4 superfamily protein, metastasis controlling peptide, and human CD9 sequence, which are thought to be important in development of cancer, immune system development and functions.

Gnee NO: 4 is expressed primarily in cancers of several different tissues and to a lesser extent in normal tissue like prostate, skin and kidney.

Therefore, polynucleotides or polypeptides of the invention are useful as reagents for differential identification of the tissue(s) or cell type(s) present in a biological sample and for diagnosis of diseases and conditions which include, but are not limited to, cancers and disorders of the immune system, prostate and kidney. Similarly, polypeptides and antibodies directed to these polypeptides are useful in providing immunological probes for differential identification of the tissue(s) or cell type(s). For a number of disorders of the above tissues or cells, particularly of the kidney, skin, prostate and immune system, expression of this gene at significantly higher or lower levels may routinely be detected in certain tissues (e.g. kidney, skin and prostate, and cancerous and wounded tissues) or bodily fluids (e.g. seminal fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology of Gene NO: 4 to tetraspan transmembrane surface molecules such as human metastasis tumor suppressor gene, CO-029 tumor associated antigen protein, CD53 hematopoietic antigen, human membrane antigen TM4 superfamily protein, metastasis controlling peptide, and human CD9 sequence, indicates that polypeptides and polynucleotides corresponding to Gene NO: 4 are involved with the cellular control of growth and differentiation. Therefore, the translation product of this gene is believed to be useful for diagnosis and treatment of neoplasia and disorders of the kidney, skin and prostate. For example, recombinant protein can be produced in transformed host cells for diagnostic and prognostic applications. Alterations in the protein sequence are indicative of the presence of malignant cancer, or of a predisposition to malignancy, in a subject. Gene therapy can be used to restore the wild-type gene product to a subject. Additionally, the antibodies are a useful tool for the identification of hematopoietic neoplasms, and may prove helpful for identifying morphologically poorly defined cells. Moreover, this protein can be used to isolate cognate receptors and ligands and identify potential agonists and antagonists using techniques known in the art. The protein also has immunomodulatory activity, regulates hematopoiesis and stimulates growth and regeneration as a male/female contraceptive, increases fertility depending on activin and inhibin like activities. Other uses are as a chemotactic agent for lymphocytes, treatment of coagulation disorders, an anti-inflammatory agent, an antimicrobial or analgesic and as a modulator of behavior and metabolism. The DNA can be used in genetic diagnosis or gene therapy, and for the production of recombinant protein. It can also be used to identify protein expressing cells, isolate related sequences, prepare primers for genetic fingerprinting and generate anti-protein or anti-DNA antibodies. In addition, residues 1–71, in the translation product for this gene are believed to be the extracellular domain. Thus, polypeptide comprising residues 1–71 or derivatives (including fragments) or analogs thereof, are useful as a soluble polypeptide which may be routinely used therapeutically to antagonize the activities of the receptor.

Preferred epitopes include those comprising a sequence shown in SEQ ID NO: 137 as residues: Lys-118 to Phe-127, Asn-145 to Ala-160, and Thr-177 to Val-188.

Many polynucleotide sequences, such as EST sequences, are publicly available and accessible through sequence databases. Some of these sequences are related to SEQ ID NO: 14 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1362 of SEQ ID NO: 14, b is an integer of 15 to 1376, where both a and b correspond to the positions of nucleotide residues shown in SEQ ID NO: 14, and where b is greater than or equal to a+14.

Features of Protein Encoded by Gene No: 5

Gene NO: 5 is expressed primarily in human testes.

Therefore, polynucleotides or polypeptides of the invention are useful as reagents for differential identification of the tissue(s) or cell type(s) present in a biological sample and for diagnosis of diseases and conditions which include, but are not limited to, diseases of the testes including cancer and reproductive disorders. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may routinely be detected in certain tissues (e.g. testes and cancerous and wounded tissues) or bodily fluids (e.g. seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution of Gene NO: 5 indicates that the protein product of this gene is useful for treatment/diagnosis of diseases of the testes, particularly testicular cancer since expression is observed primarily in the testes.

Preferred epitopes include those comprising a sequence shown in SEQ ID NO: 138 as residue: Gly-22 to Gln-30.

Many polynucleotide sequences, such as EST sequences, are publicly available and accessible through sequence databases. Some of these sequences are related to SEQ ID NO: 15 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 488 of SEQ ID NO:

15, b is an integer of 15 to 502, where both a and b correspond to the positions of nucleotide residues shown in SEQ ID NO: 15, and where b is greater than or equal to a+14.

Features of Protein Encoded by Gene No: 6

The translation product of Gene NO: 6 shares sequence homology with GALNS (N-acetylgalactosamine 6-sulphatase) which is thought to be important in the storage of the glycosaminoglycans, keratan sulfate and chondroitin 6-sulfate. See Genbank accession no. gil618426. Based on the sequence similarity, the translation product of this gene is expected to share biological activities with GALNS.

Gene NO: 6 is expressed primarily in human bone marrow.

Therefore, polynucleotides or polypeptides of the invention are useful as reagents for differential identification of the tissue(s) or cell type(s) present in a biological sample and for diagnosis of diseases and conditions which include, but are not limited to, storage disorders of glycosaminoglycans, keratan sulfate and chondroitin 6-sulfate, e.g. Morquio A syndrome. Similarly, polypeptides and antibodies directed to these polypeptides are useful in providing inmunological probes for differential identification of the tissue(s) or cell type(s). For a number of disorders of the above tissues or cells, particularly involving cell storage disorder, expression of this gene at significantly higher or lower levels may routinely be detected in certain tissues (e.g. immune, bone marrow and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology of Gene NO: 6 to N-acetylgalactosamine 6-sulphatase indicates that polypeptides and polynucleotides corresponding to Gene NO: 6 are useful for the treatment and diagnosis of storage disorders of glycosaminoglycans, keratin sulfate and chondroitin 6-sulfate. Such disorders are known in the art and include, e.g. Morquio A syndrome which is caused by an error of mucopolysaccharide metabolism with excretion of keratan sulfate in urine. Morquio A syndrome is characterized by severe skeletal defects with short stature, severe deformity of spine and thorax, long bones with irregular epiphyses but with shafts of normal length, enlarged joints, flaccid ligaments, and waddling gait; autosomal recessive inheritance.

Preferred epitopes include those comprising a sequence shown in SEQ ID NO: 139 as residues: Gly-29 to Pro-36 and Glu-57 to Leu-64.

Many polynucleotide sequences, such as EST sequences, are publicly available and accessible through sequence databases. Some of these sequences are related to SEQ ID NO: 16 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 411 of SEQ ID NO: 16, b is an integer of 15 to 425, where both a and b correspond to the positions of nucleotide residues shown in SEQ ID NO: 16, and where b is greater than or equal to a+14.

Features of Protein Encoded by Gene No: 7

The translation product of Gene NO: 7 shares sequence homology with carboxy peptidase E and H (carboxypeptidase E is thought to be important in the biosynthesis of numerous peptide hormones and neurotransmitters). The translation product of this gene also shares sequence homology with bone-related carboxypeptidase "OSF-5" from the mouse. See European patent application EP-588118-A. Based on the sequence similarity to OSF-5, the translation product of this gene will hereinafter sometimes be referred to as "human-OSF-5" or "hOSF-5".

Gene NO: 7 is expressed primarily in tumor cell lines derived from connective tissues including chondrosarcoma, synovial sarcoma, Wilm's tumor and rhabdomyosarcoma and to a lesser extent in a myeloid progenitor cell line, bone marrow, and placenta.

Therefore, polynucleotides or polypeptides of the invention are useful as reagents for differential identification of the tissue(s) or cell type(s) present in a biological sample and for diagnosis of diseases and conditions which include, but are not limited to, various cancers involving the skeletal system and connective tissues in general, in particular at cartilage interfaces. Similarly, polypeptides and antibodies directed to these polypeptides are useful in providing immunological probes for differential identification of the tissue(s) or cell type(s). For a number of disorders of the above tissues or cells, particularly of the skeletal system and various other tumor tissues, expression of this gene at significantly higher or lower levels may routinely be detected in certain tissues (e.g. immune, skeletal, muscle, connective tissues and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The restricted tissue distribution and homology of Gene NO: 7 to carboxypeptidase E and mouse OSF-5 indicates that polypeptides and polynucleotides corresponding to Gene NO: 7 are for processing of peptides to their mature form that may have various activities similar to the activities of neuropeptides but in the periphery. In addition the abundance of expression in cancer tissues indicates that aberrant expression and subsequent processing may play a role in the progression of malignancies, e.g. growth factor and/or adhesion factor activities. In particular, the expression of this gene is restricted to connective tissues and embryonic tissues. Furthermore, it is overexpressed in cancers of these same tissues (i.e., in sarcomas). Moreover, hOSF-5 shares very strong sequence similarity with mOSF-5 which is a known bone growth factor and is thought to be useful in obtaining products for the diagnosis and treatment of bone metabolic diseases, e.g. osteoporosis and Paget's disease. Like OSF-5, the translation product of this gene is believed to be a bone-specific carboxypeptidase which acts as an adhesion molecule/growth factor and takes part in osteogenesis at the site of bone induction. hOSF-5 can, therefore, be used to treat bone metabolic diseases, osteoporosis, Paget's disease, osteomalacia, hyperostosis or osteopetrosis. Furthermore, hOSF-5 can be used to stimulate the regeneration of bone at the site of mechanical damage, e.g. accidentally or surgically caused fractures.

Preferred epitopes include those comprising a sequence shown in SEQ ID NO: 140 as residues: Leu-24 to Val-30, Ala-89 to Lys-94, Phe-150 to Trp-157, Leu-162 to Asp-167, Asp-187 to Ser-199, His-241 to Asp-254, and Pro-362 to Asp-376.

Many polynucleotide sequences, such as EST sequences, are publicly available and accessible through sequence databases. Some of these sequences are related to SEQ ID NO:

17 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1302 of SEQ ID NO: 17, b is an integer of 15 to 1316, where both a and b correspond to the positions of nucleotide residues shown in SEQ ID NO:17, and where b is greater than or equal to a+14.

Features of Protein Encoded by Gene No: 8

Gene NO: 8 is expressed primarily in bone marrow, and to a lesser extent in an erythroleukemia cell line.

Therefore, polynucleotides or polypeptides of the invention are useful as reagents for differential identification of the tissue(s) or cell type(s) present in a biological sample and for diagnosis of diseases and conditions which include, but are not limited to, hematological disorders including cancer and anemia. Similarly, polypeptides and antibodies directed to these polypeptides are useful in providing immunological probes for differential identification of the tissue(s) or cell type(s). For a number of disorders of the above tissues or cells, particularly of the immune and hematologic systems, expression of this gene at significantly higher or lower levels may routinely be detected in certain tissues and cell types (e.g. bone marrow, immune, kidney, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 8 are useful as a growth factor for hematopoietic stem cells or progenitor cells, e.g. in the treatment of bone marrow stem cell loss in chemotherapy patients and in the treatment of kidney disease.

Preferred epitopes include those comprising a sequence shown in SEQ ID NO: 141 as residues: Gly-30 to Lys-35.

Many polynucleotide sequences, such as EST sequences, are publicly available and accessible through sequence databases. Some of these sequences are related to SEQ ID NO: 18 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 422 of SEQ ID NO: 18, b is an integer of 15 to 436, where both a and b correspond to the positions of nucleotide residues shown in SEQ ID NO: 18, and where b is greater than or equal to a+14.

Features of Protein Encoded by Gene No: 9

Gene NO: 9 is expressed primarily in neutrophils.

Therefore, polynucleotides or polypeptides of the invention are useful as reagents for differential identification of the cell type present in a biological sample and for diagnosis of diseases and conditions which include, but are not limited to, inflammatory diseases. Similarly, polypeptides and antibodies directed to these polypeptides are useful in providing immunological probes for differential identification of the cell type indicated. For a number of disorders of the above tissues or cells, particularly of the immune system, expression of this gene at significantly higher or lower levels may routinely be detected in certain tissues or cell types (e.g. neutrophils, bone marrow, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 9 are useful for immune modulation or as a growth factor to stimulate neutrophil differentiation or proliferation that may be useful in the treatment of neutropenia.

Preferred epitopes include those comprising a sequence shown in SEQ ID NO: 142 as residues: Thr-22 to Pro-37.

Many polynucleotide sequences, such as EST sequences, are publicly available and accessible through sequence databases. Some of these sequences are related to SEQ ID NO: 19 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 489 of SEQ ID NO: 19, b is an integer of 15 to 503, where both a and b correspond to the positions of nucleotide residues shown in SEQ ID NO: 19, and where b is greater than or equal to a+14.

Features of Protein Encoded by Gene No: 10

Gene NO: 10 is expressed primarily in the epidermis.

Therefore, polynucleotides or polypeptides of the invention are useful as reagents for differential identification of the tissue(s) or cell type(s) present in a biological sample and for diagnosis of diseases and conditions which include, but are not limited to, diseases of the epidermis such as psoriasis or eczema or may be involved in the normal proliferation or differentiation of the epithelial cells or fibroblasts constituting the skin. Similarly, polypeptides and antibodies directed to these polypeptides are useful in providing inmmunological probes for differential identification of the tissue(s) or cell type(s). For a number of disorders of the above tissues or cells, particularly of the skin, expression of this gene at significantly higher or lower levels may routinely be detected in certain tissues or cell types (e.g. epidermis and cancerous and wounded tissues) or bodily fluids (e.g. lymph, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 10 are useful for diagnosis and treatment of skin conditions and as an aid in the healing of various epidermal injuries including wounds, and diabetic ulcers.

Preferred epitopes include those comprising a sequence shown in SEQ ID NO: 143 as residues: Ser-3 to Ser-9 and Trp-27 to Glu-32.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 344 of SEQ ID NO:20, b is an integer of 15 to 358, where both a and b correspond to the positions of nucleotide residues shown in SEQ ID NO:20, and where b is greater than or equal to a+14.

Features of Protein Encoded by Gene No: 11

The translation product of Gene NO: 11 shares sequence homology with phosphatidylcholine 2-acylhydrolase (PLA2). See, for example, Genbank accession no. gil190004. PLA2 is involved in inflammation, where it is responsible for the conversion of cell membrane phospholipids into arachidonic acid. Arachidonic acid in turn feeds into both the lipoxygenase and cyclooxygenase pathways to produce leukotrienes (involved in chemotaxis, vasoconstriction, bronchoconstriction, and increased vascular permeability) and prostaglandins (responsible for vasodilation, potentiate edema, and increased pain). Diseases in which PLA2 is implicated as a major factor include rheumatoid arthritis, sepsis, ischemia, and thrombosis. The inventors refer to the translation product of this gene as PLA2-like protein based on the sequence similarity. Furthermore, owing to the sequence similarity PLA2 and PLA2-like protein are expected to share certain biological activities.

Gene NO: 11 is expressed primarily in human cerebellum and in T-cells.

Therefore, polynucleotides or polypeptides of the invention are useful as reagents for differential identification of the tissue(s) or cell type(s) present in a biological sample and for diagnosis of diseases and conditions which include, but are not limited to, cerebellum disorders, rheumatoid arthritis, sepsis, ischemia, and thrombosis. Similarly, polypeptides and antibodies directed to these polypeptides are useful in providing immunological probes for differential identification of the tissue(s) or cell type(s). For a number of disorders of the above tissues or cells, particularly of the cerebellum and Purkinje cells, expression of this gene at significantly higher or lower levels may routinely be detected in certain tissues and cell types (e.g. brain, bone marrow, T-cells, immune, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 11 are useful for diagnosis and treatment of cerebellum disorders, rheumatoid arthritis, sepsis, ischemia, and thrombosis. This gene is also useful as a chromosome marker. It is believed to map to Chr.15, D15S118-D15S123.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1912 of SEQ ID NO:21, b is an integer of 15 to 1926, where both a and b correspond to the positions of nucleotide residues shown in SEQ ID NO:21, and where b is greater than or equal to a+14.

Features of Protein Encoded by Gene No: 12

Gene NO: 12 is expressed primarily in highly vascularized tissues such as placenta, uterus, tumors, fetal liver, fetal spleen and also in the C7MCF7 cell line treated with estrogen.

Therefore, polynucleotides or polypeptides of the invention are useful as reagents for differential identification of the tissue(s) or cell type(s) present in a biological sample and for diagnosis of diseases and conditions which include, but are not limited to, endometriosis, endometritis, endometrial carcinoma, primary hepatocellular carcinoma, and spleen-related diseases. Similarly, polypeptides and antibodies directed to these polypeptides are useful in providing immunological probes for different identification of the tissue(s) or cell type(s). For a number of disorders of the above tissues or cells, particularly of the endometrium, liver and spleen, expression of this gene at significantly higher or lower levels may routinely be detected in certain tissues (e.g. endometrium, liver, and spleen, and cancerous and wounded tissues) or bodily fluids (e.g. amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 12 are useful for diagnosis and treatment of diseases of the endometrium (such as endometrial carcinoma, endometriosis, and endometritis), liver diseases (such as primary hepatocellular carcinoma), and spleen-related diseases.

SEQ ID NO: 145 as residues: Ala-29 to Leu-35, Leu-50 to Ser-57, Glu-96 to Glu-105, Asp-140 to Asp-148, and Asn-191 to Ser-197.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1210 of SEQ ID NO:22, b is an integer of 15 to 1224, where both a and b correspond to the positions of nucleotide residues shown in SEQ ID NO:22, and where b is greater than or equal to a+14.

Features of Protein Encoded by Gene No: 13

Gene NO: 13 is expressed primarily in B cell lymphoma and to a lesser extent in other tissues.

Therefore, polynucleotides or polypeptides of the invention are useful as reagents for differential identification of the tissue(s) or cell type(s) present in a biological sample and for diagnosis of diseases and conditions which include, but are not limited to, B cell lymphoma; hematopoietic disorders; immune dysfunction. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues and cell types (e.g. bone marrow and B-cells and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Enhanced expression of this gene product in B cell lymphoma indicates that it may play a role in the proliferation of hematopoietic cells. It is also believed to be involved in the survival and/or differentiation of various hematopoietic lineages. Expression in lymphoma also indicates that it may be involved in other cancers and abnormal cellular proliferation. The tissue distribution, therefore, indicates that polypeptides and polynucleotides corresponding to Gene NO: 13 are useful for the diagnosis and/or therapeutic treatment of hematopoietic disorders, particularly B cell lymphoma. Furthermore, since overexpression of this gene is associated with the development of B cell lymphoma, antagonists of this protein are useful to interfere with the progression of the disease. This protein is useful in assays for identifying such antagonists. Assays for identifying antagonists are known in the art and are described briefly elsewhere herein. Preferred antagonists include antibodies and antisense nucleic acid molecules. Preferred are antagonists which inhibit B-cell proliferation.

Many polynucleotide sequences, such as EST sequences, are publicly available and accessible through sequence databases. Some of these sequences are related to SEQ ID NO: 23 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 680 of SEQ ID NO:23, b is an integer of 15 to 694, where both a and b correspond to the positions of nucleotide residues shown in SEQ ID NO:23, and where b is greater than or equal to a+14.

Features of Protein Encoded by Gene No: 14

The translation product of Gene NO: 14 shares sequence homology with very low density lipoprotein receptor which is thought to be important in transport of lipoproteins. Owing to the sequence similarity the translation product of this gene is believed to share certain biological activities with VLDL receptors. Assaying such activity may be achieved by assays known in the art and set forth elsewhere herein.

This gene is expressed primarily in human synovium, umbilical vein endothelial cells, CD34+ cells, Jurkat cells, and HL60 cells, and to a lesser extent in thymus, meningioma, hypothalmus, adult testis, and fetal liver and spleen.

Therefore, polynucleotides or polypeptides of the invention are useful as reagents for differential identification of the tissue(s) or cell type(s) present in a biological sample and for diagnosis of diseases and conditions which include, but are not limited to, atherosclerosis, ataxia malabsortion, vascular damage, hyperlipidemia, and other cardiovascular diseases. Similarly, polypeptides and antibodies directed to these polypeptides are useful in providing immunological probes for differential identification of the tissue(s) or cell type(s). For a number of disorders of the above tissues or cells, particularly of the cardiovascular and hematological systems, expression of this gene at significantly higher or lower levels may routinely be detected in certain tissues (e.g. endothelium, thymus meningioma, hypothalmus, testes, liver, and spleen and cancerous and wounded tissues) or bodily fluids (e.g. lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in the vascular endothelial cells and homology to VLDL receptors indicates that polypeptides and polynucleotides corresponding to Gene NO: 14 are useful for diagnosis and treatment of atherosclerosis, ataxia malabsortion, and hyperlipidemia. These and other factors often result in other cardiovascular diseases. Additionally, the presence of the gene product in cells of blood lineages indicates that it may be useful in hematopoietic regulation and hemostasis.

Preferred epitopes include those comprising a sequence shown in SEQ ID NO: 147 as residues: Pro-39 to Ser-52, Trp-71 to Thr-76, and Pro-94 to His-100.

A Many polynucleotide sequences, such as EST sequences, are publicly available and accessible through sequence databases. Some of these sequences are related to SEQ ID NO: 24 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 782 of SEQ ID NO:24, b is an integer of 15 to 796, where both a and b correspond to the positions of nucleotide residues shown in SEQ ID NO:24, and where b is greater than or equal to a+14.

Features of Protein Encoded by Gene No: 15

The translation product of Gene NO: 15 shares sequence homology with kallikrein which is thought to be important in blood pressure and renal secretion. Furthermore, this gene has now been characterized as a novel hepatitis B virus X binding protein that inhibits viral replication. See, for example, J. Virol. 72 (3), 1737–1743 (1998).

This gene is expressed primarily in kidney, placenta, lung, aorta and other endothelial cells, caudate nucleus and to a lesser extent in melanocytes, liver, adipose tissue.

Therefore, polynucleotides or polypeptides of the invention are useful as reagents for differential identification of the tissue(s) or cell type(s) present in a biological sample and for diagnosis of diseases and conditions which include, but are not limited to, renovascular hypertension, renal secretion, electrolyte metabolism, toxemia of pregnancy. Similarly, polypeptides and antibodies directed to these polypeptides are useful in providing immunological probes for differential identification of the tissue(s) or cell type(s). For a number of disorders of the above tissues or cells, particularly of the renovascular or respiratory vascular systems, expression of this gene at significantly higher or lower levels may routinely be detected in certain tissues and cell types (e.g. kidney, placenta, lung, endothelial cells, melanocytes, liver, and adipose tissue, and cancerous and wounded tissues) or bodily fluids (e.g. lymph, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to kallikrein indicates that polypeptides and polynucleotides corresponding to Gene NO: 15 are useful for treating renovascular hypertension, renal secretion, electrolyte metabolism, toxemia of pregnancy and hydronephrosis. The protein expression in the organs like kidney, lung and vascular endothelial cells indicates the gene involvement in hemodynamic regulatory functions. The translation product of this gene is also useful in the treatment of viral infection, particularly liver infection, and particularly hepatitis B virus(es).

Preferred epitopes include those comprising a sequence shown in SEQ ID NO: 148 as residues: Leu-9 to Asn-15 and Thr-56 to Asp-61.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 648 of SEQ ID NO:25, b is an integer of 15 to 662, where both a and b correspond to the positions of nucleotide residues shown in SEQ ID NO:25, and where b is greater than or equal to a+14.

Features of Protein Encoded by Gene No: 16

The translation product of Gene NO: 16 shares sequence homology with secretory component protein, immunoglobulins and their receptors which are thought to be important in immunological functions. The amino acid sequence of secretory component protein can be accessed as accession no. pirlA02112, incorporated herein by reference. When tested against sensory neuron cell lines, supernatants removed from cells containing this gene activated the interferon-sensitive responsive promoter element. Thus, it is likely that this gene activates neuronal cells through the Jaks-STAT signal transduction pathway. The EGR1 pathway is a signal transduction pathway in which the EGR1 promoter is induced in various tissues and cell types upon activation, leading the cells to undergo differentiation and proliferation.

Gene NO: 16 is expressed primarily in macrophages, monocytes and dendritic cells and to a lesser extent in placenta and brain.

Therefore, polynucleotides or polypeptides of the invention are useful as reagents for differential identification of the tissue(s) or cell type(s) present in a biological sample and for diagnosis of diseases and conditions which include, but are not limited to, inflammation and tumors. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues or cells (e.g. macrophages, monocytes, dendritic cells, plancenta and brain, and cancerous and wounded tissues) or bodily fluids (e.g. lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to immunoglobulins and secretory component protein indicates that polypeptides and polynucleotides corresponding to Gene NO: 16 are useful for diagnosis and treatment of inflammation and bacterial infection, and other diseases where immunomodulation would be beneficial. Alternatively, the activity demonstrated in the EGR1 assays, coupled with the tissue distribution and homology, suggests that the gene product may perform an important function in immunological responses, immune cell differentiation and proliferation, or antigen presentation. Protein, as well as, antibodies directed against the protein may show utility as a tumor marker and/or immunotherapy targets for the above listed tissues.

Preferred epitopes include those comprising a sequence shown in SEQ ID NO: 149 as residues: Pro-37 to Cys-51, Gln-53 to Cys-60, Asn-99 to Gly-106, Gly-145 to Glu-151, and Ile-159 to Ser-164.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1091 of SEQ ID NO:26, b is an integer of 15 to 1105, where both a and b correspond to the positions of nucleotide residues shown in SEQ ID NO:26, and where b is greater than or equal to a+14.

Features of Protein Encoded by Gene No: 17

The translation product of Gene NO: 17 is evolutionarily conserved and shares sequence homology with proteins from yeast and C. elegans. See, for example, Genbank accession no. gil746540. As is known in the art, strong sequence similarity to a secreted protein from C. elegans is predictive of cellular location of human proteins.

Gene NO: 17 is expressed primarily in colon carcinoma cell lines, messangial cells, many tumors like T cell lymphoma, osteoclastoma, Wilm's tumor, adrenal gland tumor, testes tumor, synovial sarcoma, and to a lesser extent in placenta, lung and brain.

Therefore, polynucleotides or polypeptides of the invention are useful as reagents for differential identification of the tissue(s) or cell type(s) present in a biological sample and for diagnosis of diseases and conditions which include, but are not limited to, rapidly growing/dividing cells such as cancerous tissue, including, colon carcinoma, lymphomas, and sarcomas. Similarly, polypeptides and antibodies directed to these polypeptides are useful in providing immunological probes for differential identification of the tissue(s) or cell type(s). For a number of disorders of the above tissues or cells, particularly of the gastrointestinal, hematological and immune systems, expression of this gene at significantly higher or lower levels may routinely be detected in certain tissues and cell types (e.g. placenta, lung, brain, colon, messangial cells, adrenal gland, T-cells, testes, and lymph tissue, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in colon cancer and many other tumors indicates that the polynucleotides and polypeptides of Gene NO: 17 are useful for cancer diagnosis and therapeutic targeting. The extracellular nature may contribute to solid tumor immunosuppression, angiogenesis and cell growth stimulation. The tissue distribution of this gene in cells of the immune system indicates that polypeptides and polynucleotides corresponding to Gene NO: 17 are useful for treatment, prophylaxis and diagnosis of immune and autoimmune diseases, such as lupus, transplant rejection, allergic reactions, arthritis, asthma, immunodeficiency diseases, leukemia, and AIDS. Its expression predominantly in hematopoietic cells also indicates that the gene could be important for the treatment and/or detection of hematopoietic disorders such as graft versus host reaction, graft versus host disease, transplant rejection, myelogenous leukemia, bone marrow fibrosis, and myeloproliferative disease. The protein can also be used to enhance or protect proliferation, differentiation and functional activation of hematopoietic progenitor cells such as bone marrow cells, which could be useful for cancer patients undergoing chemotherapy or patients undergoing bone marrow transplantation. The protein may also be useful to increase the proliferation of peripheral blood leukocytes, which could be useful in the combat of a range of hematopoietic disorders including immunodeficiency diseases, leukemia, and septicemia.

Preferred epitopes include those comprising a sequence shown in SEQ ID NO: 150 as residues: Val-131 to Asn-136.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1003 of SEQ ID NO:27, b is an integer of 15 to 1017, where both a and b correspond to the positions of nucleotide residues shown in SEQ ID NO:27, and where b is greater than or equal to a+14.

Features of Protein Encoded by Gene No: 18

The translation product of Gene NO: 18 shares sequence homology with immunoglobulin, which is thought to be important in immunoreactions.

Gene NO: 18 is expressed primarily in macrophage.

Therefore, polynucleotides or polypeptides of the invention are useful as reagents for differential identification of the tissue(s) or cell type(s) present in a biological sample and for diagnosis of diseases and conditions which include, but are not limited to, inflammation. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues and cell types (e.g. immune, hematopoietic, macrophage and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution in macrophages and the weak homology to immunoglobin indicates that polypeptides and polynucleotides corresponding to Gene NO: 18 are useful for diagnosing and treating immune response disorders, including inflammation, antigen presentation and iimmunosurveillance.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 377 of SEQ ID NO:28, b is an integer of 15 to 391, where both a and b correspond to the positions of nucleotide residues shown in SEQ ID NO:28, and where b is greater than or equal to a+14.

Features of Protein Encoded by Gene No: 19

The translation product of Gene NO: 19 shares sequence homology with proline rich proteins which are thought to be important in protein-protein interaction.

This gene has a wide range of tissue distribution, but is expressed primarily in normal prostate, synovial fibroblasts, brain amygdala depression, fetal bone and fetal cochlea, and to a lesser extent in adult retina, umbilical vein endothelial cells, atrophic endometrium, osteoclastoma, melanocytes, pancreatic carcinoma and smooth muscle.

Therefore, polynucleotides or polypeptides of the invention are useful as reagents for differential identification of the tissue(s) or cell type(s) present in a biological sample and for diagnosis of diseases and conditions which include, but are not limited to, cancer metastasis, wound healing, tissue repair. Similarly, polypeptides and antibodies directed to these polypeptides are useful in providing immunological probes for differential identification of the tissue(s) or cell type(s). For a number of disorders of the above tissues or cells, particularly of the skeletal, connective tissues, reproductive and central nervous system, expression of this gene at significantly higher or lower levels may routinely be detected in certain tissues and cell types (e.g. brain, prostrate, fibroblasts, bone, cochlea, retina, endothelial cells, endometrium, pancreas and smooth muscle, and cancerous and wounded tissues) or bodily fluids (e.g. lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to proline-rich proteins indicates that the protein is a extracellular matrix protein or an ingredient of bodily fluid. Polypeptides and polynucleotides corresponding to Gene NO: 19 are useful for cancer metastasis intervention, tissue culture additive, bone modeling, wound healing and tissue repair. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1125 of SEQ ID NO:29, b is an integer of 15 to 1139, where both a and b correspond to the positions of nucleotide residues shown in SEQ ID NO:29, and where b is greater than or equal to a+14.

Features of Protein Encoded by Gene No: 20

Gene NO: 20 is expressed primarily in prostate cancer, leukocytes, meningima, adult liver, pancreas, brain, and to a lesser extent in lung.

Therefore, polynucleotides or polypeptides of the invention are useful as reagents for differential identification of the tissue(s) or cell type(s) present in a biological sample and for diagnosis of diseases and conditions which include, but are not limited to, prostate cancers. Similarly, polypeptides and antibodies directed to these polypeptides are useful in providing immunological probes for differential identification of the tissue(s) or cell type(s). For a number of disorders of the above tissues or cells, particularly of the prostate and brain, expression of this gene at significantly higher or lower levels may routinely be detected in certain tissues and cell types (e.g. prostate, leukocytes, memingima, liver, brain, pancreas and lung, and cancerous and wounded tissues) or bodily fluids (e.g. bile, pulmonary surfactant, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Prostate cancer cell lines are known to be responsive to estrogen and androgen. The protein expression of Gene NO: 20 appears to be influenced by both estrogen and androgen levels. The prostate cancer tissue distribution indicates that polypeptides and polynucleotides corresponding to Gene NO: 20 are is useful in the intervention and detection of prostate hyperplasia and prostate cancer. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO: 30 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 451 of SEQ ID NO:30, b is an integer of 15 to 465, where both a and b correspond to the positions of nucleotide residues shown in SEQ ID NO:30, and where b is greater than or equal to a+1.

Features of Protein Encoded by Gene No: 21

The translation product of Gene NO: 21 is identical to the human wnt-7a gene. Wnt-7a is a secreted signaling molecule, thought to be important in signaling and the regulation of cell fate and pattern formation during embryogenesis. Specifically, knock out studies in mice have demonstrated that wnt7a plays a critical role in the development of the dorsal-ventral patterning in the developing limb, and to a lesser extent plays a role in the development of anterior-posterior patterning. Overexpression of wnt7a can induce transformation of cultured mammary cells, suggesting that it is an oncogene. Preferred polypeptides comprise the following amino acid sequence: NKRPTFLKIKKPL-SYRKPMDTDLVYIEKSPNYCEEDPVTGS-VGTQGRACNKT APQASGCDLMCCGRGYNTHQ-YARVWQCNCKFHWCCYVKCNTCSERT (SEQ ID NO:260). Also preferred are the polynucleotides encoding these proteins.

Expression of Gene NO: 21 has only been observed in testes.

Therefore, polynucleotides or polypeptides of the invention are useful as reagents for differential identification of the tissue(s) or cell type(s) present in a biological sample and for diagnosis of diseases and conditions which include, but are not limited to, testicular cancer; abnormal limb development. Similarly, polypeptides and antibodies directed to these polypeptides are useful in providing immunological probes for differential identification of the testes or developing embryo. For a number of disorders of the above tissues or cells, particularly of the developing embryo, expression of this gene at significantly higher or lower levels may routinely be detected in the developing embryo or amniotic fluid taken from a pregnant individual and compared relative to the standard gene expression level, i.e., the expression level in healthy tissue or bodily fluid from an individual not having the disorder. Also, expression of this gene at significantly higher or lower levels may routinely be detected in the testes of patient suffering from testicular cancer and compared relative to the standard gene expression level, i.e., the expression level in healthy tissue or bodily fluid from an individual not having the disorder.

The tissue distribution and homology to mouse wnt7a indicates that polypeptides and polynucleotides corresponding to Gene NO: 21 are useful to restore abnormal limb development in an affected individual. Furthermore, its oncogenic potential and tissue distribution indicates that it could serve as a diagnostic for testicular cancer. Protein, as well as, antibodies directed against the protein may show utility as a tumor marker and/or immunotherapy targets for the above listed tissues.

Preferred epitopes include those comprising a sequence shown in SEQ ID NO: 154 as residues: Gly-22 to Arg-28.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 688 of SEQ ID NO:31, b is an integer of 15 to 702, where both a and b correspond to the positions of nucleotide residues shown in SEQ ID NO:31, and where b is greater than or equal to a+1.

Features of Protein Encoded by Gene No: 22

Gene NO: 22 is expressed primarily in fetal liver/spleen, breast, testes and placenta and to a lesser extent in brain, and a series of cancer tissues.

Therefore, polynucleotides or polypeptides of the invention are useful as reagents for differential identification of the tissue(s) or cell type(s) present in a biological sample and for diagnosis of diseases and conditions which include, but are not limited to, immune disorders, brain diseases, male infertility, and disposition to pregnant miscarriages. Similarly, polypeptides and antibodies directed to these polypeptides are useful in providing immunological probes for differential identification of the tissue(s) or cell type(s). For a number of disorders of the above tissues or cells, particularly of the immune system, hematopoietic system, and sexual organs, expression of this gene at significantly higher or lower levels may routinely be detected in certain tissues or cell types (e.g. liver, spleen, testes, placenta, and brain, and cancerous and wounded tissues) or bodily fluids (e.g. seminal fluid, breast milk, bile, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution of this gene indicates that polypeptides and polynucleotides corresponding to Gene NO: 22 are useful as a marker for non-differentiated, dividing cells and hence could serve as an oncogenic marker. Its high expression in fetal liver, suggests an involvement in hematopoiesis and/or the immune system. Hence it is useful as a factor to enhance an individuals immune system, e.g. in individuals with immune disorders. It is also thought to affect the survival, proliferation, and differentiation of a number of hematopoietic cell lineages, including hematopoietic stem cells. Its disruption, e.g. mutation or altered expression, may also be a marker of immune disorder. Its expression in the testes, suggests it may be important in controlling male fertility. Expression of this gene in breast further reflects a role in immune function and immune surveillance (breast lymph node). This gene is believed to be useful as a marker for breast cancer. Protein, as well as, antibodies directed against the protein may show utility as a tumor marker and/or immunotherapy targets for the above listed tissues.

Preferred epitopes include those comprising a sequence shown in SEQ ID NO: 155 as residues: Gln-57 to Lys-70 and Ala-91 to Pro-100.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1128 of SEQ ID NO:32, b is an integer of 15 to 1142, where both a and b correspond to the positions of nucleotide residues shown in SEQ ID NO:32, and where b is greater than or equal to a+1.

Features of Protein Encoded by Gene No: 23

Gene NO: 23 is expressed primarily in bone marrow and brain (whole and fetal).

Therefore, polynucleotides or polypeptides of the invention are useful as reagents for differential identification of the tissue(s) or cell type(s) present in a biological sample and for diagnosis of diseases and conditions which include, but are not limited to, neurological, immune and hematopoietic disorders. Similarly, polypeptides and antibodies directed to these polypeptides are useful in providing immunological probes for differential identification of the tissue(s) or cell type(s). For a number of disorders of the above tissues or cells, particularly of the central nervous and hematopoietic systems, expression of this gene at significantly higher or lower levels may routinely be detected in certain tissues or cell types (e.g. bone marrow, brain, and cancerous and wounded tissues) or bodily fluids (e.g. lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 23 are useful in the diagnosis and treatment of disorders related to the central nervous system (e.g. neuro-degenerative conditions, trauma, and behavior abnormalities) and hematopoiesis. In addition, the expression in fetal brain indicates a role for this gene product in diagnosis of predisposition to developmental defects of the brain.

Preferred epitopes include those comprising a sequence shown in SEQ ID NO: 156 as residues: Thr-23 to Tyr-29.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 914 of SEQ ID NO:33, b is an integer of 15 to 928, where both a and b correspond to the positions of nucleotide residues shown in SEQ ID NO:33, and where b is greater than or equal to a+1.

Features of Protein Encoded by Gene No: 24

Gene NO: 24 is expressed primarily in smooth muscle, placenta, prostate, and osteoblasts.

Therefore, polynucleotides or polypeptides of the invention are useful as reagents for differential identification of the tissue(s) or cell type(s) present in a biological sample and for diagnosis of diseases and conditions which include, but are not limited to, cardiovascular pathologies. Similarly, polypeptides and antibodies directed to these polypeptides are useful in providing immunological probes for differential identification of the tissue(s) or cell type(s). For a number of disorders of the above tissues or cells, particularly of the cardiovascular, reproductive and skeletal systems, expression of this gene at significantly higher or lower levels may routinely be detected in certain tissues and cell types (e.g. placenta, smooth muscle, prostrate, and osteoblasts, and cancerous and wounded tissues) or bodily fluids (e.g. seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 24 are useful for detection and treatment of neoplasias and developmental abnormalities associated with these tissues.

Preferred epitopes include those comprising a sequence shown in SEQ ID NO: 157 as residues: Asn-21 to Thr-26.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 759 of SEQ ID NO:34, b is an integer of 15 to 773, where both a and b correspond to the positions of nucleotide residues shown in SEQ ID NO:34, and where b is greater than or equal to a+1.

Features of Protein Encoded by Gene No: 25

The translation product of Gene NO: 25 shares sequence homology with Pregnancy Associated Mouse Protein (PAMP)-1. (See, FEBS Lett 1993 May 17;322(3):219–222). Based on the sequence similarity the translation product of this gene is expected to share certain biological activities with PAMP-1.

Gene NO: 25 is expressed primarily in 12-week-old human embryos and prostate.

Therefore, polynucleotides or polypeptides of the invention are useful as reagents for differential identification of the tissue(s) or cell type(s) present in a biological sample and for diagnosis of diseases and conditions which include, but are not limited to, prostate disorders (cancer). Similarly, polypeptides and antibodies directed to these polypeptides are useful in providing immunological probes for differential identification of the tissue(s) or cell type(s). For a number of disorders of the above tissues or cells, particularly of the prostate, expression of this gene at significantly higher or lower levels may routinely be detected in certain tissues or cell types (e.g. embryonic tissue, and prostate, and cancerous and wounded tissues) or bodily fluids (e.g. amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 25 are useful for the diagnosis and treatment of prostate disorders (such as cancer) and developmental abnormalities and fetal deficiencies. The homology to PAMP-1 indicates that this gene and gene product are useful in detecting pregnancy.

Preferred epitopes include those comprising a sequence shown in SEQ ID NO: 158 as residues: Pro-23 to Glu-28 and Ser-44 to Gly-55.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 439 of SEQ ID NO:35, b is an integer of 15 to 453, where both a and b correspond to the positions of nucleotide residues shown in SEQ ID NO:35, and where b is greater than or equal to a+1.

Features of Protein Encoded by Gene No: 26

When tested against Jurkat T-cell cell lines, supernatant removed from cells containing this gene activated the GAS promoter element. Thus, it is likely that this gene activates T-cells through the Jaks-STAT signal transduction pathway. GAS is a promoter element found upstream in many genes which are involved in the Jaks-STAT pathway. The Jaks-STAT pathway is a large, signal transduction pathway involved in the differentiation and proliferation of cells. Therefore, activation of the Jaks-STAT pathway, reflected by the binding of the GAS element, can be used to indicate proteins involved in the proliferation and differentiation of cells.

Gene NO: 26 is expressed primarily in testes and to a lesser extent in epididymis.

Therefore, polynucleotides or polypeptides of the invention are useful as reagents for differential identification of the tissue(s) or cell type(s) present in a biological sample and for diagnosis of diseases and conditions which include, but are not limited to, reproductive and endocrine disorders, as well as testicular cancer. Similarly, polypeptides and antibodies directed to these polypeptides are useful in providing immunological probes for differential identification of the tissue(s) or cell type(s). For a number of disorders of the above tissues or cells, particularly of the male reproductive and endocrine systems, expression of this gene at significantly higher or lower levels may routinely be detected in certain tissues or cell types (e.g. reproductive, testes, and epididymis, and cancerous and wounded tissues) or bodily fluids (e.g. seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 26 are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents as such agents (antagonists) are useful as male contraceptive agents. Similarly, the protein is believed to by useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Preferred epitopes include those comprising a sequence shown in SEQ ID NO: 159 as residues: Pro-24 to Gly-33 and Arg-70 to Gly-76.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 445 of SEQ ID NO:36, b is an integer of 15 to 459, where both a and b correspond to the positions of nucleotide residues shown in SEQ ID NO:36, and where b is greater than or equal to a+1.

Features of Protein Encoded by Gene No: 27

The translation product of Gene NO: 27 shares sequence homology with salivary protein precursors which are thought to be important in immune response and production of secreted proteins.

Gene NO: 27 is expressed primarily in salivary gland tissue.

Therefore, polynucleotides or polypeptides of the invention are useful as reagents for differential identification of the tissue(s) or cell type(s) present in a biological sample and for diagnosis of diseases and conditions which include, but are not limited to, immune disorders, diseases of the salivary gland. Similarly, polypeptides and antibodies directed to these polypeptides are useful in providing immunological probes for differential identification of the tissue(s) or cell type(s). For a number of disorders of the above tissues or cells, particularly of the immune system, digestive system, expression of this gene at significantly higher or lower levels may routinely be detected in certain tissues or cell types (e.g. salivary gland, and cancerous and wounded tissues) or bodily fluids (e.g. serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to salivary secreted protein indicates that polypeptides and polynucleotides corresponding to Gene NO: 27 are useful for treatment of immune disorders and diagnostic uses related to secretion of protein in disease states. For example, the gene product can be used as an anti-microbial agent, an ingredient for oral or dental hygiene, treatment of xerostomia, sialorrhea, intervention for inflammation including parotitis, and an indication for tumors in the salivary gland (adenomas, carcinomas).

Preferred epitopes include those comprising a sequence shown in SEQ ID NO: 160 as residues: Asp-21 to Gly-28, Asp-30 to Glu-43, Glu-49 to Glu-62, and Thr-75 to Pro-83.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 495 of SEQ ID NO:37, b is an integer of 15 to 509, where both a and b correspond to the positions of nucleotide residues shown in SEQ ID NO:37, and where b is greater than or equal to a+1.

Features of Protein Encoded by Gene No: 28

Gene NO: 28 is expressed primarily in human fetal heart tissue and to a lesser extent in olfactory tissue.

Therefore, polynucleotides or polypeptides of the invention are useful as reagents for differential identification of the tissue(s) or cell type(s) present in a biological sample and for diagnosis of diseases and conditions which include, but are not limited to, immune, olfactory and cardiovascular disorders. Similarly, polypeptides and antibodies directed to these polypeptides are useful in providing immunological probes for differential identification of the tissue(s) or cell type(s). For a number of disorders of the above tissues or cells, particularly of the immune, olfactory and vascular systems, expression of this gene at significantly higher or lower levels may routinely be detected in certain tissues or cell types (e.g. olfactory tissue, and heart, and cancerous and wounded tissues) or bodily fluids (e.g. amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 28 are useful for diagnosis and treatment of immune, olfactory and vascular disorders.

Preferred epitopes include those comprising a sequence shown in SEQ ID NO: 161 as residues: Cys-33 to Gly-44, Arg-71 to Arg-78, Ser-130 to Gly-142, Lys-150 to Gly-157, and Thr-159 to Asp-177.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 584 of SEQ ID NO:38, b is an integer of 15 to 598, where both a and b correspond to the positions of nucleotide residues shown in SEQ ID NO:38, and where b is greater than or equal to a+1.

Features of Protein Encoded by Gene No: 29

Gene NO: 29 is expressed primarily in brain and to a lesser degree in activated macrophages, endothelial and smooth muscle cells, and some bone cancers.

Therefore, polynucleotides or polypeptides of the invention are useful as reagents for differential identification of brain and endothelial present in a biological sample and for diagnosis of diseases and conditions which include, but are not limited to, neurodegeneration, inflammation and other immune disorders, fibrotic conditions. Similarly, polypeptides and antibodies directed to these polypeptides are useful in providing immunological probes for differential identification brain, smooth muscle, and endothelium. For a number of disorders of the above tissues or cells, particularly of the brain and endothelium, expression of this gene at significantly higher or lower levels may routinely be detected in certain tissues or cell types (e.g. brain, endothelial cells, macrophages, smooth muscle, and bone, and cancerous and wounded tissues) or bodily fluids (e.g. serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

Tissue distribution suggests polypeptides and polynucleotides corresponding to Gene NO: 29 are useful in study and treatment of neurodegenerative and immune disorders.

Preferred epitopes include those comprising a sequence shown in SEQ ID NO: 162 as residues: Asn-18 to Glu-20, Ser-33 to Gln-48, Cys-55 to Ser-56, Pro-67 to Cys-69.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 440 of SEQ ID NO:39, b is an integer of 15 to 454, where both a and b correspond to the positions of nucleotide residues shown in SEQ ID NO:39, and where b is greater than or equal to a+1.

Features of Protein Encoded by Gene No: 30

Gene NO: 30 is expressed primarily in early stage human brain and to a lesser extent in cord blood, heart, and some tumors.

Therefore, polynucleotides or polypeptides of the invention are useful as reagents for differential identification of developing CNS tissue present in a biological sample and for diagnosis of diseases and conditions which include, but are not limited to, cardiovascular and neurodegenerative disorders. Similarly, polypeptides and antibodies directed to these polypeptides are useful in providing immunological probes for differential identification of the tissue(s) or cell type(s). For a number of disorders of the above tissues or cells, particularly of the nervous and immune systems, expression of this gene at significantly high or lower levels may routinely be detected in certain tissues (e.g. brain and heart, and cancerous and wounded tissues) or bodily fluids (e.g. serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that that polypeptides and polynucleotides corresponding to Gene NO: 30 are useful for the treatment of cancer and of neurodegenerative and cognitive disorders, such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 411 of SEQ ID NO:40, b is an integer of 15 to 425, where both a and b correspond to the positions of nucleotide residues shown in SEQ ID NO:40, and where b is greater than or equal to a+1.

Features of Protein Encoded by Gene No: 31

Gene NO: 31 is expressed primarily in brain and thymus and to a lesser extent in several other organs and tissues including the hematopoietic system, liver skin and bone.

Therefore, polynucleotides or polypeptides of the invention are useful as reagents for differential identification of the tissue(s) or cell type(s) present in a biological sample and for diagnosis of diseases and conditions which include, but are not limited to, CNS disorders, hematopoietic system disorders, disorders of the endocrine system, bone, and skin. Similarly, polypeptides and antibodies directed to these polypeptides are useful in providing immunological probes for differential identification of the tissue(s) or cell type(s). For a number of disorders of the above tissues or cells, particularly CNS disorders, hematopoietic system disorders, disorders of the endocrine system, bone, and skin, expression of this gene at significantly higher or lower levels may routinely be detected in certain tissues and cell types (e.g. hematopoietic cells, brain, thymus, liver, bone, and epidermis, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 31 are useful for treatment and diagnosis of CNS disorders, hematopoietic system disorders, disorders of the endocrine system, and of bone and skin. Protein, as well as, antibodies directed against the protein may show utility as a tumor marker and/or immunotherapy targets for the above listed tissues.

Preferred epitopes include those comprising a sequence shown in SEQ ID NO: 164 as residues: Thr-35 to Arg-40, Pro-55 to His-75, Pro-93 to Ala-98, Ala-111 to Pro-119, and Pro-132 to Glu-138.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2457 of SEQ ID NO:41, b is an integer of 15 to 2471, where both a and b correspond to the positions of nucleotide residues shown in SEQ ID NO:41, and where b is greater than or equal to a+1.

Features of Protein Encoded by Gene No: 32

Gene NO: 32 is expressed primarily in organs and tissue of the nervous system and to a lesser extent in various developing tissues and organs.

Therefore, polynucleotides or polypeptides of the invention are useful as reagents for differential identification of the tissue(s) or cell type(s) present in a biological sample and for diagnosis of diseases and conditions which include, but are not limited to, disorders of the central nervous system and disorders of developing and growing tissues and organs. Similarly, polypeptides and antibodies directed to these polypeptides are useful in providing immunological probes for differential identification of the tissue(s) or cell type(s). For a number of disorders of the above tissues or cells, particularly disorders of the CNS, expression of this gene at significantly higher or lower levels may routinely be detected in certain tissues or cell types (e.g. tissue of the nervous system and cancerous and wounded tissues) or bodily fluids (e.g. amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 32 are useful for diagnosis and treatment of disorders of the central nervous system, general neurological diseases and neoplasias, such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and perception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues.

Preferred epitopes include those comprising a sequence shown in SEQ ID NO: 165 as residues: Ser-33 to Lys-41 and Glu-86 to Glu-91.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2645 of SEQ ID NO:42, b is an integer of 15 to 2659, where both a and b correspond to the positions of nucleotide residues shown in SEQ ID NO:42, and where b is greater than or equal to a+1.

Features of Protein Encoded by Gene No: 33

Residues 141–156 in the translation product for Gene NO: 33 as shown in the sequence listing matches phosphopantetheine binding site motifs. Phosphopantetheine (or pantetheine 4' phosphate) is the prosthetic group of acyl carrier proteins (ACP) in some multienzyme complexes where it serves as a 'swinging arm' for the attachment of activated fatty acid and amino-acid groups. Phosphopantetheine is attached to a serine residue in these proteins. ACP proteins or domains have been found in various enzyme systems which are listed below. Fatty acid synthetase (FAS), which catalyzes the formation of long-chain fatty acids from acetyl-CoA, malonyl-CoA and NADPH. Bacterial and plant chloroplast FAS are composed of eight separate subunits which correspond to the different enzymatic activities; ACP is one of these polypeptides. Fungal FAS consists of two multifunctional proteins, FAS1 and FAS2; the ACP domain is located in the N-terminal section of FAS2. Vertebrate FAS consists of a single multifunctional enzyme; the ACP domain is located between the beta-ketoacyl reductase domain and the C-terminal thioesterase domain. Based on the presence of a phosphopantetheine binding site in the translation product of this gene, it is believed to share activities fatty acid synthetase polypeptides. Such activities may be assayed by methods known in the art.

This gene is expressed primarily in developing and rapidly growing tissues like placenta fetal heart and endometrial tumor and to a lesser extent in B and T cell lymphoma tissues Therefore, polynucleotides or polypeptides of the invention are useful as reagents for differential identification of the tissue(s) or cell type(s) present in a biological sample and for diagnosis of diseases and conditions which include, but are not limited to, cancer and disorders of developing tissues and organs. Similarly, polypeptides and antibodies directed to these polypeptides are useful in providing immunological probes for differential identification of the tissue(s) or cell type(s). For a number of disorders of the above tissues or cells, particularly of the hematopoietic tissues and developing organs and tissues, expression of this gene at significantly higher or lower levels may routinely be detected in certain tissues and cell types (e.g. embryonic tissue, endometrium, B-cells, and T-cells, and cancerous and wounded tissues) or bodily fluids (e.g. amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 33 are useful for treatment and diagnosis of cancer in the hematopoietic system developing organs and tissues. It may also be useful for induction of cell growth in disorders of the hematopoietic system and other tissue and organs. The homology to fatty acid synthetases indicates that this gene product is useful in the diagnosis and treatment of lipid metabolism disorders such as hyperlipidemia.

Preferred epitopes include those comprising a sequence shown in SEQ ID NO: 166 as residues: Arg-27 to Glu-34.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1621 of SEQ ID NO:43, b is an integer of 15 to 1635, where both a and b correspond to the positions of nucleotide residues shown in SEQ ID NO:43, and where b is greater than or equal to a+1.

Features of Protein Encoded by Gene No: 34

Gene NO: 34 is expressed primarily in breast and testes tissues and to a lesser extent in hematopoietic tissues including tonsils, T cells and monocytes.

Therefore, polynucleotides or polypeptides of the invention are useful as reagents for differential identification of the tissue(s) or cell type(s) present in a biological sample and for diagnosis of diseases and conditions which include, but are not limited to, diseases of the reproductive organs and systems, including cancer, autoimmune diseases and inflammatory diseases. Similarly, polypeptides and antibodies directed to these polypeptides are useful in providing immunological probes for differential identification of the tissue(s) or cell type(s). For a number of disorders of the above tissues or cells, particularly of the reproductive organs and hematopoietic tissues, expression of this gene at significantly higher or lower levels may routinely be detected in certain tissues and cell types (e.g. hemotopoietic cells, T-cells and monocytes, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Nucleic acids comprising sequence of this gene are also useful as chromosome markers since this gene maps to Chr.15, D 15S 118–D15S123.

The tissue distribution indicates that polypeptides and polynucleotides corresponding to Gene NO: 34 are useful for treatment of diseases of the reproductive organs and hematopoietic system including cancer, autoimmune diseases and inflammatory diseases, such as rheumatoid arthritis, lupus, scleroderma, and dermatomyositis as well as dwarfism, spinal deformation, and specific joint abnormalities as well as chondrodysplasias ie. spondyloepiphyseal dysplasia congenita, familial osteoarthritis, Atelosteogenesis type II, and metaphyseal chondrodysplasia type Schmid. Protein, as well as, antibodies directed against the protein may show utility as a tumor marker and/or immunotherapy targets for the above listed tissues.

Preferred epitopes include those comprising a sequence shown in SEQ ID NO: 167 as residues: Phe-81 to Lys-86.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 766 of SEQ ID NO:44, b is an integer of 15 to 780, where both a and b correspond to the positions of nucleotide residues shown in SEQ ID NO:44, and where b is greater than or equal to a+1.

Features of Protein Encoded by Gene No: 35

The translation product of Gene NO: 35 shares sequence similarity with the mouse cytokine-inducible inhibitor of signaling. See, e.g. Nature 1997 Jun 26;387(6636):917–921. Cytokines are secreted proteins that regulate important cellular responses such as proliferation and differentiation. Key events in cytokine signal transduction are well defined: cytokines induce receptor aggregation, leading to activation of members of the JAK family of cytoplasmic tyrosine kinases. In turn, members of the STAT family of transcription factors are phosphorylated, dimerize and increase the transcription of genes with STAT recognition sites in their promoters. Less is known of how cytokine signal transduction is switched off. Expression of the mouse SOCS-1 protein inhibited both interleukin-6-induced receptor phosphorylation and STAT activation. We have also cloned two relatives of SOCS-1, named SOCS-2 and SOCS-3, which together with the previously described CIS form a new family of proteins. Transcription of all four SOCS genes is increased rapidly in response to interleukin-6, in vitro and in vivo, suggesting they may act in a classic negative feedback loop to regulate cytokine signal transduction. The translation product of this gene is believed to have similar biological activities as this family of mouse genes. The biological activity of the translation product of this gene may be assayed by methods shown in Nature 1997 Jun 26;387 (6636): 917–921, which is incorporated herein by reference in its entirety. One embodiment of this clone comprises polypeptides of the following amino acid sequence: SAEP-AGTFLIRDSSDQRHFFTLSVKTQSGTKNLRIQCE GGSFSLQSDPRSTQPVPRFDCVLKLVH-HYMPPPGAPSFPSPPTEPSSEVPEQPSAQPLPGS PPRRAYYIYSGGEKIPLVLSRPLSSN-VATLQHLCRKTVNGHLDSYEKVTQLPGPIREFLDQ YDAPL (SEQ ID NO:261), MVTHSKFPAAGMSR-PLDTSLRLKTFSSKSEYQLVV NAVRK (SEQ ID NO:262), QESGFYWSAVTGGEANLLLSAEPAGTF-LIRDSS (SEQ ID NO:263). An additional embodiment would be the polynucleotides encoding these polypeptides.

Gene NO: 35 is expressed primarily in tissues of hematopoietic origin including activated monocytes, neutrophils, activated T-cells and to a lesser extent in breast, adipose tissue and dendritic cells.

Therefore, polynucleotides or polypeptides of the invention are useful as reagents for differential identification of the tissue(s) or cell type(s) present in a biological sample and for diagnosis of diseases and conditions which include, but are not limited to, diseases of the hematopoietic system including cancer autoimmune diseases and inflammatory diseases. Similarly, polypeptides and antibodies directed to these polypeptides are useful in providing immunological probes for differential identification of the tissue(s) or cell type(s). For a number of disorders of the above tissues or cells, particularly of the hematopoietic system expression of this gene at significantly higher or lower levels may routinely be detected in certain tissues and cell types (e.g. hematopoietic cells and cancerous and wounded tissues) or bodily fluids (e.g. lymph, breast milk, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to cytokine inducible inhibitor of signaling indicates that polypeptides and polynucleotides corresponding to Gene NO: 35 are useful for diagnosis and treatment of diseases of the hematopoietic system including autoimmune diseases, inflammatory diseases, infectious diseases and neoplasia. For example, administration of, or upregulation of this gene could by used to decrease the response of immune-system to lymphokines and cytokines.

Preferred epitopes include those comprising a sequence shown in SEQ ID NO: 168 as residues: Arg-23 to His-30, Ala-35 to Gly-42.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2364 of SEQ ID NO:45, b is an integer of 15 to 2378, where both a and b correspond to the positions of nucleotide residues shown in SEQ ID NO:45, and where b is greater than or equal to a+1.

Features of Protein Encoded by Gene No: 36

When tested against K562 cell lines, supernatant removed from cells containing the gene activated the SRE assay. Thus, it is likely that this gene activates leukemia cells through the Jaks-STAT signal transduction pathway. The interferon-sensitive response element is a promoter found upstream in many genes which are involved in the Jaks-STAT pathway. The Jaks-STAT pathway is a large, signal transduction pathway involved in the differentiation and proliferation of cells. Therefore, activation of the Jaks-STAT pathway, reflected by the binding of the ISRE element, can be used to indicate proteins involved in the proliferation and differentiation of cells.

Gene NO: 36 is expressed primarily in infant brain and to a lesser extent in osteoclastoma, placenta, and a wide variety of other tissues.

Therefore, polynucleotides or polypeptides of the invention are useful as reagents for differential identification of the tissue(s) or cell type(s) present in a biological sample and for diagnosis of diseases and conditions which include, but are not limited to, neurological disorders. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may routinely be detected in certain tissues and cell types (e.g. osteoclastoma, placenta, and tissue of the central nervous system, and cancerous and wounded tissues) or bodily fluids (e.g. amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 36 are useful for diagnosis and treatment of neurologic disorders, such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Alternatively, the tissue distribution, as well as the activation of leukemia cells in the SRE assay, suggest that the gene product of this clone may function in the regulation and proliferation of certain types of cancerous cells. Protein, as well as, antibodies directed against the protein may show utility as a tissue-specific marker and/or immunotherapy target for the above listed tissues.

Preferred epitopes include those comprising a sequence shown in SEQ ID NO: 169 as residues: Gln-31 to Ser-37, Ile-49 to Gly-54, Tyr-57 to Asp-67, Gln-141 to Pro-151, and Val-207 to Thr-219.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1758 of SEQ ID NO:46, b is an integer of 15 to 1772, where both a and b correspond to the positions of nucleotide residues shown in SEQ ID NO:46, and where b is greater than or equal to a+1.

Features of Protein Encoded by Gene No: 37

Gene NO: 37 is expressed primarily in osteoclastoma stromal cells, dendritic cells, liver, and placenta.

Therefore, polynucleotides or polypeptides of the invention are useful as reagents for differential identification of the tissue(s) or cell type(s) present in a biological sample and for diagnosis of diseases and conditions which include, but are not limited to, cancer, wound, pathological conditions. Similarly, polypeptides and antibodies directed to these polypeptides are useful in providing immunological probes for differential identification of the tissue(s) or cell type(s). For a number of disorders of the above tissues or cells, expression of this gene at significantly higher or lower levels may routinely be detected in certain tissues or cell types (e.g. stromal cells, dendritic cells, liver, and placenta and, cancerous and wounded tissues) or bodily fluids (e.g. lymph, bile, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 37 are useful for fundamental role in basic growth and development of human.

Preferred epitopes include those comprising a sequence shown in SEQ ID NO: 170 as residues: Leu-32 to Thr-37 and Arg-48 to Pro-55.

Many polynucleotide sequences, such as EST sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1093 of SEQ ID NO:47, b is an integer of 15 to 1107, where both a and b correspond to the positions of nucleotide residues shown in SEQ ID NO:47, and where b is greater than or equal to a+1.

Features of Protein Encoded by Gene No: 38

The translation product of Gene NO: 38 shares sequence homology with a yeast protein, Lpe 10p, which may be involved in mRNA processing. (See Accession Nos. 2104457 and 1079682.) It is likely that an upstream signal sequence exists, other than the predicted sequence described in Table 1. Preferred polypeptide fragments comprise the open reading frame upstream from the predicted signal sequence, as well as polynucleotide fragments encoding these polypeptide fragments.

This gene is expressed primarily in skin, and to a lesser extent in embryonic tissues, and fetal liver.

Therefore, polynucleotides or polypeptides of the invention are useful as reagents for differential identification of the tissue(s) or cell type(s) present in a biological sample and for diagnosis of diseases and conditions which include, but are not limited to, defects of the skin. Similarly, polypeptides and antibodies directed to these polypeptides are useful in providing immunological probes for differential identification of the tissue(s) or cell type(s). For a number of disorders of the above tissues or cells, particularly of the skin, expression of this gene at significantly higher or lower levels may routinely be detected in certain tissues or cell types (e.g. epidermis, liver, and embryanic tissues, and cancerous and wounded tissues) or bodily fluids (e.g. bile, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 38 are useful for diagnosis and treatment of defects of the skin, including congenital disorders (i.e. nevi, moles, freckles, Mongolian spots, hemangiomas, port-wine syndrome), integumentary tumors (i.e. keratoses, Bowentis disease, basal cell carcinoma, squamous cell carcinoma, malignant melanoma, Pagetís disease, mycosis fungoides, and Kaposifs sarcoma), injuries and inflammation of the skin (i.e.wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm). Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 791 of SEQ ID NO:48, b is an integer of 15 to 805, where both a and b correspond to the positions of nucleotide residues shown in SEQ ID NO:48, and where b is greater than or equal to a+1.

Features of Protein Encoded by Gene No: 39

Gene NO: 39 is expressed primarily in amygdala, activated monocytes, testis, and fetal liver. Moreover, the gene encoding the disclosed cDNA is thought to reside on chromosome 4. Accordingly, polynucleotides related to this invention are useful as a marker in linkage analysis for chromosome 4.

Therefore, polynucleotides and polypeptides of the invention are useful as reagents for differential identification of the tissue(s) or cell type(s) present in a biological sample and for diagnosis of diseases and conditions which include, but are not limited to, defects of the brain, immune system and testis. Similarly, polypeptides and antibodies directed to these polypeptides are useful in providing immunological probes for differential identification of the tissue(s) or cell type(s). For a number of disorders of the above tissues or cells, particularly of the brain, immune system and testis, expression of this gene at significantly higher or lower levels may routinely be detected in certain tissues and cell types (e.g. amygdala, monocytes, testes, and liver and cancerous and wounded tissues) or bodily fluids (e.g. seminal fluid, lymph, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 39 are useful for detecting defects of the brain, immune system and testis because of its abundance in these tissues. Expression of this gene product in liver and spleen tissue suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells an d progenitors of various blood lineages, and in the differentiation and/or proliferation of various cell types. In addition, this gene product may be useful in the treatment of male infertility, and/or could be used as a male contraceptive. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1394 of SEQ ID NO:49, b is an integer of 15 to 1408, where both a and b correspond to the positions of nucleotide residues shown in SEQ ID NO:49, and where b is greater than or equal to a+1.

Features of Protein Encoded by Gene No: 40

The translation product of Gene NO: 40 shares sequence homology with lymphoma 3-encoded protein (bcl-3) which is thought to contribute to leukemogenesis when abnormally expressed.

This gene is expressed primarily in human neutrophils, and to a lesser extent in human osteoclastoma stromal cells (unamplified), hepatocellular tumor, and human neutrophils, (activated).

Therefore, polynucleotides or polypeptides of the invention are useful as reagents for differential identification of the tissue(s) or cell type(s) present in a biological sample and for diagnosis of diseases and conditions which include, but are not limited to, chronic lymphocytic leukemia. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues and cell types (e.g. neutrophils, osteoclastoma, and kidney, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to lymphoma 3-encoded protein (bcl-3) indicates that polypeptides and polynucleotides corresponding to Gene NO: 40 are useful for treatment of lymphoma and related cancers. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1799 of SEQ ID NO:50, b is an integer of 15 to 1813, where both a and b correspond to the positions of nucleotide residues shown in SEQ ID NO:50, and where b is greater than or equal to a+1.

Features of Protein Encoded by Gene No: 41

Gene NO: 41 is expressed primarily in ovary tumor, and to a lesser extent in endometrial stromal cells and fetal brain.

Therefore, polynucleotides or polypeptides of the invention are useful as reagents for differential identification of the tissue(s) or cell type(s) present in a biological sample and for diagnosis of diseases and conditions which include, but are not limited to, ovarian or endometrial cancer. Similarly, polypeptides and antibodies directed to these polypeptides are useful in providing immunological probes for differential identification of the tissue(s) or cell type(s). For a number of disorders of the above tissues or cells, particularly of the female reproductive system and the developing central nervous system, expression of this gene at significantly higher or lower levels may routinely be detected in certain tissues or cell types (e.g. ovary, endometrium and brain, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 41 are useful for development of factors involved in ovarian or endometrial and general reproductive organ disorders.

Preferred epitopes include those comprising a sequence shown in SEQ ID NO: 174 as residues: Glu-22 to Trp-31, Asn-84 to Asp-90, and Ser-144 to Asp-151.

Many polynucleotide sequences, such as EST sequences, are publicly available and accessible through sequence databases. Some of these sequences are related to SEQ ID NO:S51 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2056 of SEQ ID NO:51, b is an integer of 15 to 2070, where both a and b correspond to the positions of nucleotide residues shown in SEQ ID NO:51, and where b is greater than or equal to a+1.

Features of Protein Encoded by Gene No: 42

The translation product of Gene 42 has sequence identity with a gene designated PTHrP(B). The PTHrP(B) polypeptide inhibits parathyroid hormone related peptide (PTHrP) activity.

This gene is expressed primarily in adult testis, and to a lesser extent in pituitary.

Therefore polynucleotides or polypeptides of the invention are useful as reagents for differential identification of the tissue(s) or cell type(s) present in a biological sample and for diagnosis of male reproductive disorders. Similarly, polypeptides and antibodies directed to these polypeptides are useful in providing immunological probes for differential identification of the tissue(s) or cell type(s). For a number of disorders of the above tissues or cells, particularly of the male reproductive system, expression of this gene at significantly higher or lower levels may routinely be detected in certain tissues or cell types (e.g. testes, and pituitary, and cancerous and wounded tissues) or bodily fluids (e.g. seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Furthermore, based in part on sequence identity with PTlHrP(B), nucleic acids and polypeptides of the present invention may be used to diagnose or treat such conditions as hypercalcemia, osteoporosis, and disorders related to calcium metabolism.

The tissue distribution indicates that polypeptides and polynucleotides corresponding to Gene NO: 42 are useful for treatment of male reproductive disorders, hypercalcemia, osteoporosis, and other disorders related to calcium metabolism.

Preferred epitopes include those comprising a sequence shown in SEQ ID NO: 175 as residues: Tyr-81 to Met-86, Gly-103 to Ser-108, Glu-127 to Pro-128, Pro-175 to Ser-180, Glu-196 to Lys-203, Pro-235 to Ser-241, and Ala-249 to Ser-264.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1412 of SEQ ID NO:52, b is an integer of 15 to 1426, where both a and b correspond to the positions of nucleotide residues shown in SEQ ID NO:52, and where b is greater than or equal to a+1.

Features of Protein Encoded by Gene No: 43

The translation product of Gene NO: 43 shares sequence homology with brevican, which is thought to be important as a proteoglycan core protein of the aggrecan/versican family. The translation product of this gene may also contain a hyaluronan (HA)-binding region domain in frame with, but downstream of, the predicted open reading frame (Barta, et al., Biochem. J. 292:947–949 (1993)). The HA-binding domain, also termed the link domain, is found in proteins of vertebrates that are involved in the assembly of extracellular matrix, cell adhesion, and migration. It is about 100 amino acids in length. The structure has been shown to consist of two alpha helices and two antiparallel beta sheets arranged around a large hydrophobic core similar to that of C-type lectin. This domain typically contains four conserved cysteines involved in two disulfide bonds.

This gene is expressed primarily in early stage human brain and to a lesser extent in frontal cortex and epileptic tissues.

Therefore, polynucleotides or polypeptides of the invention are useful as reagents for differential identification of the tissue(s) or cell type(s) present in a biological sample and for diagnosis of disorders associated with, or observed during, neuronal development. Similarly, polypeptides and antibodies directed to these polypeptides are useful as immunological probes for differential identification of neuronal and associated tissues and cell types. For a number of disorders of the above tissues or cells, particularly for those of the nervous system, expression of this gene at significantly higher or lower levels may routinely be detected in certain tissues or cell types (e.g. brain and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to brevican indicates that polypeptides and polynucleotides corresponding to Gene NO: 43 are useful for neuronal regulation and signaling. The uses include directing or inhibiting axonal growth for the treatment of neuro-fibromatosis and in detection of glioses.

Preferred epitopes include those comprising a sequence shown in SEQ ID NO: 176 as residues: Asp-28 to Arg-33 and Arg-126 to Arg-131.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1706 of SEQ ID NO:53, b is an integer of 15 to 1720, where both a and b correspond to the positions of nucleotide residues shown in SEQ ID NO:53, and where b is greater than or equal to a+1.

Features of Protein Encoded by Gene No: 44

Gene NO: 44 is the human homolog of Notch-2 (Accession No. 477495) and mouse EGF repeat transmembrane protein (Accession No. 1336628), both genes are important in differentiation and development of an organism. The EGF repeat transmembrane protein is regulated by insulin like growth factor Type I receptor. These proteins are involved in cell-cell signaling and cell fate determination. Based on homology, it is likely that this gene products also involved in cell differentiation and development. Although the predicted signal sequence is indicated in Table 1, it is likely that a second signal sequence is located further upstream. Moreover, further translated coding regions are likely found downstream from the disclosed sequence, which can easily be obtained using standard molecular biology techniques. A frameshift occurs somewhere around nucleotide 714, causing a frame shift in amino acid sequence from frame +2 to frame +3. However, using the homology of Notch-2 and EGF repeat transmembrane protein, the complete open reading frame can be elucidated. Preferred polynucleotide fragments comprise nucleotides 146–715, 281–715, and 714–965. Other preferred polypeptide fragments comprise the following EGF-like motifs: CRCASGFTGEDC (SEQ ID NO:264), CTCQVGFTGKEC (SEQ ID NO:265), CLNLPGSYQCQC (SEQ ID NO:266), CKCLTGFTGQKC (SEQ ID NO:267), and CQCLQGFTGQYC (SEQ ID NO:268). When tested against Jurkat T-cell cell lines, supernatants removed from cells containing the gene activated the GAS assay. Additionally, when tested against K562 leukemia cell lines, supernatants removed from cells containing this gene activated the ISRE assay. Thus, it is likely that this gene activates T-cells and leukemia cells, respectively, through the Jaks-STAT signal transduction pathway. Gamma activation site (GAS) is a promoter element found upstream in many genes which are involved in the Jaks-STAT pathway. The interferon-sensitive response element (ISRE) is also a promoter element found upstream in many genes which are involved in the Jaks-STAT pathway. The Jaks-STAT pathway is a large, signal transduction pathway involved in the differentiation and proliferations of cells. Therefore, activation of the Jaks-STAT pathway, reflected by the binding of both the GAS and ISRE elements, can be used to indicate proteins involved in the proliferation and differentiation of cells.

Gene NO: 44 is expressed primarily in placenta and to a lesser extent in stromal and immune cells.

Therefore, polynucleotides and polypeptides of the invention are useful as reagents for differential identification of the tissue(s) or cell type(s) present in a biological sample and for diagnosis of diseases and conditions which include, but are not limited to, hemophelia and other blood disorders, central nervous system disorders, muscle disorders, and any other disorder resulting from abnormal development. Similarly, polypeptides and antibodies directed to these polypeptides are useful in providing immunological probes for differential identification of the tissue(s) or cell type(s). For a number of disorders of the above tissues or cells, particularly of the immune, hematopoietic and vascular systems, expression of this gene at significantly higher or lower levels may routinely be detected in certain tissues and cell types (e.g. placenta, stromal and immune cells and cancerous and wounded tissues) or bodily fluids (e.g. amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution, homology to Notch-2, and activity in the GAS and ISRE assays indicates that the polypeptides and polynucleotides corresponding to Gene NO: 44 are useful for diagnosing and treating disorders relating to abnormal regulation of cell fate, induction, and differentiation of cells (e.g. cancer, epidermal growth factors, axonal path finding, and hematopoiesis.)

Preferred epitopes include those comprising a sequence shown in SEQ ID NO: 177 as residues: Gln-27 to Tyr-32, His-45 to Glu-55, Tyr-61 to Gly-77, Glu-99 to Ser-106, Ser-125 to Cys-131, and Thr-138 to Trp-144.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1103 of SEQ ID NO:54, b is an integer of 15 to 1117, where both a and b correspond to the positions of nucleotide residues shown in SEQ ID NO:54, and where b is greater than or equal to a+1.

Features of Protein Encoded by Gene No: 45

The translation product of this gene shares sequence homology with Laminin A which is thought to be important in the binding of epithelial cells to basement membrane and is associated with tumor invasion. Moreover, the translated protein is homologous to the Drosophila LAMA gene (Accession No. 1314864), a gene expressed in the first optic ganglion of Drosophila. Thus, it is likely that the gene product from this gene is involved in the development of the eye. Nucleotide fragments comprising nucleotides 822–1223, 212–475, 510–731, and 1677–1754 are preferred. Also preferred are the polypeptide fragments encoded by these polynucleotide fragments. It is likely that a frame shift occurs somewhere between nucleotides 475 to 510, shifting the open reading frame from +2 to +3. However, the open reading frame can be clarified using known molecular biology techniques.

This gene is expressed primarily in human testes tumor and to a lesser extent in placenta and activated monocytes.

Therefore, polynucleotides or polypeptides of the invention are useful as reagents for differential identification of the tissue(s) or cell type(s) present in a biological sample and for diagnosis of diseases and conditions which include, but are not limited to, invasive cancers or tumors of the epithelium, as well as disorders relating to eye development. Similarly, polypeptides and antibodies directed to these polypeptides are useful as immunological probes for differential identification of the tissue(s) or cell type(s). For a number of disorders of the above tissues or cells, particularly of neoplastic conditions. expression of this gene at significantly higher or lower levels may routinely be detected in certain tissues and cell types (e.g. testes, placenta, reproductive, and monocytes and cancerous and wounded tissues) or bodily fluids (e.g. seminal fluid, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to Laminin A indicates that polypeptides and polynucleotides corresponding to Gene NO: 45 are useful for study and diagnosis of malignant or benign tumors, fibrotic disorders, and eye disorders. Protein, as well as, antibodies directed against the protein may show utility as a tumor marker and/or immunotherapy targets for the above listed tissues.

Preferred epitopes include those comprising a sequence shown in SEQ ID NO: 178 as residues: Met-1 to Gly-8, Glu-32 to Ala-37, Met-113 to Asn-119, and Glu-139 to Gln-153.

Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1889 of SEQ ID NO:55, b is an integer of 15 to 1903, where both a and b correspond to the positions of nucleotide residues shown in SEQ ID NO:55, and where b is greater than or equal to a+1.

Features of Protein Encoded by Gene No: 46

The translation product of Gene NO: 46 is novel and shares sequence homology with the product of the Drosophila tissue polarity gene frizzled. In vertebrates, it appears that there is a family of proteins that represent frizzled gene homologs. (See, e.g. Accession Nos. 1946343 and AFO17989.) The Drosophila frizzled protein is thought to transmit polarity signals across the plasma membrane of epidermal cells. The structure of frizzled proteins suggest that they may function as a G-protein-coupled receptor. The frizzled proteins are thought to represent receptors for Wnt gene products—secreted proteins that control tissue differentiation and the development of embryonic and adult structures. Inappropriate expression of Wnts has also been demonstrated to contribute to tumor formation. Moreover, mammalian secreted frizzled related proteins are thought to regulate apoptosis. (See Accession No. AFO17989.) The human homolog has also been recently cloned by other groups. (See Accession No. H2415415.) Thus, the protein encoded by this gene plays a role in mediating tissue differentiation, proliferation, tumorigenesis and apoptosis. Preferred polypeptide fragments lack the signal sequence as described in Table 1, as well as N-terminal and C-terminal deletions. Preferred polynucleotide fragments encode these polypeptide fragments.

Gene NO: 46 is expressed primarily in fetal tissues—particularly fetal lung—and adult cancers, most notably pancreas tumor and Hodgkin's lymphoma. Together, this distribution is consistent with expression in tissues undergoing active proliferation. The gene is also expressed to a lesser extent in other organs, including stomach, prostate, and thymus.

Therefore, polynucleotides and polypeptides of the invention are useful as reagents for differential identification of the tissue(s) or cell type(s) present in a biological sample and for diagnosis of diseases and conditions which include, but are not limited to, cancer (particularly pancreatic cancer and/or Hodgkin's lymphoma), as well as other forms of aberrant cell proliferation. Similarly, polypeptides and antibodies directed to these polypeptides are useful in providing immunological probes for differential identification of the tissue(s) or cell type(s). For a number of disorders of the above tissues or cells, particularly of the immune system and hyperproliferative disorders, expression of this gene at significantly higher or lower levels may routinely be detected in certain tissues or cell types (e.g. fetal tissue, pancreas, and tissue of the immune system, and cancerous and wounded tissues) or bodily fluids (e.g. amniotic fluid, pulmonary surfactant, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to frizzled indicates that polypeptides and polynucleotides corresponding to Gene NO: 46 are useful for influencing cell proliferation, differentiation, and apoptosis. The full-length protein or a truncated domain could potentially bind to and regulate the function of specific factors, such as Wnt proteins or other apoptotic genes, and thereby inhibit uncontrolled cellular proliferation. Expression of this protein within a cancer—such as via gene therapy or systemic administration—could effect a switch from proliferation to differentiation, thereby arresting the progression of the cancer. Protein, as well as, antibodies directed against the protein may show utility as a tumor marker and/or immunotherapy targets for the above listed tissues.

Preferred epitopes include those comprising a sequence shown in SEQ ID NO: 179 as residues: Pro-31 to Arg-37.

Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1855 of SEQ ID NO:56, b is an integer of 15 to 1869, where both a and b correspond to the positions of nucleotide residues shown in SEQ ID NO:56, and where b is greater than or equal to a+1.

Features of Protein Encoded by Gene No: 47

The translation product of Gene NO: 47 shares sequence homology with members of the Rh/T2/S-glycoprotein family of ribonuclease-encoding genes. These ribonuclease proteins are found predominantly in fungi, plants, and bacteria and have been implicated in a number of functions, including phosphate-starvation response, self-incompatibility, and responses to wounding. A second group has recently cloned this same gene, calling it a ribonuclease 6 precursor. (See Accession No. 2209029.) The gene encoding the disclosed cDNA is thought to reside on chromosome 6. Accordingly, polynucleotides related to this invention are useful as a marker in linkage analysis for chromosome 6.

Gene NO: 47 is expressed primarily in hematopoietic cells and tissues, including macrophages, eosinophils, CD34 positive cells, T-cells, and spleen. It is also expressed to a lesser extent in brain and spinal cord.

Therefore, polynucleotides and polypeptides of the invention are useful as reagents for differential identification of the tissue(s) or cell type(s) present in a biological sample and for diagnosis of diseases and conditions which include, but are not limited to, tumors of a hematopoietic origin, graft rejection, wounding, inflammation, and allergy. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues and cell types (e.g. hematopoietic cells, and tissues and cells of the immune system, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to the Rh/T2/S-glycoprotein family of ribonuclease-encoding genes indicates that polypeptides and polynucleotides corresponding to Gene NO: 47 are useful as a cytotoxin that could be directed against specific cell types (e.g. cancer cells; HIV-infected cells), and that would be well tolerated by the human immune system.

Preferred epitopes include those comprising a sequence shown in SEQ ID NO: 180 as residues: Ala-24 to Asp-30, Ile-51 to Tyr-61, Pro-69 to Ser-78, Pro-105 to Phe-110, Asn-129 to Phe-135, Pro-187 to Glu-192, Lys-205 to Gln-224, and Pro-250 to His-256.

Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1245 of SEQ ID NO: 57, b is an integer of 15 to 1259, where both a and b correspond to the positions of nucleotide residues shown in SEQ ID NO:57, and where b is greater than or equal to a+1.

Features of Protein Encoded by Gene No: 48

The translation product of Gene NO: 48 shares sequence homology with dolichyl-phosphate glucosyltransferase, a transmembrane-bound enzyme of the endoplasmic reticulum which is thought to be important in N-linked glycosylation, by catalyzing the transfer of glucose from UDP-glucose to dolichyl phosphate. (See Accession No. 535141.) Based on homology, it is likely that this gene product also plays a role similar in humans. Preferred polynucleotide fragments comprise nucleotides 132–959. Also preferred are the polypeptide fragments encoded by this nucleotide fragment.

Gene NO: 48 is expressed primarily in endothelial cells and to a lesser extent in hematopoietic cells and brain.

Therefore, polynucleotides and polypeptides of the invention are useful as reagents for differential identification of the tissue(s) or cell type(s) present in a biological sample and for diagnosis of diseases and conditions which include, but are not limited to, defects in proper N-linked glycosylation of proteins, such as Wiskott-Aldrich syndrome; tumors of an endothelial cell origin. Similarly, polypeptides and antibodies directed to these polypeptides are useful in providing immunological probes for differential identification of the tissue(s) or cell type(s). For a number of disorders of the above tissues or cells, particularly of the vascular and hematopoietic systems, as well as brain, expression of this gene at significantly higher or lower levels may routinely be detected in certain tissues and cell types (e.g. endothelial cells, hematopoietic cells, and brain, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to dolichyl-phosphate glucosyltransferase indicates that polypeptides and polynucleotides corresponding to Gene NO: 48 are useful in diagnosing and treating defects in N-linked glycosylation pathways that contribute to disease conditions and/or pathologies.

Preferred epitopes include those comprising a sequence shown in SEQ ID NO: 181 as residues: Lys-50 to Thr-55, Ser-73 to Arg-79, Glu-92 to Pro-99, Asp-110 to Ser-117, Gln-125 to Lys-131, Gly-179 to Asn-188, Ile-231 to Cys-236, and Glu-318 to Asn-324.

Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1172 of SEQ ID NO:58, b is an integer of 15 to 1186, where both a and b correspond to the positions of nucleotide residues shown in SEQ ID NO:58, and where b is greater than or equal to a+1.

Features of Protein Encoded by Gene No: 49

Gene NO: 49 is expressed primarily in brain, most notably in the hypothalamus and amygdala. This gene is also mapped to chromosome X, and therefore, can be used in linkage analysis as a marker for chromosome X.

Therefore, polynucleotides and polypeptides of the invention are useful as reagents for differential identification of the tissue(s) or cell type(s) present in a biological sample and for diagnosis of diseases and conditions which include, but are not limited to, tumors of a brain origin; neurodegenerative disorders, and sex-linked disorders. Similarly, polypeptides and antibodies directed to these polypeptides are useful in providing immunological probes for differential identification of the tissue(s) or cell type(s). For a number of disorders of the above tissues or cells, particularly of the brain, expression of this gene at significantly higher or lower levels may routinely be detected in certain tissues or cell types (e.g. brain and cancerous and wounded tissues) or bodily fluids (e.g. serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 49 are useful for the diagnosis of tumors of a brain origin, and the treatment of neurodegenerative disorders, such as Parkinson's disease, and sex-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 414 of SEQ ID NO:59, b is an integer of 15 to 428, where both a and b correspond to the positions of nucleotide residues shown in SEQ ID NO:59, and where b is greater than or equal to a+1.

Features of Protein Encoded by Gene No: 50

The translation product Gene NO: 50 shares sequence homology with canine phospholemman, a major plasma membrane substrate for cAMP-dependent protein kinases A and C. (See Accession No. M63934; see also Accession No. A40533.) In fact, a group also recently cloned the human phospholemman gene, and mapped this gene to chromosome 19. (See Accession No.1916010.) Phospholemman is a type I integral membrane protein that gets phosphorylated in response to specific extracellular stimuli such as insulin and adrenalin. Phospholemman forms ion channels in the cell membrane and appears to regulate taurine transport, suggesting an involvement in cell volume regulation. It has been proposed that phospholemman is a member of a superfamily of membrane proteins, characterized by single transmembrane domains, which function in transmembrane ion flux. They are capable of linking signal transduction to the regulation of such cellular processes as the control of cell volume. Additionally, when tested against U937 myeloid cell lines, supernatants removed from cells containing this gene activated the GAS assay. Thus, it is likely that this gene activates myeloid cells through the Jaks-STAT signal transduction pathway. The Gamma activation site (GAS) is a promoter element found upstream in many genes which are involved in the Jaks-STAT pathway. The Jaks-STAT pathway is a large, signal transduction pathway involved in the differentiation and proliferation of cells. Therefore, activation of the jaks-STAT pathway, reflected by the binding of the GAS element, can be used to indicate proteins involved in the proliferation and differentiation of cells. One embodiment of this clone comprises polypeptides of the following amino acid sequence: PKEHDPFTYDYQSLQIGGLVI-AGILFILG ILIVLSRRCRCKFNQQQRTGEPDEEEGT-FRSSIRRLSTRRR (SEQ ID NO:269). An additional embodiment would be the polynucleotides encoding these polypeptides.

Gene No 50 is expressed primarily in fetal liver and to a lesser extent in adult brain and kidney, as well as other organs.

Therefore, polynucleotides and polypeptides of the invention are useful as reagents for differential identification of the tissue(s) or cell type(s) present in a biological sample and for diagnosis of diseases and conditions which include, but are not limited to, insulin and/or adrenalin defects; diabetes; aberrant ion channel signaling; defective taurine transport; and defects in cell volume regulation. Similarly, polypeptides and antibodies directed to these polypeptides are useful in providing immunological probes for differential identification of the tissue(s) or cell type(s). For a number of disorders of the above tissues or cells, particularly of the brain and/or immune system, expression of this gene at significantly higher or lower levels may routinely be detected in certain tissues (e.g. liver, brain, and kidney, and cancerous and wounded tissues) or bodily fluids (e.g. amniotic fluid, lymph, bile, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to phospholemman indicates that polypeptides and polynucleotides corresponding to Gene NO: 50 are useful for treatment of disorders involving the transport of ions and small molecules, in particular taurine. It could also be beneficial for control of pathologies or diseases wherein aberrancies in the control of cell volume are a distinguishing feature, due to the predicted role for phospholemman in the normal control of cell volume. It also may play a role in disorders involving abnormal circulating levels of insulin and/or adrenalin—along with other active secreted molecules—as revealed by its phosphorylation upon stimulation with insulin or adrenalin.

Preferred epitopes include those comprising a sequence shown in SEQ ID NO: 183 as residues: Ala-20 to Gln-34, Arg-58 to Thr-79, and Leu-87 to Arg-92.

Many polynucleotide sequences, such as EST sequences, are publicly available and accessible through sequence databases. Some of these sequences are related to SEQ ID NO:60 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 487 of SEQ ID NO:60, b is an integer of 15 to 501, where both a and b correspond to the positions of nucleotide residues shown in SEQ ID NO:60, and where b is greater than or equal to a+1.

Features of Protein Encoded by Gene No: 52

Gene NO: 52 is expressed primarily in metastic melanoma and to a lesser extent in infant brain.

Therefore, polynucleotides or polypeptides of the invention are useful as reagents for differential identification of the tissue(s) or cell type(s) present in a biological sample and for diagnosis of diseases and conditions which include, but are not limited to, cancer and cancer metastasis. Similarly, polypeptides and antibodies directed to these polypeptides are useful in providing immunological probes for differential identification of the tissue(s) or cell type(s). For a number of disorders of the above tissues or cells, expression of this gene at significantly higher or lower levels may routinely be detected in certain tissues or cell types (e.g. epidermis, and brain, fetal, and cancerous and wounded tissues) or bodily fluids (e.g. lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 52 are useful for diagnosis and treatment of melanoma. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:62 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 581 of SEQ ID NO:62, b is an integer of 15 to 595, where both a and b correspond to the positions of nucleotide residues shown in SEQ ID NO:62, and where b is greater than or equal to a+1.

Features of Protein Encoded by Gene No: 53

The translation product of Gene NO: 53 shares sequence homology with mucin which is thought to be important cell surface molecule. It also exhibits sequence identity with a calcium channel blocker of Agelenopsis aperta. In particular, with those calcium channel blockers which affect neuronal and muscle cells.

Gene NO: 53 is expressed primarily in prostate, endothelial cells, smooth muscle and fetal tissues and to a lesser extent in T cells and placenta.

Therefore, polynucleotides or polypeptides of the invention are useful as reagents for differential identification of the tissue(s) or cell type(s) present in a biological sample and for diagnosis of diseases and conditions which include, but are not limited to, prostate cancer, immune disorders, angina, hypertension, cardiomyopathies, supraventricular arrhythmia, oesophogeal achalasia, premature labour, and Raynaud's disease. Similarly, polypeptides and antibodies directed to these polypeptides are useful in providing immunological probes for differential identification of the tissue(s) or cell type(s). For a number of disorders of the above a tissues or cells, particularly of the immune system, expression of this gene at significantly higher or lower levels may routinely be detected in certain tissues or cell types (e.g. prostrate, and tissue and cells of the immune system, and cancerous and wounded tissues) or bodily fluids (e.g. seminal fluid, amniotic fluid, lymph, serum, plasma, urine, synovial fluid or spinal fluid) or another tissue or cell sample or another tissue or cell sample taken from an individual having such a disorder, relative to the standard gene expression level, i.e., the expression level in healthy tissue or bodily fluid from an individual not having the disorder.

The tissue distribution and homology to mucin indicates that polypeptides and polynucleotides corresponding to Gene NO: 53 are useful as a surface antigen for diagnosis of diseases such as prostate cancer and as tumor vaccine. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:63 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1464 of SEQ ID NO:63, b is an integer of 15 to 1478, where both a and b correspond to the positions of nucleotide residues shown in SEQ ID NO:63, and where b is greater than or equal to a+1.

Features of Protein Encoded by Gene No: 54

Gene NO: 54 encodes a polypeptide which exhibits sequence identity with the rab receptor and VAMP-2 receptor proteins. (Martincic, et al., J. Biol. Chem. 272 (1997).). The gene encoding the disclosed cDNA is believed to reside on chromosome 3. Accordingly, polynucleotides related to this invention are useful as a marker in linkage analysis for chromosome 3. On embodiment of this clone comprises polypeptides of the following amino acid sequence: M D V N I A P L R A W D D F F P G S D R F A R P D F R D - I S K W N N R V V S N L L Y Y Q T N Y L V V A A M M I S I V G F L S P F N (SEQ ID NO:270).

An additional embodiment would be the polynucleotides encoding these polypeptides.

Gene NO: 54 is expressed primarily in placenta, fetal liver, osteoclastoma and smooth muscle and to a lesser extent in T cell, fetal lung and colon cancer.

Therefore, polynucleotides or polypeptides of the invention are useful as reagents for differential identification of the tissue(s) or cell type(s) present in a biological sample and for diagnosis of diseases and conditions which include, but are not limited to, cancers, osteoporosis and immuno-related diseases. Similarly, polypeptides and antibodies directed to these polypeptides are useful in providing immunological probes for differential identification of the tissue(s) or cell type(s). For a number of disorders of the above tissues or cells, particularly of the immune system, hematopoiesis system and bone system, expression of this gene at significantly higher or lower levels may routinely be detected in certain tissues and cell types (e.g. placenta, liver, osteoclastama, smooth muscle, T-cells, and lung, and colon, and cancerous and wounded tissues) or bodily fluids (e.g. bile, amniotic fluid, lymph, serum, plasma, urine, synovial fluid or spinal fluid) or another tissue or cell sample or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 54 are useful for treating cancer, osteoporosis and immuno-disorders. Expression within embryonic tissue and other cellular sources marked by proliferating cells suggests that this protein may play a role in the regulation of cellular division. Additionally, the expression in hematopoietic cells and tissues suggests that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus, this protein may also be involved in apoptosis or tissue differentiation and could again be useful in cancer therapy. Protein, as well as, antibodies directed against the protein may show utility as a tumor marker and/or immunotherapy targets for the above listed tissues.

Preferred epitopes include those comprising a sequence shown in SEQ ID NO: 187 as residues: Pro-16 to Phe-21, Pro-24 to Arg-35, Arg-92 to Pro-98, Asn-143 to Lys-151, and Leu-169 to Ile-176.

Many polynucleotide sequences, such as EST sequences, are publicly available and accessible through sequence databases. Some of these sequences are related to SEQ ID NO:64 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2019 of SEQ ID NO:64, b is an integer of 15 to 2033, where both a and b correspond to the positions of nucleotide residues shown in SEQ ID NO:64, and where b is greater than or equal to a+1.

Features of Protein Encoded by Gene No: 55

Gene NO: 55 encodes a protein having sequence identity to the rat galanin receptor GALR2.

Gene NO: 55 is expressed primarily in ovarian cancer.

Therefore, polynucleotides or polypeptides of the invention are useful as reagents for differential identification of the tissue(s) or cell type(s) present in a biological sample and for diagnosis of ovarian cancer. Similarly, polypeptides and antibodies directed to those polypeptides are useful in providing immunological probes for differential identification of the tissue(s) or cell type(s). For a number of disorders of the above tissues or cells, particularly of the immune system and reproductive system, expression of this gene at significantly higher or lower levels may routinely be detected in certain tissues or cell types (e.g. ovary, and tissues and cells of the immune system, and cancerous and wounded tissues) or bodily fluids (e.g. serum, plasma, urine, synovial fluid or spinal fluid) or another tissue or cell sample or another tissue or cell sample taken from an individual having such a disorder, relative to the standard gene expression level, i.e., the expression level in healthy tissue or bodily fluid from an individual not having the disorder. GALR2 antagonists can be used to treat obesity, bulimia, or Alzheimer's disease, while GALR2 agonists can be used to treat anorexia or pain, or to decrease conception (claimed). Agonists and antagonists can also be used to treat numerous other disorders, including cognitive disorders, sensory disorders, motion sickness, convulsion/epilepsy, hypertension, diabetes, glaucoma, reproductive disorders, gastric and intestinal ulcers, inflammation, immune disorders, and anxiety.

The tissue distribution indicates that polypeptides and polynucleotides corresponding to Gene NO: 55 are useful for diagnosis and treatment of ovarian cancer. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:65 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 426 of SEQ ID NO:65, b is an integer of 15 to 440, where both a and b correspond to the positions of nucleotide residues shown in SEQ ID NO:65, and where b is greater than or equal to a+1.

Features of Protein Encoded by Gene No: 56

As indicated in Table 1, the predicted signal sequence of Gene NO: 56 relates to an open reading frame that is homologous to the mouse major histocompatibility locus class 1 ml. (See Accession No. 2564953.) Any frame shift mutations that alter the correct open reading frame can easily be clarified using known molecular biology techniques. Moreover, in the opposite orientation, a second translated product is disclosed. This second translation product of this contig is identical in sequence to intracellular protein lysophosphatidic acid acyltransferase. The nucleotide and amino acid sequences of this translated product have since been published by Stamps and colleagues (Biochem. J. 326 (Pt 2), 455–461 (1997)), West and coworkers (DNA Cell Biol. 6, 691–701 (1997)), Rowan (GenBank Accession No. U89336), and Soyombo and Hofmann (GenBank Accession No. AF020544). This gene is thought to enhance cytokine signaling response in cells. It is likely that a signal peptide is located upstream from this translated product. Preferred polypeptide fragments comprise the amino acid sequence: GLACWLAGVIFI DRKRTGDAIS-VMSEVAQTLLTQDVXVWVF-PEGTRNHNGSMLPFKRGAFHLAVQAQVPIV PIV-MSSYQDFYCKKERRFTSGQCQVRVLPPVPTEGL TPDVPALADRVRHSMLHCF(SEQ ID NO: 271); PSAKY-FFKMAFYNGWILFLAVLAIPVCAVRGRN-VENMKILRLMLLHIKY LYGIRVEVRGAHBF-PPSQPYVVVSNHQSSLDLLGMMEVLPGRCVPIAKR (SEQ ID NO:272); TVFREISTD (SEQ ID NO:273); or LWAGSAGWPAG (SEQ ID NO: 274). Also provided are polynucleotide fragments encoding these polypeptide fragments. When tested against aortic smooth muscle cell lines, supernatants removed from cells containing this gene induced a calcium flux in the FLIPR assay (small molecule concentration and membrane permeability assays). Thus, it is likely that this gene activates aortic smooth muscle cells via the binding of a ligand to a receptor. The FLIPR assay indicates binding of a ligand to a receptor, which is known to alter intracellular levels of small molecules such as calcium, potassium, sodium, and pH, as well as alter membrane potential. Alterations in small molecule concentration can be measured to identify supernatants which bind to receptors of a particular cell.

Gene NO: 56 is expressed primarily in infant adrenal gland, hypothalamus, 7 week old embryonic tissue, fetal lung, osteoclastoma stromal cells, and to a lesser extent in a large number of additional tissues.

Therefore, polynucleotides or polypeptides of the invention are useful as reagents for differential identification of the tissue(s) or cell type(s) present in a biological sample and for diagnosis of developmental disorders and osteoclastoma. Similarly, polypeptides and antibodies directed to these polypeptides are useful in providing immunological probes for differential identification of the tissue(s) or cell type(s) in which it is highly expressed. For a number of disorders of the above tissues or cells, particularly during development or of the nervous or bone systems, expression of this gene at significantly higher or lower levels may routinely be detected in certain tissues and cell types (e.g. adrenal, embryonic tissue, lung, and osteoclastomal stromal cells, and cancerous and wounded tissues) or bodily fluids (e.g. amniotic fluid, lymph, serum, plasma, urine, synovial fluid or spinal fluid) or another tissue or cell sample or another tissue or cell sample taken from an individual having such a disorder, relative to the standard gene expression level, i.e., the expression level in healthy tissue or bodily fluid from an individual not having the disorder. Further, expression of this protein can be used to alter the fatty acid composition of a given cell or membrane type.

The tissue distribution indicates that polypeptides and polynucleotides corresponding to Gene NO: 56 are useful for diagnosis and treatment of osteoclastoma and other bone and non-bone-related cancers, as well as for the diagnosis and treatment of developmental disorders. Protein, as well as, antibodies directed against the protein may show utility as a tumor marker and/or immunotherapy targets for the above listed tissues.

Preferred epitopes include those comprising a sequence shown in SEQ ID NO: 189 as residues: Gly-29 to Gly-36 and Tyr-49 to Tyr-58.

Many polynucleotide sequences, such as EST sequences, are publicly available and accessible through sequence databases. Some of these sequences are related to SEQ ID NO:66 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 3287 of SEQ ID NO:66, b is an integer of 15 to 3301, where both a and b correspond to the positions of nucleotide residues shown in SEQ ID NO:66, and where b is greater than or equal to a+1.

Features of Protein Encoded by Gene No: 57

The translation product of Gene NO: 57 shares sequence homology with longevity-assurance protein-1. (See Accession No. g 1123105.) Preferred polynucleotide fragments comprise nucleotides 6–125 and 118–432, as well as the polypeptides encoded by these polynucleotides. It is likely that a second signal sequence exists upstream from the predicted signal sequence in Table 1. Moreover, a frame shift likely occurs between nucleotides 118–125, which can be elucidated using standard molecular biology techniques.

Gene NO: 57 is expressed primarily in fetal liver, kidney, brain, thymus, and bone marrow.

Therefore, polynucleotides or polypeptides of the invention are useful as reagents for differential identification of the tissue(s) or cell type(s) present in a biological sample and for diagnosis of diseases and conditions which include, but are not limited to, immunological diseases and hyperproliferative disorders. Similarly, polypeptides and antibodies directed to these polypeptides are useful in providing immunological probes for differential identification of the tissue(s) or cell type(s). For a number of disorders of the above tissues or cells, particularly of the fetal liver, kidney, brain, thymus, and bone marrow expression of this gene at significantly higher or lower levels may routinely be detected in certain tissues or cell types (e.g. liver, kidney, brain, thymus, and bone marrow, and cancerous and wounded tissues) or bodily fluids (e.g. bile, amniotic fluid, serum, plasma, urine, synovial fluid or spinal fluid) or another tissue or cell sample or another tissue or cell sample taken from an individual having such a disorder, relative to the standard gene expression level, i.e., the expression level in healthy tissue or bodily fluid from an individual not having the disorder.

The tissue distribution and homology to longevity-assurance protein suggest that Gene NO: 57 encodes a protein useful in increasing life span and in replacement therapy for those suffering from immune system disorders or hyperproliferative disorders caused by underexpression or overexpression of this gene. Protein, as well as, antibodies directed against the protein may show utility as a tumor marker and/or immunotherapy targets for the above listed tissues.

Preferred epitopes include those comprising a sequence shown in SEQ ID NO: 190 as residues: Val-29 to Arg-46 and Gly-50 to Gly-56.

Many polynucleotide sequences, such as EST sequences, are publicly available and accessible through sequence databases. Some of these sequences are related to SEQ ID NO:67 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1521 of SEQ ID NO:67, b is an integer of 15 to 1535, where both a and b correspond to the positions of nucleotide residues shown in SEQ ID NO:67, and where b is greater than or equal to a+1.

Features of Protein Encoded by Gene No: 58

Domains of the Gene NO: 58 product are homologous to porcine surfactant protein-A receptor. (See Accession No. B48516.) The bovine gene binds surfactant protein-A receptor, modulating the secretion of alveolar surfactant. Based on this homology, the gene product encoded by this gene will likely have activity similar to the porcine gene. Preferred polynucleotide fragments comprise nucleotides 887–1039, as well as the polypeptide fragments encoded by this nucleotide fragment.

Gene NO: 58 is expressed primarily in brain and to a lesser extent in endothelial cells.

Therefore, polynucleotides or polypeptides of the invention are useful as reagents for differential identification of the tissue(s) or cell type(s) present in a biological sample and for diagnosis of diseases and conditions which include, but are not limited to, diseases of the central nervous system including dimentia, stroke, neurological disorders, respiratory distress, and diseases affecting the endothelium including inflammatory diseases, restenosis, and vascular diseases. Similarly, polypeptides and antibodies directed to these polypeptides are useful in providing immunological probes for differential identification of the tissue(s) or cell type(s). For a number of disorders of the above tissues or cells, particularly of the placenta, liver, endothelial cells, prostate, thymus, and lung, expression of this gene at significantly higher or lower levels may routinely be detected in certain tissues and cell types (e.g. brain, and endothelial cells, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology indicates that polypeptides and polynucleotides corresponding to Gene NO: 58 are useful for the diagnosis and /or treatment of diseases on the central nervous system, such as a factor that promote neuronal survival or protection, in the treatment of inflammatory disorders of the endothelium, or in disorders of the lung. In addition this protein may inhibit or promote angiogenesis and therefore is useful in the treatment of vascular disorders. Protein, as well as, antibodies directed against the protein may show utility as a tumor marker and/or immunotherapy targets for the above listed tissues.

Preferred epitopes include those comprising a sequence shown in SEQ ID NO: 191 as residues: His-66 to Pro-80, Gly-139 to Ser-146 and Ser-262 to Pro-267.

Many polynucleotide sequences, such as EST sequences, are publicly available and accessible through sequence databases. Some of these sequences are related to SEQ ID NO:68 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1230 of SEQ ID NO:68, b is an integer of 15 to 1244, where both a and b correspond to the positions of nucleotide residues shown in SEQ ID NO:68, and where b is greater than or equal to a+1.

Features of Protein Encoded by Gene No: 59

The translation product of Gene NO: 59 is homologous to the rat hypertension-induced protein which is thought to be important in hypertension, and found expressed mainly in kidneys. (See Accession No. B61209.) Thus, it is likely that this gene product is involved in hypertension in humans. Preferred polypeptide fragments comprise the short chain dehydrogenase/reductase motif SILGIISVPLSIGY-CASKHALRGFFNGLR (SEQ ID NO:275), as well as polynucleotides encoding this polypeptide fragment. Also preferred are polynucleotide fragments of 337–639, as well as the polypeptide fragments encoded by this polynucleotide fragment.

Gene NO: 59 is expressed primarily in liver, spleen, lung, brain, and prostate.

Therefore, polynucleotides and polypeptides of the invention are useful as reagents for differential identification of the tissue(s) or cell type(s) present in a biological sample and for diagnosis of diseases and conditions which include, but are not limited to, cardiovascular, immunological, and renal disorders. Similarly, polypeptides and antibodies directed to these polypeptides are useful in providing immunological probes for differential identification of the tissue(s) or cell type(s). For a number of disorders of the above tissues or cells, particularly of the cardiovascular, renal, and immune, expression of this gene at significantly higher or lower levels may routinely be detected in certain tissues or cell types (e.g. liver, spleen, lung, brain, and prostrate, and cancerous and wounded tissues) or bodily fluids (e.g. lymph, bile, seminal fluid, serum, plasma, urine, synovial fluid or spinal fluid) or another tissue or cell sample or another tissue or cell sample taken from an individual having such a disorder, relative to the standard gene expression level, i.e., the expression level in healthy tissue or bodily fluid from an individual not having the disorder.

The tissue distribution and homology to hypertension-induced protein indicates that polypeptides and polynucleotides corresponding to Gene NO: 59 are useful for treating hypertension.

Preferred epitopes include those comprising a sequence shown in SEQ ID NO: 192 as residues: Gln-40 to Glu-45, Glu-96 to Glu-102, Asn-256 to Thr-266, and Asp-308 to Asp-317.

Many polynucleotide sequences, such as EST sequences, are publicly available and accessible through sequence databases. Some of these sequences are related to SEQ ID NO:69 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1278 of SEQ ID NO:69, b is an integer of 15 to 1292, where both a and b correspond to the positions of nucleotide residues shown in SEQ ID NO:69, and where b is greater than or equal to a+1.

Features of Protein Encoded by Gene No: 60

Gene NO: 60 is expressed primarily in activated T-cell and jurkat cell and to a lesser extent in apoptic T-cell and CD34+ cell. It is likely that alternative open reading frames provide the full length amino acid sequence, which can be verified using standard molecular biology techniques.

Therefore, polynucleotides and polypeptides of the invention are useful as reagents for differential identification of the tissue(s) or cell type(s) present in a biological sample and for diagnosis of diseases and conditions which include, but are not limited to, T lymphocyte related diseases or hematopoiesis. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues and cell types (e.g. T-cells, immune, hematopoietic, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 60 are useful for diagnosis or treatment of immune system disorders. Expression of this gene product in a variety of immune cells suggests a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:70 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1017 of SEQ ID NO:70, b is an integer of 15 to 1031, where both a and b correspond to the positions of nucleotide residues shown in SEQ ID NO:70, and where b is greater than or equal to a+1.

Features of Protein Encoded by Gene No: 61

The translation product of Gene NO: 61, a vacuolar proton-ATPase, shares sequence homology with a *Caenorhabditis elegans* protein which is thought to be important in development. This protein may be a human secretory homologue that may also influence embryo development. Ludwig, J., also recently cloned this gene from chromaffin granules. (See, Accession No. 2584788.) Although Table 1 indicates the predicted signal peptide sequence, the translated product of this gene may in fact start with the upstream methionine, beginning with the amino acid sequence MAY-HGLTV (SEQ ID NO:276). Thus, polypeptides comprising this upstream sequence, as well as N-terminus deletions, are also contemplated in the present invention.

Gene NO: 61 is expressed primarily in human placenta, liver, and Hodgkin's Lymphoma and to a lesser extent in bone marrow. Modest levels of expression were also observed in dendritic cells.

Therefore, polynucleotides and polypeptides of the invention are useful as reagents for differential identification of the tissue(s) or cell type(s) present in a biological sample and for diagnosis of diseases and conditions which include, but are not limited to, hyperproliferative disorders, defects in embryonic development, and diseases or disorders caused by defects in chromaffin granules. Similarly, polypeptides and antibodies directed to these polypeptides are useful in providing immunological probes for differential identification of the tissue(s) or cell type(s). For a number of disorders of the above tissues or cells, particularly cancer, expression of this gene at significantly higher or lower levels may routinely be detected in certain tissues or cell types (e.g. placenta, liver, lymph tissue, and bone marrow, and cancerous and wounded tissues) or bodily fluids (e.g. amniotic fluid, bile, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to *Caenorhabditis elegans* indicates that polypeptides and polynucleotides corresponding to Gene NO: 61 are useful for diagnostic or therapeutic modalities for hyperproliferative disorders, embryonic development disorders, and chromaffin granules disorders.

Many polynucleotide sequences, such as EST sequences, are publicly available and accessible through sequence databases. Some of these sequences are related to SEQ ID NO:71 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 841 of SEQ ID NO:71, b is an integer of 15 to 855, where both a and b correspond to the positions of nucleotide residues shown in SEQ ID NO:71, and where b is greater than or equal to a+1.

Features of Protein Encoded by Gene No: 62

The translation product of Gene NO: 62 shares sequence homology with the murine LAG3 gene which is thought to be important in the mediation of natural killer cell (NK cell) activity as previously determined by experiments in mice containing null mutations of LAG3. The similarity of this gene to the CD4 receptor may imply that the gene product may be a secreted, soluble receptor and immune mediator. When tested against monocyte cell lines, supernatants removed from cells containing this gene induced a calcium flux in the FLIPR assay, which is a small molecule concentration and membrane permeability assay. Thus, it is likely that this gene activates monocytes via the binding of a ligand to a receptor. The FLIPR assay is indicative of the binding of a ligand to a receptor, which is known to alter intracellular levels of small molecules, such as calcium, potassium, sodium, and pH, as well as alter membrane permeability. Alterations in small molecule concentration can be measured to identify supernatants which bind to receptors of a particular cell.

Gene NO: 62 is expressed primarily in human fetal heart, meningima, and to a lesser extent in tonsils. This gene also is expressed in the breast cancer cell line MDA 36.

Therefore, polynucleotides or polypeptides of the invention are useful as reagents for differential identification of the tissue(s) or cell type(s) present in a biological sample and for diagnosis of diseases and conditions which include, but are not limited to, lymphomas, leukemias, breast cancer and any immune system dysfunction, including those dysfunctions which involve natural killer cell activities. Similarly, polypeptides and antibodies directed to these polypeptides are useful in providing immunological probes for differential identification of the tissue(s) or cell type(s). For a number of disorders of the above tissues or cells, particularly of the immune system or breast cancer, expression of this gene at significantly higher or lower levels may routinely be detected in certain tissues or cell types (e.g. heart, meningima, and tonsils and cancerous and wounded tissues) or bodily fluids (e.g. amniotic fluid, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to the LAG3 gene (murine) indicates that the polynucleotides and polypeptides corresponding to Gene NO: 62 are useful for diagnostic and/or therapeutic modalities directed at abnormalities or disease states involving defective immune systems, preferably involving natural killer cell activity, as well as breast cancer. Protein, as well as, antibodies directed against the protein may show utility as a tumor marker and/or immunotherapy targets for the above listed tissues.

Preferred epitopes include those comprising a sequence shown in SEQ ID NO: 195 as residues: Pro-10 to Trp-17, Cys-58 to Pro-67, Thr-76 to Glu-85, and Arg-93 to Asn-101.

Many polynucleotide sequences, such as EST sequences, are publicly available and accessible through sequence databases. Some of these sequences are related to SEQ ID NO:72 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1260 of SEQ ID NO:72, b is an integer of 15 to 1274, where both a and b correspond to the positions of nucleotide residues shown in SEQ ID NO:72, and where b is greater than or equal to a+1.

Features of Protein Encoded by Gene No: 63

The translation product of Gene NO: 63 shares sequence homology with a *Caenorhabditis elegans* alpha-collagen gene (Clg), which is thought to be important in organism development, as well as other collagen genes. Thus, based on sequence homology, polypeptides of this gene are expected to have activity similar to collagen, including involvement in organ development.

Gene NO: 63 is expressed primarily in human B-Cell Lymphoma, and to a lesser extent in human pituitary tissue. This gene has also demonstrated expression in keratinocytes.

Therefore, polynucleotides or polypeptides of the invention are useful as reagents for differential identification of the tissue(s) or cell type(s) present in a biological sample and for diagnosis of diseases and conditions which include, but are not limited to, B-Cell Lymphoma, other lymphomas, leukemias, and other cancers, as well as disorders related to development. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues and cell types (e.g. tissue and/or cells of the immune system, and pituitary, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to *Caenorhabditis elegans* alpha-collagen gene indicates that polypeptides and polynucleotides corresponding to Gene NO: 63 are useful for development of diagnostic and/or therapeutic modalities directed at the detection and/or treatment of cancer, specifically B-Cell Lymphomas, leukemias, or diseases related to development. Protein, as well as, antibodies directed against the protein may show utility as a tumor marker and/or immunotherapy targets for the above listed tissues.

Preferred epitopes include those comprising a sequence shown in SEQ ID NO: 196 as residues: Thr-22 to Arg-27 and Ser-29 to Thr-39.

Many polynucleotide sequences, such as EST sequences, are publicly available and accessible through sequence databases. Some of these sequences are related to SEQ ID NO:73 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 674 of SEQ ID NO:73, b is an integer of 15 to 688, where both a and b correspond to the positions of nucleotide residues shown in SEQ ID NO:73, and where b is greater than or equal to a+1.

Features of Protein Encoded by Gene No: 64

The translation product of Gene NO: 64 shares sequence homology with human extracellular molecule olfactomedin, which is thought to be important in the maintenance, growth, or differentiation of chemosensory cilia on the apical dendrites of olfactory neurons. Based on this sequence homology, it is likely that polypeptides of this gene have activity similar to the olfactomedin, particularly the differentiation or proliferation of neurons. The gene encoding the disclosed cDNA is believed to reside on chromosome 1. Accordingly, polynucleotides related to this invention are useful as a marker in linkage mapping analysis for chromosome 1. When tested against U937 myeloid cell lines, supernatants removed from cells containing this gene activated the GAS assay. Thus, it is likely that this gene activates myeloid cells through the Jaks-STAT signal transduction pathway. The gamma activation site (GAS) is a promoter element found upstream in many genes which are involved in the Jaks-STAT pathway. The Jaks-STAT pathway is a large, signal transduction pathway involved in the differentiation and proliferation of cells. Therefore, activation of the Jaks-STAT pathway, reflected by the binding of the GAS element, can be used to indicate proteins involved in the proliferation and differentiation of cells. When tested against Jurkat E cell lines, supernatants removed from cells containing this gene activated the NF-κB assay. Thus, it is likely that this gene activates T-cells via an interaction with the NF-κB promoter element. The NF-κB promoter element is a transcription factor activated by a wide variety of agents, leading to cell activation, differentiation, or apoptosis. Reporter constructs utilizing the NF-κB promoter element are used to screen supernatants for such activity. When tested against monocyte cell lines, supernatants removed from cells containing this gene activated the FLIPR assay. Thus, it is likely that this gene activates monocyte cells through an interaction between a ligand and a receptor. The FLIPR assay indicates binding of a ligand to a receptor via the alteration of intracellular levels of small molecules, such as calcium, potassium, sodium, and pH, as well as through the alteration of membrane potential. Alterations in small molecule concentration can be measured to identify supernatants which bind to receptors of a particular cell.

Gene NO: 64 is expressed primarily in fetal lung tissue.

Therefore, polynucleotides or polypeptides of the invention are useful as reagents for differential identification of the tissue(s) or cell type(s) present in a biological sample and for diagnosis of diseases and conditions which include, but are not limited to, diseases of the lung as well as neural development, particularly of the lung. Similarly, polypeptides and antibodies directed to these polypeptides are useful in providing immunological probes for differential identification of the tissue(s) or cell type(s). For a number of disorders of the above tissues or cells, particularly of the pulmonary system, expression of this gene at significantly higher or lower levels may routinely be detected in certain tissues or cell types (e.g. lungs and cancerous and wounded tissues) or bodily fluids (e.g. amniotic fluid, pulmonary surfactant, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to the olfactomedin family indicates that polypeptides and polynucleotides corresponding to Gene NO: 64 are useful for the development of diagnostic and/or therapeutic modalities directed at detection and/or treatment of pulmonary disease states, e.g. cystic fibrosis. Protein, as well as, antibodies directed against the protein may show utility as a tumor marker and/or immunotherapy targets for the above listed tissues.

Preferred epitopes include those comprising a sequence shown in SEQ ID NO: 197 as residues: Gly-17 to Gln-23, Gln-45 to Arg-50, Arg-56 to Lys-61, Glu-70 to Leu-76, Asp-88 to Glu-93, Pro-117 to Met-131, Asp-161 to Glu-167, Arg-224 to Asn-237, Asp-302 to Trp-312, Pro-315 to Asn-320, and Thr-337 to Ser-341.

Many polynucleotide sequences, such as EST sequences, are publicly available and accessible through sequence databases. Some of these sequences are related to SEQ ID NO:74 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1876 of SEQ ID NO:74, b is an integer of 15 to 1890, where both a and b correspond to the positions of nucleotide residues shown in SEQ ID NO:74, and where b is greater than or equal to a+1.

Features of Protein Encoded by Gene No: 65

The translation product of Gene NO: 65 shares sequence homology with *Saccharomyces cerevisiae* hypothetical protein YKL166 (Accession No. gi/687880) which is thought to be important in secretory and/or vesicular transport mechanisms. Based on this homology, it is likely that the gene product would have similar activity to YKL166, particularly secretory or transport mechanisms. Preferred polypeptide fragments of this gene include those fragments starting with the amino acid sequence ISAARV (SEQ ID NO:277). Other polypeptide fragments include the former fragment, which ends with the amino acid sequence PDVSEFMTRLF (SEQ ID NO:278). Further preferred fragments include those polypeptide fragments comprising the amino acid sequence FDPVRVDITSKGKMRAR (SEQ ID NO:279). Also preferred are polypeptide fragments having exogenous signal sequences fused to the polypeptide. One embodiment of this clone comprises polypeptides of the following amino acid sequence: MAAALWGFFPVLLLLLL SGDVQSSEVP-GAAAEGSGGSGVGIGDRFKIEGRAV-VPGVKPQDWISAARVLVDGEEHVG FLKTDGSFVVH-DIPSGSYVVEVVSPAYRFDPVRVDrFSKGKMRARY VNYIKTSEVVRLPY PLQMKSSGPPSYFIKRESWGWT-DFLMNPMVMM (SEQ ID NO:280). An additional embodiment would be the polynucleotides encoding these polypeptides.

Gene No 65 is expressed primarily in placenta, testis, osteoclastoma and to a lesser extent in adrenal gland.

Therefore, polynucleotides or polypeptides of the invention are useful as reagents for differential identification of the tissue(s) or cell type(s) present in a biological sample and for diagnosis of diseases and conditions which include, but are not limited to, cancer and/or diseases involving defects in protein secretion. Similarly, polypeptides and antibodies directed to these polypeptides are useful in providing immunological probes for differential identification of the tissue(s) or cell type(s). For a number of disorders of the above tissues or cells, particularly of the reproductive system, cartilage and bone, expression of this gene at significantly higher or lower levels may routinely be detected in certain tissues and cell types (e.g. placenta, testis, adrenal gland, and osteoclastoma, and cancerous and wounded tissues) or bodily fluids (e.g. seminal fluid, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to the yeast YKL1GG protein indicates that polypeptides and polynucleotides corresponding to Gene NO: 65 are useful for the development of therapeutic and/or diagnostic modalities targeted at cancer or secretory anomalies, such as genetically caused secretory diseases. Protein, as well as, antibodies directed against the protein may show utility as a tumor marker and/or immunotherapy targets for the above listed tissues.

Preferred epitopes include those comprising a sequence shown in SEQ ID NO: 198 as residues: Ser-18 to Ser-29 and Lys-53 to Arg-74.

Many polynucleotide sequences, such as EST sequences, are publicly available and accessible through sequence databases. Some of these sequences are related to SEQ ID NO:75 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1119 of SEQ ID NO:75, b is an integer of 15 to 1133, where both a and b correspond to the positions of nucleotide residues shown in SEQ ID NO:75, and where b is greater than or equal to a+1.

Features of Protein Encoded by Gene No: 66

The translation product of Gene NO: 66 shares sequence homology with the human papilloma virus (HPV) E5 ORF region which is thought to be important as a secreted growth factor. Although this is described as a viral gene product, it is believed to have several cellular secretory homologues. Therefore, based on the sequence similarity between the HPV E5 ORF and the translated product of this gene, this gene product is likely to have activity similar to HPV E5 ORF. The gene encoding the disclosed cDNA is believed to reside on chromosome 1. Accordingly, polynucleotides related to this invention are useful as a marker in linkage analysis for chromosome 1.

Gene NO: 66 is expressed primarily in activated T-Cells, monocytes, cerebellum and to a lesser extent in infant brain.

Therefore, polynucleotides or polypeptides of the invention are useful as reagents for differential identification of the tissue(s) or cell type(s) present in a biological sample and for diagnosis of diseases and conditions which include, but are not limited to, cancer and/or human papilloma virus infection. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues and cell types (e.g. brain, lymph tissue, monocytes, and T-cells, developmental, and cancerous and wounded tissues) or bodily fluids (e.g. lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Moreover, polynucleotides of this gene have been mapped to chromosome 1. Therefore, polynucleotides of the present invention can be used in linkage analysis as a marker for chromosome 1.

The tissue distribution and homology to human papilloma virus E5 region indicates that polypeptides and polynucleotides corresponding to Gene NO: 66 are useful for development of diagnostic and/or therapeutic modalities directed at the diagnosis and/or treatment of cancer and/or human papilloma virus infection (HPV). Protein, as well as, antibodies directed against the protein may show utility as a tumor marker and/or immunotherapy targets for the above listed tissues.

Preferred epitopes include those comprising a sequence shown in SEQ ID NO: 199 as residues: Asn-31 to Arg-36 and Leu-102 to Ser-112.

Many polynucleotide sequences, such as EST sequences, are publicly available and accessible through sequence databases. Some of these sequences are related to SEQ ID NO:76 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 571 of SEQ ID NO:76, b is an integer of 15 to 585, where both a and b correspond to the positions of nucleotide residues shown in SEQ ID NO:76, and where b is greater than or equal to a+1.

Features of Protein Encoded by Gene No: 67

The translation product of Gene NO: 67 shares sequence homology with the 8hs20 protein precursor [Mus musculus] which is thought to be important in B-Cell mu chain assembly. (See, Accession No. PID/d1002996; Shiraswa, T., EMBO. J. 12(5): 1827–1834 (1993).) A polypeptide fragment starting at amino acid 53 is preferred, as well as 1–20 amino acid N-terminus and/or C-terminus deletions. Based on the sequence similarity between 8hs20 protein and the translation product of this gene, the two polypeptides are expected to share certain biological activities, particularly immunologic activities. Precursors of B cells, which constitute a subpopulation of the lymphocytes in bone marrow, can be identified by their surface expression of nonimmunoglobulin markers and the absence of immunoglobulin kappa and lambda light chains. Most pre-B cells synthesize mu heavy chains but, without light-chain partners, these undergo rapid cytoplasmic degradation. Late stage pre-B cells, like their neoplastic counterparts, express low levels of a surface receptor composed of mu chains paired with a surrogate light-chain complex formed by Vpre-B and lambda 5-like proteins. This pre-B cell receptor presumably triggers early steps of B cell differentiation.

Gene NO: 67 is expressed primarily in human B-cells and to a lesser extent in Hodgkin's Lymphoma. It is also likely that the polypeptide will be expressed in B-cell specific cells, bone marrow, and spleen, as is observed with 8hs20.

Therefore, polynucleotides or polypeptides of the invention are useful as reagents for differential identification of the tissue(s) or cell type(s) present in a biological sample and for diagnosis of diseases and conditions which include, but are not limited to, Hodgkin's Lymphoma, Common Variable Immunodeficiency, and/or other B-cell lymphomas. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues and cell types (e.g. bone marrow, spleen, lymph tissue, and B-cells, and cancerous and wounded tissues) or bodily fluids (e.g. lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution and homology to 8hs20 protein precursor [Mus musculus], indicates that polypeptides and polynucleotides corresponding to Gene NO: 67 are useful for therapeutic and/or diagnostic purposes, targeting Hodgkin's Lymphoma, B-cell lymphomas, Common Variable Immunodeficiency, or other immune disorders.

Preferred epitopes include those comprising a sequence shown in SEQ ID NO: 200 as residues: Asp-51 to Trp-56, Arg-72 to Asp-85, and Gln-106 to Asp-112.

Many polynucleotide sequences, such as EST sequences, are publicly available and accessible through sequence databases. Some of these sequences are related to SEQ ID NO:77 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 563 of SEQ ID NO:77, b is an integer of 15 to 577, where both a and b correspond to the positions of nucleotide residues shown in SEQ ID NO:77, and where b is greater than or equal to a+1.

Features of Protein Encoded by Gene No: 68

Gene NO: 68 is expressed primarily in fetal liver/spleen, rhabdomyosarcoma, and to a lesser extent in 9 week-old early stage human embryo and bone marrow.

Therefore, polynucleotides or polypeptides of the invention are useful as reagents for differential identification of the tissue(s) or cell type(s) present in a biological sample and for diagnosis of diseases and conditions which include, but are not limited to, rhabdomyosarcoma and other cancers, hematopoietic disorders, and immune dysfunction. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may routinely be detected in certain tissues or cell types (e.g. embryonic tissue, striated muscle, liver, spleen, and bone marrow, and cancerous and wounded tissues) or bodily fluids (e.g. amniotic fluid, bile, lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that the protein product of Gene NO: 68 is useful for diagnostic and/or therapeutic purposes directed to cancer, preferably rhabdomyosarcoma. Enhanced expression of this gene in fetal liver, spleen, and bone marrow indicates that this gene plays an active role in hematopoiesis. Polypeptides or polynucleotides of the present invention may therefore help modulate survival, proliferation, and/or differentiation of various hematopoietic lineages, including the hematopoietic stem cell. Thus, polynucleotides or polypeptides can be used treat various hematopoietic disorders and influence the development and differentiation of blood cell lineages, including hematopoeitic stem cell expansion. The polypeptide does contain a thioredoxin family active site at amino acids 64–82. Polypeptides comprising this thioredoxin active site are contemplated.

Many polynucleotide sequences, such as EST sequences, are publicly available and accessible through sequence databases. Some of these sequences are related to SEQ ID NO:78 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 2264 of SEQ ID NO:78, b is an integer of 15 to 2278, where both a and b correspond to the positions of nucleotide residues shown in SEQ ID NO:78, and where b is greater than or equal to a+1.

Features of Protein Encoded by Gene No: 69

Gene NO: 69 is expressed primarily in liver and kidney and to a lesser extent in macrophages, uterus, placenta, and testes.

Therefore, polynucleotides or polypeptides of the invention are useful as reagents for differential identification of the tissue(s) or cell type(s) present in a biological sample and for diagnosis of diseases and conditions which include, but are not limited to, renal disorders, neoplasms (e.g. soft tissue cancer, hepatacellular tumors), immune disorders, endocrine imbalances, and reproductive disorders. Similarly, polypeptides and antibodies directed to these polypeptides are useful in providing immunological probes for differential identification of the tissue(s) or cell type(s). For a number of disorders of the above tissues or cells, particularly of the hepatic, urogenital, immune, and reproductive systems, expression of this gene at significantly higher or lower levels may routinely be detected in certain tissues and cell types (e.g. liver, kidney, uterus, placenta, testes, and macrophages and cancerous and wounded tissues) or bodily fluids (e.g. bile, lymph, amniotic fluid, seminal fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 69 are useful for diagnosis and treatment of disorders in the hepatic, urogenital, immune, and reproductive systems. Protein, as well as, antibodies directed against the protein may show utility as a tumor marker and/or immunotherapy targets for the above listed tissues.

Preferred epitopes include those comprising a sequence shown in SEQ ID NO: 202 as residues: Arg-41 to Ser-50, Glu-138 to Asn-148, Ser-155 to Arg-172, Pro-219 to Glu-228.

Many polynucleotide sequences, such as EST sequences, are publicly available and accessible through sequence databases. Some of these sequences are related to SEQ ID NO:79 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 1129 of SEQ ID NO:79, b is an integer of 15 to 1143, where both a and b correspond to the positions of nucleotide residues shown in SEQ ID NO:79, and where b is greater than or equal to a+1.

Features of Protein Encoded by Gene No: 70

The gene which encodes for the disclosed cDNA is thought to reside on chromosome 19. Accordingly, polynucleotides related to this invention are useful for linkage analysis for chromosome 19.

Gene NO: 70 is expressed primarily in the immune system, including macrophages, T-cells, and dendritic cells and to a lesser extent in fetal tissue.

Therefore, polynucleotides or polypeptides of the invention are useful as reagents for differential identification of the tissue(s) or cell type(s) present in a biological sample and for diagnosis of diseases and conditions which include, but are not limited to, immune disorders, inflammatory diseases, lymph node disorders, fetal development, and cancers. Similarly, polypeptides and antibodies directed to these polypeptides are useful in providing immunological probes for differential identification of the tissue(s) or cell type(s). For a number of disorders of the above tissues or cells, particularly of the immune and hematopoietic systems, expression of this gene at significantly higher or lower levels may routinely be detected in certain tissues and certain cell types (e.g. macrophages, T-cells, dendritic cells, and fetal tissue, and cancerous and wounded tissues) or bodily fluids (e.g. lymph, amniotic fluid, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder.

The tissue distribution indicates that polypeptides and polynucleotides corresponding to Gene NO: 70 are useful for treatment, prophylaxis, and diagnosis of immune and autoimmune diseases, such as lupus, transplant rejection, allergic reactions, arthritis, asthma, immunodeficiency diseases, leukemia, and AIDS. The polypeptides or polynucleotides of the present invention are also useful in the treatment, prophylaxis, and detection of thymus disorders, such as Graves Disease, lymphocytic thyroiditis, hyperthyroidism, and hypothyroidism. The expression observed predominantly in hematopoietic cells also indicates that the polynucleotides or polypeptides are important in treating and/or detecting hematopoietic disorders, such as graft versus host reaction, graft versus host disease, transplant rejection, myelogenous leukemia, bone marrow fibrosis, and myeloproliferative disease. The polypeptides or polynucleotides are also useful to enhance or protect proliferation, differentiation, and functional activation of hematopoietic progenitor cells (e.g. bone marrow cells), useful in treating cancer patients undergoing chemotherapy or patients undergoing bone marrow transplantation. The polypeptides or polynucleotides are also useful to increase the proliferation of peripheral blood leukocytes, which can be used in the combat of a range of hematopoietic disorders, including immunodeficiency diseases, leukemia, and septicemia.

Preferred epitopes include those comprising a sequence shown in SEQ ID NO: 203 as residues: Thr-21 to Ser-27, Pro-33 to Ser-38, and Arg-73 to Lys-84.

Many polynucleotide sequences, such as EST sequences, are publicly available and accessible through sequence databases. Some of these sequences are related to SEQ ID NO: 80 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 543 of SEQ ID NO:80, b is an integer of 15 to 557, where both a and b correspond to the positions of nucleotide residues shown in SEQ ID NO:80, and where b is greater than or equal to a+1.

TABLE 1

| Gene No. | cDNA Clone D | ATCC Deposit No: Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 1 | HGCMD20 | 97901 02/26/97 209047 05/15/97 | pSport1 | 11 | 1739 | 25 | 1658 | 54 | 54 | 134 | 1 | 28 | 29 | 467 |

TABLE 1-continued

| Gene No. | cDNA Clone D | ATCC Deposit No: Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 2 | HLDBG33 | 97898 02/26/97 209044 05/15/97 | pCMVSport 3.0 | 12 | 844 | 1 | 844 | 39 | 39 | 135 | 1 | 28 | 29 | 221 |
| 2 | HLDBG33 | 97898 02/26/97 209044 05/15/97 | pCMVSport 3.0 | 81 | 795 | 1 | 434 | 10 | 10 | 204 | 1 | 29 | 30 | 35 |
| 3 | HTGEW86 | 97899 02/26/97 209045 05/15/97 | Uni-ZAP XR | 13 | 776 | 134 | 676 | 173 | 173 | 136 | 1 | 35 | 36 | 156 |
| 4 | HKCSR70 | 97900 02/26/97 209046 05/15/97 | pBluescript | 14 | 1376 | 727 | 1343 | 202 | 202 | 137 | 1 | 20 | 21 | 232 |
| 4 | HKCSR70 | 97900 02/26/97 209046 05/15/97 | pBluescript | 82 | 1324 | 741 | 1309 | | 861 | 205 | 1 | 31 | 32 | 43 |
| 4 | HETBI87 | 209010 04/28/97 209085 05/29/97 | Uni-ZAP XR | 83 | 1494 | 1 | 1484 | 51 | 51 | 206 | 1 | 34 | 35 | 84 |
| 5 | HTEAU17 | 97897 02/26/97 209043 05/15/97 | Uni-ZAP XR | 15 | 502 | 1 | 502 | 143 | 143 | 138 | 1 | 33 | 34 | 61 |
| 6 | HBMCY91 | 97897 02/26/97 209043 05/15/97 | pBluescript | 16 | 425 | 1 | 425 | 56 | 56 | 139 | 1 | 17 | 18 | 72 |
| 7 | HSSGE07 | 97897 02/26/97 209043 05/15/97 | Uni-ZAP XR | 17 | 1316 | 1 | 1298 | 45 | 45 | 140 | 1 | 26 | 27 | 376 |
| 7 | HSSGE07 | 97897 02/26/97 209043 05/15/97 | Uni-ZAP XR | 84 | 1285 | 1 | 1271 | 15 | 15 | 207 | 1 | 28 | 29 | 208 |
| 8 | HBMBX59 | 97897 02/26/97 209043 05/15/97 | pBluescript | 18 | 436 | 87 | 384 | 157 | 157 | 141 | 1 | 21 | 22 | 43 |
| 9 | HNGIT22 | 97897 02/26/97 209043 05/15/97 | Uni-ZAP XR | 19 | 503 | 1 | 503 | 23 | 23 | 142 | 1 | 19 | 20 | 41 |
| 10 | HERAD57 | 97897 02/26/97 209043 05/15/97 | Uni-ZAP XR | 20 | 358 | 1 | 358 | 147 | 147 | 143 | 1 | 31 | 32 | 70 |
| 11 | HCENJ40 | 97898 02/26/97 209044 05/15/97 | Uni-ZAP XR | 21 | 1926 | 573 | 1926 | 157 | 157 | 144 | 1 | 30 | 31 | 483 |
| 11 | HCENJ40 | 97898 02/26/97 209044 05/15/97 | Uni-ZAP XR | 85 | 394 | 1 | 394 | 166 | 166 | 208 | 1 | 20 | 21 | 24 |
| 11 | HCENJ40 | 97898 02/26/97 209044 05/15/97 | Uni-ZAP XR | 86 | 1925 | 573 | 1925 | 157 | 157 | 209 | 1 | 30 | 31 | 482 |
| 11 | HCENJ40 | 97898 02/26/97 209044 05/15/97 | Uni-ZAP XR | 87 | 1818 | 30 | 1298 | | 1137 | 210 | 1 | | | 13 |
| 12 | HCSRA90 | 97898 02/26/97 209044 05/15/97 | Uni-ZAP XR | 22 | 1224 | 64 | 557 | 80 | 80 | 145 | 1 | 30 | 31 | 226 |

TABLE 1-continued

| Gene No. | cDNA Clone D | ATCC Deposit No: Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 13 | HBJFC03 | 97898 02/26/97 209044 05/15/97 | Uni-ZAP XR | 23 | 694 | 1 | 694 | 181 | 181 | 146 | 1 | 39 | 40 | 44 |
| 13 | HBJFC03 | 97898 02/26/97 209044 05/15/97 | Uni-ZAP XR | 88 | 539 | 1 | 539 | 215 | 215 | 211 | 1 | 18 | 19 | 20 |
| 14 | HSNBL85 | 97899 02/26/97 20945 05/15/97 | Uni-ZAP XR | 24 | 796 | 405 | 796 | 1 | 1 | 147 | 1 | 30 | 31 | 131 |
| 14 | HSNBL85 | 97899 02/26/97 20945 05/15/97 | Uni-ZAP XR | 89 | 855 | 300 | 855 | 513 | 513 | 212 | 1 | 37 | 38 | 55 |
| 15 | HTEBY26 | 97899 02/26/97 20945 05/15/97 | Uni-ZAP XR | 25 | 662 | 205 | 653 | 77 | 77 | 148 | 1 | 30 | 31 | 91 |
| 15 | HTEBY26 | 97899 02/26/97 20945 05/15/97 | Uni-ZAP XR | 90 | 628 | 198 | 625 |  | 275 | 213 | 1 | 31 | 32 | 35 |
| 16 | HMABH07 | 97899 02/26/97 20945 05/15/97 | Uni-ZAP XR | 26 | 1105 | 40 | 1105 | 88 | 88 | 149 | 1 | 18 | 19 | 164 |
| 16 | HMABH07 | 97899 02/26/97 20945 05/15/97 | Uni-ZAP XR | 91 | 1053 | 61 | 1009 | 79 | 79 | 214 | 1 | 22 | 23 | 230 |
| 16 | HMAAD57 | 209236 09/04/97 | Uni-ZAP XR | 92 | 1075 | 68 | 1059 | 95 | 95 | 215 | 1 | 22 | 23 | 230 |
| 17 | HSKNY94 | 97899 02/26/97 20945 05/15/97 | pBluescript | 27 | 1017 | 1 | 1017 | 97 | 97 | 150 | 1 | 30 | 31 | 138 |
| 17 | HSKNY94 | 97899 02/26/97 20945 05/15/97 | pBluescript | 93 | 2492 | 1 | 943 | 100 | 100 | 216 | 1 | 27 | 28 | 127 |
| 18 | HMCDA67 | 97899 02/26/97 20945 05/15/97 | Uni-ZAP XR | 28 | 391 | 1 | 391 | 169 | 169 | 151 | 1 | 29 | 30 | 58 |
| 19 | HOSFF45 | 97899 02/26/97 20945 05/15/97 | Uni-ZAP XR | 29 | 1139 | 6 | 1139 | 109 | 109 | 152 | 1 | 44 | 45 | 47 |
| 19 | HOSFF45 | 97899 02/26/97 20945 05/15/97 | Uni-ZAP XR | 94 | 3058 | 1795 | 2847 | 1868 | 1868 | 217 | 1 | 46 | 47 | 47 |
| 20 | HMJAA51 | 97899 02/26/97 20945 05/15/97 | pSport1 | 30 | 465 | 1 | 370 | 47 | 47 | 153 | 1 | 28 | 29 | 41 |
| 20 | HMJAA51 | 97899 02/26/97 20945 05/15/97 | pSport1 | 95 | 1099 | 664 | 1000 | 669 | 669 | 218 | 1 | 33 | 34 | 41 |
| 21 | HTEBF05 | 97899 02/26/97 20945 05/15/97 | Uni-ZAP XR | 31 | 702 | 1 | 702 | 403 | 403 | 154 | 1 | 24 | 25 | 72 |
| 22 | HTEAL31 | 97899 02/26/97 20945 05/15/97 | Uni-ZAP XR | 32 | 1142 | 1 | 518 | 49 | 49 | 155 | 1 | 47 | 48 | 105 |

TABLE 1-continued

| Gene No. | cDNA Clone D | ATCC Deposit No: Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 22 | HTEAL31 | 97899 02/26/97 20945 05/15/97 | Uni-ZAP XR | 96 | 1580 | 23 | 422 | 32 | 32 | 219 | 1 | 47 | 48 | 105 |
| 23 | HBMCT32 | 97899 02/26/97 20945 05/15/97 | pBluescript | 33 | 928 | 1 | 928 | 48 | 48 | 156 | 1 | 27 | 28 | 29 |
| 23 | HBMCT32 | 97899 02/26/97 20945 05/15/97 | pBluescript | 97 | 678 | 72 | 593 | 89 | 89 | 220 | 1 | 27 | 28 | 29 |
| 24 | HSKXE91 | 97899 02/26/97 20945 05/15/97 | pBluescript | 34 | 773 | 1 | 773 | 39 | 39 | 157 | 1 | 22 | 23 | 52 |
| 24 | HSKXE91 | 97899 02/26/97 20945 05/15/97 | pBluescript | 98 | 1253 | 507 | 1253 | 507 | 507 | 221 | 1 | | | 17 |
| 25 | HPWTB39 | 97899 02/26/97 20945 05/15/97 | Uni-ZAP XR | 35 | 453 | 1 | 453 | 40 | 40 | 158 | 1 | 25 | 26 | 75 |
| 26 | HTLEV12 | 97899 02/26/97 20945 05/15/97 | Uni-ZAP XR | 36 | 459 | 1 | 459 | 25 | 25 | 159 | 1 | 24 | 25 | 81 |
| 27 | HSPAF93 | 97900 02/26/97 209046 05/15/97 | pSport1 | 37 | 509 | 1 | 509 | 1 | 1 | 160 | 1 | 19 | 20 | 138 |
| 27 | HSPAF93 | 97900 02/26/97 209046 05/15/97 | pSport1 | 99 | 447 | 1 | 447 | 7 | 7 | 222 | 1 | 23 | 24 | 138 |
| 28 | HHFGL62 | 97900 02/26/97 209046 05/15/97 | Uni-ZAP XR | 38 | 598 | 1 | 598 | 1 | 1 | 161 | 1 | 21 | 22 | 177 |
| 28 | HHFGL62 | 97900 02/26/97 209046 05/15/97 | Uni-ZAP XR | 100 | 611 | 37 | 611 | 17 | 17 | 223 | 1 | 26 | 27 | 50 |
| 29 | HCE1U14 | 97900 02/26/97 209046 05/15/97 | Uni-ZAP XR | 39 | 454 | 1 | 454 | 1 | 1 | 162 | 1 | 21 | 22 | 71 |
| 29 | HCE1U14 | 97900 02/26/97 209046 05/15/97 | Uni-ZAP XR | 101 | 609 | 176 | 609 | 237 | 237 | 224 | 1 | | | 15 |
| 30 | HEBDA39 | 97900 02/26/97 209046 05/15/97 | Uni-ZAP XR | 40 | 425 | 1 | 376 | 223 | 223 | 163 | 1 | 18 | 19 | 67 |
| 31 | HTHBA79 | 97900 02/26/97 209046 05/15/97 | Uni-ZAP XR | 41 | 2471 | 141 | 2471 | 213 | 213 | 164 | 1 | 30 | 31 | 154 |
| 31 | HTHBA79 | 97900 02/26/97 209046 05/15/97 | Uni-ZAP XR | 102 | 1770 | 47 | 1721 | 119 | 119 | 225 | 1 | 31 | 32 | 154 |
| 31 | HTHBA79 | 97900 02/26/97 209046 05/15/97 | Uni-ZAP XR | 103 | 1832 | 96 | 1777 | 138 | 138 | 226 | 1 | | | 10 |
| 32 | HAGBB70 | 97900 02/26/97 209046 05/15/97 | Uni-ZAP XR | 42 | 2659 | 1172 | 2659 | 119 | 119 | 165 | 1 | 18 | 19 | 103 |

TABLE 1-continued

| Gene No. | cDNA Clone D | ATCC Deposit No: Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 32 | HAGBB70 | 97900 02/26/97 209046 05/15/97 | Uni-ZAP XR | 104 | 2237 | 878 | 2237 | 1134 | 1134 | 227 | 1 | | | 20 |
| 33 | HETDG84 | 97900 02/26/97 209046 05/15/97 | Uni-ZAP XR | 43 | 1635 | 100 | 1580 | 299 | 299 | 166 | 1 | 20 | 21 | 81 |
| 34 | HTEGA81 | 97900 02/26/97 209046 05/15/97 | Uni-ZAP XR | 44 | 780 | 19 | 717 | 10 | 10 | 167 | 1 | 23 | 24 | 93 |
| 34 | HKGAJ40 | 209236 09/04/97 | pSport1 | 105 | 1822 | 1 | 1023 | 272 | 272 | 228 | 1 | 23 | 24 | 93 |
| 34 | HKMLK44 | 209084 05/29/97 | pBluescript | 106 | 1712 | 1 | 1669 | 168 | 168 | 229 | 1 | 21 | 22 | 93 |
| 35 | HTXAK60 | 97900 02/26/97 209046 05/15/97 | Uni-ZAP XR | 45 | 2378 | 1337 | 2378 | 1437 | 1437 | 168 | 1 | 30 | 31 | 57 |
| 35 | HTXAK60 | 97900 02/26/97 209046 05/15/97 | Uni-ZAP XR | 107 | 1969 | 1068 | 1892 | 989 | 989 | 230 | 1 | 23 | 24 | 37 |
| 36 | HMHBN40 | 97901 02/26/97 209047 05/15/97 | Uni-ZAP XR | 46 | 1772 | 69 | 1772 | 129 | 129 | 169 | 1 | 30 | 31 | 231 |
| 36 | HMHBN40 | 97901 02/26/97 209047 05/15/97 | Uni-ZAP XR | 108 | 1734 | 65 | 1734 | 100 | 100 | 231 | 1 | 29 | 30 | 81 |
| 37 | HFVGS85 | 97901 02/26/97 209047 05/15/97 | pBluescript | 47 | 1107 | 70 | 1107 | 83 | 83 | 170 | 1 | 30 | 31 | 72 |
| 38 | HERAH81 | 97901 02/26/97 209047 05/15/97 | Uni-ZAP XR | 48 | 805 | 167 | 764 | 167 | 167 | 171 | 1 | 23 | 24 | 65 |
| 39 | HMSEU04 | 97901 02/26/97 209047 05/15/97 | Uni-ZAP XR | 49 | 1408 | 131 | 1258 | 364 | 364 | 172 | 1 | 22 | 23 | 75 |
| 40 | HNEDJ57 | 97901 02/26/97 209047 05/15/97 | Uni-ZAP XR | 50 | 1813 | 1 | 1184 | 2 | 2 | 173 | 1 | 1 | 2 | 334 |
| 41 | HNTME13 | 97901 02/26/97 209047 05/15/97 | pSport1 | 51 | 2070 | 74 | 2070 | 142 | 142 | 174 | 1 | 20 | 21 | 195 |
| 41 | HNTME13 | 97901 02/26/97 209047 05/15/97 | pSport1 | 109 | 2003 | 15 | 1957 | 68 | 68 | 232 | 1 | 22 | 23 | 301 |
| 42 | HSXBI25 | 97901 02/26/97 209047 05/15/97 | Uni-ZAP XR | 52 | 1426 | 1 | 1426 | 158 | 158 | 175 | 1 | 25 | 26 | 264 |
| 42 | HSXBI25 | 97901 02/26/97 209047 05/15/97 | Uni-ZAP XR | 110 | 1320 | 80 | 1311 | 41 | 41 | 233 | 1 | 29 | 30 | 313 |
| 43 | HSXCK41 | 97901 02/26/97 209047 05/15/97 | Uni-ZAP XR | 53 | 1720 | 1 | 1720 | 161 | 161 | 176 | 1 | 22 | 23 | 137 |
| 43 | HSXCK41 | 97901 02/26/97 209047 05/15/97 | Uni-ZAP XR | 111 | 1962 | 299 | 1962 | | 566 | 234 | 1 | 33 | 34 | 48 |

TABLE 1-continued

| Gene No. | cDNA Clone D | ATCC Deposit No: Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 44 | HE8CJ26 | 97902 02/26/97 209048 05/15/97 | Uni-ZAP XR | 54 | 1117 | 1 | 1107 | 218 | 218 | 177 | 1 | 25 | 26 | 178 |
| 44 | HE8CJ26 | 97902 02/26/97 209048 05/15/97 | Uni-ZAP XR | 112 | 1785 | 30 | 1087 | | 225 | 235 | 1 | 23 | 24 | 34 |
| 45 | HTTDS54 | 97902 02/26/97 209048 05/15/97 | Uni-ZAP XR | 55 | 1903 | 1 | 1903 | 119 | 119 | 178 | 1 | 31 | 32 | 154 |
| 45 | HTTDS54 | 97902 02/26/97 209048 05/15/97 | Uni-ZAP XR | 113 | 1842 | 1 | 1832 | 80 | 80 | 236 | 1 | 36 | 37 | 313 |
| 46 | HLHDY31 | 97902 02/26/97 209048 05/15/97 | Uni-ZAP XR | 56 | 1869 | 133 | 1838 | 124 | 124 | 179 | 1 | 24 | 25 | 295 |
| 46 | HLHDY31 | 97902 02/26/97 209048 05/15/97 | Uni-ZAP XR | 114 | 1960 | 90 | 1960 | 165 | 165 | 237 | 1 | 24 | 25 | 295 |
| 47 | HMCBP63 | 97902 02/26/97 209048 05/15/97 | Uni-ZAP XR | 57 | 1259 | 320 | 1010 | 352 | 352 | 180 | 1 | 26 | 27 | 256 |
| 48 | HEMGE83 | 97902 02/26/97 209048 05/15/97 | Uni-ZAP XR | 58 | 1186 | 33 | 557 | 12 | 12 | 181 | 1 | 18 | 19 | 324 |
| 49 | HHSDC22 | 97902 02/26/97 209048 05/15/97 | Uni-ZAP XR | 59 | 428 | 1 | 304 | 172 | 172 | 182 | 1 | 34 | 35 | 47 |
| 50 | HRSDZ57 | 97902 02/26/97 209048 05/15/97 | Uni-ZAP XR | 60 | 501 | 1 | 501 | 40 | 40 | 183 | 1 | 62 | 63 | 92 |
| 50 | HHSDZ57 | 97902 02/26/97 209048 05/15/97 | Uni-ZAP XR | 115 | 536 | 73 | 536 | 73 | 73 | 238 | 1 | 22 | 23 | 92 |
| 51 | HCRBS80 | 97958 03/13/97 209072 05/22/97 | Uni-ZAP XR | 61 | 1197 | 513 | 880 | 6 | 6 | 184 | 1 | 30 | 31 | 167 |
| 51 | HAICS58 | 97903 02/26/97 209049 05/15/97 | Uni-ZAP XR | 116 | 790 | 466 | 699 | 484 | 484 | 239 | 1 | 28 | 29 | 71 |
| 51 | HCRBS80 | 97958 03/13/97 209072 05/22/97 | Uni-ZAP XR | 117 | 776 | 402 | 776 | 514 | 514 | 240 | 1 | 30 | 31 | 71 |
| 52 | HMMAB12 | 97903 02/26/97 209049 05/15/97 | pSport1 | 62 | 595 | 1 | 595 | 308 | 308 | 185 | 1 | 29 | 30 | 42 |
| 52 | HMMAB12 | 97903 02/26/97 209049 05/15/97 | pSport1 | 118 | 453 | 1 | 453 | 198 | 198 | 241 | 1 | 26 | 27 | 28 |
| 53 | HSKDW02 | 97903 02/26/97 209049 05/15/97 | Uni-ZAP XR | 63 | 1478 | 40 | 1436 | 176 | 176 | 186 | 1 | 39 | 40 | 58 |
| 53 | HSKDW02 | 97903 02/26/97 209049 05/15/97 | Uni-ZAP XR | 119 | 2016 | 211 | 1957 | 317 | 317 | 242 | 1 | 25 | 26 | 58 |

TABLE 1-continued

| Gene No. | cDNA Clone D | ATCC Deposit No: Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 54 | HETGL41 | 97903 02/26/97 209049 05/15/97 | Uni-ZAP XR | 64 | 2033 | 1 | 2033 | 225 | 225 | 187 | 1 | 22 | 23 | 123 |
| 54 | HETGL41 | 97903 02/26/97 209049 05/15/97 | Uni-ZAP XR | 120 | 2136 | 110 | 2134 | 296 | 296 | 243 | 1 | 23 | 24 | 123 |
| 55 | HODAZ50 | 97903 02/26/97 209049 05/15/97 | Uni-ZAP XR | 65 | 440 | 1 | 440 | 1 | 1 | 188 | 1 | 26 | 27 | 146 |
| 55 | HODAZ50 | 97903 02/26/97 209049 05/15/97 | Uni-ZAP XR | 121 | 219 | 1 | 219 | | 1 | 244 | 1 | 10 | 11 | 73 |
| 56 | HSDGE59 | 97903 02/26/97 209049 05/15/97 | Uni-ZAP XR | 66 | 3301 | 349 | 1478 | 341 | 341 | 189 | 1 | 30 | 31 | 84 |
| 57 | HE6ES13 | 97903 02/26/97 209049 05/15/97 | Uni-ZAP XR | 67 | 1535 | 1 | 1535 | 331 | 331 | 190 | 1 | 26 | 27 | 57 |
| 57 | HE6ES13 | 97903 02/26/97 209049 05/15/97 | Uni-ZAP XR | 122 | 1686 | 239 | 1678 | | 367 | 245 | 1 | 27 | 28 | 49 |
| 58 | HSSEP68 | 97903 02/26/97 209049 05/15/97 | Uni-ZAP XR | 68 | 1244 | 402 | 1244 | 57 | 57 | 191 | 1 | 30 | 31 | 310 |
| 58 | HSSEP68 | 97903 02/26/97 209049 05/15/97 | Uni-ZAP XR | 123 | 1211 | 1 | 1211 | 80 | 80 | 246 | 1 | 30 | 31 | 338 |
| 58 | HSSEP68 | 97903 02/26/97 209049 05/15/97 | Uni-ZAP XR | 124 | 1804 | 402 | 1526 | 501 | 501 | 247 | 1 | | | 18 |
| 59 | HRDEV41 | 97903 02/26/97 209049 05/15/97 | Uni-ZAP XR | 69 | 1292 | 1 | 1278 | 70 | 70 | 192 | 1 | 28 | 29 | 317 |
| 59 | HRDEV41 | 97903 02/26/97 209049 05/15/97 | Uni-ZAP XR | 125 | 1282 | 31 | 1088 | 70 | 70 | 248 | 1 | 21 | 22 | 339 |
| 60 | HILCJ01 | 97903 02/26/97 209049 05/15/97 | pBluescript SK- | 70 | 1031 | 498 | 1031 | 536 | 536 | 193 | 1 | 30 | 31 | 53 |
| 61 | HSATP28 | 97904 02/26/97 209050 05/15/97 | Uni-ZAP XR | 71 | 855 | 178 | 855 | 187 | 187 | 194 | 1 | 28 | 29 | 42 |
| 62 | HHFGL41 | 97904 02/26/97 209050 05/15/97 | Uni-ZAP XR | 72 | 1274 | 58 | 1274 | 133 | 133 | 195 | 1 | 39 | 40 | 96 |
| 62 | HHFGL41 | 97904 02/26/97 209050 05/15/97 | Uni-ZAP XR | 126 | 1296 | 88 | 1237 | 133 | 133 | 249 | 1 | 39 | 40 | 96 |
| 63 | HBJEM49 | 97904 02/26/97 209050 05/15/97 | Uni-ZAP XR | 73 | 688 | 1 | 688 | 173 | 173 | 196 | 1 | 18 | 19 | 44 |
| 63 | HBJEM49 | 97904 02/26/97 209050 05/15/97 | Uni-ZAP XR | 127 | 737 | 1 | 737 | 174 | 174 | 250 | 1 | 20 | 21 | 79 |

TABLE 1-continued

| Gene No. | cDNA Clone D | ATCC Deposit No: Z and Date | Vector | NT SEQ ID NO:X | Total NT Seq. | 5' NT of Clone Seq. | 3' NT of Clone Seq. | 5' NT of Start Codon | 5' NT of First AA of Signal Pep | AA SEQ ID NO:Y | First AA of Sig Pep | Last AA of Sig Pep | First AA of Secreted Portion | Last AA of ORF |
|---|---|---|---|---|---|---|---|---|---|---|---|---|---|---|
| 64 | HSLDJ95 | 97904 02/26/97 209050 05/15/97 | Uni-ZAP XR | 74 | 1890 | 1 | 1890 | 112 | 112 | 197 | 1 | 21 | 22 | 354 |
| 64 | HSLDJ95 | 97904 02/26/97 209050 05/15/97 | Uni-ZAP XR | 128 | 1925 | 1 | 1829 | 87 | 87 | 251 | 1 | 23 | 24 | 354 |
| 65 | HSREG44 | 97904 02/26/97 209050 05/15/97 | Uni-ZAP XR | 75 | 1133 | 408 | 1133 | 531 | 531 | 198 | 1 | 18 | 19 | 74 |
| 66 | HTXCT40 | 97904 02/26/97 209050 05/15/97 | Uni-ZAP XR | 76 | 585 | 1 | 585 | 1 | 1 | 199 | 1 | 69 | 70 | 112 |
| 66 | HTXCT40 | 97904 02/26/97 209050 05/15/97 | Uni-ZAP XR | 129 | 2713 | 2023 | 2713 | 2133 | 2133 | 252 | 1 | 39 | 40 | 109 |
| 67 | HRGDF73 | 97904 02/26/97 209050 05/15/97 | Uni-ZAP XR | 77 | 577 | 1 | 577 | 51 | 51 | 200 | 1 | 23 | 24 | 123 |
| 68 | HRDBF52 | 97904 02/26/97 209050 05/15/97 | Uni-ZAP XR | 78 | 2278 | 1458 | 1935 | 25 | 25 | 201 | 1 | 23 | 24 | 314 |
| 68 | HRDBF52 | 97904 02/26/97 09050 05/15/97 | Uni-ZAP XR | 130 | 1011 | 479 | 1011 | 701 | 701 | 253 | 1 | 20 | 21 | 45 |
| 68 | HKMND45 | 209081 05/29/97 97976 04/04/97 | pBluescript | 131 | 2278 | 1 | 1929 | 25 | 25 | 254 | 1 | 27 | 28 | 314 |
| 69 | HPEBD70 | 97904 02/26/97 209050 05/15/97 | Uni-ZAP XR | 79 | 1143 | 601 | 1097 | 95 | 95 | 202 | 1 | 6 | 7 | 235 |
| 69 | HPEBD70 | 97904 02/26/97 209050 05/15/97 | Uni-ZAP XR | 132 | 1088 | 535 | 1043 | 588 | 588 | 255 | 1 | 27 | 28 | 53 |
| 70 | HMCAB89 | 97904 02/26/97 209050 05/15/97 | Uni-ZAP XR | 80 | 557 | 1 | 557 | 132 | 132 | 203 | 1 | 25 | 26 | 93 |
| 70 | HCFNP60 | 209125 06/19/97 | pSport1 | 133 | 553 | 21 | 546 | 132 | 132 | 256 | 1 | 18 | 19 | 92 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion."

Finally, the amino acid position of SEQ ID NO:Y of the last amino acid in the open reading frame is identified as "Last AA of ORF."

SEQ ID NO:X and the translated SEQ ID NO:Y are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used to generate antibodies which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs. Species homologs may be isolated and identified by making suitable probes or primers from the sequences provided herein and screening a suitable nucleic acid source for the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, prosequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified by the one-step method described in Smith and Johnson, Gene 67:31–40 (1988). Polypeptides of the invention also can be purified from natural or recombinant sources using antibodies of the invention raised against the secreted protein in methods which are well known in the art.

Signal Sequences

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10: 1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., +or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. These polypeptides, and the polynucleotides encoding such polypeptides, are contemplated by the present invention.

Polynucleotide and Polypeptide Variants

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragement specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is becuase the FASTDB program does not account for 5' and 3' truncations of the subject sequence when calculating percent identity. For subject sequences truncated at the 5' or 3' ends, relative to the the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/ alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in Table 1 or to the amino acid sequence encoded by deposited DNA clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is becuase the FASTDB program does not account for N- and C-terminal truncations of the subject sequence when calculating global percent identity. For subject sequences truncated at the N- and C-termini, relative to the the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g. to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Polynucleotide and Polypeptide Fragments

In the present invention, a "polynucleotide fragment" refers to a short polynucleotide having a nucleic acid sequence contained in the deposited clone or shown in SEQ ID NO:X. The short nucleotide fragments are preferably at least about 15 nt, and more preferably at least about 20 nt, still more preferably at least about 30 nt, and even more preferably, at least about 40 nt in length. A fragment "at least 20 nt in length," for example, is intended to include 20 or more contiguous bases from the cDNA sequence contained in the deposited clone or the nucleotide sequence shown in SEQ ID NO:X. These nucleotide fragments are useful as diagnostic probes and primers as discussed herein. Of course, larger fragments (e.g. 50, 150, 500, 600, 2000 nucleotides) are preferred.

Moreover, representative examples of polynucleotide fragments of the invention, include, for example, fragments having a sequence from about nucleotide number 1–50, 51–100, 101–150, 151–200, 201–250, 251–300, 301–350, 351–400, 401–450, 451–500, 501–550, 551–600, 651–700, 701–7509 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In the present invention, a "polypeptide fragment" refers to a short amino acid sequence contained in SEQ ID NO:Y or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotide fragments encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotide fragments encoding these domains are also contemplated.

Other preferred fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

Epitopes & Antibodies

In the present invention, "epitopes" refer to polypeptide fragments having antigenic or immunogenic activity in an animal, especially in a human. A preferred embodiment of the present invention relates to a polypeptide fragment comprising an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., Proc. Natl. Acad. Sci. USA 81:3998–4002 (1983).)

Fragments which function as epitopes may be produced by any conventional means. (See, e.g. Houghten, R. A., Proc. Natl. Acad. Sci. USA 82:5131–5135 (1985) further described in U.S. Pat. No. 4,631,211.) In the present invention, antigenic epitopes preferably contain a sequence of at least seven, more preferably at least nine, and most preferably between about 15 to about 30 amino acids. Antigenic epitopes are useful to raise antibodies, including monoclonal antibodies, that specifically bind the epitope. (See, for instance, Wilson et al., Cell 37:767–778 (1984); Sutcliffe, J. G. et al., Science 219:660–666 (1983).) Similarly, immunogenic epitopes can be used to induce antibodies according to methods well known in the art. (See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g. in Western blotting.)

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24:316–325 (1983).) Thus, these fragments are preferred, as well as the products of a FAB or other immunoglobulin expression library. Moreover, antibodies of the present invention include chimeric, single chain, and humanized antibodies.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).) Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the A fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,0004,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

In addition to the foregoing, a polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g. hair or skin, or body fluids, e.g. blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides of the present invention can be used to treat disease. For example, patients can be administered a polypeptide of the present invention in an effort to replace absent or decreased levels of the polypeptide (e.g. insulin), to supplement absent or decreased levels of a different polypeptide (e.g. hemoglobin S for hemoglobin B), to inhibit the activity of a polypeptide (e.g. an oncogene), to activate the activity of a polypeptide (e.g. by binding to a receptor), to reduce the activity of a membrane bound receptor by competing with it for free ligand (e.g. soluble TNF receptors used in reducing inflammation), or to bring about a desired response (e.g. blood vessel growth).

Similarly, antibodies directed to a polypeptide of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides and polypeptides of the present invention can be used in assays to test for one or more biological activities. If these polynucleotides and polypeptides do exhibit activity in a particular assay, it is likely that these molecules may be involved in the diseases associated with the biological activity. Thus, the polynucleotides and polypeptides could be used to treat the associated disease.

Immune Activity

A polypeptide or polynucleotide of the present invention may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g. by chemotherapy or toxins), or infectious. Moreover, a polynucleotide or polypeptide of the present invention can be used as a marker or detector of a particular immune system disease or disorder.

A polynucleotide or polypeptide of the present invention may be useful in treating or detecting deficiencies or disorders of hematopoietic cells. A polypeptide or polynucleotide of the present invention could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polypeptide or polynucleotide of the present invention could also be used to modulate hemostatic (the stopping of bleeding) or thrombolytic activity (clot formation). For example, by increasing hemostatic or thrombolytic activity, a polynucleotide or polypeptide of the present invention could be used to treat blood coagulation disorders (e.g. afibrinogenemia, factor deficiencies), blood platelet disorders (e.g. thrombocytopenia), or wounds resulting from trauma, surgery, or other causes. Alternatively, a polynucleotide or polypeptide of the present invention that can decrease hemostatic or thrombolytic activity could be used to inhibit or dissolve clotting. These molecules could be important in the treatment of heart attacks (infarction), strokes, or scarring.

A polynucleotide or polypeptide of the present invention may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of a polypeptide or polynucleotide of the present invention that inhibits an immune response, particularly the proliferation, differentiation, or chemotaxis of T-cells, may be an effective therapy in preventing autoimmune disorders.

Examples of autoimmune disorders that can be treated or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated by a polypeptide or polynucleotide of the present invention. Moreover, these molecules can be used to treat anaphylaxis, hypersensitivity to an antigenic molecule, or blood group incompatibility.

A polynucleotide or polypeptide of the present invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polypeptide or polynucleotide of the present invention that inhibits an immune response, particularly the proliferation, differentiation, or chemotaxis of T-cells, may be an effective therapy in preventing organ rejection or GVHD.

Similarly, a polypeptide or polynucleotide of the present invention may also be used to modulate inflammation. For example, the polypeptide or polynucleotide may inhibit the proliferation and differentiation of cells involved in an inflammatory response. These molecules can be used to treat inflammatory conditions, both chronic and acute conditions, including inflammation associated with infection (e.g. septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g. TNF or IL-1.)

Hyperproliferative Disorders

A polypeptide or polynucleotide can be used to treat or detect hyperproliferative disorders, including neoplasms. A polypeptide or polynucleotide of the present invention may inhibit the proliferation of the disorder through direct or indirect interactions. Alternatively, a polypeptide or polynucleotide of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by a polynucleotide or polypeptide of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by a polynucleotide or polypeptide of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Infectious Disease

A polypeptide or polynucleotide of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, the polypeptide or polynucleotide of the present invention may also directly inhibit the infectious agent, without necessarily eliciting an immune response.

Viruses are one example of an infectious agent that can cause disease or symptoms that can be treated or detected by a polynucleotide or polypeptide of the present invention. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g. Paramyxoviridae, Morbillivirus, Rhabdoviridae), Orthomyxoviridae (e.g. Influenza), Papovaviridae, Parvoviridae, Picornaviridae, Poxviridae (such as Smallpox or Vaccinia), Reoviridae (e.g. Rotavirus), Retroviridae (HTLV-I, HTLV-II, Lentivirus), and Togaviridae (e.g. Rubivirus). Viruses falling within these families can cause a variety of diseases or symptoms, including, but not limited to: arthritis, bronchiollitis, encephalitis, eye infections (e.g. conjunctivitis, keratitis), chronic fatigue syndrome, hepatitis (A, B, C, E, Chronic Active, Delta), meningitis, opportunistic infections (e.g. AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g. Kaposi's, warts), and viremia. A polypeptide or polynucleotide of the present invention can be used to treat or detect any of these symptoms or diseases.

Similarly, bacterial or fungal agents that can cause disease or symptoms and that can be treated or detected by a polynucleotide or polypeptide of the present invention include, but not limited to, the following Gram-Negative and Gram-positive bacterial families and fungi: Actinomycetales (e.g. Corynebacterium, Mycobacterium, Norcardia), Aspergillosis, Bacillaceae (e.g. Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Kiebsiella, Salmonella, Serratia, Yersinia), Erysipelothrix, Helicobacter, Legionellosis, Leptospirosis, Listeria, Mycoplasmatales, Neisseriaceae (e.g. Acinetobacter, Gonorrhea, Menigococcal), Pasteurellacea Infections (e.g. Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g. AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g. cellulitis, dermatocycoses), toxemia, urinary tract infections, wound infections. A polypeptide or polynucleotide of the present invention can be used to treat or detect any of these symptoms or diseases.

Moreover, parasitic agents causing disease or symptoms that can be treated or detected by a polynucleotide or polypeptide of the present invention include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g. dysentery, giardiasis), liver disease, lung disease, opportunistic infections (e.g. AIDS related), Malaria, pregnancy complications, and toxoplasmosis. A polypeptide or polynucleotide of the present invention can be used to treat or detect any of these symptoms or diseases.

Preferably, treatment using a polypeptide or polynucleotide of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g. pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide of the present invention may increase regeneration of tissues difficult to heal. For example, increased tendon/ligament regeneration would quicken recovery time after damage. A polynucleotide or polypeptide of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide of the present invention to proliferate and differentiate nerve cells. Diseases that could be treated using this method include central and peripheral nervous system diseases, neuropathies, or mechanical and traumatic disorders (e.g. spinal cord disorders, head trauma, cerebrovascular disease, and stoke). Specifically, diseases associated with peripheral nerve injuries, peripheral neuropathy (e.g. resulting from chemotherapy or other medical therapies), localized neuropathies, and central nervous system diseases (e.g. Alzheimer's disease, Parkinson's disease, Huntington's disease, amyotrophic lateral sclerosis, and Shy-Drager syndrome), could all be treated using the polynucleotide or polypeptide of the present invention.

Chemotaxis

A polynucleotide or polypeptide of the present invention may have chemotaxis activity. A chemotaxic molecule attracts or mobilizes cells (e.g. monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that a polynucleotide or polypeptide of the present invention may inhibit chemotactic activity. These molecules could also be used to treat disorders. Thus, a polynucleotide or polypeptide of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g. receptors),or small molecules.

Preferably, the molecule is closely related to the natural ligand of the polypeptide, e.g. a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g. active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g. biological sample) using a monoclonal or polyclonal antibody. The antibody can measure polypeptide level or activity by either binding, directly or indirectly, to the polypeptide or by competing with the polypeptide for a substrate.

All of these above assays can be used as diagnostic or prognostic markers. The molecules discovered using these assays can be used to treat disease or to bring about a particular result in a patient (e.g. blood vessel growth) by activating or inhibiting the polypeptide/molecule. Moreover, the assays can discover agents which may inhibit or enhance the production of the polypeptide from suitably manipulated cells or tissues.

Therefore, the invention includes a method of identifying compounds which bind to a polypeptide of the invention comprising the steps of: (a) incubating a candidate binding compound with a polypeptide of the invention; and (b) determining if binding has occurred. Moreover, the invention includes a method of identifying agonists/antagonists comprising the steps of: (a) incubating a candidate compound with a polypeptide of the invention, (b) assaying a biological activity, and (b) determining if a biological activity of the polypeptide has been altered.

Other Activities

A polypeptide or polynucleotide of the present invention may also increase or decrease the differentiation or proliferation of embryonic stem cells, besides, as discussed above, hematopoietic lineage.

A polypeptide or polynucleotide of the present invention may also be used to modulate mammalian characteristics, such as body height, weight, hair color, eye color, skin, percentage of adipose tissue, pigmentation, size, and shape (e.g. cosmetic surgery). Similarly, a polypeptide or polynucleotide of the present invention may be used to modulate mammalian metabolism affecting catabolism, anabolism, processing, utilization, and storage of energy.

A polypeptide or polynucleotide of the present invention may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide or polynucleotide of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

EXAMPLE

Example 1

Isolation of a Selected cDNA Clone From the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128, 256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for Sacd and "K" is for KpnI which are the first sites on each respective end of the linker). "+" or "−" refer to the orientation of the f1 origin of replication ("ori"), such that in one orientation, single stranded rescue initiated from the f1 origin generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, N.Y.) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, a-each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g. Maniatis et al., Molecular Cloning: A Laboratory Manual, Cold Spring Harbor Press, Cold Spring, NY (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g. ampicillin) to a density of about 150 transformants (colonies) per plate. These plates are screened using Nylon membranes according to routine methods for bacterial colony screening (e.g. Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 $\mu$l of reaction mixture with 0.5 ug of the above cDNA template. A convenient reaction mixture is 1.5–5 mM $MgCl_2$, 0.01% (w/v) gelatin, 20 $\mu$M each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic PI library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHIII and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPFG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an E. coli origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g. Filtron), equilibrated with 40 mM sodium acetate, pH 6.0 is employed. The filtered sample is loaded onto a cation exchange resin (e.g. Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa califomica* nuclear polyhedrosis virus (AcMNPV) followed by convenient restriction sites such as BamnHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five jig of a plasmid containing the polynucleotide is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One μg of BaculoGold™ virus DNA and 5 μg of the plasmid are mixed in a sterile well of a microtiter plate containing 50 μg of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g. Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 RCi of $^{35}$S-methionine and 5 μRCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g. RSV, HTLVI, HIVI and the early promoter of the cytomegalovirus (CMV). However, cellular elements can also be used (e.g. the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g. Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10: 169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g. with the restriction enzyme cleavage sites BamHIII, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g. WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB 101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five µg of the expression plasmid pC6 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHIII site.

Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g. WO 96/34891.)

Human IgG Fc region:

GGGATCCGGAGCCCAAATCTTCTGA-CAAAACTCACACATGCCCACCGTGCC CAG-CACCTGAATTCGAGGGTGCACCGT-CAGTCTTCCTCTTCCCCCCAAAACC CAAGGACACCCTCATGATCTCCCG-GACTCCTGAGGTCACATGCGTGGTGGT GGACGTAAGCCACGAAGACCCTGAGGT-CAAGTTCAACTGGTACGTGGACG GCGTGGAG-GTGCATAATGCCAAGACAAAGCCGCGG-GAGGAGCAGTACAAC AGCACGTACCGTGTGGTCAGCGTCCT-CACCGTCCTGCACCAGGACTGGCTG AATG-GCAAGGAGTACAAGTGCAAGGTCTCCAA-CAAAGCCCTCCCAACCCCC ATCGAGAAAACCATCTCCAAAGC-CAAAGGGCAGCCCCGAGAACCACAGGT GTA-CACCCTGCCCCCATCCCGGGATGAGCT-GACCAAGAACCAGGTCAGCCT GACCTGCCTGGTCAAAGGCTTCTATC-CAAGCGACATCGCCGTGGAGTGGGA GAG-CAATGGGCAGCCGGAGAACAACTACAA-GACCACGCCTCCCGTGCTGG ACTCCGACGGCTCCTTCTTCCTCTACAG-CAAGCTCACCGTGGACAAGAGCA GGTG-GCAGCAGGGGAACGTCTTCTCATGCTC-CGTGATGCATGAGGCTCTGC ACAACCACTACACGCAGAAGAGCCTCTC-CCTGTCTCCGGGTAAATGAGTGC GACGGC-CGCGACTCTAGAGGAT (SEQ ID NO: 1)

Example 10

Production of an Antibody from a Polypeptide

The antibodies of the present invention can be prepared by a variety of methods. (See, Current Protocols, Chapter 2.) For example, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Patent No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production Of Secreted Protein For High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at 2×10$^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17–602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each wen. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using al2-channel pipetter with tips on every other channel, adds the 200 ul of DNA/Lipofectamine/Optimem I complex to the odd wells first, then to the even wells, to each row on the 24-well plates. Incubate at 37° C. for 6 hours.

While cells are incubating, prepare appropriate media, either 1%BSA in DMEM with 1×penstrep, or CHO-5 media (116.6 mg/L of CaCl2 (anhyd); 0.00130 mg/L CuSO$_4$-5H$_2$O; 0.050 mg/L of Fe(NO$_3$)$_3$-9H$_2$O; 0.417 mg/L of FeSO$_4$-7H$_2$O; 311.80 mg/L of Kcl; 28.64 mg/L of MgCl$_2$; 48.84 mg/L of MgSO$_4$; 6995.50 mg/L of NaCl; 2400.0 mg/L of NaHCO$_3$; 62.50 mg/L of NaH$_2$PO$_4$-H$_2$O; 71.02 mg/L of Na$_2$HPO4; 0.4320 mg/L of ZnSO$_4$-7H$_2$O; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L- Alanine; 147.50 mg/ml of L-Arginine-HCL; 7.50 mg/ml of L-Asparagine-H$_2$O; 6.65 mg/ml of L-Aspartic Acid; 29.56 mg/ml of L-Cystine-2HCL-H$_2$O; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-H$_2$0; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2H$_2$0; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin B$_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2mm glutamine and 1×penstrep. (BSA (81-068-3 Bayer) 100 gm dissolved in 1L DMEM for a 10% BSA stock solution). Filter the media and collect 50 ul for endotoxin assay in 15ml polystyrene conical.

The transfection reaction is terminated, preferably by tag-teaming, at the end of the incubation period. Person A aspirates off the transfection media, while person B adds 1.5ml appropriate media to each well. Incubate at 37° C. for 45 or 72 hours depending on the media used: 1%BSA for 45 hours or CHO-5 for 72 hours.

On day four, using a 300 ul multichannel pipetter, aliquot 600 ul in one 1 ml deep well plate and the remaining supernatant into a 2ml deep well. The supernatants from each well can then be used in the assays described in Examples 13–20.

It is specifically understood that when activity is obtained in any of the assays described below using a supernatant, the activity originates from either the polypeptide directly (e.g. as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proxial region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

|  | JAKs | | | | | GAS(elements) |
|---|---|---|---|---|---|---|
| Ligand | tyk2 | Jak1 | Jak2 | Jak3 | STATS | or ISRE |
| IFN family | | | | | | |
| IFN-a/B | + | + | − | − | 1,2,3 | ISRE |
| IFN-g |  | + | + | − | 1 | GAS (IRF1 > Lys6 > IFP) |
| Il-10 | + | ? | ? | − | 1,3 | |
| gp130 family | | | | | | |
| IL-6 (Pleiotrohic) | + | + | + | ? | 1,3 | GAS (IRF1 > Lys6 > IFP) |
| Il-11 (Pleiotrohic) | ? | + | ? | ? | 1,3 | |
| OnM (Pleiotrohic) | ? | + | + | ? | 1,3 | |
| LIF (Pleiotrohic) | ? | + | + | ? | 1,3 | |
| CNTF (Pleiotrohic) | −/+ | + | + | ? | 1,3 | |
| G-CSF (Pleiotrohic) | ? | + | ? | ? | 1,3 | |
| IL-12 (Pleiotrohic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS(B − CAS > IRF1 = IFP >> Ly6) |

|  | JAKs | | | | | GAS(elements) |
|---|---|---|---|---|---|---|
| Ligand | tyk2 | Jak1 | Jak2 | Jak3 | STATS | or ISRE |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:
5':GCGCCTCGAGATTTCCCCGAAATCTA-GATTTCCCCGAAATGATTTCCCCG AAATGATTTC-CCCGAAATATCTGCCATCTCAATTAG:3' (SEQ ID NO:3)

The downstream primer is complementary to the SV40 promoter and is flanked with a Hind m site: 5':GCG-GCAAGCTTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:
5':CTCGAGATTTCCCCGAAATCTAGATTC-CCCGAAATGATTCCCCGAAATG ATTTC-CCCGAAATATCTGCCATCTCAATTAGT-CAGCAACCATAGTCCCGCCC CTAACTCCGCCCATCCCGCCCCTAACTC-CGCCCAGTTCCGCCCATTCTCCGC CCCATGGCT-GACTAATTTTTTATGCAGAGGCCGAGGC-CGCCTCGGC CTCTGAGCTATTCCAGAAGTAGTGAG-GAGGCTTTTTrGGAGGCCTAGGCTTT TGCAAAAAGCTT:3' (SEQ ID NO:5)

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g. GAS/NF-KB/EGR, GAS/NF-KB, II-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13
High-Throughput Screening Assay for T-cell Activity.

The following protocol is used to assess T-cell activity by identifying factors, such as growth factors and cytokines, that may proliferate or differentiate T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMREE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mils of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells (107 per transfection), and resuspend in OPI-MEM to a final concentration of 107 cells/ml. Then add 1 ml of $1 \times 10^7$ cells in OPTI-MEM to T25 flask and incubate at 37° C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing a polypeptide as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100, 000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20° C. until SEAP assays are performed according to Example 17. The plates containing the remaining treated cells are placed at 40C and serve as a source of material for repeating the assay on a specific well if desired.

As a positive control, 100 Unit/ml interferon gamma can be used which is known to activate Jurkat T cells. Over 30 fold induction is typically observed in the positive control wells.

Example 14
High-Throughput Screening Assay Identifying Myeloid Activity

The following protocol is used to assess myeloid activity by identifying factors, such as growth factors and cytokines, that may proliferate or differentiate myeloid cells.

Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2 \times 10e^7$ U937 cells and wash with 10 PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37° C. for 45 min.

Wash the cells with RPMI 1640 medium containing 10% FBS and then resuspend in 10 ml complete medium and incubate at 37° C. for 36 hr.

The GAS-SEAPIU937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5 \times 10^5$ cells/ml. Plate 200 ul cells per well in the 96-well plate (or $1 \times 10^5$ cells/well).

Add 50 ul of the supernatant prepared by the protocol described in Example 11.

Incubate at 37° C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGRL is responsible for such induction. Using the EGR1 promoter linked to reporter molecules, activation of cells can be assessed.

Particularly, the following protocol is used to assess neuronal activity in PC12 cell lines. PC 12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGRL gene expression is activated during this treatment. Thus, by stably transfecting PC12 cells with a construct containing an EGR promoter linked to SEAP reporter, activation of PC 12 cells can be assessed.

The EGR/SEAP reporter construct can be assembled by the following protocol. The EGR-1 promoter sequence (-633 to +1)(Sakamoto K et al., Oncogene 6:867–871 (1991)) can be PCR amplified from human genomic DNA using the following primers:

5' GCGCTCGAGGGATGACAGCGATAGAACCCCGG-3' (SEQ ID NO:6)

5' GCGAAGCTTCGCGACTCCCCGGATCCGCCTC-3' (SEQ ID NO:7)

Using the GAS:SEAP/Neo vector produced in Example 12, EGRL amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCEENCES, Cat. #12449–78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5 \times 10^5$ cells/ml.

Add 200 ul of the cell suspension to each well of 96-well plate (equivalent to $1 \times 10^5$ cells/well). Add 50 ul supernatant produced by Example 11, 370C for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-cell Activity

NF-κB (Nuclear Factor κB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-κB regulates the expression of genes involved in immune cell activation, control of apoptosis (NF-κB appears to shield cells from apoptosis), B and T-cell development, anti-viral and antimicrobial responses, and multiple stress responses.

In non-stimulated conditions, NF-κB is retained in the cytoplasm with I-κB (Inhibitor KB). However, upon stimulation, I-κB is phosphorylated and degraded, causing NF-κB to shuttle to the nucleus, thereby activating transcription of target genes. Target genes activated by NF-κB include IL-2, IL-6, GM-CSF, ICAM-1 and class 1 MHC.

Due to its central role and ability to respond to a range of stimuli, reporter constructs utilizing the NF-κB promoter element are used to screen the supernatants produced in Example 11. Activators or inhibitors of NF-κB would be useful in treating diseases. For example, inhibitors of NF-κB could be used to treat those diseases related to the acute or chronic activation of NF-κB, such as rheumatoid arthritis.

To construct a vector containing the NF-κB promoter element, a PCR based strategy is employed. The upstream primer contains four tandem copies of the NF-κB binding site (GGGGACTTTCCC) (SEQ ID NO:8), 18 bp of sequence complementary to the 5' end of the SV40 early promoter sequence, and is flanked with an XhoI site:
5':GCGGCCTCGAGGGGACTTTCCCGGG-GACTTTCCGGGGACTTTCCGGGAC TTTCCATCCT-GCCATCTCAATTAG:3' (SEQ ID NO:9)

The downstream primer is complementary to the 3' end of the SV40 promoter and is flanked with a Hind III site:
5':GCGGCAAGCTTTnGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:
5':CTCGAGGGGACTTTCCCGGGGACTTTC-CGGGGACTTTCCGGGACTTTCC ATCTGCCATCT-CAATTAGTCAGCAACCATAGTCCCGC-CCCTAACTCCGCCCA
TCCCGCCCCTAACTCCGCCCAGTTCCGC-CCATTCTCCGCCCCATGGCTGACT AATTTTTATT- TATGCAGAGGCCGAGGCCGCCTCGGC-
CTCTGAGCTATTC
CAGAAGTAGTGAGGAGGCTTGGAGGC-
CTAGGCTTTTGCAAAAAGCTT: 3' (SEQ ID NO: 10)

Next, replace the SV40 minimal promoter element present in the pSEAP2-promoter plasmid (Clontech) with this NF-κB/SV40 fragment using XhoI and HindIII. However, this vector does not contain a neomycin resistance gene, and therefore, is not preferred for mammalian expression systems.

In order to generate stable mammalian cell lines, the NF-κB/SV40/SEAP cassette is removed from the above NF-κB/SEAP vector using restriction enzymes SalI and NotI, and inserted into a vector containing neomycin resistance. Particularly, the NF-KIB/SV40/SEAP cassette was inserted into pGFP-1 (Clontech), replacing the GFP gene, after restricting pGFP-1 with SalI and NotI.

Once NF-κB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1,1, 10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5×Dilution Buffer and dispense 15 μl of 2.5×dilution buffer into Optiplates containing 35 μl of a supernatant. Seal the plates with a plastic sealer and incubate at 65° C. for 30 min. Separate the Optiplates to avoid uneven heating.

Cool the samples to room temperature for 15 minutes. Empty the dispenser and prime with the Assay Buffer. Add 50 μl Assay Buffer and incubate at room temperature 5 min. Empty the dispenser and prime with the Reaction Buffer (see the table below). Add 50 μl Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |

Reaction Buffer Formulation:

| # of plates | Rxn buffer diluent (ml) | CSPD (ml) |
|---|---|---|
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small mocules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-3, used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-3 is made in 10% pluronic acid DMSO. To load the cells with fluo-3, 50 ul of 12 ug/ml fluo-3 is added to each well. The plate is incubated at 37° C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5\times10^6$ cells/ml with HBSS in a 50-ml conical tube. 4 ul of 1 mg/ml fluo-3 solution in 10% pluronic acid DMSO is added to each ml of cell suspension. The tube is then placed in a 37° C. water bath for 30–60 min. The cells are washed twice with HBSS, resuspended to $1\times10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-3. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca^{++}$ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g. src, yes, Ick, lyn, fyn) and non-receptor linked and cytosolic protein tyrosine kinases, such as the Jak family, members of which mediate signal transduction triggered by the cytokine superfamily of receptors (e.g. the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g. primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 40C. Cell growth on these plates is assayed by seeding 5,000 cells/well in growth medium and indirect quantitation of cell number through use of 3–5' alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest HI cell culture plates can also be used in some proliferation experiments.

To prepare extracts, A431 cells are seeded onto the nylon membranes of Loprodyne plates (20,000/200ml/well) and cultured overnight in complete medium. Cells are quiesced by incubation in serum-free basal medium for 24 hr. After 5–20 minutes treatment with EGF (60ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boehringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4° C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 nM ATP/50 mM $MgCl_2$), then 10 ul of 5×Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate(1 mM), and then 5 ul of water. Mix the components gently and preincubate the reaction mix at 30° C. for 2 min. Initial the reaction by adding 10 ul of the control enzyme or the filtered supernatant.

The tyrosine kinase assay reaction is then terminated by adding 10 ul of 120mm EDTA and place the reactions on ice.

Tyrosine kinase activity is determined by transferring 50 ul aliquot of reaction mixture to a microtiter plate (MTP) module and incubating at 37° C. for 20 min. This allows the streptavadin coated 96 well plate to associate with the biotinylated peptide. Wash the MTP module with 300 ul/well of PBS four times. Next add 75 ul of anti-phosphotyrosine antibody conjugated to horse radish peroxidase(anti-P-Tyr-POD(0.5 u/ml)) to each well and incubate at 37° C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (10 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4° C. until use.

A431 cells are seeded at 20,000/well in a 96-well Loprodyne filterplate and cultured overnight in growth medium. The cells are then starved for 48 hr in basal medium (DMEM) and then treated with EGF (6ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95° C. for 30 seconds; 60–120 seconds at 52–58° C.; and 60–120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton, T. A. and Graham, M. W., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

The secreted polypeptide is also suitably administered by sustained-release systems. Suitable examples of sustained-release compositions include semi-permeable polymer matrices in the form of shaped articles, e.g. films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g. polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g. 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 24

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g. Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confiming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated protein comprising amino acid residues 27 to 146 of SEQ ID NO:188.

2. The isolated protein of claim 1 which comprises amino acid residues 2 to 146 of SEQ ID NO:188.

3. The isolated protein of claim 1 which comprises amino acid residues 1 to 146 of SEQ ID NO:188.

4. The protein of claim 1 which comprises a heterologous polypeptide sequence.

5. A composition comprising the protein of claim 1 and a pharmaceutically acceptable carrier.

6. An isolated protein produced by the method comprising:

(a) expressing the protein of claim 1 by a cell; and (b) recovering said protein.

7. The isolated protein of claim 6, wherein said cell is isolated from recombinant cell culture.

8. The isolated protein of claim 6, wherein said cell is isolated from a biological sample.

9. An isolated protein comprising the amino acid sequence of the secreted portion of the polypeptide encoded by the HODAZ50 cDNA contained in ATCC Deposit No. 97903.

10. The isolated protein of claim 9 which comprises the amino acid sequence of the complete polypeptide encoded by the HODAZ50 cDNA contained in ATCC Deposit No. 97903, excepting the N-terminal methionine.

11. The isolated protein of claim 9 which comprises the amino acid sequence of the complete polypeptide encoded by the HODAZ50 cDNA contained in ATCC Deposit No. 97903.

12. The protein of claim 9 which comprises a heterologous polypeptide sequence.

13. A composition comprising the protein of claim 9 and a pharmaceutically acceptable carrier.

14. An isolated protein produced b the method comprising:
   (a) expressing the protein of claim 9 by a cell; and
   (b) recovering said protein.

15. The isolated protein of claim 14, wherein said cell is isolated from recombinant cell culture.

16. The isolated protein of claim 14, wherein said cell is isolated from a biological sample.

17. An isolated protein comprising a fragment of SEQ ID NO:188, wherein said fragment generates an antibody that specifically binds to a polypeptide having an amino acid sequence consisting of amino acid residues 27 to 146 of SEQ ID NO:188.

18. The isolated protein of claim 17, wherein said fragment comprises at least 30 contiguous amino acid residues of amino acid residues 27 to 146 of SEQ ID NO:188.

19. The isolated protein of claim 17, wherein said fragment comprises at least 50 contiguous amino acid residues of amino acid residues 27 to 146 of SEQ ID NO:188.

20. The protein of claim 17 which further comprises a heterologous polypeptide sequence.

21. A composition comprising the protein of claim 17 and a pharmaceutically acceptable carrier.

22. An isolated protein produced by the method comprising:
   (a) expressing the protein of claim 11 by a cell; and
   (b) recovering said protein.

23. The isolated protein of claim 22, wherein said cell is isolated from recombinant cell culture.

24. The isolated protein of claim 22, wherein said cell is isolated from a biological sample.

25. An isolated protein comprising a fragment of the secreted portion of the polypeptide encoded by the HODAZ50 cDNA contained in ATCC Deposit No. 97903, wherein said fragment generates an antibody that specifically binds to the secreted portion of the polypeptide encoded by the HODAZ50 cDNA contained in ATCC Deposit No. 97903.

26. The isolated protein of claim 25, wherein said fragment comprises at least 30 contiguous amino acid residues of the secreted portion of the polypeptide encoded by the HODAZ50 cDNA contained in ATCC Deposit No. 97903.

27. The isolated protein of claim 25, wherein said fragment comprises at least 50 contiguous amino acid residues of the secreted portion of the polypeptide encoded by the HODAZ50 cDNA contained in ATCC Deposit No. 97903.

28. The protein of claim 25, which further comprises a heterologous polypeptide sequence.

29. A composition comprising the protein of claim 25 and a pharmaceutically acceptable carrier.

30. An isolated protein produced by the method comprising:
   (a) expressing the protein of claim 25 by a cell; and
   (b) recovering said protein.

31. The isolated protein of claim 30, wherein said cell is isolated from recombinant cell culture.

32. The isolated protein of claim 30, wherein said cell is isolated from a biological sample.

33. An isolated protein comprising a fragment of SEQ ID NO:188, wherein said fragment generates an antibody that specifically binds to a polypeptide having an amino acid sequence consisting of amino acid residues 1 to 146 of SEQ ID NO:188.

34. The isolated protein of claim 33, wherein said fragment comprises at least 30 contiguous amino acid residues of amino acid residues 1 to 146 of SEQ ID NO:188.

35. The isolated protein of claim 33, wherein said fragment comprises at least 50 contiguous amino acid residues of amino acid residues 1 to 146 of SEQ ID NO:188.

36. The protein of claim 33 which further comprises a heterologous polypeptide sequence.

37. A composition comprising the protein of claim 33 and a pharmaceutically acceptable carrier.

38. An isolated protein produced by the method comprising:
   (a) expressing the protein of claim 33 by a cell; and
   (b) recovering said protein.

39. The isolated protein of claim 38, wherein said cell is isolated from recombinant cell culture.

40. The isolated protein of claim 38, wherein said cell is isolated from a biological sample.

41. An isolated protein comprising a fragment of the complete polypeptide encoded by the HODAZ50 cDNA contained in ATCC Deposit No. 97903, wherein said fragment generates an antibody that specifically binds to the complete polypeptide encoded by the HODAZ50 cDNA contained in ATCC Deposit No. 97903.

42. The isolated protein of claim 41, wherein said fragment comprises at least 30 contiguous amino acid residues of the complete polypeptide encoded by the HODAZ50 cDNA contained in ATCC Deposit No. 97903.

43. The isolated protein of claim 41, wherein said fragment comprises at least 50 contiguous amino acid residues of the complete polypeptide encoded by the HODAZ50 cDNA contained in ATCC Deposit No. 97903.

44. The protein of claim 41 which further comprises a heterologous polypeptide sequence.

45. A composition comprising the protein of claim 41 and pharmaceutically acceptable carrier.

46. An isolated protein produced by the method comprising:
   (a) expressing the protein of claim 41 by a cell; and
   (b) recovering said protein.

47. The isolated protein of claim 46, wherein said cell is isolated from recombinant cell culture.

48. The isolated protein of claim 46, wherein said cell is isolated from a biological sample.

* * * * *

UNITED STATES PATENT AND TRADEMARK OFFICE
CERTIFICATE OF CORRECTION

PATENT NO. : 6,590,075 B2
DATED : July 8, 2003
INVENTOR(S) : Rosen et al.

It is certified that error appears in the above-identified patent and that said Letters Patent is hereby corrected as shown below:

<u>Title page,</u>
Insert Item:
-- [63] Continuation-in-part of PCT/US98/04482, filed March 6, 1998. --.

<u>Column 451,</u>
Line 5, delete "protein produced b" and insert -- protein produced by; --.
Line 30, delete "expressing the protein of claim 11 by a cell; and" and insert
-- expressing the protein of claim 17 by a cell; and --.

Signed and Sealed this

Tenth Day of January, 2006

JON W. DUDAS
*Director of the United States Patent and Trademark Office*

SEQUENCE LISTING

<160> NUMBER OF SEQ ID NOS: 280

<210> SEQ ID NO 1
<211> LENGTH: 733
<212> TYPE: DNA
<213> ORGANISM: Homo sapiens

<400> SEQUENCE: 1

| | | | | | |
|---|---|---|---|---|---|
| gggatccgga | gcccaaatct | tctgacaaaa | ctcacacatg | cccaccgtgc | ccagcacctg | 60 |
| aattcgaggg | tgcaccgtca | gtcttcctct | tcccccaaa | acccaaggac | accctcatga | 120 |
| tctcccggac | tcctgaggtc | acatgcgtgg | tggtggacgt | aagccacgaa | gaccctgagg | 180 |
| tcaagttcaa | ctggtacgtg | gacggcgtgg | aggtgcataa | tgccaagaca | aagccgcggg | 240 |
| aggagcagta | caacagcacg | taccgtgtgg | tcagcgtcct | caccgtcctg | caccaggact | 300 |
| ggctgaatgg | caaggagtac | aagtgcaagg | tctccaacaa | agccctccca | acccccatcg | 360 |
| agaaaaccat | ctccaaagcc | aaagggcagc | cccgagaacc | acaggtgtac | accctgcccc | 420 |
| catcccggga | tgagctgacc | aagaaccagg | tcagcctgac | ctgcctggtc | aaaggcttct | 480 |
| atcccagcga | catcgccgtg | gagtgggaga | gcaatgggca | gccggagaac | aactacaaga | 540 |
| ccacgcctcc | cgtgctggac | tccgacggct | ccttcttcct | ctacagcaag | ctcaccgtgg | 600 |
| acaagagcag | gtggcagcag | gggaacgtct | tctcatgctc | cgtgatgcat | gaggctctgc | 660 |
| acaaccacta | cacgcagaag | agcctctccc | tgtctccggg | taaatgagtg | cgacggccgc | 720 |
| gactctagag | gat | | | | | 733 |

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally
      ocurring L-amino acids

<400> SEQUENCE: 2

Trp Ser Xaa Trp Ser
 1               5

<210> SEQ ID NO 3
<211> LENGTH: 86
<212> TYPE: DNA
<213> ORGANISM: Homo sapiens

<400> SEQUENCE: 3

| | | | | | |
|---|---|---|---|---|---|
| gcgcctcgag | atttccccga | aatctagatt | tccccgaaat | gatttccccg | aaatgatttc | 60 |
| cccgaaatat | ctgccatctc | aattag | | | | 86 |

<210> SEQ ID NO 4
<211> LENGTH: 27
<212> TYPE: DNA
<213> ORGANISM: Homo sapiens

<400> SEQUENCE: 4
gcggcaagct ttttgcaaag cctaggc          27

<210> SEQ ID NO 5
<211> LENGTH: 271

-continued

<212> TYPE: DNA
<213> ORGANISM: Homo sapiens

<400> SEQUENCE: 5

```
ctcgagattt ccccgaaatc tagatttccc cgaaatgatt tccccgaaat gatttccccg      60
aaatatctgc catctcaatt agtcagcaac catagtcccg ccctaactc cgcccatccc     120
gcccctaact ccgcccagtt ccgcccattc tccgccccat ggctgactaa tttttttat     180
ttatgcagag gccgaggccg cctcggcctc tgagctattc cagaagtagt gaggaggctt     240
ttttggaggc ctaggctttt gcaaaaagct t                                   271
```

<210> SEQ ID NO 6
<211> LENGTH: 32
<212> TYPE: DNA
<213> ORGANISM: Homo sapiens

<400> SEQUENCE: 6

```
gcgctcgagg gatgacagcg atagaaccccc gg                                  32
```

<210> SEQ ID NO 7
<211> LENGTH: 31
<212> TYPE: DNA
<213> ORGANISM: Homo sapiens

<400> SEQUENCE: 7

```
gcgaagcttc gcgactcccc ggatccgcct c                                    31
```

<210> SEQ ID NO 8
<211> LENGTH: 12
<212> TYPE: DNA
<213> ORGANISM: Homo sapiens

<400> SEQUENCE: 8

```
ggggactttc cc                                                         12
```

<210> SEQ ID NO 9
<211> LENGTH: 73
<212> TYPE: DNA
<213> ORGANISM: Homo sapiens

<400> SEQUENCE: 9

```
gcggcctcga ggggactttc ccggggactt tccggggact ttccgggact ttccatcctg      60
ccatctcaat tag                                                        73
```

<210> SEQ ID NO 10
<211> LENGTH: 256
<212> TYPE: DNA
<213> ORGANISM: Homo sapiens

<400> SEQUENCE: 10

```
ctcgagggga ctttcccggg gactttccgg ggactttccg ggactttcca tctgccatct      60
caattagtca gcaaccatag tcccgcccct aactccgccc atcccgcccc taactccgcc     120
cagttccgcc cattctccgc ccatggctg actaattttt tttatttatg cagaggccga     180
ggccgcctcg gcctctgagc tattccagaa gtagtgagga ggcttttttg gaggcctagg     240
cttttgcaaa aagctt                                                    256
```

<210> SEQ ID NO 11
<211> LENGTH: 1739
<212> TYPE: DNA

<213> ORGANISM: Homo sapiens
<220> FEATURE:
<221> NAME/KEY: SITE
<222> LOCATION: (772)
<223> OTHER INFORMATION: n equals a,t,g, or c
<220> FEATURE:
<221> NAME/KEY: SITE
<222> LOCATION: (1716)
<223> OTHER INFORMATION: n equals a,t,g, or c
<220> FEATURE:
<221> NAME/KEY: SITE
<222> LOCATION: (1731)
<223> OTHER INFORMATION: n equals a,t,g, or c

<400> SEQUENCE: 11

```
gcgctcccga ggccgcggga cctgcagaga ggacagccgg cctgcgccgg gacatgcggc      60
cccaggagct ccccaggctc gcgttcccgt tgctgctgtt gctgttgctg ctgctgccgc     120
cgccgccgtg ccctgcccac agcgccacgc gtttcgaccc cacctgggag tccctggacg     180
cccgccagct gcccgcgtgg tttgaccagg ccaagttcgg catcttcatc cactggggag     240
tgttttccgt gccagcttc ggtagcgagt ggttctggtg gtattggcaa aaggaaaaga     300
taccgaagta tgtggaattt atgaaagata attaccctcc tartttcaaa tatgaagatt     360
ttggaccact atttacagca aaatttttta atgccaacca rtgggcarat attttycagg     420
cctctggtgc caaatacatt gtcttaactt ccaaacatca tgaaggcttt accttgtggg     480
ggtcagaata ttcgtggaac tggaatgcca tagatgaggg gcccaagagg gacattgtca     540
aggaacttga ggtagccatt aggaacagaa ctgacctgcg ttttggactg tactattccc     600
tttttgaatg gtttcatccg ctcttccttg aggatgaatc cagttcattc cataagcggc     660
aatttccagt ttctaagaca ttgccagagc tctatgagtt agtgaacaac tatcagcctg     720
aggttctgtg gtcggatggt gacggaggag caccggatca atactggaac ancacaggct     780
tcttggcctg gttatataat gaaagcccag ttcgggcac agtagtcacc aatgatcgtt     840
ggggagctgg tagcatctgt aagcatggtg gcttctatac ctgcagtgat cgttataacc     900
caggacatct tttgccacat aaatgggaaa actgcatgac aatagacaaa ctgtcctggg     960
gctataggag ggaagctgga atctctgact atcttacaat tgaagaattg gtgaagcaac    1020
ttgtagagac agtttcatgt ggaggaaatc ttttgatgaa tattgggccc acactagatg    1080
gcaccatttc tgtagttttt gaggagcgac tgaggcaaat ggggtcctgg ctaaaagtca    1140
atggagaagc tatttatgaa acccataccat ggcgatccca gaatgacact gtcaccccag    1200
atgtgtggta cacatccaag cctaaagaaa aattagtcta tgccattttt cttaaatggc    1260
ccacatcagg acagctgttc cttggccatc ccaaagctat tctgggggca acagaggtga    1320
aactactggg ccatggacag ccacttaact ggatttcttt ggagcaaaat ggcattatgg    1380
tagaactgcc acagctaacc attcatcaga tgccgtgtaa atggggctgg gctctagccc    1440
tractaatgt gatctaaagt gcagcagagt ggctgatgct gcaagttatg tctaaggcta    1500
ggaactatca ggtgtctata attgtagcac atggagaaag caaatgtaaa actggataag    1560
aaaattattt tggcagttca gcccttttccc ttttttcccac taaatttttt cttaaattac    1620
ccatgtaacc attttaactc tccagtgcac tttgccatta agtctcttc acattgaaaa    1680
aaaaaaaaaa aaaacccccg ggggggggc ccgggnaccc catttcgccc ntaaagggg     1739
```

<210> SEQ ID NO 12
<211> LENGTH: 844
<212> TYPE: DNA
<213> ORGANISM: Homo sapiens

<400> SEQUENCE: 12

```
ggcccctggg cccgaggggc tggagccggg ccggggcgat gtggagcgcg ggccgcggcg      60
gggctgcctg gccggtgctg ttggggctgc tgctggcgct gttagtgccg ggcggtggtg     120
ccgccaagac cggtgcggag ctcgtgacct gcgggtcggt gctgaagctg ctcaatacgc     180
accaccgcgt gcggctgcac tcgcacgaca tcaaatacgg atccggcagc ggccagcaat     240
cggtgaccgg cgtagaggcg tcggacgacg ccaatagcta ctggcggatc cgcggcggct     300
cggagggcgg gtgccgccgc gggtccccgg tgcgctgcgg gcaggcggtg aggctcacgc     360
atgtgcttac gggcaagaac ctgcacacgc accacttccc gtcgccgctg tccaacaacc     420
aggaggtgag tgcctttggg gaagacggcg agggcgacga cctggaccta tggacagtgc     480
gctgctctgg acagcactgg gagcgtgagg ctgctgtgcg cttccagcat gtgggcacct     540
ctgtgttcct gtcagtcacg ggtgagcagt atggaagccc catccgtggg cagcatgagg     600
tccacggcat gcccagtgcc aacacgcaca atacgtggaa ggccatggaa ggcatcttca     660
tcaagcctag tgtggagccc tctgcaggtc acgatgaact ctgagtgtgt ggatggatgg     720
gtggatggag ggtggcaggt ggggcgtctg cagggccact cttggcagag actttgggtt     780
tgtaggggtc ctcaagtgcc tttgtgatta agaatgttg gtctatgaaa aaaaaaaaa     840
aaaa                                                                 844
```

<210> SEQ ID NO 13
<211> LENGTH: 776
<212> TYPE: DNA
<213> ORGANISM: Homo sapiens

<400> SEQUENCE: 13

```
ttcgaaataa aagatctgct caagagagcc gcagaaaaag aaggtgtatg ttgggggttt      60
agagagcagg gtcttgaaat acacagccca gaatatggag cttcagaaca agtacagct     120
tctggaggaa cagaatttgt cccttctaga tcaactgagg aaactccagg ccatggtgat     180
tgagatatca aacaaaacca gcagcagcag cacctgcatc ttggtcctac tagtctcctt     240
ctgcctcctc cttgtacctg ctatgtactc ctctgacaca agggggagcc tgccagctga     300
gcatggagtg ttgtcccgcc agcttcgtgc cctccccagt gaggacccctt accagctgga     360
gctgcctgcc ctgcagtcag aagtgccgaa agacagcaca caccagtggt tggacggctc     420
agactgtgta ctccaggccc ctggcaacac ttcctgcctg ctgcattaca tgcctcaggc     480
tcccagtgca gagcctcccc tggagtggcc attccctgac ctcttctcag agcctctctg     540
ccgaggtccc atcctccccc tgcaggcaaa tctcacaagg aagggaggat ggcttcctac     600
tggtagccc tctgtcattt tgcaggacag atactcaggc tagatatgag gatatgtggg     660
gggtctcagc aggagcctgg ggggctcccc atctgtgtcc aaataaaaag cggtgggcaa     720
gggctggccg cagctcctgt gccctgtcag gacgactgag ggctcaaaca caccac        776
```

<210> SEQ ID NO 14
<211> LENGTH: 1376
<212> TYPE: DNA
<213> ORGANISM: Homo sapiens
<220> FEATURE:
<221> NAME/KEY: SITE
<222> LOCATION: (1070)
<223> OTHER INFORMATION: n equals a,t,g, or c

<400> SEQUENCE: 14

-continued

```
gaattcggca cgaggcgcct accctgcctg caggtgagca gtggtgtgtg agagccaggc      60
gtccctctgc ctgcccactc agtggcaaca cccgggagct gttttgtcct tgtggagcc      120 tcagcagttc cctctttcag aactcactgc aagagccc gaacaggagc caccatgcag       180
tgcttcagct tcattaagac catgatgatc ctcttcaatt tgctcatctt tctgtgtggt     240
gcagccctgt tggcagtggg catctgggtg tcaatcgatg gggcatcctt tctgaagatc     300
ttcgggccac tgtcgtccag tgccatgcag tttgtcaacg tgggctactt cctcatcgca     360
gccggcgttg tggtctttgc tcttggtttc ctgggctgct atggtgctaa gactgagagc     420
aagtgtgccc tcgtgacgtt cttcttcatc ctcctcctca tcttcattgc tgaggttgca     480
gctgctgtgg tcgccttggt gtacaccaca atggctgagc acttcctgac gttgctggta     540
gtgcctgcca tcaagaaaga ttatggttcc caggaagact tcactcaagt gtggaacacc     600
accatgaaag ggctcaagtg ctgtggcttc accaactata cggattttga ggactcaccc     660
tacttcaaag agaacagtgc ctttccccca ttctgttgca atgacaacgt caccaacaca     720
gccaatgaaa cctgcaccaa gcaaaaggct cacgaccaaa agtagaggg ttgcttcaat      780 cagcttttgt atgacatccg aactaatgca gtcaccgtgg gtggtgtggc agctggaatt     840 ggggggcctcg agctggctgc catgattgtg tccatgtatc tgtactgcaa tctacaataa   900
gtccacttct gcctctgcca ctactgctgc acatggaac ctgtgaagag gcaccctggc      960
aagcagcagt gattgggga ggggacagga tctaacaatg tcacttggc cagaatggac     1020 ctgcccttc tgctccagac ttggggctag atagggacca ctccttttan gcgatgcctg    1080
actttccttc cattggtggg tggatgggtg ggggcattc cagagcctct aaggtagcca    1140
gttctgttgc ccattccccc agtctattaa acccttgata tgcccctag gcctagtggt    1200 gatcccagtg ctctactggg ggatgagaga aaggcatttt atagcctggg cataagtgaa   1260
atcagcagag cctctgggtg gatgtgtaga aggcacttca aaatgcataa acctgttaca   1320
atgtttaaaa aaaaaaaaa aaaaaaaaa aaaaaaytcg agggggtcc cgtacc          1376
```

<210> SEQ ID NO 15
<211> LENGTH: 502
<212> TYPE: DNA
<213> ORGANISM: Homo sapiens
<220> FEATURE:
<221> NAME/KEY: SITE
<222> LOCATION: (269)
<223> OTHER INFORMATION: n equals a,t,g, or c

<400> SEQUENCE: 15

```
taaaacagtg cctgcctcaa agggaggact cagtcaatat ctgttgaatg aatgaatgaa      60
taattgcctg ggtcaacgaa tgaatggctg aatgaatgat ttctcctttc cctcggcact     120
gtctggagtc cccaggacag gcatgggcag cagtcgctgg tctgtggcct gtcccactgg     180
acttggggtt ctcatgcttg gtctgggcgg agatcaccca ccaggctccc aggtcgatcc     240
tctgctcatg gaarctgcg tccggcccna gctgccagaa ctcactgcas ggtgaggga      300 ararcaggra cgatctgcga gcgcctgaac agcgcacaag agccgaggag ccgctgctta    360
aaatgcaggc gttgagagga gtttcgcctc ctttttttgag ttgaatatga gatttccgag   420
cagccatgac gagttgggtt ggtggaagtg gggagtccgt tcctcagtca gatggaggag    480 ggggtccccct tggatctcct ct                                            502
```

<210> SEQ ID NO 16
<211> LENGTH: 425

```
<212> TYPE: DNA
<213> ORGANISM: Homo sapiens

<400> SEQUENCE: 16
atctctagtg gtggctgccg tcgctccaga caatcggaat cctgccttca ccaccatggg      60 ctggctttt  ctaaaggttt tgttggcggg agtgagtttc tcaggatttc tttatcctct     120
tgtggatttt tgcatcagtg ggaaaacaag aggacagaag ccaaactttg tgattatttt     180
ggccgatgac atgggtggg  gtgactgggg agcaaactgg gcagaaacaa aggacactgc     240
caaccttgat aagatggctt cggagggaat gargtgartc ttgaratgcc argccagctt     300
tctttggawg tcttactccc gttcttgaaa agggaaaggg gcgtgcaaag cacttaarga     360
wtcatkgatg gacccatgtg atttarttaa tttattaatt aatttggttt ggaarccagc     420
atagc                                                                  425

<210> SEQ ID NO 17
<211> LENGTH: 1316
<212> TYPE: DNA
<213> ORGANISM: Homo sapiens

<400> SEQUENCE: 17
ggcacgagga gctgggggag cctgaggtgc gctacgtggc tggcatgcat gggaacgagg      60
ccctggggcg ggagttgctt ctgctcctga tgcagttcct gtgccatgag ttcctgcgag     120
ggaacccacg ggtgacccgg ctgctctctg agatgcgcat tcacctgctg ccctccatga     180
accctgatgg ctatgagatc gcctaccacc ggggttcaga gctggtgggc tgggccgagg     240
gccgctggaa caaccagagc atcgatctta accataattt tgctgacctc aacacaccac     300
tgtgggaagc acaggacgat gggaaggtgc cccacatcgt ccccaaccat cacctgccat     360 tgccccactta ctacccctg cccaatgcca ccgtggctcc tgaaacgcgg gcagtaatca     420
agtggatgaa gcggatcccc tttgtgctaa gtgccaacct ccacggggggt gagctcgtgg     480 tgtcctaccc attcgacatg actcgcaccc cgtgggctgc ccgcgagctc acgcccacac     540
cagatgatgc tgtgtttcgc tggctcagca ctgtctatgc tggcagtaat ctggccatgc     600
aggacaccag ccgccgaccc tgccacagcc aggacttctc cgtgcacggc aacatcatca     660
acggggctga ctggcacacg gtccccggga gcatgaatga cttcagctac ctacacacca     720
actgctttga ggtcactgtg gagctgtcct gtgacaagtt ccctcacgag aatgaattgc     780
cccaggagtg ggagaacaac aaagacgccc tcctcaccta cctggagcag gtgcgcatgg     840
gcattgcagg agtggtgagg acaaggaca  cggagcttgg gattgctgac gctgtcattg     900
ccgtggatgg gattaaccat gacgtgacca cggcgtgggg cggggattat tggcgtctgc     960 tgacccagg  ggactacatg gtgactgcca gtgccgaggg ctaccattca gtgacacgga    1020
actgtcgggt caccttgaa gagggccct tcccctgcaa tttcgtgctc accaagactc    1080
ccaaacagag gctgcgcgag ctgctggcag ctggggccaa ggtgccccg  gaccttcgca    1140 ggcgcctgga gcggctaagg ggacagaagg attgatacct gcggtttaag agccctaggg    1200
caggctggac ctgtcaagac gggaagggga agagtagaga gggagggaca aagtgaggaa    1260
aaggtgctca ttaaagctac cgggcacctt aaaaaaaaaa aaaaaaaaaa aaaaaa       1316

<210> SEQ ID NO 18
<211> LENGTH: 436
<212> TYPE: DNA
<213> ORGANISM: Homo sapiens
```

<400> SEQUENCE: 18

| aaaaaaattc aatggatatt atgaaaataa gagagtattt ccagaagtat ggatatagtc | 60 |
| cacgtgtcaa gaaaaattca gtacacgagc aagaagccat taactctgac ccagagttgt | 120 |
| ctaattgtga aaattttcag aagactgatg tgaaagatga tctgtctgat cctcctgttg | 180 |
| caagcagttg tatttctgag aagtctccac gtagtccaca actttcagat tttggacttg | 240 |
| agcggtacat cgtatcccaa gttctaccaa accctccaca ggcagtgaac aactataagg | 300 |
| aagagcccgt aattgtaacc ccacctacca acaatcact agtaaaagta ctaaaaactc | 360 |
| caaaatgtgc actaaaatgg atgattttga gtgtgtactc ctaaattaga cactttggt | 420 |
| atctctgaat atacta | 436 |

<210> SEQ ID NO 19
<211> LENGTH: 503
<212> TYPE: DNA
<213> ORGANISM: Homo sapiens
<220> FEATURE:
<221> NAME/KEY: SITE
<222> LOCATION: (441)
<223> OTHER INFORMATION: n equals a,t,g, or c
<220> FEATURE:
<221> NAME/KEY: SITE
<222> LOCATION: (450)
<223> OTHER INFORMATION: n equals a,t,g, or c
<220> FEATURE:
<221> NAME/KEY: SITE
<222> LOCATION: (461)
<223> OTHER INFORMATION: n equals a,t,g, or c
<220> FEATURE:
<221> NAME/KEY: SITE
<222> LOCATION: (463)
<223> OTHER INFORMATION: n equals a,t,g, or c

<400> SEQUENCE: 19

| tgtgcatatc ctggggaaaa aaatggtaca tgttttagaa attttactgt ttataacaat | 60 |
| gcaggcagtc agtttcccgt ttcaaacaca gatagataca tgcaacactc aagatcctgc | 120 |
| agagaggcag ccagcatcta ttgtttaaaa aggtttcaaa aagaattcgg attgctcktt | 180 |
| tctcttttga atctgtgtgc caaatgacag ggaccaatat tcgtcttctt tttckgtaaa | 240 |
| aytcagaaag amacatgaaa gaaccccagaa tgcatttctt aaagggattt agtgcagtta | 300 |
| ttttaaataa tttatgcacg cacacacaca tacatatatc ccccgagtac atattttttc | 360 |
| cctttttact tgtgtgcaat cagtagctac aatgactgaa atccacttct ttgggactgt | 420 |
| gacatttaag caaatcttgt ntctagaaan cgaaatgcca nantctcgca caaagctgct | 480 |
| ccgtctgggg caacaaatcc aca | 503 |

<210> SEQ ID NO 20
<211> LENGTH: 358
<212> TYPE: DNA
<213> ORGANISM: Homo sapiens
<220> FEATURE:
<221> NAME/KEY: SITE
<222> LOCATION: (358)
<223> OTHER INFORMATION: n equals a,t,g, or c

<400> SEQUENCE: 20

| gggctgtctc cccagtagta acttgctggc cctgcccttg aagtggggaa actgtgaagg | 60 |
| gctccttgat caagcttgtc ctcttttctt acctcttcct ctcttctgtt tccgctgcag | 120 |
| ctgaacaggc cagcaggcaa cctgccatgg ggtcctgctc caagaaccgg tccttcttct | 180 |
| ggatgactgg gctcctggta ttcatcagcc tcctcctcag tgagtggcag ggtccctggg | 240 |

| aagggagggc aattggagag ggctgggcta gctgggctct gaccaacggg tgggctgttc | 300 |
| aacttctgat gtctttgggc aacaacacag aaaaacactc tgttatgatt tacgaaan | 358 |

<210> SEQ ID NO 21
<211> LENGTH: 1926
<212> TYPE: DNA
<213> ORGANISM: Homo sapiens
<220> FEATURE:
<221> NAME/KEY: SITE
<222> LOCATION: (54)
<223> OTHER INFORMATION: n equals a,t,g, or c
<220> FEATURE:
<221> NAME/KEY: SITE
<222> LOCATION: (1689)
<223> OTHER INFORMATION: n equals a,t,g, or c

<400> SEQUENCE: 21

| agtgaaggga gctggccgtg cgactgggct tcgggccctg tgccagagga gcangccttc | 60 |
| ctgagcagga ggaagcaggt ggtggccgcg gccttgaggc aggccctgca gctggatgga | 120 |
| gacctgcagg aggatgagat cccagtggta gctattatgg ccactggtgg tgggatccgg | 180 |
| gcaatgactt ccctgtatgg gcagctggct ggcctgaagg agctgggcct cttggattgc | 240 |
| ktctcctaca tcaccggggc ctcgggctcc acctgggcct tggccaacct ttataaggac | 300 |
| ccagagtggt ctcagaagga cctggcaggg cccactgagt tgctgaagac ccaggtgacc | 360 |
| aagaacaagc tgggtgtgct ggcccccagc cagctgcagc ggtaccggca ggagctggcc | 420 |
| gagcgtgccc gcttgggcta cccaagctgc ttcaccaacc tgtgggccct catcaacgag | 480 |
| gcgctgctgc atgatgagcc ccatgatcac aagctctcag atcaacggga ggccctgagt | 540 |
| catggccaga accctctgcc catctactgt gccctcaaca ccaaagggca gagcctgacc | 600 |
| acttttgaat tgggggagtg gtgcgagttc tctccctacg aggtcggctt ccccaagtac | 660 |
| ggggccttca tccctctga gctctttggc tccgagttct ttatggggca gctgatgaag | 720 |
| aggcttcctg agtcccgcat ctgcttctta gaaggtatct ggagcaacct gtatgcagcc | 780 |
| aacctccagg acagcttata ctgggcctca gagcccagcc agttctggga ccgctgggtc | 840 |
| aggaaccagg ccaacctgga caaggagcag gtccccctc tgaagataga agaaccaccc | 900 |
| tcaacagccg gcagaatagc tgagttttc accgatcttc tgacgtggcg tccactggcc | 960 |
| caggccacac ataatttcct gcgtggcctc catttccaca agactactt tcagcatcct | 1020 |
| cacttctcca catggaaagc taccactctg gatgggctcc ccaaccagct gacaccctcg | 1080 |
| gagccccacc tgtgcctgct ggatgttggc tacctcatca ataccagctg cctgccctc | 1140 |
| ctgcagccca ctcgggacgt ggacctcatc ctgtcattgg actacaacct ccacggagcc | 1200 |
| ttccagcagt tgcagctcct gggccggttc tgccaggagc aggggatccc gttcccaccc | 1260 |
| atctcgccca gccccgaaga gcagctccag cctcgggagt gccacacctt ctccgacccc | 1320 |
| acctgccccg gagcccctgc ggtgctgcac tttcctctgg tcagcgactc cttccgggag | 1380 |
| tactcggccc tggggtccg gcggacaccc gaggaggcgg cagctgggga ggtgaacctg | 1440 |
| tcttcatcgg actctcccta ccactacacg aaggtgacct acagccagga ggacgtggac | 1500 |
| aagctgctgc acctgacaca ttacaatgtc tgcaacaacc aggagcagct gctggaggct | 1560 |
| ctgcgccagg cagtgcagcg gaggcggcag cgcaggcccc actgatggcc ggggcccctg | 1620 |
| ccacccctaa ctctcattca ttccctggct gctgagttgc aggtgggaac tgtcatcacg | 1680 |
| cagtgcttnc agagcctcgg gctcaggtgg cactgtccca gggtccaggc tgagggctgg | 1740 |

-continued

| | |
|---|---|
| gagctccctt gcgcctcagc agtttgcagt ggggtaagga ggccaagccc atttgtgtaa | 1800 |
| tcacccaaaa ccccccggcc tgtgcctgtt ttcccttctg cgctaccttg agtagttgga | 1860 |
| gcacttgata catcacagac tcatacaaat gtgaggcgct gagaaaaaaa aaaaaaaaaa | 1920 |
| actcga | 1926 |

<210> SEQ ID NO 22
<211> LENGTH: 1224
<212> TYPE: DNA
<213> ORGANISM: Homo sapiens

<400> SEQUENCE: 22

| | |
|---|---|
| ccgccgaagc tccgtcccgc ccgcggccgg ctccgcctca cctcccggcc gcggctgccc | 60 |
| tctgcccggg ttgtccaaga tggagggcgc tccaccgggg tcgctcgccc tccggctcct | 120 |
| gctgttcgtg gcgctacccg cctccggctg gctgacgacg ggcgccccg agccgccgcc | 180 |
| gctgtccgga gccccacagg acggcatcag aattaatgta actacactga aagatgatgg | 240 |
| ggacatatct aaacagcagg ttgttcttaa cataacctat gagagtggac aggtgtatgt | 300 |
| aaatgactta cctgtaaata gtggtgtaac ccgaataagc tgtcagactt tgatagtgaa | 360 |
| gaatgaaaat cttgaaaatt tggaggaaaa agaatatttt ggaattgtca gtgtaaggat | 420 |
| tttagttcat gagtggccta tgacatctgg ttccagtttg caactaattg tcattcaaga | 480 |
| agaggtagta gagattgatg gaaaacaagt tcagcaaaag gatgtcactg aaattgatat | 540 |
| tttagttaag aaccggggag tactcagaca ttcaaactat ccctcccctt tggaagaaag | 600 |
| catgctctac tctatttctc gagacagtga cattttattt acccttccta acctctccaa | 660 |
| aaaagaaagt gttagttcac tgcaaaccac tagccagtat cttatcagga atgtggaaac | 720 |
| cactgtagat gaagatgttt tacctgggca agttacctga aactcctctc agagcagagc | 780 |
| cgccatcttc atataaggta atgtgtcagt ggatggaaaa gtttagaaaa gatctgtgta | 840 |
| ggttctggag caacgttttc ccagtattct ttcagttttt gaacatcatg gtggttggaa | 900 |
| ttacaggagc agctgtggta ataaccatct taaaggtgtt tttcccagtt ctgaataca | 960 |
| aaggaattct tcagttggat aaagtggacg tcatacctgt gacagctatc aacttatatc | 1020 |
| cagatggtcc agagaaaaga gctgaaaacc ttgaagataa aacatgtatt taaaacgcca | 1080 |
| tctcatatca tggactccga agtagcctgt tgcctccaaa tttgccactt gaatataatt | 1140 |
| ttctttaaat cgttaagaat cagtttatac actagagaaa ttgctaaact ctaagactgc | 1200 |
| ctgaaaattg acctttacag tgcc | 1224 |

<210> SEQ ID NO 23
<211> LENGTH: 694
<212> TYPE: DNA
<213> ORGANISM: Homo sapiens
<220> FEATURE:
<221> NAME/KEY: SITE
<222> LOCATION: (577)
<223> OTHER INFORMATION: n equals a,t,g, or c

<400> SEQUENCE: 23

| | |
|---|---|
| ggcacgagtc ttattgtgca ctgtagcctg aatcccccag ggtaattaat atgaagtgca | 60 |
| aaaagttgaa tgttccagtc taaaaggcag tgggagaaat tacatagcat ggaaataata | 120 |
| aaatgaactc ttattaatga gaacgaggct cttgcagtgg caagttctgc tggtcacccg | 180 |
| atggggatgg gagcctttca agcttttttt tgggtaatac tcacagtttc caacgtctgt | 240 |
| gtacttttca aaatgagctt gttcttcctt ctgacactca tctcaaagct ccatggtgac | 300 |

```
gcagaggtct gttgaaggtc acaggtcctc gcttgcattg catacggtc  ctgtagcatc      360 acttgttagc ccactgctgc ttgaaggaac taagagtatt cagggataga gagctgaaaa      420
taggattaat tccttccttt tgactctccc ctcaagatgt ccttgctttg gtctgaaaac      480
ctctcctgac aacttttgcc caaagcaaac catctgcctt ttctgaactc tgagtgaata      540
tattagcatc ttcccttctg agccctcgta ctgccangtt tgtttgtttg tttgtttcca      600
agagactgtg tcttgctctg tcacccagga gtttgaaacc agcctggcaa catagcaaga      660
ccctatctct acaaaaaaaa aaaaaaaaaa aaaa                                  694

<210> SEQ ID NO 24
<211> LENGTH: 796
<212> TYPE: DNA
<213> ORGANISM: Homo sapiens

<400> SEQUENCE: 24
atgagcggcg gttggatggc gcaggttgga gcgtggcgaa caggggctct gggcctggcg      60
ctgctgctgc tgctcggcct cggactaggc ctggaggcgc cgcgagcccg ctttccaccc      120
cgacctctgc ccaggccgca cccgagctca ggctcgtgcc cacccaccaa gttccagtgc      180
cgcaccagtg gcttatgcgt gcccctcacc tggcgctgcg acaggacttg gactgcagcg      240
atggcagcga tgaggaggag tgcaggattg agccatgtac ccagaaaggg caatgcccac      300
cgccccctgg cctcccctgc cctgcaccgg cgtcagtga ctgctctggg ggaactgaca      360
agaaactgcg caactgcagc cgcctggcct gcctagcags gragskcmcg wkgcacgctg      420
agcgatgact gcattccact cacgtggcgc tgcgacggcc acccagactg tcccgactcc      480
agcgacgagc tcggctgtgg aaccaatgag atcctcccgg aagggggatgc cacaaccatg      540 gggcccctg tgaccctgga gagtgtcacc tctctcagga atgccacaac catggggccc      600
cctgtgaccc tggagagtgt cccctctgtc gggaatgcca catcctcctc tgccggagac      660
cagtctggaa gcccaactgc ctatggggtt attgcagctg ctgcggtgct cagtgcaagc      720
ctggtcaccg ccacctcct cctttgtcc tggctccgag cccaggagcg cctccgccca      780
ctggggttac tggtgg                                                     796

<210> SEQ ID NO 25
<211> LENGTH: 662
<212> TYPE: DNA
<213> ORGANISM: Homo sapiens
<220> FEATURE:
<221> NAME/KEY: SITE
<222> LOCATION: (647)
<223> OTHER INFORMATION: n equals a,t,g, or c

<400> SEQUENCE: 25
taattcggca cgaggctgtg gtggagaagg acgtgccgtg ccgctgggtt ctgagccgga      60
gtggtcggtg ggtgggatgg aggcgacctt ggagcagcac ttggaagaca caatgaagaa      120
tccctccatt gttggagtcc tgtgcacaga ttcacaagga cttaatctgg gttgcgcgg      180 gaccctgtca gatgagcatg ctggagtgat atctgttcta gcccagcaag cagctaagct      240
aacctctgac cccactgata ttcctgtggt gtgtctagaa tcagataatg gaacattat       300 gatccagaaa cacgatggca tcacggtggc agtgcacaaa atggcctctt gatgctcata      360
tctgttcttc agcagcctgt cataggaact ggatcctacc tatgttaatt accttataga      420
actactaaag ttccagtagt taggccattc atttaatgtg cattaggcac ttttctgttt      480
```

| | |
|---|---|
| atttaagagt caattgcttt ctaatgctct atggaccgac tatcaagata ttagtaagaa | 540 |
| aggatcatgt tttgaagcag caggtccagg tcactttgta tatagaattt tgctgtattc | 600 |
| aataaatctg tttggaggaa aaaaaaaaaa aaaaaaatta ctgcggnccg acaagggaat | 660 |
| tc | 662 |

<210> SEQ ID NO 26
<211> LENGTH: 1105
<212> TYPE: DNA
<213> ORGANISM: Homo sapiens

<400> SEQUENCE: 26

| | |
|---|---|
| cctgatcctc tcttttctgc agttcaaggg aaagacgaga tcttgcacaa ggcactctgc | 60 |
| ttctgccctt ggctggggaa gggtggcatg gagcctctcc ggctgctcat cttactcttt | 120 |
| gtcacagagc tgtccggagc ccacaacacc acagtgttcc agggcgtggc gggccagtcc | 180 |
| ctgcaggtgt cttgcccta tgactccatg aagcactggg ggaggcgcaa ggcctggtgc | 240 |
| cgccagctgg gagagaaggg cccatgccag cgtgtggtca gcacgcacaa cttgtggctg | 300 |
| ctgtccttcc tgaggaggtg aatgggagc acagccatca cagacgatac cctgggtggc | 360 |
| actctcacca ttacgctgcg gaatctacaa ccccatgatg cgggtctcta ccagtgccag | 420 |
| agcctccatg gcagtgaggc tgacaccctc aggaaggtcc tggtggaggt gctcgcagac | 480 |
| cccctggatc accgggatgc tggagatctc tggttccccg gggagtctga gagcttcgag | 540 |
| gatgcccatg tggagcacag catctccagg agctcttckt aggaaaggcc gcaaattccc | 600 |
| attccttccc ctcttgccta tcyttctcct ccaagayctg catctttctc atcaagattc | 660 |
| tagcagccag cgccctctgg gctgcagcct ggcatggaca gaagccaggg acacatccac | 720 |
| ccagtgaact ggactgtggc catgacccag ggtatcagct ccaaactctg ccagggctga | 780 |
| gagacacgtg aaggaagatg atgggaggaa agcccagga gaagtccacc agggaccag | 840 |
| cccagcctgc atacttgcca cttggccacc aggactcctt gttctgctct ggcaagagac | 900 |
| tactctgcct gaacactgct ctcctgac cctggaagca gggactggtt gagggagtgg | 960 |
| ggaggtggta agaacacctg caacttctg atattggac attttaaaca cttacaaata | 1020 |
| aatccaagac tgtcatattt aaaaaaaaaa aaaaaaaama aaarrrrrrc cccggtaccc | 1080 |
| aattcgccct atagtgagtc gtata | 1105 |

<210> SEQ ID NO 27
<211> LENGTH: 1017
<212> TYPE: DNA
<213> ORGANISM: Homo sapiens

<400> SEQUENCE: 27

| | |
|---|---|
| ctcgcctggg ctgtttcccg gcttcatttc tcccgactca gcttcccacc ctgggctttc | 60 |
| cgaggtgctt tcgccgctgt ccccaccact gcagccatga tctccttaac ggacacgcag | 120 |
| aaaattggaa tggattaac aggatttgga gtgttttcc tgttctttgg aatgattctc | 180 |
| ttttttgaca aagcactact ggctattgga aatgttttat ttgtagccgg cttggctttt | 240 |
| gtaattggtt tagaaagaac attcagattc ttcttccaaa aacataaaat gaaagctaca | 300 |
| ggttttttc tgggtggtgt atttgtagtc cttattggtt ggcctttgat aggcatgatc | 360 |
| ttcgaaattt atgattttt tctcttgttc aggggcttct ttcctgtcgt tgttggcttt | 420 |
| attagaagag tgccagtcct tggatccctc ctaaatttac ctggaattag atcatttgta | 480 |
| gataaagttg gagaaagcaa caatatggta taacaacaag tgaatttgaa gactcattta | 540 |

```
aaatattgtg ttatttataa agtcatttga agaatattca gcacaaaatt aaattacatg      600
aaatagcttg taatgttctt tacaggagtt taaaacgtat agcctacaaa gtaccagcag      660
caaattagca aagaagcagt gaaaacaggc ttctactcaa gtgaactaag aagaagtcag      720
caagcaaact gagagaggtg aaatccatgt taatgatgct taagaaactc ttgaaggcta      780
tttgtgttgt ttttccacaa tgtgcgaaac tcagccatcc ttagagaact gtggtgcctg      840
tttcttttct ttttattttg aaggctcagg agcatccata ggcatttgct ttttagaaat      900
gtccactgca atggcaaaaa tatttccagt tgcactgtat ctctggaagt gatgcatgaa      960
ttcgattgga ttgtgtcatt ttaaagtatt aaaaccaagg gaaacccccaa aaaaaaa     1017
```

```
<210> SEQ ID NO 28
<211> LENGTH: 391
<212> TYPE: DNA
<213> ORGANISM: Homo sapiens
<220> FEATURE:
<221> NAME/KEY: SITE
<222> LOCATION: (281)
<223> OTHER INFORMATION: n equals a,t,g, or c

<400> SEQUENCE: 28
ccctggaaag aggaactgat gtttgagggg acagatgtgg gtcactttcc ctggcagtgc       60
cctctagcct tgctgccttg gctttctgac cccttccagg cttcaggggc ctgggagatc      120
tcatgcctca gcccaggaaa catttaatag ggaaagcaga acatgtcat gtcagcccca      180 cagacaagaa tttctagagc acttgtcctg ttgttccttg ccccgacatt actcagtctg      240
ggccatggaa tccatccaat aaacacagca acacccctatg ntactgacca agcaaagctt      300 gccctggta ccaaagagct aaatcatgac caaagtgtga catgaatgta actgaaatgc      360
gggttagttg ctcaatgtat gcaaagtccc a                                    391
```

```
<210> SEQ ID NO 29
<211> LENGTH: 1139
<212> TYPE: DNA
<213> ORGANISM: Homo sapiens

<400> SEQUENCE: 29
ggtgatatct tcatagtggg ctattacagg caggaaaatg ttttaactgg tttacaaaat       60
ccatcaatac ttgtgtcatt ccctgtaaaa ggcaggagac atgtgattat gatcaggaaa      120
ctgcacaaaa ttattgtttt cagcccccgt gttattgtcc ttttgaactg ttttttttt      180 attaaagcca aatttgtgtt gtatatattc gtattccatg tgttagatgg aagcatttcc      240
tatccagtgt gaataaaaag aacagttgta gtaaattatt ataaagccga tgatatttca      300
tggcaggtta ttctaccaag ctgtgcttgt tggtttttcc catgactgta ttgcttttat      360
aaatgtacaa atagttactg aaatgacgag acccttgttt gcacagcatt aataagaacc      420
ttgataagaa ccatattctg ttgacagcca gctcacagtt tcttgcctga agcttggtgc      480
accctccagt gagacacaag atctctcttt taccaaagtt gagaacagag ctggtggatt      540
aattaatagt cttcgatatc tggccatggg taacctcatt gtaactatca tcagaatggg      600
cagagatgat cttgaagtgt cacatacact aaagtccaaa cactatgtca gatggggta      660 aaatccatta agaacagga aaaataatt ataagatgat aagcaaatgt ttcagcccaa      720
tgtcaaccca gttaaaaaaa aaattaatgc tgtgtaaaat ggttgaatta gtttgcaaac      780
tatataaaga catatgcagt aaaaagtctg ttaatgcaca tcctgtggga atggagtgtt      840
```

```
ctaaccaatt gccttttctt gttatctgag ctctcctata ttatcatact cagataacca      900
aattaaaaga attagaatat gattttaaat acacttaaca ttaaactctt ctaactttct      960
tctttctgtg ataattcaga agatagttat ggatcttcaa tgcctctgag tcattgttat     1020
aaaaaatcag ttatcactat accatgctat aggagactgg gcaaaacctg tacaatgaca     1080
accctggaag ttgcttttt taaaaaaata ataaatttct aaatcaaaa aaaaaaaaa        1139
```

<210> SEQ ID NO 30
<211> LENGTH: 465
<212> TYPE: DNA
<213> ORGANISM: Homo sapiens

<400> SEQUENCE: 30

```
ccacgcgtcc gcggacgcgt ggggaaggtt tgtgccagta gacattatgt tactaaatca       60
gcactttaaa atctttggtt ctctaattca tatgaatttg ctgtttgctc taatttcttt      120
gggctcttct aatttgagtg gagtacaatt ttgttgtgaa acagtccagt gaaactgtgc      180
agggaaatga agtagaatt ttgggaggta ataatgatgt gaaacataaa gatttaataa       240
ttactgtcca acacagtgga gcagcttgtc cacaaatata gtaattacta tttattgctc      300
taaggaagat taaaaaaga tagggaaaag ggggaaactt ctttgaaaaa tgaaacatct      360
gttacattaa tgtctaatta taaaatttta atccttactg catttcttct gttcctacaa      420
atgtattaaa cattcagttt aactggtaaa aaaaaaaaaa aaaaa                     465
```

<210> SEQ ID NO 31
<211> LENGTH: 702
<212> TYPE: DNA
<213> ORGANISM: Homo sapiens
<220> FEATURE:
<221> NAME/KEY: SITE
<222> LOCATION: (299)
<223> OTHER INFORMATION: n equals a,t,g, or c
<220> FEATURE:
<221> NAME/KEY: SITE
<222> LOCATION: (488)
<223> OTHER INFORMATION: n equals a,t,g, or c
<220> FEATURE:
<221> NAME/KEY: SITE
<222> LOCATION: (699)
<223> OTHER INFORMATION: n equals a,t,g, or c

<400> SEQUENCE: 31

```
gcaacaagcg gcccaccttc ctgaagatca agaagccact gtcgtaccgc aagcccatgg       60
acacggacct ggtgtacatc gagaagtcgc ccaactactg cgaggaggac ccggtgaccg      120
gcagtgtggg cacccagggc cgcgcctgca acaagacggc tccccaggcc agcggctgtg      180
acctcatgtg ctgtgggcgt ggctacaaca cccaccagta cgcccgcgtg tggcagtgca      240
actgtaagtt ccactggtgc tgctatgtca agtgcaacac gtgcagcgag cgcacggang      300
atgtacacgt gcaagtgagc cccgtgtgca caccaccctc ccgctgcaag tcagattgct      360
gggaggactg gaccgtttcc aagctgcggg ctccctggca ggatgctgag cttgtctttt      420
ctgctgagga gggtactttt cctgggtttc ctgcaggcat ccgtggggga aaaaaaatct      480
ctcagagncc tcaactattc tgttccacac ccaatgctgs tccaccctcc cccagacaca      540
gcccaggtcc ctccgcggct ggagcgaagc cttctgcagc aggaactctg gaccctggg       600 cctcatcaca gcaatatta acaatttatt cctgataaaa ataatattaa tttattaat       660 taaaagaat tcttccaaaa aaaaaaaaaa aaaaaacnt cg                          702
```

<210> SEQ ID NO 32
<211> LENGTH: 1142
<212> TYPE: DNA
<213> ORGANISM: Homo sapiens

<400> SEQUENCE: 32

```
cggcacgagg aagaaatggc agagactgga atctctcttc atgaaaaaat gcagcccctt      60
aacttcagtt cgacagagtg cagctccttc tctccaccca ccacagtgat tctccttatc     120
ctgctgtgct ttgagggcct gctcttcctc attttcacat cagtgatgtt tgggacccag     180
gtgcactcca tctgcacaga tgagacggga atagaacaat tgaaaaagga agagagaaga     240
tgggctaaaa aaacaaaatg gatgaacatg aaagccgttt ttggccaccc cttctctcta     300
ggctgggcca gcccctttgc cacgccagac caagggaagg cagacccgta ccagtatgtg     360
gtctgaagga ccccgaccgg catggccact cagacacaag tccacaccac agcactaccg     420
tcccatccgt tctcatgaat gtttaaatcg aaaaagcaaa acaactactc ttaaaacttt     480
ttttatgtct caagtaaaat ggctgagcat tgcagagara aaaaaaagtc cccacatttt     540
attttttaaa aaccatcctt tcgatttctt ttggtgaccg aagctgctct cttttccttt     600
taaaatcact tctctggcct ctggtttctc tctgctgtct gtctggcatg actaatgtag     660
agggcgctgt ctcgcgctgt gcccattcta ctaactgagt gagacatgac gctgtgctgg     720
gatggaatag tctggacacc tggtgggga tgcatgggaa agccaggagg gccctgacct      780
tcccactgcc caggaggcag tggcgggctc cccgatggga cataaaacct caccgaagat     840
ggatgcttac cccttgaggc ctgagaaggg caggatcaga agggaccttg gcacagcgac     900
ctcatccccc aagtggacac ggtttgcctg ctaactcgca aagcaattgc ctgccttgta     960
ctttatgggc ttggggtgtg tagaatgatt ttgcggggga gtgggggaga aagatgaaag    1020
aggtcttatt tgtattctga atcagcaatt atattccctg tgattatttg gaagagtgtg    1080
taggaaagac gtttttccag ttcaaaatgc cttatacaat caagaggaaa aaaaaaaaa    1140
ag                                                                 1142
```

<210> SEQ ID NO 33
<211> LENGTH: 928
<212> TYPE: DNA
<213> ORGANISM: Homo sapiens

<400> SEQUENCE: 33

```
ggcacgaggt ctaatgaggg ctctcttgtt tgctagagat gagagaaatg tatactaatc      60
attttaattt gtacttaaaa tacattttac taatcatatt gattttaaat atgacaaatt     120
cttctagtag atactaatct ttcttgttta tcatattgtc ctagagaagc ctaggtaaaa     180
atgggttcca cctagtctgt ttgtataaca ccttcccccg tccctctcc atccctgcca      240
attgggctct atgcatattg acaagcaaat aagaaaacct taggttcttg tatttgaatt     300
tccaaaacaa taaaggtttt tgactcaaga tttgcattca agaagaggca gaaattttgt     360
cttatctttt tatcattttg tgaacttgtg tttctctgta tgcttagaaa atttacacac     420
aaggaatgtt tgaaaaagtg agaatttag agtgcttggg tggtttttat ttggtcagtg      480
ctgatgtgtt aggtgtttag ggaaataatg cttcaggacc tttttgacaa cacagcttca     540
tgaatgactg ggggatattt atgtttgtgc tgagaaaagg gagggagtgg gcaggttgga     600
gtggggacct ttccattgaa agcagtgcag tcagctgttt cgtagatgca tttttttctt     660
atgcttgtaa cattgttctt gtgtccataa ttgactgaaa tgtcaagctc caggaatgca     720
```

-continued

| | |
|---|---|
| aggcatttat caggtgacca gaagtagaac cttgttgatt atgaaatgga agaataatgt | 780 |
| caaggtagtg ggggtaaaat gacaaataag attttactgg tgaatttcca tgcttagtat | 840 |
| gtacattaac ctctttttaa gttgcatgtt aatctggtat aacgtattgt gtctggttta | 900 |
| tgctttgagt aaaaaaaaaa aaaaaaa | 928 |

<210> SEQ ID NO 34
<211> LENGTH: 773
<212> TYPE: DNA
<213> ORGANISM: Homo sapiens

<400> SEQUENCE: 34

| | |
|---|---|
| ggcacgagtt ctggcctctc atttccttac actctgacat gaatgaatta ttattatttt | 60 |
| tcttttcttt ttttttttt acattttgta tagaaacaaa ttcatttaaa caaacttatt | 120 |
| attattattt tttacaaaat atatatatgg agatgctccc tccccctgtg aaccccccag | 180 |
| tgcccccgtg gggctgagtc tgtgggccca ttcggccaag ctggattctg tgtacctagt | 240 |
| acacaggcat gactgggatc ccgtgtaccg agtacacgac ccaggtatgt accaagtagg | 300 |
| caccttggg cgcacccact ggggccaggg gtcgggggat gttgggagcc tcctcccac | 360 |
| cccacctccc tcacttcact gcattccaga ttggacatgt tccatagcct tgctggggaa | 420 |
| gggcccactg ccaactccct ctgccccagc cccacccttg gccatctccc tttgggaact | 480 |
| agggggctgc tggtgggaaa tgggagccag ggcagatgta tgcattcctt tatgtccctg | 540 |
| taaatgtggg actacaagaa gaggagctgc ctgagtggta ctttctcttc ctggtaatcc | 600 |
| tctggcccag ccttatggca gaatagaggt atttttaggc tattttttgta atatggcttc | 660 |
| tggtcaaaat ccctgtgtag ctgaattccc aagccctgca ttgtacagcc ccccactccc | 720 |
| ctcaccacct aataaaggaa tagttaacac tcaaaaaaaa aaaaaaaaaa aaa | 773 |

<210> SEQ ID NO 35
<211> LENGTH: 453
<212> TYPE: DNA
<213> ORGANISM: Homo sapiens

<400> SEQUENCE: 35

| | |
|---|---|
| taaaatgtta cacgcttgtc atattccagg cactgcacta tgtatgccgt ttatcaacag | 60 |
| ttagctcagc taaccctcat ggtaaccttg ttagccccga ttttgccaga tgagcaaagt | 120 |
| gaggttttg aggccttaag taacttgccc aaggtcacgt ggctgggaag taactctccc | 180 |
| agttctgaga tgcccgagcc tggacgcttt gtcattgtac accatcaact cagtgctgcc | 240 |
| agtcattcca gcagccagct agcgtagtca aggtttctcc accttagcac tgttgacatt | 300 |
| tcgagccaga taattctctg tggtgaggag ctgtcctatg ccttgtagga tatacaacag | 360 |
| catcytggct ttacccacca gatgytggaa cacctcccca gtcgtgacag cccaaaatgt | 420 |
| ctatagacgt tgccacgtat acccagggt tcc | 453 |

<210> SEQ ID NO 36
<211> LENGTH: 459
<212> TYPE: DNA
<213> ORGANISM: Homo sapiens

<400> SEQUENCE: 36

| | |
|---|---|
| gtgactgccg ccctgcccgc agccatgtgg ccccgctgt tgctgctgct gctgctgctc | 60 |
| ccggccgcc cggtccccac cgccaaagcc gctcccacc cggatgctaa cacccaggaa | 120 |
| ggccttcaga acctgctcca aggagtcggg gctggcggag acggagagct gcgggcagac | 180 |

```
tcacacctgg ccccgggctc tggctgtatt gatggggctg tggtggccac gcgaccagaa      240
agccggggag gaagacctgc ggttccgtga gaggcgtcca gggctgcagg ccacggcgac      300
aggctccggg gaacatgggg ctttccctgt ccactcccaa ggagtgtggg cctcaacgca      360
ttggcagggg acggccgtgt gccctctyca gaccccaccc ccagatgcat ttattagaaa      420
taataaattc tttcttagct aaaaaaaaaa aaaaaaat                              459
```

<210> SEQ ID NO 37
<211> LENGTH: 509
<212> TYPE: DNA
<213> ORGANISM: Homo sapiens

<400> SEQUENCE: 37

```
atgaaattta ccactctcct cttcttggca gctgtagcag gggccctggt ctatgctgaa       60
gatgcctcct ctgactcgac gggtgctgat cctgcccagg aagctgggac ctctaagcct      120
aatgaagaga tctcaggtcc agcagaacca gcttcacccc cagagacaac cacaacagcc      180
caggagactt cggcggcagc agttcagggg acagccaagg tcacctcaag caggcaggaa      240
ctaaaccccc tgaaatccat agtggagaaa agtatcttac taacagaaca agcccttgca      300
aaagcaggaa aaggaatgca cggaggcgtg ccaggtggaa acaattcat cgaaaatgga       360 agtgaatttg cacaaaaatt actgaagaaa ttcagtctat taaaaccatg gcatgagaa       420 gctgaaaaga atgggatcat tggacttaaa gccttaaata cccttgtagc ccagagctat      480
taaaacgaaa gcatccaaaa aaaaaaaa                                         509
```

<210> SEQ ID NO 38
<211> LENGTH: 598
<212> TYPE: DNA
<213> ORGANISM: Homo sapiens

<400> SEQUENCE: 38

```
atgtttgggct gtgggatccc agcgctgggc ctgctcctgc tgctgcaggg ctcggcagac      60
ggaaatggaa tccagggatt cttctaccca tggagctgtg agggtgacat atgggaccgg     120
gagagctgtg ggggccaggc ggccatcgat agccccaacc tctgcctgcg tctccggtgc     180
tgctaccgca atgggtctg ctaccaccag cgtccagacg aaaacgtgcg gaggaagcac      240
atgtgggcgc tggtctggac gtgcagcggc ctcctcctcc tgagctgcag catctgcttg     300
ttctggtggg ccaagcgccg ggacgtgctg catatgcccg gtttcctggc gggtccgtgt     360
gacatgtcca gtccgtctc gctgctctcc aagcaccgag ggaccaagaa gacgccgtcc      420
acgggcagcg tgccagtcgc cctgtccaaa gagtccaggg atgtggaggg aggcaccgag      480
ggggaaggga cggaggaggg tgaggagaca gagggcgagg aagaggagga ttagggagt      540 ccccggggga ctggtcaata cagatacggt ggacggaaaa aaaaaaaaa aaaaaaa         598
```

<210> SEQ ID NO 39
<211> LENGTH: 454
<212> TYPE: DNA
<213> ORGANISM: Homo sapiens

<400> SEQUENCE: 39

```
atggaggctg tttttacagt ttttttttt gttgttgttt tgtttttaaa gaatacagaa       60
ggagccaagc ttttttgcac tttgtatcca gctgcaagct cagggcagag tcaagggcct      120
gggttggaaa aacctgactc acaggaatgc ataattgacc cttgcagcta cccaatagcc      180
```

```
cttggagctg gcactgaacc aggctgcaag atttgactgc cttaaaaaca caaggccctc      240
taggcctggc agggatgtcc ctgtgcccag cactgggggc tcgaagactg gtttctagca      300
ctaccggtca cggccatgtc gtcctagaag ggtccagaag attattttac gttgagtcca      360
tttttaatgt tctgatcacc tgacagggca ccccaaaccc ccaactccca ataaaagccg      420
tgacgttcgg acaaaaaaaa aaaaaaaaaa aaaa                                  454

<210> SEQ ID NO 40
<211> LENGTH: 425
<212> TYPE: DNA
<213> ORGANISM: Homo sapiens

<400> SEQUENCE: 40
gctaaaggcc attccctccg caggcattt gcgtcgggt gggagggaa aacgcatctt         60 gttaattatt tttaatctta tttattgtac atacctgggg caggggcttg ggaggtgga      120 gggggragaa gggtcccctc tctctgcccc tcccactcct tttctacggc gatttgtctg     180
tgtctggccc ccacccactg mccatccccc attgttgtct ggatgtggtt ctattttta     240 tcggtctcct ttccctcct ccccgttytc gcccccgmcc caccccctgc tcccactacc     300
ctttgtctct tgctctttct tgggyttctg tacaactcaa cttgtataca ctgtgtacac     360
acaaccagyc waacgcaaaa cccaacggca aacactttaa aaaaaaaaaa aaaaactgg     420 ggggt                                                                  425

<210> SEQ ID NO 41
<211> LENGTH: 2471
<212> TYPE: DNA
<213> ORGANISM: Homo sapiens
<220> FEATURE:
<221> NAME/KEY: SITE
<222> LOCATION: (42)
<223> OTHER INFORMATION: n equals a,t,g, or c
<220> FEATURE:
<221> NAME/KEY: SITE
<222> LOCATION: (1932)
<223> OTHER INFORMATION: n equals a,t,g, or c
<220> FEATURE:
<221> NAME/KEY: SITE
<222> LOCATION: (1957)
<223> OTHER INFORMATION: n equals a,t,g, or c
<220> FEATURE:
<221> NAME/KEY: SITE
<222> LOCATION: (1983)
<223> OTHER INFORMATION: n equals a,t,g, or c
<220> FEATURE:
<221> NAME/KEY: SITE
<222> LOCATION: (1989)
<223> OTHER INFORMATION: n equals a,t,g, or c
<220> FEATURE:
<221> NAME/KEY: SITE
<222> LOCATION: (2003)
<223> OTHER INFORMATION: n equals a,t,g, or c
<220> FEATURE:
<221> NAME/KEY: SITE
<222> LOCATION: (2018)
<223> OTHER INFORMATION: n equals a,t,g, or c

<400> SEQUENCE: 41
ggcacgagta tggcttcccg tggactcagc ctcttccccg antcctggca cgagggggct      60
tcgcgtctgt gcttcctgtg gctgacgtca tctggaggag atttgctttc ttttctcca     120 aaagggagg aaattgaaac tgagtggccc acgatgggaa gaggggaaag cccagggta     180 caggaggcct ctgggtgaag gcagaggcta acatgggtt cggagcgacc ttggccgttg      240
gcctgaccat ctttgtgctg tctgtcgtca ctatcatcat ctgcttcacc tgctcctgct      300
```

```
gctgccttta caagacgtgc cgccgaccac gtccggttgt caccaccacc acatccacca    360
ctgtggtgca tgcccttat cctcagcctc caagtgtgcc gcccagctac cctggaccaa     420
gctaccaggg ctaccacacc atgccgcctc agccagggat gccagcagca ccctacccaa    480
tgcagtaccc accaccttac ccagcccagc ccatgggccc accggcctac cacgagaccc    540
tggctggaga gcagccgcgc cctacccgc cagccagcct ccttacaacc cggcctacat     600
ggatgccccg aaggcggccc tctgagcatt ccctggcctc tctggctgcc acttggttat    660
gttgtgtgtg tgcgtgagtg gtgtgcaggc gcggttcctt acgccccatg tgtgctgtgt    720
gtgtccaggc acggttcctt acgccccatg tgtgctgtgt gtgtcctgcc tgtatatgtg    780
gcttcctctg atgctgacaa ggtggggaac aatccttgcc agagtgggct gggaccagac    840
tttgttctct tcctcacctg aaattatgct tcctaaaatc tcaagccaaa ctcaaagaat    900
ggggtggtgg gggcaccct gtgaggtggc ccctgagagg tggggcctc tccagggcac      960
atctggagtt cttctccagc ttaccctagg gtgaccaagt agggcctgtc acaccagggt    1020
ggcgcagctt tctgtgtgat gcagatgtgt cctggtttcg gcagcgtacc agctgctgct    1080
tgaggccatg gctccgtccc cggagttggg ggtacccgtt gcagagccag gacatgatg     1140
caggcgaagt tggggatctg gccaagttgg actttgatcc tttgggcaga tgtcccattg    1200
ctccctggag cctgtcatgc ctgttgggga tcaggcagcc tcctgatgcc agaacacctc    1260
aggcagagcc ctactcagct gtacctgtct gcctggactg tcccctgtcc ccgcatctcc    1320
cctgggacca gctggagggc acatgcaca cacagcctag ctgcccccag ggagctctgc     1380
tgcccttgct ggccctgccc ttcccacagg tgagcagggc tcctgtccac cagcacactc    1440
agttctcttc cctgcagtgt tttcatttta ttttagccaa acattttgcc tgttttctgt    1500
ttcaaacatg atagttgata tgagactgaa acccctgggt tgtggaggga aattggctca    1560
gagatggaca acctggcaac tgtgagtccc tgcttcccga ccagcctc atggaatatg      1620
caacaactcc tgtaccccag tccacggtgt tctggcagca gggacacctg gccaatgggg    1680
ccatctggac caaaggtggg gtgtggggcc ctggatggca gctctggccc agacatgaat    1740
acctcgtgtt cctcctccct ctattactgt ttcaccagag ctgtcttagc tcaaatctgt    1800
tgtgtttctg agtctagggt ctgtacactt gtttataata aatgcaatcg tttggaaaaa    1860
aaaaaaaaaa aaactcgtag ggggggcccg tacccaatgg gcycmmarat agtagarwac    1920
raaaayamca antgcaacca aagagggggcc agggganttt taagagggcc ccctttttggg    1980
ggnatccant ttagccgggg ttnttaaggg aagttgcntg gcggggggtta gggcccsgtt    2040
kytwcttcca accaagggtt ytygtggtta ggccgggttg ggcccmatgg gctgggctgg    2100
gtaaagtggt gggtmaytgc mattgggtag ggtgctgctg gcattcctgg ctgaggcggc    2160
atggtgtggt agccctggta gcttggtcca gggtagctgg gcggcacact tggaggctga    2220
ggataagggg catgcaccca cagtggtgga tgtggtggtg gtgacaaccg gacgtggtcg    2280
gcggcacgtc ttgtaaaggc agcagcagga gcaggtgaag cagatgatga tagtgacgac    2340
agacagcaca aagatggtcc agccaacggc caaggtcgct ccgaaccca tgttagcctc     2400
tgccttcacc cagaggcctc ctgtaccct gggctttccc ctcttcccat cgtgggccac     2460
tcactcgtgc c                                                          2471
```

<210> SEQ ID NO 42
<211> LENGTH: 2659
<212> TYPE: DNA

<213> ORGANISM: Homo sapiens

<400> SEQUENCE: 42

| | | | | | |
|---|---|---|---|---|---|
| ggcacgagct | tttctctaga | gtctgaaaga | tgctagaaag | aaataaaatt | taacttactt | 60 |
| aagagaatta | tggatctttt | attaataaaa | attaacttga | tgatttgaac | taacagttat | 120 |
| gataattctg | gtatttatag | cttttttttat | tccctgcag | aaaaccatag | gcaaaattgc | 180 |
| aacatgcttg | gaattgcgaa | gtgcagcttt | acagtccaca | cagtctcaag | aagaatttaa | 240 |
| actggaggac | ctgaagaagc | tagaaccaat | cctaaagaat | attcttacat | ataataaaga | 300 |
| attcccattt | gatgttcagc | ctgtcccatt | aagaagaatt | ttggcacctg | gtgaagaaga | 360 |
| gaatttggaa | tttgaagaag | atgaagaaga | gggtggtgct | ggagcaggtc | tcctgattct | 420 |
| ttcctgctag | agttcccggt | actttattac | caaggttgcc | atcggaacca | ggaatgacat | 480 |
| tactcactat | cagaattgag | aaaattggtt | tgaaagatgc | tgggcagtgc | atcgatccct | 540 |
| atattacagt | tagtgtaaag | gatctgaatg | gcatagactt | aactcctgtg | caagatactc | 600 |
| ctgtggcttc | aagaaaagaa | gatacatatg | ttcattttaa | tgtggacatt | gagctccaga | 660 |
| agcatgttga | aaaattaacc | aaaggtgcag | ctatcttctt | tgaattcaaa | cactacaagc | 720 |
| ctaaaaaaag | gtttaccagc | accaagtgtt | ttgctttcat | ggagatggat | gaaattaaac | 780 |
| ctgggccaat | tgtaatagaa | ctatacaaga | aacccactga | ctttaaaaga | aagaaattgc | 840 |
| aattattgac | caagaaacca | ctttatcttc | atctacatca | aactttgcac | aaggaatgat | 900 |
| cctgacatga | tgaacctgga | acttctgtga | attttaccac | tcagtagaaa | ccatcatagc | 960 |
| tctgtgtagc | atattcaccc | ttcaacaggc | aggaagcaag | ccgtacccag | accagtaggc | 1020 |
| cggacggagt | caaatgcaaa | gctgtaccac | agaattcaga | gtccagcaca | tcacactgac | 1080 |
| gtataggact | ccttgggata | caggtttatt | gtagattttg | aaacatgttt | ttactttttct | 1140 |
| attaattgtg | caattaatag | tctattttct | aatttaccac | tactcctacc | ctgcttcctg | 1200 |
| gaacaatact | gttgtgggta | ggatgtgctc | atcttcagac | ttaatacagc | aataagaatg | 1260 |
| tgctagagtt | tacacatctg | ttcacttttg | ctccaatatg | ctcttttgac | ttaacgtcaa | 1320 |
| gctttgggtt | gatgtgggta | gggtagtgtc | aaactgcttt | gagaggaatg | ggaccagttc | 1380 |
| tgctgcctaa | gaaggtctgt | ctggatgttt | ataggcagca | cctctgaagt | ggcctaaatt | 1440 |
| caccctgatc | tgatagtttt | cctgcttaga | aagtgtgcct | tggccagatc | agtatcccac | 1500 |
| atgggagtgt | tccctaggtt | gtagctgtga | ttgtttccag | atgaccagat | tgttttttctg | 1560 |
| aaaatgagca | tatttttagt | catgtcgatt | agctgttctt | ctacatcaca | ttgttactct | 1620 |
| ttctgatgat | gattctaggg | ttaacattgg | aaccatctca | aaataattac | aaagttttag | 1680 |
| atgggtttac | aatgtcttct | aaacaatgta | atctaaaaat | aattgagtca | gatgctaacg | 1740 |
| agatactgca | ggcataactg | ctgttttttct | gacaactgat | tgtgaaacct | taaaacctgc | 1800 |
| atacctcttc | ttacagtgag | gagtatgcaa | aatctggaaa | gatattctat | ttttttttata | 1860 |
| taggtagata | ggatcgccat | ttatttccta | tttagatata | ctgacattca | tccatatgaa | 1920 |
| aatatgcagg | tcattagctt | actataattt | acttttgact | taatgggca | taaataaaac | 1980 |
| tttcatagta | cacatgaggt | ggatatttga | tacacagaac | atttgcggtg | ggctttctgt | 2040 |
| gggttagatg | taaagcccac | atattttaat | attcactatt | ttaaatgagc | aatgcatgag | 2100 |
| gggaatgcag | tgtcagtacc | tggcctattt | ttaaactagt | gtaatcaccc | tagtcatacc | 2160 |
| attcagtatg | tttgcttttt | aaaataagta | accacaatta | agttgttgta | gcccttgcac | 2220 |
| ttcaagagat | ctagtctttta | ctttcagttg | tctgttaggt | ccattctgtt | tactagacgg | 2280 |

| | |
|---|---|
| atgttaataa aaactatgcg agcctggaat ggaattctcc agccaaattt tagtcttgtc | 2340 |
| ctctccatct tgattggatt aattccaaat tctaaaatga ttcagtccac aatagctcta | 2400 |
| ggggatgaag aatttgcctt actttgccca gttcctaaga ctgtgagttg tcaaatccct | 2460 |
| agactgtaag ctcttcaagg agcaagaggc gcattttctc cgtgtcatgt aattttttcta | 2520 |
| aggtgtttgg cagcactctg taccctgtgg agtactcagt accttttgtt tgatgttgct | 2580 |
| gacaagacct gaaaaaaaat cccttaaaaa aaaaacccat taaagtgtag caaaaccgaa | 2640 |
| awaaaaaaaa aaaaaaaaa | 2659 |

<210> SEQ ID NO 43
<211> LENGTH: 1635
<212> TYPE: DNA
<213> ORGANISM: Homo sapiens
<220> FEATURE:
<221> NAME/KEY: SITE
<222> LOCATION: (1626)
<223> OTHER INFORMATION: n equals a,t,g, or c

<400> SEQUENCE: 43

| | |
|---|---|
| cgaggaggtc atgaacaagg aggcgggaga ggtggacgtg gtggctatga ccatggtggc | 60 |
| cgaggggggag gaagaggaaa taagcatcaa ggaggctgga cagatggagg gagtggtgga | 120 |
| ggaggtggct accaagatgg tggttatcga gattcaggtt tccagccagg tggctatcat | 180 |
| ggtggccaca gcagtggtgg ctatcaaggc ggaggttatg gtggcttcca acatcttct | 240 |
| tcatatacag gaagtggata ccagggtggt ggctaccagc aggacaatag ataccaagat | 300 |
| ggcgggcacc atggtgatcg tggtggtggt cgtggtgggc gaggtggtcg tggaggccga | 360 |
| ggtggtcgtg caggccaggg aggaggctgg ggaggaagag ggagccagaa ttatcaccaa | 420 |
| gggggtcaat ttgaacagca tttccagcat ggaggttatc agtataatca ttctggattt | 480 |
| ggacagggaa gacattacac tagttgaggc taccgaacct tacattttgc tagagctcaa | 540 |
| gtaatagaaa cttagtttca gaatcctgaa ttcagcacct attttgaatt aatgtgagac | 600 |
| cacaggtggc aggcagattc ctgcttggca taagcatttg taggtcttca ttcaattctg | 660 |
| ttagattttt ttattggact tacataatgc cgtttatttg agaaacacat aacatctctc | 720 |
| cttttctatga aaaattttt aaaggtggt taaaattgcc tttaattgcc cagtagacta | 780 |
| attccacagt cagaacatgc aaacttttttt gaagaaatta cttgaataag tagttttcat | 840 |
| gttttcaata tgcagttttg aaaatgagga ttcacctaga cttttttaga tttactacya | 900 |
| ggaaaccttc cycatatgaa taaccattta tatgtgtttt gcttaaagta ttccaatgcc | 960 |
| tattttccaa gcacagttct gccccccggt tgactttttat gccacgtgtg cttcatgatg | 1020 |
| gaacttttag gtcagttcct attaaatgag ctcttytgca gatagcacat tcagtagcct | 1080 |
| tattttgttg atggaatact gtatcatatg ctcaactctg aaaaccttga acacggccaa | 1140 |
| aatccataaa gattataaaa gcaaactaag ttgtgaagct atagtacatg taggcattta | 1200 |
| gttaagtata gcaattcaaa ctgacctgca tccatccaaa acaaattcct ccttcaacct | 1260 |
| tattttact tgaaatttgc tagaagaaat agcaaaccga aatttgtttt atgcatgagt | 1320 |
| taataccact ggctcagcaa atacaagtta gtttgcttta agcaggtaac ttttttttgta | 1380 |
| atggaagaaa tgcactacaa agttaagaca gattttttgct aagtgcagga ggccctttat | 1440 |
| tattgctgca gaaaacaaaa gcctggctga gttgatgttt tacattctcc cttactgaaa | 1500 |
| tctacatgac atgatgcttc ttgctgggtt tttgtacatg taaacattgt caagctgtga | 1560 |

| | |
|---|---:|
| aagaaaatgg ctggaggtgt gctttgtgtg aaaggtgagc actgaaagta tctgttaagt | 1620 |
| tctccngaaa aaaaa | 1635 |

<210> SEQ ID NO 44
<211> LENGTH: 780
<212> TYPE: DNA
<213> ORGANISM: Homo sapiens

<400> SEQUENCE: 44

| | |
|---|---:|
| aacatggtca tgtcttttag tttcattatt ttcctactcc ttgtatgtca agaaattaca | 60 |
| ttttgcatgt cttatggaga tgctgttaat tgcttcagtg agtgcttttc taatctgcag | 120 |
| accatttaca tttcctgttt gcagcatgct gtgtgcaaac aytcagtaat ttggagtatt | 180 |
| caattatttg ttagggctct tcctatttcc aaatgtgctg aattgtctat tgatgggatt | 240 |
| ttcagatctt ttcatgagaa ctggaaatgt agctgggtgg cacctaccta ggttgctacg | 300 |
| tagtgagtag actttctctt gggtatagta agcctcagac agctttcact tttatctact | 360 |
| ttacttgtgg aaataaaaca gtcattttgt tctgaaagaa taagatagct ttctgtagag | 420 |
| aaggaattcc tacctctaaa agctgccttg agaactcaga actggcagtt ttctgaggtg | 480 |
| attttttaaat ttcagtatta gggagagtcc agcatttgct gacacagatt ctacataact | 540 |
| aatgtatgat agcaaatgca aaactattat aatgtggtgt atcttgcgca tacacaggtt | 600 |
| agaacaagta gactctggca gcagatctcc agagacccaa gtttaggttc tcatagtgta | 660 |
| tttgaagtag ttatactcct ggcttaagta gtttagtgcc tgggagaatc cattactgaa | 720 |
| aagcatttaa cttaaaaaaa aaaaaaaaaa aaaactgaaa aggtagtgaa tacagaatag | 780 |

<210> SEQ ID NO 45
<211> LENGTH: 2378
<212> TYPE: DNA
<213> ORGANISM: Homo sapiens

<400> SEQUENCE: 45

| | |
|---|---:|
| gcgaagcagc tgaagccgcc gccgcgcaga atccacgctg gctccgtgcg ccatggtcac | 60 |
| ccacagcaag tttcccgccg ccgggatgag ccgcccccctg acaccagcc tgcgcctcaa | 120 |
| gaccttcagc tccaagagcg agtaccagct ggtggtgaac gcagtgcgca agtgcaggag | 180 |
| agcggcttct actggagcgc agtgaccggc ggcgaggcga acctgctgct cagtgccgag | 240 |
| cccgccggca cctttctgat ccgcgacagc tcgggaccag cgccacttct tcacgctcag | 300 |
| cgtcaagacc cagtctggga ccaagaacct gcgcatccag tgtgaggggg gcagcttctc | 360 |
| tctgcagagc gatccccgga gcacgcagcc cgtgscccgc ttcgactgcg tgctcaagct | 420 |
| ggtgcaccac tacatgccgc cccctggagc cccctccttc ccctcgccac ctactgaacc | 480 |
| ctcctccgag gtgcccgagc agccgtctgc ccagccactc cctgggagtc cccccagaag | 540 |
| agcctattac atctactccg ggggcgagaa gatcccccctg gtgttgagcc ggcccctctc | 600 |
| ctccaacgtg gccactcttc agcatctctg tcggaagacc gtcaacggcc acctggactc | 660 |
| ctatgagaaa gtcacccagc tgccggggcc cattcgggag ttcctggacc agtacgatgc | 720 |
| cccgctttaa ggggtaaagg gcgcaaaggg catgggtcgg gagaggggac gcaggccccct | 780 |
| ctcctccgtg gcacatggca caagcacaag aagccaacca ggagagagtc ctgtagctct | 840 |
| gggggggaaag agggcggaca ggcccctccc tctgccctct ccctgcagaa tgtggcaggc | 900 |
| ggacctggaa tgtgttggag ggaaggggga gtaccacctg agtctccagc ttctccggag | 960 |
| gasccagctg tcctggtggg acgatagcaa ccacaagtgg attctccttc aattcctcag | 1020 |

```
cttcccctct gcctccaaac agggacact tcgggaatgc tgaactaatg agaactgcca   1080
gggaatcttc aaactttcca acggaacttg tttgctcttt gatttggttt aaacctgagc   1140
tggttgtgga gcctgggaaa ggtggaagag agagaggtcc tgagggcccc agggctgcgg   1200
gctggcgaag gaaatggtca caccccccgc ccaccccagg cgaggatcct ggtgacatgc   1260
tcctctccct ggctccgggg agaagggctt ggggtgacct gaaagggaac catcctggtg   1320
ccccacatcc tctcctccgg gacagtcacc gaaaacacag gttccaaagt ctacctggtg   1380
cctgagagcc caggcccctt cctccgtttt aaggggaag caacatttgg cacgagatgg   1440
gctggtcagc tggtctcctt ttcctactca tactatacct tcctgtacct gggtggatgg   1500
agcgggagga tggagagacg ggacatcttt cacctcaggc tcctggtaga aatacaggg   1560 gattctactc tgtgcctcct gactatgtct ggctaagaga ttcgccttaa atgctccctg   1620
tcccatggag agggacccag cataggaaag ccacatactc agcctggatg ggtggagagg   1680
ctgagggact cactggaggg caccaagcca gcccacagcc agggaagtgg ggagggggc   1740 ggaaacccat gcctcccagc tgagcactgg gaatgtcagc ccagtaagta ttggccagtc   1800
aggcgcctcg tggtcagagc agagccacca ggtcccactg ccccgagccc tgcacagccc   1860
tccctcctgc ctgggtgggg gaggctggag gtcattggag aggctggact gctgccaccc   1920
cgggtgctcc cgctctgcca tagcactgat cagtgacaat ttacaggaat gtagcagcga   1980
tggaattacc tggaacagtt ttttgttttt gttttgttt ttgttttgt ggggggggc   2040 aactaaacaa acacaaagta ttctgtgtca ggtattgggc tggacagggc agttgtgtgt   2100
tggggtggtt tttttctcta ttttttttgtt tgtttcttgt tttttaataa tgtttacaat   2160
ctgcctcaat cactctgtct tttataaaga ttccactcca gtcctctctc ctcccccta   2220 ctcaggccct tgaggctatt aggagatgct tgaagaactc aacaaaatcc caatccaagt   2280
caaactttgc acatatttat atttatattc agaaaagaaa catttcagta atttataata   2340
aagagcacta tttttaatg aaaaaaaaaa aaaaaaa                              2378
```

<210> SEQ ID NO 46
<211> LENGTH: 1772
<212> TYPE: DNA
<213> ORGANISM: Homo sapiens

<400> SEQUENCE: 46

```
tcgacccacg cgtccgggag gatccccagc cgggtcccaa gcctgtgcct gagcctgagc     60
ctgagcctga gccgagccgg gagccggtcg cggggggctcc gggctgtggg accgctgggc   120
ccccagcgat ggcgaccctg tggggaggcc ttcttcggct tggctccttg ctcagcctgt   180
cgtgcctggc gctttccgtg ctgctgctgg cgcactgtca gacgccgcca agaatttcga   240
ggatgtcaga tgtaaatgta tctgccctcc ctataaagaa aaattctggg catatttata   300
ataagaacat atctcagaaa gattgtgatt gccttcatgt tgtggagccc atgcctgtgc   360
gggggcctga tgtagaagca tactgtctac gctgtgaatg caaatatgaa gaagaagct   420 ctgtcacaat caaggttacc attataattt atctctccat tttgggcctt ctacttctgt   480
acatggtata tcttactctg gttgagccca tactgaagag cgcctctttt ggacatgcac   540
agttgataca gagtgatgat gatattgggg atcaccagcc ttttgcaaat gcacacgatg   600
tgctagcccg ctcccgcagt cgagccaacg tgctgaacaa ggtagaatat ggcacagcag   660
cgctggaagc ttcaagtcca agagcagcga aaagtctgtc tttgaccggc atgttgtcct   720
```

-continued

```
cagctaattg gggaattgaa ttcaaggtga ctagaaagaa acaggcagac aactggaaag      780
gaactgactg ggttttgctg ggtttcattt taataccttg ttgatttcac caactgttgc      840
tggaagattc aaaactggaa gkaaaaactt gcttgatttt tttttcttgt taacgtaata      900
atagagacat ttttaaaagc acacagctca aagtcagcca ataagtcttt tcctatttgt      960 gactttact aataaaaata aatctgcctg taaaataaat taaaaaatcc tttacctgga     1020
acaagcactc tcttttcac cacatagttt taacttgact ttccaagata attttcaggg     1080 ttttgttgt tgttgttttt tgtttgtttg ttttggtggg agaggggagg gatgcctggg     1140
aagtggttaa caactttttt caagtcactt tactaaacaa acttttgtaa atagaccta     1200 ccttctattt tcgagtttca tttatatttt gcagtgtagc cagcctcatc aaagagctga     1260
cttactcatt tgacttttgc actgactgta ttatctgggt atctgctgtg tctgcacttc     1320
atggtaaacg ggatctaaaa tgcctggtgg cttttcacaa aaagcagatt ttcttcatgt     1380
actgtgatgt ctgatgcaat gcatcctaga acaaactggc catttgctag tttactctaa     1440
agactaaaca tagtcttggt gtgtgtggtc ttactcatct tctagtacct ttaaggacaa     1500
atcctaagga cttggacact tgcaataaag aaatttttatt ttaaacccaa gcctccctgg     1560
attgataata tatacacatt tgtcagcatt tccggtcgtg gtgagaggca gctgtttgag     1620
ctccaatgtg tgcagctttg aactagggct ggggttgtgg gtgcctcttc tgaaaggtct     1680
aaccattatt ggataactgg ctttttttct tcctctttgg aatgtaacaa taaaaataat     1740
ttttgaaaca tcaaaaaaaa aaaaaaaaa aa                                    1772
```

<210> SEQ ID NO 47
<211> LENGTH: 1107
<212> TYPE: DNA
<213> ORGANISM: Homo sapiens

<400> SEQUENCE: 47

```
cgggcgagaa gggcagacgg gacatgcagc ctcttccgcc tgagccccgg aagtgatgtg       60
gctgcggcat cgcggcctcg ctatgtctgc cattttcaat tttcagagtc tattgactgt      120
aatcttgctg cttatatgta cctgtgctta tattcgatcc ttggcaccca gcctcctgga      180
cagaaataaa actggattgt tgggtatatt ttggaagtgt gccagaattg gtgaacggaa      240
gagtccttat gttgcagtat gctgtatagt aatggccttc agcatcctct tcatacagta      300 gctgggaaa atgccagaat gtagttgcca tcagatttga ttgtgaacaa ggactgactg      360
cagaaaataa tggaaggat gtttaactct tttatctccg aacattgaat gagataaatt      420
tccagatgct gttctctatt ttaatgttat tggaccaatg ttctgtataa acaattaaga      480
tgtaaccatt taatagtctg taacaatcaa cctcagtact gtcactacaa tattacattc      540
tgcaaatgtt attctgttgt atcagataca aaatttagt gaggtatctc taaggcacat      600
agtagaaaac aaaattggtt aattactcaa gttcctttca ctgtgatttg gaaatgattt      660
aatctttata gaatgagaac ctttttgga ctagcttttt tattaaaatg gctcaatttg      720
tgttgataag gattgcatta atatttaata gtgcttgctt ttcctctggg cacaccattt      780
tgatcattaa ccagagtacc tctactctta gcaaactcta gtttatgaca agtatttaaa      840
atatttaaaa caagcttatg cagttcttaa ggacgaaggt aaatgagatg taacttaaaa      900
atagtattgg gaaatgttg atagttaaca ttagtggatt tagactagcc aaatgacata      960
gtaggctctg aaacatcttg tcaagtatat gtattttgtg catgaatttt tgctggaaag     1020
ctgtctttct ctgaaaaaca caacgttctt agaatgaaaa gaacaattat aaaataaaaa     1080
```

```
aaaaatttaa aaaaaactgg gcggggg                                    1107
```

<210> SEQ ID NO 48
<211> LENGTH: 805
<212> TYPE: DNA
<213> ORGANISM: Homo sapiens

<400> SEQUENCE: 48

```
tgcagaagag atggagttgc tgttggaaaa ctactaccga ttggctgacg atctctccaa   60
tgcagctcgt gagcttaggg tgctgattga tgattcacaa agtattattt tcattaatct  120
ggacagccac cgaaacgtga tgatgaggtt gaatctacag ctgaccatgg gaaccttctc  180
tctttcgctc tttggactaa tgggagttgc ttttggaatg aatttggaat cttcccttga  240
agaggaccat agaattttt ggctgattac aggaattatg ttcatgggaa gtggcctcat   300
ctggaggcgc ctgctttcat tccttggacg acagctagaa gctccattgc ctcctatggt  360
atgaaggata tggttcacgg cggtattgtg aagggttat gatcatgggc cctaaagtca   420
gagcgcctgg gattaagttg tcacaggcac tatggcccct gcgagttgct ttctcaaact  480
tccttcagtt tccctatctg tcagttaagt cggtattacc tgcttcatag ggttatggga  540
agaattaaac aatatgtgta aagcacttac tagcacactg cctaacacaa taagttagaa  600
atataatttg tgtagaactc tgacaacata catttaaaca gatgttagta attctggtat  660
aaggtttgtc ataaccaaat ggaaatgtag gaaacattta taatgttctt aaaagatagr  720
aaattcacct ccatttttctt tgtacttgaa gatggcacca ctggaataaa acttaagac  780
actgaaaaaa aaaaaaaaaa aactc                                       805
```

<210> SEQ ID NO 49
<211> LENGTH: 1408
<212> TYPE: DNA
<213> ORGANISM: Homo sapiens

<400> SEQUENCE: 49

```
tcattattta ttcatgtggc tgaaagagta tattaattat gtttagattt ttggaaaaag   60
tctgaacaaa aaaggacct atacagtgct caaactatat ttttaaaaat actattttat   120
ttttactcac atatgaaaaa aatggctgta ctatcatgtt tacatacata ctaacattgg  180
aaacagaata acgaattgta tttaaatttt atgaagaaca cacaaacatt aaaacactga  240
ttggttacag aaagcagagt ttgaggaaaa aacattagct ataattttca ttttcattaa  300
agagcagcac cctctgagaa taatcaaact gattagtaat attcatctat actgcaaaat  360
aatatgtaca aggaaagtt agtgattgta ctgatttat tacttttacc aagccatttt   420
atgttcctca ctcaatgcaa agaaataaaa cataatctga agaaaaatat gtccttatta  480
ttattcacaa taaaaagttg gctttattct gcaagcctgg gcatattgta caattggcag  540
cacttaacgg ctcaagtgga tcaatgtacc agtttgattc tgatccactg aatagaatct  600
ctcatccata tctggtgacc agactaactc catgggagct gtgatagact gaaccatttc  660
tgtggtatcc ctagatctca ctaaataaga aagaccctac accagaaat atagcaactg    720
atctatctat aaattcacatc tatatgctag ctctttagta taagttggaa aaaggggccc  780
tttcttgagc acatggataa aagtattatt gtagtctaaa gattgctgga ttgatattgt  840
gttgttataa tgaagataag gtacacactg aaaccactgt cagattaaga aacttccaca  900
acttgtctca gttcttcaaa caatggagca agttcctttt ctaggctgac aattagtcct  960
```

```
gtattggcac tgctgctggc tatgaaactc accaccaaag gtaaacgatt aaattgaacc    1020
acctggtagg tgttatagta acagatgata cttttatttt tggaaagtcc aagtttgctt    1080
ccttggtctg ttgcaagggc aaaagtggat aagaaaccag gtcgcaaagc atgctctgga    1140
gcattgtcat ttgccacttt aataacaggt actccatctc tatctgacac aacaatggca    1200
tggagcccct caacacttgg taactttta tacaagaatc gctttaggtc atccgccatg     1260
atgaaccccc ttctctcgca ggatcaatct ccacgcctgg ggtttctggg ctgcctggtt    1320
ctctccgctg tcacttcagg gacagcttta aagacaggtt cctcctcaag ccaccgtcac    1380
atgattcatg acctcgtctg cgctccag                                       1408

<210> SEQ ID NO 50
<211> LENGTH: 1813
<212> TYPE: DNA
<213> ORGANISM: Homo sapiens

<400> SEQUENCE: 50
catggtgggg cacgagatgg cctctractc ttcwaacact tcactgccat tctcaaacat      60
gggaaatcca atgaacacca cacagttagg gaaatcactt tttcagtggc aggtggagca     120
ggaagaaagc aaattggcaa atatttccca agaccagttt ctttcaaagg atgcagatgg     180
tgacacgttc cttcatattg ctgttgccca agggagaagg gcactttcct atgttcttgc     240
aagaaagatg aatgcacttc acatgctgga tattaaagag cacaatggac agagtgcctt     300
tcaggtggca gtggctgcca atcagcatct cattgtgcag gatctggtga acatcggggc     360
acaggtgaac accacagact gctggggaag aacacctctg catgtgtgtg ctgagaaggg     420
ccactcccag gtgcttcagg cgattcagaa gggagcagtg gaagtaatca gtttgtgga     480 tcttgaggca actaactatg atggcctgac tcccttcac tgtgcagtca tagcccacaa      540
tgctgtggtc catgaactcc agagaaatca acagcctcat tcacctgaag ttcaggagct     600
tttactgaag aataagagtc tggttgatac cattaagtgc ctaattcaaa tgggagcagc    660
ggtggaagcg aaggatcgca aaagtggccg cacagccctg catttggcag ctgaagaagc    720
aaatctggaa ctcattcgcc tcttttgga gctgcccagt tgcctgtctt ttgtgaatgc     780
aaaggcttac aatggcaaca ctgccctcca tgttgctgcc agcttgcagt atcggttgac    840
acaattagat gctgtccgcc tgttgatgag gaagggagca gacccaagta ctcggaactt    900
ggagaacgaa cagccagtgc atttggttcc cgatggccct gtgggagaac agatccgacg    960
tatcctgaag gggaaagtcca ttcagcagag agctccaccg tattagctcc attagcttgg  1020
agcctggcta gcaacactca ctgtcagtta ggcagtcctg atgtatctgt acatagacca    1080
tttgccttat attggcaaat gtaagttgtt tctatgaaac aaacatattt agttcactat     1140
tatatagtgg gttatattaa agaaaagaa raaaaatatc taattwctct ggcagatt      1200 gcatatttca tacccaggta tctggatcta gacatctgaa tttgatctca atggtaacat    1260
tgccttcaat taacagtagc ttttgagtag gaaaggactt tgatttgtgg cacaaaacat    1320
tattaatata gctattgaca gtttcaaagc aggtaaattg taaatgtttc tttaagaaaa    1380
agcatgtgaa aggaaaaagg taaatacagc attgaggctt catttggcct tagtccctgg    1440
gagttactgg cgttggacag gcttcagtca ttggactaga tgaaaggtgt ccatggttag    1500
aatttgatct ttgcaaactg tatataattg ttatttttgt ccttaaaaat attgtacata    1560
cttggttgtt aacatggtca tatttgaaat gtataagtcc ataaaataga aagaacaag    1620 tgaattgttg ctatttaaaa aaattttaca attcttacta aggagttttt attgtgtaat    1680
```

| | |
|---|---|
| cactaagtct tgtagataa agcagatggg gagttacgga gttgttcctt tactggctga | 1740 |
| aagatatatt cgaattgtaa agatgctttt yctcatgcat tgaaattata cattatttgt | 1800 |
| agggaattgc atg | 1813 |

<210> SEQ ID NO 51
<211> LENGTH: 2070
<212> TYPE: DNA
<213> ORGANISM: Homo sapiens

<400> SEQUENCE: 51

| | |
|---|---|
| ccacgcgtcc ggaagagcgc ggcacttccg ctggccgctg gctcgctggc cgctcctgga | 60 |
| ggcggcggcg ggagcgcagg gggcgcgcgg cccggggact cgcattcccc ggttcccccct | 120 |
| ccacccacg cggcctggac catggacgcc agatggtggg cagtggtggt gctggctgcg | 180 |
| ttcccctccc taggggcagg tggggagact cccgaagccc ctccggagtc atggacccag | 240 |
| ctatggttct tccgatttgt ggtgaatgct gctggctatg ccagctttat ggtaccaggc | 300 |
| tacctcctgg tgcagtactt caggcggaag aactacctgg agaccggtag ggcctctgc | 360 |
| tttcccctgg tgaaagcttg tgtgtttggc aatgagccca aggcctctga tgaggttccc | 420 |
| ctggcgcccc gaacagaggc ggcagagacc accccgatgt ggcaggccct gaagctgctc | 480 |
| ttctgtgcca cagggctcca ggtgtcttat ctgacttggg gtgtgctgca ggaaagagtg | 540 |
| atgacccgca gctatggggc cacagccaca tcaccgggtg agcgctttac ggactcgcag | 600 |
| ttcctggtgc taatgaaccg agtgctggca ctgattgtgg ctggcctctc ctgtgttctc | 660 |
| tgcaagcagc cccggcatgg ggcacccatg taccggtact cctttttgcca gcctgtccaa | 720 |
| tgtgcttagc agctggtgcc aatacgaagc tcttaagttc gtcagcttcc ccacccaggt | 780 |
| gctggccaag gcctctaagg tgatccctgt catgctgatg ggaaagcttg tgtctcggcg | 840 |
| cagtaacgaa cactgggagt acctgacagc caccctcatc tccattgggg tcagcatgtt | 900 |
| tctgctatcc agcggaccag agccccgcag ctccccagcc accacactct caggcctcat | 960 |
| cttactggca ggttatattg cttttgaaca gcttcacctc aaactggcag gatgccctgt | 1020 |
| ttgcctataa gatgtcatcg gtgcagatga tgtttggggg tcaatttctt ctcctgcctc | 1080 |
| ttcacagtgg gctcactgct agaaacaggg ggccctactg gagggaaccc gcttcatggg | 1140 |
| gcgacacagt gagtttgctg cccatgccct gctactctcc atctgctccg catgtggcca | 1200 |
| gctcttcatc ttttacacca ttgggcagtt tggggctgcc gtcttcacca tcatcatgac | 1260 |
| cctccgccag gcctttgcca tccttctttc ctgccttctc tatggccaca ctgtcactgt | 1320 |
| ggtgggaggg ctgggggtgg ctgtggtctt tgctgccctc ctgctcagag tctacgcgcg | 1380 |
| gggccgtcta agcaacggg gaaagaaggc tgtgcctgtt gagtctcctg tgcagaaggt | 1440 |
| ttgagggtgg aaagggcctg aggggtgaag tgaaataggca ccctcccacc atccccttct | 1500 |
| gctgtaacct ctgagggagc tggctgaaag ggcaaaatgc aggtgttttc tcagtatcac | 1560 |
| agaccagctc tgcagcaggg gattggggag cccaggaggc agccttccct tttgccttaa | 1620 |
| gtcacccatc ttccagtaag cagtttattc tgagccccgg gggtagacag tcctcagtga | 1680 |
| ggggttttgg ggagtttggg gtcaagagag cataggtagg ttccacagtt actcttccca | 1740 |
| caagttccct taagtcttgc cctagctgtg ctctgccacc ttccagactc actcccctct | 1800 |
| gcaaatacct gcatttctta ccctggtgag aaaagcacaa gcggtgtagg ctccaatgct | 1860 |
| gctttcccag gagggtgaag atggtgctgt gctgaggaaa ggggatgcag agccctgccc | 1920 |

-continued

| | |
|---|---|
| agcaccacca cctcctatgc tcctggatcc ctaggctctg ttccatgagc ctgttgcagg | 1980 |
| ttttggtact ttagaaatgt aacttttttgc tcttataatt ttattttatt aaattaaatt | 2040 |
| actgcaaaaa aaaaaaaaaa aaaaaaaaaa | 2070 |

<210> SEQ ID NO 52
<211> LENGTH: 1426
<212> TYPE: DNA
<213> ORGANISM: Homo sapiens

<400> SEQUENCE: 52

| | |
|---|---|
| ccctcactaa agggaacaaa agctggagct ccaccgcggt ggcggccgct ctagaactag | 60 |
| tggatccccc gggctgcagg aattcggcac acggatcggc gtccgcagcg ggcggctgct | 120 |
| gagctgcctt gaggtgcagt gttggggatc cagagccatg tcggacctgc tactactggg | 180 |
| cctgattggg ggcctgactc tcttactgct gctgacgctg ctggcctttg ccgggtactc | 240 |
| agggctactg gctggggtgg aagtgagtgc tgggtcaccc ccatccgca acgtcactgt | 300 |
| ggcctacaag ttccacatgg ggctctatgg tgagactggg cggcttttca ctgagagctg | 360 |
| cagcatctct cccaagctcc gctccatcgc tgtctactat gacaaccccc acatggtgcc | 420 |
| ccctgataag tgccgatgtg ccgtgggcag catcctgagt gaaggtgagg aatcgccctc | 480 |
| ccctgagctc atcgacctct accagaaatt tggcttcaag gtgttctcct tcccggaacc | 540 |
| cagccatgtg gtgacagcca cctttcccct aacaccacca ttctgtccca tctggctggg | 600 |
| ctaccgccg tgtccatcct gccttggaca cctacatcaa ggagcggaag ctgtgtgcct | 660 |
| atcctcggct ggsgatctac caggaagacc agaatccatt tcatgtgccc actggcacgg | 720 |
| ccagggagac ttctatgtgc ctgagatgaa ggagacagag tggaaatggc gggggcttgt | 780 |
| ggaggccatt gacacccagg tggatggcac aggagctgac acaatgagtg cacgagttc | 840 |
| tgtaagcttg gaagtgagcc ctgcagccg ggagacttca gctgccacac tgtcacctgg | 900 |
| ggcgagcagc cgtggctggg atgacggtga cacccgcagc gagcacagct aacagcgagt | 960 |
| caggtgccag cggctcctct tttgaggagc tggactttgg agggcgaggg gcccttaagg | 1020 |
| ggagtcacgg ctgaccctg ggacttgagc ccctggggga ctaccaagtg gctctgggag | 1080 |
| cccactgccc ctgagaaggg caaggagtaa cccatggcct gcaccctcct gcagtgcagt | 1140 |
| tgctgaggaa ctgagcagac tctccagcag actctccagc cctcttcctc cttcctctgg | 1200 |
| gggahgaggg gttcctgagg gacctgactt ccctgctcc aggcctcttg ctaagccttc | 1260 |
| tcctcactgc cctttaggct cccagggcca gaggagccag ggactatttt ctgcaccagc | 1320 |
| ccccagggct gccgccctg ttgtgtcttt ttttcagact cacagtggag cttccaggac | 1380 |
| ccagaataaa gccaatgatt tacttgttaa aaaaaaaaaa aaaaaa | 1426 |

<210> SEQ ID NO 53
<211> LENGTH: 1720
<212> TYPE: DNA
<213> ORGANISM: Homo sapiens

<400> SEQUENCE: 53

| | |
|---|---|
| ggcacgagtg cggcccccagc ctctcctcac gctcgcgcag tctccgccgc agtctcagct | 60 |
| gcagctgcag gactgagccg tgcacccgga ggagacccccc ggaggaggcg acaaacttcg | 120 |
| cagtgccgcg acccaacccc agccctgggt agcctcagc atgcccagc tgttcctgcc | 180 |
| cctgctggca gccctggtcc tggcccaggc tcctgcagct ttagcagatg ttctggaagg | 240 |
| agacagctca gaggaccgcg cttttcgcgt gcgcatcgcg ggcgacgcgc cactgcaggg | 300 |

```
cgtgctcggc ggcgccctca ccatcccttg ccacgtccac tacctgcggc caccgccgag      360
ccgccgggct gtgctgggct ctccgcgggt caagtggact ttcctgtccc ggggccggga      420
ggcagaagtg ctggtggcgc ggggagtgcg cgtcaaggtg aacgaggcct accggttccg      480
cgtggcactg cctgcgtacc cagcgtcgct caccgacgtc tcccctggcg ctgagcgagc      540
tgcgccccaa cgactcaggt atctatcgct gtgaggtcca gcacggcatc gatgacagca      600
gcgacgctgt ggaggtcaag gtcaaaggta tcccatccag accccacgag aggcctgtta      660
cggagacatg gatggcttcc ccggggtccg gaactatggt gtggtggacc cggatgacct      720
ctatgatgtg tactgttatg ctgaagacct aaatggagaa ctgttcctgg gtgaccctcc      780
agagaagctg acattggagg aagcacgggc gtactgccag gagcggggtg cagagattgc      840
caccacgggc caactgtatg cagcctggga tggtggcctg gaccactgca gcccagggtg      900
gctagctgat ggcagtgtgc gctacccat cgtcacaccc agccagcgct gtggtggggg     960
cttgcctggt gtcaagactc tcttcctctt ccccaaccag actggcttcc ccaataagca     1020
cagccgcttc aacgtctact gcttccgaga ctcggcccca cttctgccat ccctgaggcc     1080
tccaacccag cctccaaccc agctttgatg gactagaggc tatcgtcaca gtgacagaga     1140
ccctggagga actgcagctg cctcaggaag ccacagagag tgaatcccgt ggggccatct     1200
actccatccc catcatggag gacggaggag gtggaagctc cactccagaa gacccagcag     1260
aggcccctag gacgctccta gaatttgaaa cacaatccat ggtaccgccc acggggttct     1320
cagaagagga aggtaaggca ttggaggaag aagagaaata tgaagatgaa gaagagaaag     1380
aggaggaaga agaagaggag gaggtggagg atgaggctct gtgggcatgg cccagcgagc     1440
tcagcagccc gggccctgag gcctctctcc ccactgagcc agcagcccag gaggagtcac     1500
tctcccaggc gccagcaagg gcagtcctgc agcctggtgc atcaccactt cctgatggag     1560
agtcagaagc ttccaggcct ccaagggtcc atggaccacc tactgagact ctgcccactc     1620
ccagggagag gaacctagca tcccatcac cttccactct ggttgaggca agagaggtgg     1680
gggaggcaac tggtggtcct gagctatctg ggtccctcga                          1720
```

<210> SEQ ID NO 54
<211> LENGTH: 1117
<212> TYPE: DNA
<213> ORGANISM: Homo sapiens

<400> SEQUENCE: 54

```
ggcacgaggc caaacttcgg gcggctgagg cggcggccga ggagcggcgg actccgggcg       60
cggggagtcg aggcatttgc gcctgggctt cggagcgtac ccaggcctg agcctttgaa      120
gcaggaggag gggaggagag agtggggctc ctctatcggg accccctccc catgtggatc     180
tgcccaggcg gcgcggcgg aggaggcgac cgagaagatg cccgccctgc gccccgctct     240
gctgtgggcg ctgctggcgc tctggctgtg ctgcgcgacc cccgcgcatg cattgcagtg     300
tcgagatggc tatgaaccct gtgtaaatga aggaatgtgt gttacctacc acaatggcac     360
aggatactgc aaaggtccag aaggcttctt ggggaatat tgtcaacatc gagacccctg     420
tgagaagaac cgctgccaga atggtgggac ttgtgtggcc caggccatgc tgggaaagc      480
cacgtgccga tgtgcctcag ggtttacagg agaggactgc cagtactcga catctcatcc     540
atgctttgtg tctcgacctt gcctgaatgg cggcacatgc catatgctca gccgggatac     600
ctatgagtgc acctgtcaag tcgggtttac aggtaaggag tgccaatgga ccgatgcctg     660
```

```
cctgtctcat ccctgtgcaa atggaagtac ctgtaccact gtggccaacc atttcctgca    720
aatgcctcac aggcttcaca gggcagaagt gtgagactga tgtcaatgag tgtgacattc    780
caggacactg ccagcatggt ggcacctgcc tcaacctgcc tggttcctac cagtgccagt    840
gccttcaggg cttcacaggc cagtactgtg acagcctgta tgtgccctgt gcaccctcgc    900
cttgtgtcaa tggaggcacc tgtcggcaga ctggtgactt cacttttgag tgcaactgcc    960
ttccagaaac agtgagaaga ggaacagagc tctgggaaag agacagggaa gtctggaatg    1020
gaaaagaaca cgatgagaat tagacactgg aaaatatgta tgtgtggtta ataaagtgct    1080
ttaaactgaa aaaaaaaaaa aaaaaaaaa aaaaaaa                              1117

<210> SEQ ID NO 55
<211> LENGTH: 1903
<212> TYPE: DNA
<213> ORGANISM: Homo sapiens

<400> SEQUENCE: 55
ggcacgagct cggagaggcg gcgcccctga gtaggccagg agcctctctt gcaacttctg     60
ccaccgcggg ccaccgcggc cgcctgatcc cgcagaggaa ggtcgcggcc gtggagcgat    120
gacccgcggc ggtccgggcg ggcgcccggg gctgccacag ccgccgccgc ttctgctgct    180
gctgctgctg ccgctgttgt tagtcaccgc ggagccgccg aaacctgcag gagtctacta    240
tgcaactgca tactgatgc ctgctgaaaa gacagtacaa gtcaaaaatg taatggacaa    300
gaatggggac gcctatggct tttacaataa ctctgtgaaa accacaggct ggggcatcct    360
ggagatcaga gctggctatg gctctcaaac cctgagcaat gagatcatca tgtttgtggc    420 tggcttttg gagggttacc tcattgcccc acacatgaat gaccactaca caaacctcta    480
cccacagctg atcacgaaac cttccatcat ggataaagtg caggatttta tggagaagca    540
agataaggtg gacccggaaa atatcaaag aatacaagac tgattcattt tggagacata    600
caggctatgt gatggcacaa atagatggcc tctatgtagg agcaaagaag agggctatat    660
tagaagggac aaagccaatg accctgttcc agattcagtt cctgaatagt gttggagatc    720
tattggatct gattccctca ctctctccca caaaaacgg cagcctaaag gttttttaaga    780 gatgggacat gggacattgc tccgctctta tcaaggttct tcctggattt gagaacatcc    840
tttttgctca ctcaagctgg tacacgtatg cagccatgct caggatatat aaacactggg    900
acttcaacat catagataaa gataccagca gtagtcgcct ctctttcagc agttacccag    960
ggtttttgga gtctctggat gatttttaca ttcttagcag tggattgata ttgctgcaga   1020
ccacaaacag tgtgtttaat aaaaccctgc taaagcaggt aatacccgag actctcctgt   1080
cctggcaaag agtccgtgtg gccaatatga tggcagatag tggcaagagg tgggcagaca   1140
tcttttcaaa atacaactct ggcacctata caatcaata catggttctg gacctgaaga   1200
aagtaaagct gaaccacagt cttgacaaag gcactctgta cattgtggag caaattccta   1260
catatgtaga atattctgaa caaactgatg ttctacggaa aggatattgg ccctcctaca   1320
atgttccttt ccatgaaaaa atctacaact ggagtggcta tccactgtta gttcagaagc   1380
tgggcttgga ctactcttat gatttagctc cacgagccaa aattttccgg cgtgaccaag   1440
ggaaagtgac tgatacggca tccatgaaat atatcatgcg atacaacaat tataagaagg   1500
atccttacag tagaggtgac ccctgtaata ccatctgctg ccgtgaggac cctgaactca   1560
cctaacccaa gtccttggag gttgttatga cacaaaaggt ggcagatata tacctagcat   1620
ctcagtacac atcctatgcc ataagtggtc ccacagtaca aggtggcctc cctgttttc    1680
```

```
gctgggaccg tttcaacaaa actctacatc agggcatgcc agaggtctac aactttgatt   1740
ttattaccat gaaaccaatt ttgaaacttg atataaaatg aaggagggag atgacggact   1800
agaagactgt aaataagata ccaaaggcac tattttagct atgttttttcc catcagaatt   1860 atgcaataaa atatattaat ttgtcaaaaa aaaaaaaaaa aaa                     1903
```

<210> SEQ ID NO 56
<211> LENGTH: 1869
<212> TYPE: DNA
<213> ORGANISM: Homo sapiens
<220> FEATURE:
<221> NAME/KEY: SITE
<222> LOCATION: (236)
<223> OTHER INFORMATION: n equals a,t,g, or c

<400> SEQUENCE: 56

```
acagcttttc ggggcccgag tcgcacccag cgaagagagc gggcccggga caagctcgaa    60
ctccggccgc ctcgcccttc cccggctccg ctccctctgc cccctcgggg tcgcgcgccc   120
acgatgctgc agggccctgg ctcgctgctg ctgctcttcc tcgcctcgca ctgctgcctg   180
ggctcggcgc gcgggctctt cctctttggc cagcccgact tctcctacaa gcgcancaat   240
tgcaagccca tcccggtcaa cctgcagctg tgccacggca tcgaatacca gaacatgcgg   300
ctgcccaacc tgctgggcca cgagaccatg aaggaggtgc tggagcaggc cggcgcttgg   360
atcccgctgg tcatgaagca gtgccacccg gacaccaaga agttcctgtg ctcgctcttc   420
gcccccgtct gcctcgatga cctagacgag accatccagc catgccactc gctctgcgtg   480
caggtgaagg accgctgcgc cccggtcatg tccgccttcg gyttcccctg gcccgacatg   540
cttgagtgcg accgtttccc ccaggacaac gacctttgca tcccctcgc tagcagcgac   600 cacctcctgc cagccaccga ggaagctcca aaggtatgtg aagcctgcaa aaataaaaat   660
gatgatgaca acgacataat ggaaacgctt tgtaaaaatg attttgcact gaaaataaaa   720
gtgaaggaga taacctacat caaccgagat accaaaatca tcctggagac caagagcaag   780
accatttaca agctgaacgg tgtgtccgaa agggacctga agaaatcggt gctgtggctc   840
aaagacagct tgcagtgcac ctgtgaggag atgaacgaca tcaacgcgcc ctatctggtc   900
atgggacaga aacagggtgg ggagctggtg atcacctcgg tgaagcggtg gcagaagggg   960
cagagagagt tcaagcgcat ctcccgcagc atccgcaagc tgcagtgcta gtcccggcat  1020
cctgatggct ccgacaggcc tgctccagag cacggctgac catttctgct ccgggatctc  1080
agctcccgtt ccccaagcac actcctagct gctccagtct cagcctgggc agcttccccc  1140
tgccttttgc acgtttgcat ccccagcatt tcctgagtta taaggccaca ggagtggata  1200
gctgttttca cctaaaggaa aagcccaccc gaatcttgta gaaatattca aactaataaa  1260
atcatgaata ttttatgaa gtttaaaaat agctcacttt aaagctagtt ttgaataggt  1320
gcaactgtga cttgggtctg gttggttgtt gtttgttgtt ttgagtcagc tgattttcac  1380
ttcccactga ggttgtcata acatgcaaat tgcttcaatt ttctctgtgg cccaaacttg  1440
tgggtcacaa accctgttga gataaagctg gctgttatct caacatcttc atcagctcca  1500
gactgagact cagtgtctaa gtcttacaac aattcatcat tttataccttt caatgggaac  1560 ttaaactgtt acatgtatca cattccagct acaatacttc catttattag aagcacatta  1620
accatttcta tagcatgatt tcttcaagta aaaggcaaaa gatataaatt ttataattga  1680
cttgagtact ttaagccttg tttaaaacat ttcttactta acttttgcaa attaaaccca  1740
```

| ttgtagctta cctgtaatat acatagtagt ttacctttaa aagttgtaaa aatattgctt | 1800 |
| taaccaacac tgtaaatatt tcagataaac attatattct tgtatataaa ctttacatcc | 1860 |
| tgttttacc | 1869 |

<210> SEQ ID NO 57
<211> LENGTH: 1259
<212> TYPE: DNA
<213> ORGANISM: Homo sapiens
<220> FEATURE:
<221> NAME/KEY: SITE
<222> LOCATION: (171)
<223> OTHER INFORMATION: n equals a,t,g, or c
<220> FEATURE:
<221> NAME/KEY: SITE
<222> LOCATION: (251)
<223> OTHER INFORMATION: n equals a,t,g, or c
<220> FEATURE:
<221> NAME/KEY: SITE
<222> LOCATION: (342)
<223> OTHER INFORMATION: n equals a,t,g, or c
<220> FEATURE:
<221> NAME/KEY: SITE
<222> LOCATION: (1186)
<223> OTHER INFORMATION: n equals a,t,g, or c
<220> FEATURE:
<221> NAME/KEY: SITE
<222> LOCATION: (1196)
<223> OTHER INFORMATION: n equals a,t,g, or c

<400> SEQUENCE: 57

| accgtggtcg tgggcggacg gcggctgcag cgyggaggag ctggggtcgc tgtgggtcgc | 60 |
| gaacagagcc cgggacgtgc gcgcttggtg cacgatcctg aagggagct ccgaggggcc | 120 |
| cgggtckcca gggctgctgc ggccattccc ggagcccggc gcggggcccg nragatactg | 180 |
| gtttaggccg tcccagggct ccgggcgcac ccgktggccg ctgctgcagc ggagggagcg | 240 |
| cggcggcgsg ngggctcgga gacagcgttt ctcccggaat cttcctcggg cagcargtgg | 300 |
| gaagtgggag ccggagcggc actggcarcg ttctctccgc angtcggcac catgcgccct | 360 |
| gcagccctgc gcggggccct gctgggctgc ctctgcctgg cgttgctttg cctgggcggt | 420 |
| gcggacaagc gcctgcgtga caaccatgag tggaaaaaac taattatggt tcagcactgg | 480 |
| cctgagacag tatgcgagaa aattcaaaac gactgtagag accctccgga ttactggaca | 540 |
| atacatggac tatgcccga taaaagtgaa ggatgtaata gatcgtggcc cttcaattta | 600 |
| gaagagatta aggatctttt gccagaaatg agggcatact ggcctgacgt aattcactcg | 660 |
| tttcccaatc gcagccgctt ctggaagcat gagtgggaaa agcatgggac ctgcgccgcc | 720 |
| caggtggatg cgctcaactc ccagaagaag tactttggca gaagcctgga actctacagg | 780 |
| gagctggacc tcaacagtgt gcttctaaaa ttggggataa aaccatccat caattactac | 840 |
| caagttgcag attttaaaga tgcccttgcc agagtatatg gagtgatacc caaaatccag | 900 |
| tgccttccac caagccagga tgaggaagta cagacaattg gtcagataga actgtgcctc | 960 |
| actaagcaag accagcagct gcaaaactgc accgagccgg gggagcagcc gtcccccaag | 1020 |
| caggaagtct ggctggcaaa tgggggccgcc gagagccggg gtctgagagt ctgtgaagat | 1080 |
| ggcccagtct tctatccccc acctaaaaag accaagcatt gatgcccaag ttttggaaat | 1140 |
| attctgtttt aaaagcaag agaaattcac aaactgcagc tttctnaaaa aaaaanaaaa | 1200 |
| aaaaattggg gggttttttt gggsgcccg gggcccttgg tttttccccc cggggggt | 1259 |

<210> SEQ ID NO 58
<211> LENGTH: 1186

<212> TYPE: DNA
<213> ORGANISM: Homo sapiens

<400> SEQUENCE: 58

| | | | | | |
|---|---|---|---|---|---|
| cggcatggag | aatggctccg | cttctgttgc | agctggcggt | gctcggcgcg | gcgctggcgg | 60 |
| ccgcagccct | cgtactgatt | tccatcgttg | catttacaac | tgctacaaaa | atgccagcac | 120 |
| tccatcgaca | tgaagaagag | aaattcttct | taaatgccaa | aggccagaaa | gaaactttac | 180 |
| ccagcatatg | ggactcacct | accaaacaac | tttctgtcgt | tgtgccttca | tacaatgaag | 240 |
| aaaaacggtt | gcctgtgatg | atggatgaag | ctctgagcta | tctagagaag | agacagaaac | 300 |
| gagatcctgc | gttcacttat | gaagtgatag | tagttgatga | tggcagtaaa | gatcagacct | 360 |
| caaaggtagc | ttttaaatat | tgccagaaat | atggaagtga | caaagtacgt | gtgataaccc | 420 |
| tggtgaagaa | tcgtggaaaa | ggtggagcga | ttagaatggg | tatattcagt | tctcgaggag | 480 |
| aaaagatcct | tatggcagat | gctgatggag | ccacaaagtt | tccagatgtt | gagaaattag | 540 |
| aaaagggct | aaatgatcta | cagccttggc | ctaatcaaat | ggctatagca | tgtggatctc | 600 |
| gagctcattt | agaaaaagaa | tcaattgctc | agcgttctta | cttccgtact | cttctcatgt | 660 |
| atgggttcca | ctttctggtg | tggttccttt | gtgtcaaagg | aatcagggac | acacagtgtg | 720 |
| ggttcaaatt | atttactcga | gaagcagctt | cacgacgt | ttcatctcta | cacgttgaac | 780 |
| gatgggcatt | tgatgtagaa | ctactgtaca | tagcacagtt | ctttaaaatt | ccaatagcag | 840 |
| aaattgctgt | caactggaca | gaaattgaag | gttctaaatt | agttccattc | tggagctggc | 900 |
| tacaaatggg | taaagaccta | cttttatac | gacttcgata | tttgactggt | gcctggaggc | 960 |
| ttgagcaaac | tcggaaaatg | aattaggttg | tttgcagtct | tcagttgtgt | tcttatgctt | 1020 |
| cagtgtcaca | tttcatttca | tttgaaacta | aattttaag | taaagctgaa | ataaacttct | 1080 |
| tgtcattgtc | tgccttttga | taattttaaa | gaaataactt | tccataagta | aaaaattata | 1140 |
| tatctctttg | gatataaatg | attttaaaa | gatgtttatt | taaaaa | | 1186 |

<210> SEQ ID NO 59
<211> LENGTH: 428
<212> TYPE: DNA
<213> ORGANISM: Homo sapiens
<220> FEATURE:
<221> NAME/KEY: SITE
<222> LOCATION: (351)
<223> OTHER INFORMATION: n equals a,t,g, or c
<220> FEATURE:
<221> NAME/KEY: SITE
<222> LOCATION: (401)
<223> OTHER INFORMATION: n equals a,t,g, or c

<400> SEQUENCE: 59

| | | | | | |
|---|---|---|---|---|---|
| gatcccccgg | ctgcaggatt | cggcacgagt | actgattctt | cactgagctt | kgttagtata | 60 |
| agcagagttc | caagtctccc | ctagggttgt | ctctacattt | ctttatcatt | ccagtgggta | 120 |
| rggtttagct | gggggaagga | catttcataa | gggttagttg | gactgagcag | tatggacatt | 180 |
| tgcttttttc | attacgtact | gttgtttttc | cttgttaggt | gtgctttggt | ggttttaata | 240 |
| ttattgtgcc | agggatgggg | aaatgggggg | ggttgtgtgg | gaagagtact | tattattgtg | 300 |
| ttttcttcag | tgtaattgtt | cttggtaatt | gatacctctc | tgttttattt | ntctcattct | 360 |
| ttcaaaataa | aacttttga | aatttgaaaa | aaaaaaaaa | naaaaactc | ggggggggc | 420 |
| ccggtacc | | | | | | 428 |

<210> SEQ ID NO 60

<211> LENGTH: 501
<212> TYPE: DNA
<213> ORGANISM: Homo sapiens

<400> SEQUENCE: 60

```
ggcacgagct ttcagcaggg gacagcccga ttggggacaa tggcgtctct tggccacatc      60
ttggttttct gtgtgggtct cctcaccatg gccaaggcag aaagtccaaa ggaacacgac     120
ccgttcactt acgactacca gtccctgcag atcggaggcc tcgtcatcgc cgggatcctc     180
ttcatcctgg gcatcctcat cgtgctgagc agaagatgcc ggtgcaagtt caaccagcag     240
cagaggactg gggaacccga tgaagaggag ggaactttcc gcagctccat ccgccgtctg     300
tccacccgca ggcggtagaa acacctggag cgatggaatc cggccaggac tcccctggca     360
cctgacatct cccacgctcc aactgcgcgc ccaccgcccc ctccgccgcc ccttccccag     420
ccctgcccccc gcagactccc cctgccgcca agacttccaa taaaacgtgc gttcctctcg     480
aaaaaaaaaa aaataaaaaa a                                                501
```

<210> SEQ ID NO 61
<211> LENGTH: 1197
<212> TYPE: DNA
<213> ORGANISM: Homo sapiens
<220> FEATURE:
<221> NAME/KEY: SITE
<222> LOCATION: (10)
<223> OTHER INFORMATION: n equals a,t,g, or c
<220> FEATURE:
<221> NAME/KEY: SITE
<222> LOCATION: (28)
<223> OTHER INFORMATION: n equals a,t,g, or c
<220> FEATURE:
<221> NAME/KEY: SITE
<222> LOCATION: (944)
<223> OTHER INFORMATION: n equals a,t,g, or c

<400> SEQUENCE: 61

```
acatgatggn taccaaagaa ttcggcanag ggcgcgcagt gcagcaggtg ctcaatatcg      60
agtgcctgcg ggacttcctg acgccccgc tgctgtccgt gcgcttccgg tacgtgggcg     120
ccccccaggc cctcaccctg aagctcccag tgaccakcaa caagttcttc cagcccaccg     180
agatggcggc ccaggatttc ttccagcgct ggaagcagct gagcctccct caacaggagg     240
cgcagaaaat cttcaaagcc aaccacccca tggacgcaga agttactaag gccaagcttc     300
tggggtttgg ctctgctctc ctggacaatg tggaccccaa ccctgagaac ttcgtggggg     360
cggggatcat ccagactaaa gccctgcagg tgggctgtct gcttcggctg gagcccaatg     420
cccaggccca gatgtaccgg ctgaccctgc gcaccagcaa ggagcccgtc tcccgtcacc     480
tgtgtgagct gctggcacag cagttctgag ccctggactc tgccccgggg gatgtggccg     540
gcactgggca gccccttgga ctgaggcagt tttggtggat gggggacctc cactggtgac     600
agagaagaca ccagggtttg ggggatgcct ggactttcc tccggccttt tgtattttta     660
tttttgttca tctgctgctg tttacattct ggggggttag ggggagtccc cctccctccc     720
tttccccccc aagcacagag gggagagggg ccagggaagt ggatgtctcc tcccctccca     780
ccccaccctg ttgtagcccc tcctacccccc tcccatcca gggctgtgt attattgtga     840
gcgaataaac agagagacgc taacagcccc atgtctgtgt ccatcaccca ctgttaggta     900
gtcaaagaag tggggtgagg gcatgcagag tgtgggtggc cagnttcgca gcccatgggt     960
gggactctgg ggagacagca gcagcagcag ccgccgaagc cccagctgca aggccaccag    1020
acgcactcct gtgcctggtt cctyagtccc caacaccagg tagcaagcty tgggcagctg    1080
```

```
ggcctggtag acctcatctt ctgtcttcty tggtggccct ggctctggtg ggaagtgcgt    1140
ggaggtgacc agggtataga agtttcggag ctgattggaa gaggattaac ttcccgc      1197
```

<210> SEQ ID NO 62
<211> LENGTH: 595
<212> TYPE: DNA
<213> ORGANISM: Homo sapiens
<220> FEATURE:
<221> NAME/KEY: SITE
<222> LOCATION: (4)
<223> OTHER INFORMATION: n equals a,t,g, or c
<220> FEATURE:
<221> NAME/KEY: SITE
<222> LOCATION: (6)
<223> OTHER INFORMATION: n equals a,t,g, or c
<220> FEATURE:
<221> NAME/KEY: SITE
<222> LOCATION: (76)
<223> OTHER INFORMATION: n equals a,t,g, or c

<400> SEQUENCE: 62

```
attnangack tkyagcctyt watacmatca ttatagggar aagctggtac gcctgmargt     60
accggtcygg aattcncggg tcgacccacg cgtccggcac agcgggagtt ggttctgaca    120
ccagatgttc tctgctcctg gttaatgtca gtgagggctg gaagttgaat aaatgagaac    180
aggagtggtc tgggcccatg taaatgatcc tcccttgaaa ggaggaacag ctttcatcat    240
ttgttccagc taagccttgc atgcattata gatctggtgc taagcagtgg gaaagatctc    300
ataagtaatg ttttatgttc tttctgtctc tcctcttctg twgttcttgg cttgtgggtt    360
gtgtttgtgt gttaactgga aaattgctat aagccagttg tctctaagtt ttaaaaacga    420
attagaaaaa ccataaaatc tctggcctat gcacattgtc cctgttttgt gaaaacatta    480
aagggtaaat aaaaggaag gagaacagtc aataatgtgc atcaaatata ttctgagttc    540
tagagaaatt aatgaccaag cattagaact agaagcaaaa aaaaaaaaaa aaaaa         595
```

<210> SEQ ID NO 63
<211> LENGTH: 1478
<212> TYPE: DNA
<213> ORGANISM: Homo sapiens
<220> FEATURE:
<221> NAME/KEY: SITE
<222> LOCATION: (300)
<223> OTHER INFORMATION: n equals a,t,g, or c
<220> FEATURE:
<221> NAME/KEY: SITE
<222> LOCATION: (1464)
<223> OTHER INFORMATION: n equals a,t,g, or c

<400> SEQUENCE: 63

```
cggcgctgag gacgcacgga tgccttccgt gccttccatc aagatctcaa ttttgtgcgc     60
aagttcctac agcccctgtt gattggagag ctggctccgg aagaacccag ccaggatgga    120
cccctgaatg cgcatggtcg aggacttccg agccctgcac caggcagccg aggacatgaa    180
gctgtttgat gccagtccca ccttctttgc tttcctactg ggccacatcc tggccatgga    240
ggtgctggcc tggctcctta tctacctcct gggtcctggc tgggtgccca gtgccctggn    300
ccgccttcat cctggccatc tctcaggctc agtcctggtc tctgcagcat gacctgggcc    360
atgctccatc ttcaagaagw cctggtggaa ccacgtggcc cagaagttcg tgatggggca    420
gctaaagggc ttctccgccc actggtgaaa cttccgccac ttccagcacc acgccaagcc    480
caacatcttc cacaaagacc cagacgtgac ggtggcgccc gtcttcctcc tgggggagtc    540
```

-continued

| | |
|---|---|
| atccgtcgag tatggcaaga agaaacgcag atacctaccc tacaaccagc agcacctgta | 600 |
| cttcttcctg atcggcccgc cgctgctcac cctggtgaac tttgaagtgg aaaatctggc | 660 |
| gtacatgctg gtgtgcatgc agtgggcgga tttgctctgg gccgccagct tctatgcccg | 720 |
| cttcttctta tcctacctcc ccttctacgg cgtccctggg gtgctgctct tctttgttgc | 780 |
| tgtcagggtc ctggaaagcc actggttcgt gtggatcaca cagatgaacc acatccccaa | 840 |
| ggagatcggc cacgagaagc accgggactg ggtcagctct cagctggcag ccacctgcaa | 900 |
| cgtggagccc tcacttttca ccaactggtt cagcgggcac ctcaacttcc agatcgagca | 960 |
| ccacctcttc cccaggatgc cgagacacaa ctacagccgg gtggcccgc tggtcaagtc | 1020 |
| gctgtgtgcc aagcacggcc tcagctacga atgaagccct tcctcaccgc gctggtggac | 1080 |
| atcgtcaggt ccctgaagaa gtctggtgac atctggctgg acgcctacct ccatcagtga | 1140 |
| aggcaacacc caggcgggca gagaagggct cagggcacca gcaaccaagc cagccccgg | 1200 |
| cgggatcgat acccccaccc ctccactggc cagcctgggg gtgccctgcc tgccctcctg | 1260 |
| gtactgttgt cttcccctcg gcccctcac atgtgtattc agcagcccta tggccttggc | 1320 |
| tctgggcctg atgggacagg ggtagaggga aggtgagcat agcacatttt cctagagcga | 1380 |
| gaattggggg aaagctgtta tttttatatt aaaatacatt cagatgtaaa aaaaaaaaa | 1440 |
| aaaaactcga gggggggccc cggnaaccaa ttcgccct | 1478 |

<210> SEQ ID NO 64
<211> LENGTH: 2033
<212> TYPE: DNA
<213> ORGANISM: Homo sapiens

<400> SEQUENCE: 64

| | |
|---|---|
| ggcacgagga agaacgcaaa gctgagaaca tggacgttaa tatcgcccca ctccgcgcct | 60 |
| gggacgattt cttcccgggt tccgatcgct ttgcccggcc ggacttcagg gacatttcca | 120 |
| aatggaacaa ccgcgtagtg agcaacctgc tctattacca gaccaactac ctggtggtgg | 180 |
| ctgccatgat gatttccatt gtggggtttc tgagtccctt caacatgatc ctgggaggaa | 240 |
| tcgtggtggt gctggtgttc acagggtttg tgtgggcagc ccacaataaa gacgtccttc | 300 |
| gccggatgaa gaagcgctac cccacgacgt tcgttatggt ggtcatgttg gcgagctatt | 360 |
| tccttatctc catgtttgga ggagtcatgg tctttgtgtt tggcattact tttcctttgc | 420 |
| tgttgatgtt tatccatgca tcgttagaga ttcggaacct caagaacaaa ctggagaata | 480 |
| aaatggaagg aataggtttg aagaggacac cgatgggcat tgtcctggat gccctagaac | 540 |
| agcaggaaga aggcatcaac agactcactg actatatcag caaagtgaag gaataaacat | 600 |
| aacttacctg agctagggtt gcagcagaaa ttgagttgca gcttgccctt gtccagacct | 660 |
| atgttctgct tgcgtttttg aaacaggagg tgcacgtacc acccaattat ctatggcagc | 720 |
| atgcatgtat aggccgaact attatcagct ctgatgtttc agagagaaga cctcagaaac | 780 |
| cgaaagaaaa ccaccaccct cctattgtgt ctgaagtttc acgtgtgttt atgaaatcta | 840 |
| atgggaaatg gatcacacga tttctttaag ggaattaaaa aaaataaaag aattacggct | 900 |
| tttacagcaa caatacgatt atcttatagg aaaaaaaaat cattgtaaag tatcaagaca | 960 |
| atacgagtaa atgaaaaggc tgttaaagta gatgacatca tgtgttagcc tgttcctaat | 1020 |
| cccctagaat tgtaatgtgt gggatataaa ttagttttta ttattctctt aaaaatcaaa | 1080 |
| gatgatctct atcactttgc cacctgtttg atgtgcagtg gaaactggtt aagccagttg | 1140 |
| ttcatacttc ctttacaaat ataagatag ctgtttagga tattttgtta cattttgta | 1200 |

```
aatttttgaa atgctagtaa tgtgttttca ccagcaagta tttgttgcaa acttaatgtc    1260
attttcctta agatggttac agctatgtaa cctgtattat tctggacgga cttattaaaa    1320
tacaaacaga caaaaaataa aacaaaactt gagttctatt taccttgcac attttttgtt    1380
gttacagtga aaaaaatggt ccaagaaaat gtttgccatt tttgcattgt ttcgttttta    1440
actggaacat ttagaaagaa ggaaatgaat gtgcatttta ttaattcctt aggggcacaa    1500
ggaggacaat aatagctgat cttttgaaat ttgaaaaacg tctttagatg accaagcaaa    1560
aagctttaaa aaatggtaat gaaaatgaaa tgcagctact gcagctaata aaaaatttta    1620
gatagcaatt gttacaacca tatgccttta tagctagaca ttagaattat gatagcatga    1680
gtttatacat tctattattt ttcctccctt tctcatgttt ttataaatag gtaataaaaa    1740
atgttttgcc tgccaattga atgatttcgt agctgaagta gaaacattta ggtttctgta    1800
gcattaaatt gtgaagacaa ctggagtggt acttactgaa gaaactctct gtatgtccta    1860
gaataagaag caatgatgtg ctgcttctga tttttcttgc attttaaatt ctcagccaac    1920
ctacagccat gatctttagc acagtgatat caccatgact tcacagacat ggtctagaat    1980
ctgtacccTt acccacatat gaagaataaa attgattaaa ggttaaaaaa aaa           2033
```

<210> SEQ ID NO 65
<211> LENGTH: 440
<212> TYPE: DNA
<213> ORGANISM: Homo sapiens
<220> FEATURE:
<221> NAME/KEY: SITE
<222> LOCATION: (417)
<223> OTHER INFORMATION: n equals a,t,g, or c

<400> SEQUENCE: 65

```
atgtttctta ctagaatact gtgtccaacc tatatagccc taactttcct ggtttacatt     60
gtggccctag tatctgggca gctgtgcatg gagatagcca gaggaaacat ttttttttctt    120 aatgaattgg tgaccacatt ttgttgttct tgcctcctat tatccgtgcc ctatttgcat     180
cctggtttct tctacagtag tttatgtaaa tgttgttttg tccttgtcgt tctcagtaga     240
attggttctg taaacgaaac ctggtcctgt aatttcagta tatgctcata tctcatcttt     300
ggctctccca ttttcacagc agtgatccct aaaagatgtg ccctagagga tatccagaac     360
aatccaattg gatgtcttct ccgctgcact ccagcctggg agacagaggg agactcnatc     420
tcaaaaaaaa ttaaaaaaaa                                                440
```

<210> SEQ ID NO 66
<211> LENGTH: 3301
<212> TYPE: DNA
<213> ORGANISM: Homo sapiens
<220> FEATURE:
<221> NAME/KEY: SITE
<222> LOCATION: (20)
<223> OTHER INFORMATION: n equals a,t,g, or c
<220> FEATURE:
<221> NAME/KEY: SITE
<222> LOCATION: (21)
<223> OTHER INFORMATION: n equals a,t,g, or c
<220> FEATURE:
<221> NAME/KEY: SITE
<222> LOCATION: (231)
<223> OTHER INFORMATION: n equals a,t,g, or c
<220> FEATURE:
<221> NAME/KEY: SITE
<222> LOCATION: (1021)
<223> OTHER INFORMATION: n equals a,t,g, or c
<220> FEATURE:

<220> FEATURE:
<221> NAME/KEY: SITE
<222> LOCATION: (1041)
<223> OTHER INFORMATION: n equals a,t,g, or c
<220> FEATURE:
<221> NAME/KEY: SITE
<222> LOCATION: (1630)
<223> OTHER INFORMATION: n equals a,t,g, or c
<220> FEATURE:
<221> NAME/KEY: SITE
<222> LOCATION: (3004)
<223> OTHER INFORMATION: n equals a,t,g, or c

<400> SEQUENCE: 66

| | |
|---|---|
| ggtcataagg ggagggttgn ngtgtgtccc tccaggttgt gcagagggga ttagaagtaa | 60 |
| gtaggttaga ggggaggtgg agggagtgtg ctggggtgtg agcttttatg atgctgaaag | 120 |
| gatcatgata tgctaaggac aggatagtgt tgggttgtac acacaggtgt aggcaatcct | 180 |
| ggtggctagt atgtaaaagt gaatgtcctg actcccttag agggtacctg ncagagtgcc | 240 |
| cttggargga ctagtgctgg agaaattaat aggagagggg acgggcatcc attaacctttt | 300 |
| tcttgcctgc agcctgtagg gtccagcgtc aaagcgaatc atgggtcca gggctgagct | 360 |
| gtgcactctc ttaggcggat tctccttcct cctgctactg ataccaggcg aggggggccaa | 420 |
| gggtggatcc ctcagagaga gtcagggagt ctgctccaag cagacactgg tggtcccgct | 480 |
| ccactacaac gagtcctaca gccaaccagt gtacaagccc tacctgacct tgtgcgctgg | 540 |
| gagcgcatct gcagcactta caggaccatg taccgcgtta tgtggcggga ggtgaggcgg | 600 |
| gaggttcagc agacccatgc agtgtgctgc cagggctgga agaagcggca ccgggggcg | 660 |
| ctcacctgtg aagccatctg cgccaagcct tgcctgaacg gaggcgtctg cgttaggcct | 720 |
| gaccagtgcg agtgcgcccc cggctgggga gggaagcact gtcatgtgga cgtggatgaa | 780 |
| tgtaggacca gcatcaccct ctgctcgcac cattgtttta atacggcarg cagcttcamc | 840 |
| tgcggctgcc ccatgaccta gtgctaggcg tggacgggcg cacctgcatg gaggggtccc | 900 |
| cagagccccc aaccagtgcc agcatactca gcgtggccst tcgggargcg gaaaaagatg | 960 |
| acgcgctctg aagcaggaga ttcacgagct gcgaggccct tgaagcggct ggagcagtgg | 1020 |
| nccggtcagc tgggccctgg ntcagacggt gctgcccgtg ccgcctgaag wgctgcagcc | 1080 |
| agaacaggtg gctgagctgt ggggccgggg tgaccggatc gaatctctca gcgaccaggt | 1140 |
| gctgctgctg gaggagaggc taggtgcctg ctcctgtgag acaacagcc tgggcctcgg | 1200 |
| cgtcaatcat cgataagaag cctctacagc accctgccc cctaatttat acagaaaccg | 1260 |
| gacccactaa tcctctggga ttggccgact gtgagctgca gataaggcta tcagccacca | 1320 |
| aagagcaatg aacaatggaa acttcagaga gctgaagaaa gggggaggcc tgtgttcttg | 1380 |
| gcctgcccct gagtcttctg gctggggca ggttgcctgg caagaactg cttcttcaat | 1440 |
| tccttaacaa atgcaaccac caacacccag atctctctct ctctttattt tcagttttt | 1500 |
| tgctgttatc cagataatta ataaaaacca accacgcaaa actgggtccc accctctcct | 1560 |
| tttgctccca gcctacctcc ccagttgtgg aacaggtct ggagtgagag cagggagtg | 1620 |
| gctaatgccn ccaggaagaa atgaaaactg gctcagagag ggggaagcct caacagaaaa | 1680 |
| agaaataaat taaagccct cctatcccct ccagccaggg ttcgttcctt tccccaactc | 1740 |
| cccagggggc agaagtgagt gcagcacctg atgtctgctt cttccccttg tgtctggtga | 1800 |
| gatggtgcag cagggctgca ggggctgggg tggggtcatg tccactgaag aactgtacta | 1860 |
| tggggacaga aaaccagaaa tgtggagact gaactggtat cccagagagt gcacgaccct | 1920 |
| gggcatctgg gcaagggcag gcatgagacc tctgaattag aagggtccag cccccactga | 1980 |

```
caggaggcta cactgggagg gaaggtgaag gtgctgagga aagctcccat gatgagcctg    2040
ggagtgcttc aggtatcagc ttccagccag agggcgagaa gtcctcctca caaatggatg    2100
agtccattga atccatggac tttggagtgg gggggatttg ttccaaagaa tggatgagtc    2160
cactggccaa tgtggggtag aggggtagag aagaccacat aggaagagac tccactgggg    2220
atggaatgtt cccctccctt gtgtaggctg agtcactgga gatgaggggg aggcaactgt    2280
cccacagaca aracagtagg aggtgggggt caagagtgga gactgcaccg aggcaagagt    2340
ccatggatgg ggccaagagg gggcaggagt ggcgctgtat ccacatttca cttcagaagt    2400
tgaagattcc aaagaggaga ataagtgggg agagggagga caaggaagag ggtttkgccc    2460
tgcttcaggg cccactgggt gggtaggtgt ggggaggaag atgggacag atgggaggag     2520 agctcagagc cagggttcac ccaccgcccc caggcttctt cagatagtca ccaccacccc    2580
ggccatcagt ggagatttcc cggaaaacag tgaagcatgg agtgccggac tctgtcagcc    2640
agagctggga cgtcatctgg tgtcagccct tccgtgggca ctgggggcag cacccgcacc    2700
tgacattgtc ccgaggtgaa gcgacgctcc ttcttgcagt agaagtcttg gtaggaggac    2760
atgactatgg ggacaatggg aacctgggcc tgcactgcaa gatggaaggc gccacgtttg    2820
aagggcagca tggagccatt gtggtttctc gttccctcag gaaacaccca gaccytcacg    2880
tcctgggtga gcagggtctg ggcgacctca gacatgacac tgatggcatc ccccgtgcgc    2940
ttccggtcga tgaagatgac tcctgccagc agcaggcca gccgcagag ccagcccaca     3000 gtantcgcgc ttggcaatgg gcacacagcg gcctggcagt acctccatca tcccaagcag    3060
atcgagagag ctctggtggt tggagacaac aacataggc tgcagggag ggaagtggtg      3120 agcccctcgc acctccactc ggatcccgta caggtatttg atgtggagca gcattagacg    3180
caagatcttc atgttctcga cgttgcgtcc tcgcacggca cacacaggga tggcgagcac    3240
agccaggaag aggatccagc cattgtagaa ggccatcttg aagaagtact tggcactggg    3300
g                                                                    3301

<210> SEQ ID NO 67
<211> LENGTH: 1535
<212> TYPE: DNA
<213> ORGANISM: Homo sapiens

<400> SEQUENCE: 67
ggcacgaggt caagcgaaag gatttcaagg aacagatcat ccaccatgtg ttcaccatca    60
ttctcatcag cttttcctgg tttgccaatt acatccgagc tgggactcta atcatggctc   120
tgcatggact cttccgatta cctgctggag tcagccaaga tgtttaacta cgcgggatgg   180
aagaacacct gcaacaacat cttcatcgtc ttcgccattg ttttttatcat cacccgactg   240 gtcatcctgc cctctggat cctgcattgc acccctggtgt acccactgga gctctatcct   300
gccttctttg gctattactt cttcaattcc atgatgggag ttctacagct gctgcatatc   360 ttctggggcct acctcatttt gcgcatggcc cacaagttca taactggaaa gctggtagaa   420
gatgaacgca gtaccgggaa gaaacagaga gctcagaggg ggaggaggct gcagctgggg   480
gaggagcaaa gagccggccc ctagccaatg gccaccccat cctcaataac aaccatcgta   540
agaatgactg aaccattatt ccagctgcct cccagattaa tgcataaagc caaggaacta   600
ccccgctccc tgcgctatag ggtcacttta agctctgggg aaaaaggaga aagtgagagg   660
agagttctct gcatcctccc tccttgcttg tcacccagtt gcctttaaac caaattctaa   720
```

| | |
|---|---|
| ccagcctatc cccaggtagg gggacgttgg ttatattctg ttagaggggg acggtcgtat | 780 |
| tttcctccct acccgccaag tcatcctttc tactgctttt gaggccctcc ctcagctctc | 840 |
| tgtgggtagg ggttacaatt cacattcctt attctgagaa tttggcccca gctgtttgcc | 900 |
| tttgactccc tgacctccag agccaggggtt gtgccttatt gtcccatctg tgggcctcat | 960 |
| tctgccaaag ctggaccaag ctaacctttc taagctccc taacttgggc cagaaaccaa | 1020 |
| agctgagctt ttaactttct ccctctatga cacaaatgaa ttgagggtag gaggagggtg | 1080 |
| cacataaccc ttaccctacc tctgccaaaa agtgggggct gtactgggga ctgctcggat | 1140 |
| gatctttctt agtgctactt ctttcagctg tccctgtagc gacaggtcta agatctgact | 1200 |
| gcctcctcct ttctctggcc tcttcccct tccctcttct cttcagctag ctagctggt | 1260 |
| ttggagtaga atggcaacta attctaattt ttatttatta aatatttggg gttttggttt | 1320 |
| taaagccaga attacggcta gcacctagca tttcagcaga gggaccattt tagaccaaaa | 1380 |
| tgtactgtta atgggttttt ttttaaaatt aaaagattaa ataaaaaata ttaaataaaa | 1440 |
| catggcaata agtgtcagac tattaggaat tgagaagggg gatcaactaa ataaacgaag | 1500 |
| agagtctttc ttatgcaaaa aaaaaaaaaa aaaaa | 1535 |

<210> SEQ ID NO 68
<211> LENGTH: 1244
<212> TYPE: DNA
<213> ORGANISM: Homo sapiens
<220> FEATURE:
<221> NAME/KEY: SITE
<222> LOCATION: (885)
<223> OTHER INFORMATION: n equals a,t,g, or c
<220> FEATURE:
<221> NAME/KEY: SITE
<222> LOCATION: (1239)
<223> OTHER INFORMATION: n equals a,t,g, or c
<220> FEATURE:
<221> NAME/KEY: SITE
<222> LOCATION: (1242)
<223> OTHER INFORMATION: n equals a,t,g, or c
<220> FEATURE:
<221> NAME/KEY: SITE
<222> LOCATION: (1243)
<223> OTHER INFORMATION: n equals a,t,g, or c

<400> SEQUENCE: 68

| | |
|---|---|
| gggcacccac cagcggcgcc gacctcagcg cgcacctatg ggctcgctac caggacatgc | 60 |
| ggagactggt gcacgacctc ctgccccccg aggtctgcag tctcctgaac ccagcagcca | 120 |
| tctacgccaa caacgagatc agcctgcgtg acgttgaggt ctacggcttt gactacgact | 180 |
| acaccctggc ccagtatgca gacgcactgc accccgagat cttcagtacc gcccgtgaca | 240 |
| tcctgatcga gcactacaag tacccagaag ggattcggaa gtatgactac aaccccagct | 300 |
| ttgccatccg tggcctccac tatgacattc agaagagcct tctgatgaag attgacgcct | 360 |
| tccactacgt gcagctgggg acagcctaca ggggcctcca gcctgtgcca gacgaggagg | 420 |
| tgattgagct gtatggggt acccagcaca tcccactata ccagatgagt ggcttctatg | 480 |
| gcaagggtcc ctccattaag cagttcatgg acatcttctc gctaccggag atggctctgc | 540 |
| tgtcctgtgt ggtggactac tttctgggcc acagcctgga gtttgaccaa gcacatctct | 600 |
| acaaggacgt gacggacgcc atccgagacg tgcatgtgaa gggcctcatg taccagtgga | 660 |
| tcgagcagga catggagaag tacatcctga gagggatga acgtttgct gtcctgagcc | 720 |
| gcctggtggc ccatgggaaa cagctgttcc tcatcaccaa cagtccttc agcttcgtag | 780 |
| acaagggggat gcggcacatg gtgggtcccg attggcgcca ctcttcgatg tggtcattgt | 840 |

-continued

| | |
|---|---|
| ccaggcagac aagcccagct tcttcactga ccggcgcaag ctttncagaa aactcgatga | 900 |
| gaagggctca cttcagtggg accggatcac ccgcttggaa aagggcaaga tctatcggca | 960 |
| gggaaacctg tttgacttct tacgcttgac ggaatggcgt ggccccgcg tgctctactt | 1020 |
| cggggaccac ctctatagtg atctggcgga tctcatgctg cggcacggct ggcgcacagg | 1080 |
| cgccatcatc cccgagctgg agcgtgagat ccgcatcatc aacacggagc agtacatgca | 1140 |
| ctcgctkacg tggcagcagg cgctcacggg gctkctkgag cgcatkcaga cctatcagga | 1200 |
| cgcggagttg aggcaggtct tgcttccttg atgaaaganc gnnt | 1244 |

<210> SEQ ID NO 69
<211> LENGTH: 1292
<212> TYPE: DNA
<213> ORGANISM: Homo sapiens

<400> SEQUENCE: 69

| | |
|---|---|
| ggcacgagca gcgacgcgac tctggtgcgg gccgtcttct tcccccgag ctgggcgtgc | 60 |
| gcggccgcaa tgaactggga gctgctgctg tggctgctgg tgctgtgcgc gctgctcctg | 120 |
| ctcttggtgc agctgctgcg cttcctgagg gctgacggcg acctgacgct actatgggcc | 180 |
| gagtggcagg gacgacgccc agaatgggag ctgactgata tggtggtgtg ggtgactgga | 240 |
| gcctcgagtg gaattggtga ggagctggct taccagttgt ctaaactagg agtttctctt | 300 |
| gtgctgtcag ccagaagagt gcatgagctg aaaggtgtga aaagaagatg cctagagaat | 360 |
| ggcaatttaa agaaaaaga tatacttgtt ttgccccttg acctgaccga cactggttcc | 420 |
| catgaagcgg ctaccaaagc tgttctccag gagtttggta gaatcgacat tctggtcaac | 480 |
| aatggtggaa tgtcccagcg ttctctgtgc atggatacca gcttggatgt ctacagaaag | 540 |
| ctaatagagc ttaactactt agggacggtg tccttgacaa aatgtgttct gcctcacatg | 600 |
| atcgagagga agcaaggaaa gattgttact gtgaatagca tcctgggtat catatctgta | 660 |
| cctctttcca ttggatactg tgctagcaag catgctctcc ggggttttttt taatggcctt | 720 |
| cgaacagaac ttgccacata cccaggtata atagtttcta acatttgccc aggacctgtg | 780 |
| caatcaaata ttgtggagaa ttccctagct ggagaagtca caaagactat aggcaataat | 840 |
| ggagaccagt cccacaagat gacaaccagt cgttgtgtgc ggctgatgtt aatcagcatg | 900 |
| gccaatgatt tgaaagaagt ttggatctca gaacaacctt tcttgtttag taacatattt | 960 |
| gtggcaatac atgccaacct gggcctggtg gataaccaac aagatgggga agaaaaggat | 1020 |
| tgagaacttt aagagtggtg tggatgcaga ctcttcttat tttaaaatct ttaagacaaa | 1080 |
| acatgactga aaagagcacc tgtacttttc aagccactgg agggagaaat ggaaaacatg | 1140 |
| aaaacagcaa tcttcttatg cttctgaata atcaaagact aatttgtgat tttacttttt | 1200 |
| aatagatatg actttgcttc caacatggaa tgaaataaaa aataaataat aaagattgc | 1260 |
| catgaatctt gcaaaaaaaa aaaaaaaaa aa | 1292 |

<210> SEQ ID NO 70
<211> LENGTH: 1031
<212> TYPE: DNA
<213> ORGANISM: Homo sapiens
<220> FEATURE:
<221> NAME/KEY: SITE
<222> LOCATION: (980)
<223> OTHER INFORMATION: n equals a,t,g, or c

<400> SEQUENCE: 70

| | |
|---|---|
| gggctgttgc ttttgaacag aaccctatat tactctcctg ggatctgagt ttctgcaggt | 60 |
| catttgtatg taggaccagg agtatctcct caggtgacca gtttttgggga cccgtatgtg | 120 |
| gcaaattcta agctgccata ttgaacatca tcccactggg agtggttatg ttgtatcccc | 180 |
| atcttggctg gcttcagttt ttgctgtagc cctagagcac tttgtttgtg ggaggctggc | 240 |
| ctcttgccta cctccttgca tggacagggg gatgaatatt tactttccca cctccttgct | 300 |
| ttttcttca ctgataccac tgaatggaac tggtgctgtg actcctgctg ctggggattt | 360 |
| atgtcccgag accttagcct ggctgagtgg agcctgagac ctgcacaaca gctcatggtc | 420 |
| atgcatgara gagaagtggc tggccacagc agagggaaca gtaacagccc aggggccttt | 480 |
| attttgggaa aggctgtccg gggctgttac tgtctcttct ggttataaag cagacatgtg | 540 |
| gccatctttt ccgcaggtta gagtgggctc ctttctttt ggaatccttt tcttctcctt | 600 |
| tggtagcagc tccctgcctc cagggcttcc gccaccagcg tctctgctgt gttgcgcagt | 660 |
| gcagtggggt gcaagggctt tgtttctgcc tgcctgaaag agagggctct ggggatggag | 720 |
| atgagaaaca acacgctctc cttcagacaa tgaggcattc tgtcctcctg ctgccattct | 780 |
| tcatctccac tgagagccag agctggtagg agccgagtgc acaggcatt ctgcattgct | 840 |
| ctactcttag gtttgtgtgt gtgatccttc ccctccctgt cgcccactcc tccctcctct | 900 |
| ggctatccta ccctgtctgt gggctctttt actaccagcc tatgctgtgg gactgtcatg | 960 |
| gcatttagtt cagagtggan gggctttggs ctgaaataaa atgcaagtat ttaaaaaaaa | 1020 |
| aaaaaaaaaa a | 1031 |

<210> SEQ ID NO 71
<211> LENGTH: 855
<212> TYPE: DNA
<213> ORGANISM: Homo sapiens
<220> FEATURE:
<221> NAME/KEY: SITE
<222> LOCATION: (852)
<223> OTHER INFORMATION: n equals a,t,g, or c
<220> FEATURE:
<221> NAME/KEY: SITE
<222> LOCATION: (854)
<223> OTHER INFORMATION: n equals a,t,g, or c
<220> FEATURE:
<221> NAME/KEY: SITE
<222> LOCATION: (855)
<223> OTHER INFORMATION: n equals a,t,g, or c

<400> SEQUENCE: 71

| | |
|---|---|
| agctattgac acttcctggt gggatccgag tgaggcgacg gggtaggggt tggcgctcag | 60 |
| gcggcgacca tggcgtatca cggcctcact gtgcctctca ttgtgatgag cgtgttctgg | 120 |
| ggcttcgtcg gcttcttggt gccttggttc atccctaagg gtcctaaccg gggagttatc | 180 |
| attaccatgt tggtgacctg ttcagtttgc tgctatctct tttggctgat tgcaattctg | 240 |
| gcccaactca accctctctt tggaccgcaa ttgaaaaatg aaaccatctg gtatctgaag | 300 |
| tatcattggc cttgaggaag aagacatgct ctacagtgct cagtctttga ggtcacgaga | 360 |
| agagaatgcc ttctagatgc aaaatcacct ccaaaccaga ccactttct tgacttgcct | 420 |
| gttttggcca ttagctgcct taaacgttaa cagcacattt gaatgcctta ttctacaatg | 480 |
| cagcgtgttt tcctttgcct tttttgcact ttggtgaatt acgtgcctcc ataacctgaa | 540 |
| ctgtgccgac tccacaaaac gattatgtac tcttctgaga tagaagatgc tgttcttctg | 600 |
| agagatacgt tactctctcc ttggaatctg tggatttgaa gatggctcct gccttctcac | 660 |
| gtgggaatca gtgaagtgtt tagaaactgc tgcaagacaa acaagactcc agtgggtgg | 720 |

| | |
|---|---:|
| tcagtaggag agcacgttca gagggaagag ccatctcaac agaatcgcac caaactatac | 780 |
| tttcaggatg aatttcttct ttctgccatc ttttggaata aatattttcc tcctttctaw | 840 |
| rraaaaaaaa anann | 855 |

<210> SEQ ID NO 72
<211> LENGTH: 1274
<212> TYPE: DNA
<213> ORGANISM: Homo sapiens

<400> SEQUENCE: 72

| | |
|---|---:|
| ggcagagctt agagtgtgga aaaggcaacc aggttggccg taagtgcctg ctggaatgcg | 60 |
| tgtgcctcca cacgggtctg ggcatccgga ctgataacca gccggccaga ctgagggatg | 120 |
| gaaggcactg agatggggc ccgtccaggc ggacacccgc agaaatggag ctttctgtgg | 180 |
| tctcttgcac tctggctgcc tcttgccctc tctgtgtctc tctttcttgg tctctccctc | 240 |
| tctcctcctc agcctggtct ttctcttttgg tgcacactta gttattgttg tgagcaatgg | 300 |
| aagttcaaag gaactccctc tccagctctt ctgaatcttg gacacagcc taaaaggac | 360 |
| aaaaagttag aagacagcat agcaactcag ctcaggagc taccagagaa aaatagcaac | 420 |
| tgatgtgggt gcttttttttt tttttttaat ttgaataaaa agaattagaa gtgatgtcct | 480 |
| tttataaaat gccttctccc ccttcccgcc tacagtctct tcctctcccc ttagagggg | 540 |
| gaaagtgtat aaacctacag ggttgtgagt ctgaaaagag gatcccctc accccaccc | 600 |
| tgggcagagc agtgggggtt gggggtgggg agaggggac acagatcctg gcacactgtg | 660 |
| gatatttctt gcagattgca gtctcttgtg gcccaaacag gttaggtaga ctatcgcctc | 720 |
| tggcaggtgc caccttttgg taccaacatg ttctgaggtg ttaggatttg ggttgggttt | 780 |
| tttttgtttg tttttttttt ccttttggtc tttttttttt tctccttta aagaaaagct | 840 |
| aaaggccgct gtgagtcctg gtggcaggct ctccatggat gtagcatatc gaagataatt | 900 |
| tttatactgc attttatgg attattttgt aatgtgtgat tccgtctgct gaggaggtgg | 960 |
| gaggggctcc agggaaagcc acccaccttc agtgaggttg ctccccagct gagcgcaccg | 1020 |
| ggcatgggat gtggaggctg cgacacacc ctgtgcctct ccaaggctgg gcgcgtgggg | 1080 |
| cgtccagagt ctctctgggt tcagatgtc catctgccac ctcttgttaa ggctctagcc | 1140 |
| agaagggagg gtgagggtag aagaaagtta ttcccgaaga aaaaaagaat gaaaagtcat | 1200 |
| tgtactgaac tgttttata tttttaaaag ttactattwa aaggtaaaaa aagggggggg | 1260 |
| cccggtaccc aatt | 1274 |

<210> SEQ ID NO 73
<211> LENGTH: 688
<212> TYPE: DNA
<213> ORGANISM: Homo sapiens

<400> SEQUENCE: 73

| | |
|---|---:|
| ggcacgagtg gaggcaatgc cagctccagg acagaggctc aggtgcccaa cgggcaaggc | 60 |
| agcccagggg gctgtgtctg ttcaagtcag gcttccccgg ccctcgcgca cagcgcttcc | 120 |
| acgggcagcc cggggcccca ccccacgcac tgaagaggcc gcctgggctg ccatggccct | 180 |
| gaccttcctg ctggtgctgc tcaccctggc cacgtctgca cacggctgca cagaaacttc | 240 |
| cgacgcgggg agagcatcta ctgggggccc acagcggaca gccaggacac agtggctgct | 300 |
| gtgctgaagc ggaggctgct gcagccctcg cgccgggtca gcgctcgcg ccggagaccc | 360 |

-continued

```
ctctcccgcc cacgccggac agcggcccgg aaggcgagag ctcggagtga cggcctggga    420
cctgccactg tggcgtgcgg ctcctcccg cgccgcgagg ccgcgacctc tgccacgtgg     480
accgcgcgcg gggcgctccc tggtggcgat ggcgcggcac tggccgagca ctgcgggggc    540
tttcctcctt gttggttgct gagtgggcgg ccaaggggag aaaaggagcc gcttctgcct    600
cccttgccaa aactccgttt ctaattaaat tattttagt agaaaaaaaa aaaaaaaaa     660 aaaaaaaaaa aaaaaaaaa aaaaaaaa                                        688
```

<210> SEQ ID NO 74
<211> LENGTH: 1890
<212> TYPE: DNA
<213> ORGANISM: Homo sapiens
<220> FEATURE:
<221> NAME/KEY: SITE
<222> LOCATION: (1876)
<223> OTHER INFORMATION: n equals a,t,g, or c

<400> SEQUENCE: 74

```
gagcaggaga gaaggcaccg ccccaccccg cctccaaagc taaccctcgg gcttgagggg    60
aagaggctga ctgtacgttc cttctactct ggcaccactc tccaggctgc catggggccc    120
agcacccctc tcctcatctt gttccttttg tcatggtcgg gacccctcca aggacagcag    180
caccaccttg tggagtacat ggaacgccga ctagctgctt tagaggaacg gctggcccag    240
tgccaggacc agagtagtcg gcatgctgct gagctgcggg acttcaagaa caagatgctg    300
ccactgctga aggtggcaga gaaggagcgg gaggcactca gaactgaggc cgacaccatc    360
tccgggagag tggatcgtct ggagcggag gtagactatc tggagaccca gaacccagct    420
ctgccctgtg tagagtttga tgagaaggtg actggaggcc ctgggaccaa aggcaaggga    480
agaaggaatg agaagtacga tatggtgaca gactgtggct acacaatctc tcaagtgaga    540
tcaatgaaga ttctgaagcg atttggtggc cagctggtc tatggaccaa ggatccactg    600
gggcaaacag agaagatcta cgtgttagat gggacacaga atgacacagc ctttgtcttc    660
ccaaggctgc gtgacttcac ccttgccatg gctgcccgga agcttcccg agtccgggtg    720 cccttcccct gggtaggcac agggcagctg gtatatggtg gctttcttta ttttgctcgg    780
aggcctcctg gaagacctgg tggaggtggt gagatggaga cactttgca gctaatcaaa    840 ttccacctgg caaaccgaac agtggtggac agctcagtat cccagcaga ggggctgatc    900 ccccctacg gcttgacagc agacacctac atcgacctgg cagctgatga ggaaggtctt    960
tgggctgtct atgccacccg ggaggatgac aggcacttgt gtctggccaa gttagatcca    1020
cagacactga acacagagca gcagtgggac acaccatgtc ccagagagaa tgctgaggct    1080
gcctttgtca tctgtgggac cctctatgtc gtctataaca cccgtcctgc cagtcgggcc    1140
cgcatccagt gctccttga tgccagcgga ccctgacccc tgaacgggca gcactccctt    1200
attttccccg cagatatggt gcccatgcca gcctccgcta taaccccga gaacgccagc    1260 tctatgcctg ggatgatggc taccagattg tctataagct ggagatgagg aagaagaggg    1320
aggaggtttg aggagctagc cttgtttttt gcatctttct cactcccata catttatatt    1380
atatccccac taaatttctt gttcctcatt cttcaaatgt gggccagttg tggctcaaat    1440
cctctatatt tttagccaat ggcaatcaaa ttctttcagc tcctttgttt catacggaac    1500
tccagatcct gagtaatcct tttagagccc gaagagtcaa aaccctcaat gttccctcct    1560
gctctcctgc cccatgtcaa caaatttcag gctaaggatg cccagaccc agggctctaa    1620 ccttgtatgc gggcaggccc agggagcagg cagcagtgtt cttccctca gagtgactgg    1680
```

| | |
|---|---|
| gggagggaga aataggagga gacgtccagc tctgtcctct cttcctcact cctcccttca | 1740 |
| gtgtcctgag gaacaggact ttctccacat tgttttgtat tgcaacattt tgcattaaaa | 1800 |
| ggaaaatcca ctgcaaaaaa aaaaaaaaaa aaaaaaaaaa aaaaaaacgg cacgagggg | 1860 |
| ggtcccgtac ccaatngccc tcacatgcat | 1890 |

<210> SEQ ID NO 75
<211> LENGTH: 1133
<212> TYPE: DNA
<213> ORGANISM: Homo sapiens
<220> FEATURE:
<221> NAME/KEY: SITE
<222> LOCATION: (1110)
<223> OTHER INFORMATION: n equals a,t,g, or c

<400> SEQUENCE: 75

| | |
|---|---|
| gccggtctga gtgcagagct gctgtcatgg cggccgctct gtggggcttc tttcccgtcc | 60 |
| tgctgctgct gctgctatcg ggggatgtcc agagctcgga ggtgcccggg gctgctgctg | 120 |
| agggatcggg agggagtggg gtcggcatag gagatcgctt caagattgag gggcgtgcag | 180 |
| ttgttccagg ggtgaagcct caggactgga tctcggcggc ccgagtgctg gtagacggag | 240 |
| aagagcacgt cggtttcctt aagacagatg ggagttttgt ggttcatgat ataccttctg | 300 |
| gatcttatgt agtggaagtt gtatctccag cttacagatt tgatcccgtt cgagtggata | 360 |
| tcacttcgaa aggaaaaatg agagcaagat atgtgaatta catcaaaaca tcagaggttg | 420 |
| tcagactgcc ctatcctctc caaatgaaat cttcaggtcc accttcttac tttattaaaa | 480 |
| gggaatcgtg gggctggaca gactttctaa tgaacccaat ggttatgatg atggttcttc | 540 |
| ctttattgat atttgtgctt ctgcctaaag tggtcaacac aagtgatcct gacatgagac | 600 |
| gggaaatgga gcagtcaatg aatatgctga attccaacca tgagttgcct gatgtttctg | 660 |
| agttcatgac aagactcttc tcttcaaaat catctggcaa atctagcagc ggcagcagta | 720 |
| aaacaggcaa aagtggggct ggcaaaagga ggtagtcagg ccgtccagag ctggcatttg | 780 |
| cacaaacacg gcaacactgg gtggcatcca agtcttgaa aaccgtgtga agcaactact | 840 |
| ataaacttga gtcatcccga cgttgatctc ttacaactgt gtatgttaac tttttagcac | 900 |
| atgttttgta cttggtacac gagaaaaccc agctttcatc ttttgtctgt atgaggtcaa | 960 |
| tattgatgtc actgaattaa ttacagtgtc ctatagaaaa tgccattaat aaattatatg | 1020 |
| aactactata cattatgtat attaattaaa acatcttaat ccagaaaaaa aaaaaaaaa | 1080 |
| aactcgaggg ggggcccggt acccaatttn ccaaatggga gtcgtaaaaa atc | 1133 |

<210> SEQ ID NO 76
<211> LENGTH: 585
<212> TYPE: DNA
<213> ORGANISM: Homo sapiens

<400> SEQUENCE: 76

| | |
|---|---|
| atgtttacaa tgttgtgtat aaatgggaca actcctcgcc ctctacctgt cccctccccc | 60 |
| tttggttgta tgattttctt cttttttaag aacccctgga agcagcgcct ccttcagggt | 120 |
| tggctgggag ctcggcccat ccacctcttg gggtacctgc ctctctctct cctgtggtgt | 180 |
| cccttccctc tcccatgtgc tcggtgttca gtggtgtata tttcttctcc cagacatggg | 240 |
| gcacacgccc caaggacat gatcctctcc ttagtcttag ctcatggggc tctttataag | 300 |
| gagttggggg gtagaggcag gaaatgggaa ccgagctgaa gcagaggctg agttaggggg | 360 |

```
ctagaggaca gtgctcctgg ccacccagcc tctgctgaga accattcctg ggattagagc    420
tgcctttccc agggaaaaag tgtcgtctcc ccgaccctcc cgtgggccct gtggtgtgat    480
gctgtgtctg tatattctat acaaaggtac ttgtcctttc cctttgtaaa ctacatttga    540
catggattaa accagtataa acagttaaaa aaaaaaaaaa aaaaa                    585
```

<210> SEQ ID NO 77
<211> LENGTH: 577
<212> TYPE: DNA
<213> ORGANISM: Homo sapiens
<220> FEATURE:
<221> NAME/KEY: SITE
<222> LOCATION: (561)
<223> OTHER INFORMATION: n equals a,t,g, or c

<400> SEQUENCE: 77

```
ggcacgaggc cttgcagaac ttctacttgc ctgcctccct gcctctggcc atggcctgcc     60
ggtgcctcag cttccttctg atggggacct tcctgtcagt ttcccagaca gtcctggccc    120
agctggatgc actgctggtc ttcccaggcc aagtggctca actctcctgc acgctcagcc    180
cccagcacgt caccatcagg gactacggtg tgtcctggta ccagcagcgg gcaggcagtg    240
cccctcgata tctcctctac taccgctcgg aggaggatca ccaccggcct gctgacatcc    300
ccgatcgatt ctcggcagcc aaggatgagg cccacaatgc ctgtgtcctc accattagtc    360
ccgtgcagcc tgaagacgac gcggattact actgctctgt tggctacggc tttagtccct    420 agggggtgggg tgtgagatgg gtgcctcccc tctgcctccc atttctgccc ctgaccttgg    480 gtcccttttta aactttctct gagccttgct tcccctctgt aaaatgggtt aataatattc    540
aacatgtcaa caacaaaaaa naaaaawaaa aactcga                             577
```

<210> SEQ ID NO 78
<211> LENGTH: 2278
<212> TYPE: DNA
<213> ORGANISM: Homo sapiens
<220> FEATURE:
<221> NAME/KEY: SITE
<222> LOCATION: (956)
<223> OTHER INFORMATION: n equals a,t,g, or c
<220> FEATURE:
<221> NAME/KEY: SITE
<222> LOCATION: (1062)
<223> OTHER INFORMATION: n equals a,t,g, or c
<220> FEATURE:
<221> NAME/KEY: SITE
<222> LOCATION: (1290)
<223> OTHER INFORMATION: n equals a,t,g, or c
<220> FEATURE:
<221> NAME/KEY: SITE
<222> LOCATION: (1442)
<223> OTHER INFORMATION: n equals a,t,g, or c

<400> SEQUENCE: 78

```
gtaattcggc acgaggcgcc caacatggcg ggtgggcgct gcggcccgca sctaacggcg     60
ctcctggccg cctggatcgc ggctgtggcg gcgacggcag gccccgagga ggccgcgctg    120
ccgccggagc agagccgggt ccagcccatg accgcctcca ctggacgct ggtgatggag     180 ggcgagtgga tgctgaaatt ttacgcccca tggtgtccat cctgccagca gactgattca    240
gaatgggagg cttttgcaaa gaatggtgaa atacttcaga tcagtgtggg gaaggtagat    300
gtcattcaag aaccaggttt gagtggccgc ttctttgtca ccactctccc agcatttttt    360
catgcaaagg atgggatatt ccgccgttat cgtgccccga gaatcttcga agacctgcag    420
aattatatct tagagaagaa atggcaatca gtcgagcctc tgactggctg gaaatccccg    480
```

```
gcttctctaa cgatgtctgg aatggctggt cttttagca tctctggcaa gatatggcat    540
cttcacaact atttcacagt gactcttgga attcctgctt ggtgttctta tgtcttttc    600 gtcatagcca ccttggtttt tggccttttt atgggtctgg tcttggtggt aatatcagaa    660
tgtttctatg tgccacttcc aaggcattta tctgagcgtt ctgagcagaa tcggagatca    720
gaggaggctc atagagctga acagttgcag gatgcgagg aggaaaaaga tgattcaaat    780
gaagaagaaa acaaagacag ccttgtagat gatgaagaag agaaagaaga tcttggcgat    840
gaggatgaag cagaggaaga agaggaggag gacaacttgg ctgctggtgt ggatgaggag    900
agaagtgagg ccaatgatca ggggccccca ggagaggacg tgtgacccg ggaggnaagt    960 agagcctgag gaggctgaag aaggcatctc tgagcaaccc tgcccagctg acacagaggt   1020
ggtggaagac tccttgaggc agcgtaaaag tcagcatgct gncaagggac tgtagattta   1080
atgatgcgtt ttcaagaata cacaccaaaa caatatgtca gcttccctt ggcctgcagt   1140 ttgtaccaaa tccttaattt ttcctgaatg agcaagcttc tcttaaaaga tgctctctag   1200
tcatttggtc tcatggcagt aagcctcatg tatactaagg agagtcttcc aggtgtgaca   1260
atcaggatat agaaaaacaa acgtagtgtn tgggatctgt ttggagactg ggatgggaac   1320
aagttcattt acttagggt cagagagtct cgaccagagg aggccattcc cagtcctaat    1380
cagcaccttc cagagacaag gctgcaggcc ctgtgaaatg aaagccaagc aggagccttg    1440
gntctgaggc atccccaaag tgtaacgtag aagccttgca tccttttctt gtgtaaagta   1500 tttattttg tcaaattgca ggaaacatca ggcaccacag tgcatgaaaa atctttcaca    1560
gctagaaatt gaaagggcct tgggtataga gagcagctca gaagtcatcc cagccctctg    1620
aatctcctgt gctatgtttt atttcttacc tttaatttt ccagcatttc caccatgggc     1680
attcaggctc tccacactct tcactattat ctcttggtca gaggactcca ataacagcca    1740
ggtttacatg aactgtgttt gttcattctg acctaagggg tttagataat cagtaaccat    1800 aaccctgaa gctgtgactg ccaaacatct caaatgaaat gttgtggcca tcagagactc     1860
aaaaggaagt aaggatttta caagacagat taaaaaaaaa ttgttttgtc caaaatatag    1920
ttgttgttga tttttttta agttttctaa gcaatatttt tcaagccaga agtcctctaa    1980
gtcttgccag tacaaggtag tcttgtgaag aaaagttgaa tactgttttg ttttcatctc    2040 aagggttcc ctgggtcttg aactacttta ataataacta aaaaaccact tctgattttc     2100
cttcagtgat gtgcttttgg tgaaagaatt aatgaactcc agtacctgaa agtgaaagat    2160
ttgattttgt ttccatcttc tgtaatcttc caaagaatta tatctttgta aatctctcaa    2220
tactcaatct actgtaagta cccagggagg ctaatttcyt taaaaaaaa aaaaaaaa      2278
```

<210> SEQ ID NO 79
<211> LENGTH: 1143
<212> TYPE: DNA
<213> ORGANISM: Homo sapiens
<220> FEATURE:
<221> NAME/KEY: SITE
<222> LOCATION: (1049)
<223> OTHER INFORMATION: n equals a,t,g, or c
<220> FEATURE:
<221> NAME/KEY: SITE
<222> LOCATION: (1050)
<223> OTHER INFORMATION: n equals a,t,g, or c
<220> FEATURE:
<221> NAME/KEY: SITE
<222> LOCATION: (1051)
<223> OTHER INFORMATION: n equals a,t,g, or c
<220> FEATURE:

-continued

```
<221> NAME/KEY: SITE
<222> LOCATION: (1103)
<223> OTHER INFORMATION: n equals a,t,g, or c
<220> FEATURE:
<221> NAME/KEY: SITE
<222> LOCATION: (1104)
<223> OTHER INFORMATION: n equals a,t,g, or c
<220> FEATURE:
<221> NAME/KEY: SITE
<222> LOCATION: (1110)
<223> OTHER INFORMATION: n equals a,t,g, or c
<220> FEATURE:
<221> NAME/KEY: SITE
<222> LOCATION: (1143)
<223> OTHER INFORMATION: n equals a,t,g, or c

<400> SEQUENCE: 79
cccctccaac tctcaaccca cttctccagc cagcgcccca gccctcccgc cgcccgctcg      60
caggtcccga ggagcgcaga ctgtgtccct gacaatggga acagccgaca gtgatgagat     120
ggccccggag gccccacagc acacccacat cgatgtgcac atccaccagg agtctgccct     180
ggccaagctc ctgctcacct gctgctctgc gctgcggccc cgggccaccc aggccagggg     240
cagcagccgg ctgctggtgg cctcgtgggt gatgcagatc gtgctgggga tcttgagtgc     300
agtcctagga ggatttttct acatccgcga ctacaccctc ctcgtcacct cgggagctgc     360
catctggaca ggggctgtgg ctgtgctggc tggagctgct gccttcattt acgagaaacg     420
gggtggtaca tactgggccc tgctgaggac tctgctagcg ctggcagctt tctccacagc     480
catcgctgcc ctcaaacttt ggaatgaaga tttccgatat ggctactctt attacaacag     540
tgcctgccgc atctccagct cgagtgactg gaacactcca gcccccactc agagtccaga     600
agaagtcaga aggctacacc tatgtacctc cttcatggac atgctgaagg ccttgttcag     660
aacccttcag gccatgctct tgggtgtctg gattctgctg cttctggcat ctctggcccc     720
tctgtggctg tactgctgga gaatgttccc aaccaaaggg aaaagagacc agaaggaaat     780
gttggaagtg agtggaatct agccatgcct ctcctgatta ttagtgcctg gtgcttctgc     840
accgggcgtc cctgcatctg actgctgaaa gaagaaccag actgaggaaa agaggctctt     900
caacagcccc agttatcctg gccccatgac cgtggccaca gccctgctcc agcagcactt     960
gcccattcct tacacccctt ccccatcctg ctccgcttca tgtcccctcc tgagtagtca    1020
tgtgataata aactctcatg ttattgttnn naaaaaaaa aaaaaaaaaa aatttggggg    1080
ggggccggta cccattgggc ctnnggggggn ggtttaaaat taatgggggg ggtttaaaag    1140 ggn                                                                 1143

<210> SEQ ID NO 80
<211> LENGTH: 557
<212> TYPE: DNA
<213> ORGANISM: Homo sapiens
<220> FEATURE:
<221> NAME/KEY: SITE
<222> LOCATION: (553)
<223> OTHER INFORMATION: n equals a,t,g, or c

<400> SEQUENCE: 80
ggcagagagc agatggcctt gacaccagca gggtgacatc cgctattgct acttctctgc      60
tcccccacag ttcctctgga cttctctgga ccacagtcct ctgccagacc cctgccagac     120
cccagtccac catgatccat ctgggtcaca tcctcttcct gcttttgctc ccagtggctg     180
cagctcagac gactccagga gagagatcat cactccctgc cttttaccct ggcacttcag     240
gctcttgttc cggatgtggg tccctctctc tgccgctcct ggcaggcctc gtggctgctg     300
```

```
atgcggtggc atcgctgctc atcgtggggg cggtgttcct gtgcgcacgc ccacgccgca    360
gccccgccca agaagatggc aaagtctaca tcaacatgcc aggcaggggc tgaccctcct    420
gcagcttgga cctttgactt ctgaccctct catcctggat ggtgtgtggt ggcacaggaa    480
cccccgcccc aacttttgga ttgtaataaa acaattgaaa caccaaaaaa aaaaaaaaaa    540
aaaaaaaaaa aantcga                                                   557

<210> SEQ ID NO 81
<211> LENGTH: 795
<212> TYPE: DNA
<213> ORGANISM: Homo sapiens
<220> FEATURE:
<221> NAME/KEY: SITE
<222> LOCATION: (772)
<223> OTHER INFORMATION: n equals a,t,g, or c

<400> SEQUENCE: 81 gccgggcga tgtggagcgc gggccgcggc ggggctgcct ggccggtgct gttggggctg     60
ctgctggcgc tgttagtgcc gggcggtggt gccgccaaga ccggtgcgga ctcgtgacct    120
gcgggtcggt gctgaagctg ctcaatacgc accaccgcgt gcgctgcact cgcacgacat    180
caaatacgga tccggcagcg gccagcaatc ggtgaccggc gtagaggcgt cggacgacgc    240
maatagctac tggcggatcc gcggcggctc ggagggcggg tgcccgcgcg gtccccggt     300 gcgctgcggg caggcggtga ggctcacgca tgtscttacg ggcaagaacy tgcacacgca    360
ccayttcccg tcgccgctgt ccaacaacca ggaggtgagt gcctttgggg aagacggcga    420
gggcgacgac ctggacctat ggacagtgcg ctgctctgga cagcactggg agcgtgaggc    480
tgctgtgcct tccagcatgt gggcacctct gtgttcctgt cagtcacggg tgagcagtat    540
ggaagcccca tccgtgggca gcatgaggtc cacggcatgc ccagtgccaa cacgcacaat    600
acgtggaagg ccatggaagg catcttcatc aagcctagtg tggagccctc tgcaggtcac    660
gatgaactct gagtgtgtgg atggatgggg ggatggaggg tggcaggtgg ggcgtctgca    720
gggccactct tggcagagac tttgggtttg taggggtcct caagtgcctt tntgattaaa    780
gaatgttggt ctatg                                                    795

<210> SEQ ID NO 82
<211> LENGTH: 1324
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c
<220> FEATURE:
<221> NAME/KEY: SITE
<222> LOCATION: (597)
<223> OTHER INFORMATION: n equals a,t,g, or c

<400> SEQUENCE: 82
naggctttaa agcgcctacc ctgcctgcag gtgagcagtg gtgtgtgaga gccaggcgtc     60
cctctgcctg cccactcagt ggcaacaccc gggagctgtt ttgtcctttg tggagcctca    120
gcagttccct ctttcagaac tcactgccaa gagccctgaa caggagccac catgcagtgc    180
ttcagcttca ttaagaccat gatgatcctc ttcaatttgc tcatctttct gtgtggtgca    240
gccctgttgg cagtgggcat ctgggtgtca atcgatgggg catcctttct gaagatcttc    300
gggccactgt cgtccagtgc catgcagttt gtcaacgtgg gctacttcct catcgcagcc    360
```

```
ggcgttgtgg tctttgctct tggtttcctg ggctgctatg gtgctaagac tgagagcaag      420
tgtgccctcg tgacgttctt cttcatcctc ctcctcatct tcattgctga ggttgcagct      480
gctgtggtcg ccttggtgta caccacaatg gctgagcact tcctgacgtt gctggtagtg      540
cctgccatca agaaagatta tggttcccag gaagacttca ctcaagtgtg aacacnacc       600 atgaaagggc tcaagtgctg tggcttcacc aactatacgg attttgagga ctcaccctac      660
ttcaaagaga acagtgcctt tccccccattc tgttgcaatg acaacgtcac caacacagcc     720
aatgaaacct gcaccaagca aaaggctcac gaccaaaaag tagagggttg cttcaatcag      780
cttttgtatg acatccgaac taatgcagtc accgtgggtg gtgtggcagc tggaattggg      840
ggcctcgagc tggctgccat gattgtktcc atgtatctgt actgcaatct acaataagtc      900
cacttctgcc tctgccacta ctgctgccac atgggaactg tgaagaggca ccctggcaag      960
cagcagtgat tgggggaggg gacaggatct aacaatgtca cttgggccag aatggacctg     1020 cccttctgc tccagacttg ggctagata gggaccactc cttttagcga tgcctgactt      1080
tccttccatt ggtgggtgga tgggtgggg gcattccaga gcctctaagg tagccagttc     1140
tgttgcccat tcccccagtc tattaaaccc ttgatatgcc ccctaggcct agtggtgatc     1200
ccagtgctct actgggggat gagagaaagg cattttatag cctgggcata agtgaaatca     1260
gcagagcctc tgggtggatg tgtagaaggc acttcaaaat gcataaacct gttacaatgt     1320
taaa                                                                  1324
```

<210> SEQ ID NO 83
<211> LENGTH: 1494
<212> TYPE: DNA
<213> ORGANISM: Homo sapiens
<220> FEATURE:
<221> NAME/KEY: SITE
<222> LOCATION: (612)
<223> OTHER INFORMATION: n equals a,t,g, or c
<220> FEATURE:
<221> NAME/KEY: SITE
<222> LOCATION: (620)
<223> OTHER INFORMATION: n equals a,t,g, or c

<400> SEQUENCE: 83

```
ctcaggcttc tgtctcactt ttccgggggg gggattaggg caaggagggc atgagggact       60
gtctctccct aaaacccaga cccctgttcc ccactcagtt cttcttcatc ctcctcctca      120
tcttcattgc tgaggttgca gctgctgtgg tcgccttggt gtacaccaca atggtgagac      180
actgggatgg aggaagggaa gaagattggg caaaaccctg ggagtgggct gtggcctgtg      240
aatggccacc ttctgtacca gcccctaaac actggcctgc ctcacccagg ctgagcactt      300
cctgacgttg ctggtagtgc ctgccatcaa gaaagattat ggttcccagg aagacttcac      360
tcaagtgtgg aacaccacca tgaaaggggt aaggttggct ggggagggtt ttagggtgga      420
gagaaagaag caaggcccca cctccaccct catcttgtct ccagctcaag tgctgtggct      480
tcaccaacta tacggatttt gaggactcac cctacttcaa agagaacagt gcctttcccc      540
cattctgttg caatgacaac gtcacccaac acagcccaat gaaacctgca ccaagcaaaa      600
ggctcacsac cnaaaartan aggtgtgggc tggcatgagt gggtggggac tgttttcatg      660
gcctcagagt ggcaaacggg gatgggagta gggcagctgc caactataaa tgctcttttc      720
tcttccygaa gggttgcttc aatcagcttt tgtatgacat ccgaactaat gcagtcaccg      780
tgggtggtgt ggcagctgga attggggggc ctcgaggtaa cagatsagga gctgggactg      840
ggacatgggc atgagaccag ggctgctcaa cccatctgag gcctctctgg aggaaacaga      900
```

| | |
|---|---|
| cttctaactg ggcctcaggt agggtgtctg tgggacaggc ttcaggatcc ctatcatgtt | 960 |
| ccctcatctc tccctgttcc tccctctcca gctggctgcc atgattgtgt ccatgtatct | 1020 |
| gtactgcaat ctacaataag tccacttctg cctctgccac tactgctgcc acatgggaac | 1080 |
| tgtgaagagg caccctggca agcagcagtg attgggggag gggacaggat ctaacaatgt | 1140 |
| cacttgggcc agaatggacc tgcccttcct gctccagact tggggctaga tagggaccac | 1200 |
| tccttttagc gatgcctgac tttccttcca ttggtgggtg gatgggtggg gggcattcca | 1260 |
| gagcctctaa ggtagccagt tctgttgccc attcccccag tctattaaac ccttgatatg | 1320 |
| cccctaggc ctagtggtga tcccagtgct ctactggggg atgagagaaa ggcattttat | 1380 |
| agcctgggca taagtgaaat cagcagagcc tctgggtgga tgtgtagaag gcacttcaaa | 1440 |
| atgcataaac ctgttacaat gttaaaaaaa aaaaaaaaa aactcgactc tgcc | 1494 |

<210> SEQ ID NO 84
<211> LENGTH: 1285
<212> TYPE: DNA
<213> ORGANISM: Homo sapiens
<220> FEATURE:
<221> NAME/KEY: SITE
<222> LOCATION: (644)
<223> OTHER INFORMATION: n equals a,t,g, or c
<220> FEATURE:
<221> NAME/KEY: SITE
<222> LOCATION: (663)
<223> OTHER INFORMATION: n equals a,t,g, or c
<220> FEATURE:
<221> NAME/KEY: SITE
<222> LOCATION: (1280)
<223> OTHER INFORMATION: n equals a,t,g, or c

<400> SEQUENCE: 84

| | |
|---|---|
| gctacgtggc tggcatgcat gggaacgagg ccctggggcg ggagttgctt ctgctcctga | 60 |
| tgcagttcct gtgccatgag ttcctgcgag sgaacccacg ggtgacccgg ctgctctctg | 120 |
| agatgcgcat tcacctgctg ccctccatga accctgatgg ctatgagatc gcctaccacc | 180 |
| ggggttcaga rctggtgggc tgggccgarg ccgctggaa caaccagagc atcgatctta | 240 |
| accataattt tgctgamctc aacacaccac tgtgggaagc acaggacgat gggaaggtgc | 300 |
| cccacatcgt ccccaaccat cacctgccat tgcccactta ctacaccctg cccaatgcca | 360 |
| ccgtggctcc tgaaacgcgg gcagtaatca agtggatgaa gcggatcccc tttgtgctaa | 420 |
| gtgccaacct ccacgggggt gagctcgtgg tgtcctaccc attcgacatg actcgcaccc | 480 |
| cgtgggctgc ccgcgagctc acgcccacac cagatgatgc tgtgtttcgc tggctcagca | 540 |
| ctgtctatgc tggcagtaat ctggccatgc aggacaccag ccgccgaccc tgccacagcc | 600 |
| aggacttctc cgtgcacggc aacatcatca acggggcytg actnggcaca cggtccccgg | 660 |
| gangcatgaa tgayttcagc tacctacaca ccaactgctt tgaggtcact gtggagctgt | 720 |
| sctgtgacaa gttccctcac gagaatgaat tgccccagga gtgggagaac aacaaagacg | 780 |
| ccctcctcac ctacctggag caggtgcgca tgggcattgc aggagtggtg agggacaagg | 840 |
| acacggagct tgggattgct gacgctgtca ttgccgtgga tgggattaac catgacgtga | 900 |
| ccacggcgtg gggcggggat tattggcgtc tgctgacccc aggggactac atggtgactg | 960 |
| ccagtkccga gggctaccat tcagtgacac ggaactgtcg ggtcaccttt gaagagggcc | 1020 |
| ccttcccctg caatttcgtg ctcaccaaga ctcccaaaca gaggctgcgc gagctgctgg | 1080 |
| cagctggggc caaggtgccc ccggaccttc gcaggcgcct ggagcggcta aggggacaga | 1140 |

```
aggattgata cctgcggttt aagagcccta gggcaggctg gacctgtcaa gacgggaagg    1200
ggaagagtag agagggaggg acaaagtgag gaaaaggtgc tcattaaagc taccgggcac    1260
cttaaaaaaa aaaaaaaaan aaaaa                                          1285

<210> SEQ ID NO 85
<211> LENGTH: 394
<212> TYPE: DNA
<213> ORGANISM: Homo sapiens
<220> FEATURE:
<221> NAME/KEY: SITE
<222> LOCATION: (32)
<223> OTHER INFORMATION: n equals a,t,g, or c

<400> SEQUENCE: 85
gcgcgctcta ggaactagtg gatccccgg gnctgcaggt gtggagtggg ccatcgtaaa      60
tagtatctgt gcataaggtg gttgtgcgat aaatgagtta atgtatgcaa agcccttggc    120
ccagagccgg cgcagagcat tgtgtaagts ctggcaggcg tcatgatgga gatatcatgt    180
ctcctcttrt tgattcagga ttctgatgag atggaggatg ggcctggggt tcaggattag    240
gccttgaggc actgctccag cctcctttgt gggccctgtc acccttggct tcatcgggcc    300
gtarcaagtc tcccctctcc cactytgcag cagargtgtt caagaactgc ctgctcacgg    360
ttcgtgttct gcaaggccat cgcctaacct ctaa                                394

<210> SEQ ID NO 86
<211> LENGTH: 1925
<212> TYPE: DNA
<213> ORGANISM: Homo sapiens
<220> FEATURE:
<221> NAME/KEY: SITE
<222> LOCATION: (54)
<223> OTHER INFORMATION: n equals a,t,g, or c

<400> SEQUENCE: 86
agtgaaggga gctggccgtg cgactgggct tcgggccctg tgccagagga gcangccttc     60
ctgagcagga ggaagcaggt ggtggccgcg gccttgaggc aggccctgca gctggatgga    120
gacctgcagg aggatgagat cccagtggta gctattatgg ccactggtgg tgggatccgg    180
gcaatgactt ccctgtatgg gcagctggct ggcctgaagg agctgggcct cttggattgc    240
ktctcctaca tcaccggggc ctcgggctcc acctgggcct tggccaacct ttataaggac    300
ccagagtggt ctcagaagga cctggcaggg cccactgagt tgctgaagac ccaggtgacc    360
aagaacaagc tgggtgtgct ggcccccagc cagctgcagc ggtaccggca ggagctggcc    420
gagcgtgccc gcttgggcta cccaagctgc ttcaccaacc tgtgggccct catcaacgag    480
gcgctgctgc atgatgagcc ccatgatcac aagctctcag atcaacggga ggccctgagt    540
catggccaga accctctgcc catctactgt gccctcaaca ccaaagggca gagcctgacc    600 actttttgaat ttggggagtg gtgcgagttc tctccctacg aggtcggctt ccccaagtac    660
ggggccttca tccctctga gctctttggc tccgagttct ttatgggggca gctgatgaag    720 aggcttcctg agtcccgcat ctgcttctta gaaggtatct ggagcaacct gtatgcagcc    780
aacctccagg acagcttata ctgggcctca gagcccagcc agttctggga ccgctgggtc    840
aggaaccagg ccaacctgga caaggagcag gtccccctc tgaagataga agaaccaccc    900
tcaacagccg gcagaatagc tgagtttttc accgatcttc tgacgtggcg tccactggcc    960
caggccacac ataatttcct gcgtggcctc catttccaca aagactactt tcagcatcct   1020
cacttctcca catggaaagc taccactctg gatgggctcc ccaaccagct gacaccctcg   1080
```

-continued

```
gagccccacc tgtgcctgct ggatgttggc tacctcatca ataccagctg cctgcccctc    1140
ctgcagccca ctcgggacgt ggacctcatc ctgtcattgg actacaacct ccacggagcc    1200
ttccagcagt tgcagctcct gggccggttc tgccaggagc agggatccc gttcccaccc    1260 atctcgccca gccccgaaga gcagctccag cctcgggagt ccacaccctt ctccgacccc    1320
acctgccccg gagccctgc ggtgctgcac tttcctctgg tcagcgactc cttccgggag    1380
tactcggccc ctggggtccg gcggacaccc gaggaggcgg cagctgggga ggtgaacctg    1440
tcttcatcgg actctcccta ccactacacg aaggtgacct acagccagga ggacgtggac    1500
aagctgctgc acctgacaca ttacaatgtc tgcaacaacc aggagcagct gctggaggct    1560
ctgcgccagg cagtgcagcg gaggcggcag cgcaggcccc actgatggcc ggggcccctg    1620 ccaccccta ctctcattca ttccctggct gctgagttgc aggtgggaac tgtcatcacg    1680
cagtgcttca gagcctcggg ctcaggtggc actgtcccag gtccaggct gagggctggg    1740 agctcccttg cgcctcagca gtttgcagtg gggtaaggag gccaagccca tttgtgtaat    1800
cacccaaaac ccccggcct gtgcctgttt tcccttctgc gctaccttga gtagttggag    1860
cacttgatac atcacagact catacaaatg tgaggcgctg agaaaaaaaa aaaaaaaaa    1920 ctcga                                                                  1925
```

<210> SEQ ID NO 87
<211> LENGTH: 1818
<212> TYPE: DNA
<213> ORGANISM: Homo sapiens
<220> FEATURE:
<221> NAME/KEY: SITE
<222> LOCATION: (13)
<223> OTHER INFORMATION: n equals a,t,g, or c
<220> FEATURE:
<221> NAME/KEY: SITE
<222> LOCATION: (16)
<223> OTHER INFORMATION: n equals a,t,g, or c
<220> FEATURE:
<221> NAME/KEY: SITE
<222> LOCATION: (18)
<223> OTHER INFORMATION: n equals a,t,g, or c
<220> FEATURE:
<221> NAME/KEY: SITE
<222> LOCATION: (237)
<223> OTHER INFORMATION: n equals a,t,g, or c

<400> SEQUENCE: 87

```
ccgggccccc ccncgngntt tttttttttt tttttttttk tatgagtctg tratgtatca      60
agtgctccaa ctactcaagg tagcgcagaa gggaaaacag gcacaggccg ggggttttg     120 ggtgattaca caaatgggct tggcctcctt accccactgc aaactgctga ggcgcaaggg    180
agctcccagc cctcagcctg gaccctggga cagtgccacc tgagcccgag gctctgnaag    240
cactgcgtga tgacagttcc cacctgcaac tcagcagcca gggaatgaat gagagttagg    300
ggtggcaggg gccccggcca tcagtgggc ctgcgctgcc gcctccgctg cactgcctgg    360
cgcagagcct ccagcagctg ctcctggttg ttgcagacat tgtaatgtgt caggtgcagc    420
agcttgtcca cgtcctcctg gctgtaggtc accttcgtgt agtggtaggg agagtccgat    480
gaagacaggt tcacctcccc agctgccgcc tcctcgggtg tccgccggac ccaggggcc     540 gagtactccc ggaaggagtc gctgaccaga ggaaagtgca gcaccgcagg ggctccgggg    600
caggtggggt cggagaaggt gtggcactcc cgaggctgga gctgctcttc ggggctgggc    660
gagatgggtg ggaacgggat cccctgctcc tggcagaacc ggcccaggag ctgcaactgc    720
```

```
tggaaggctc cgtggaggtt gtagtccaat gacaggatga ggtccacgtc ccgagtgggc    780
tgcaggaggg gcaggcagct ggtattgatg aggtagccaa catccagcag gcacaggtgg    840
ggctccgagg gtgtcagctg gttggggagc ccatccagag tggtagcttt ccatgtggag    900
aagtgaggat gctgaaagta gtctttgtgg aaatggaggc cacgcaggaa attatgtgtg    960
gcctgggcca gtggacgcca cgtcagaaga tcggtgaaaa actcagctat tctgccggct   1020
gttgagggtg gttcttctat cttcagaagg gggacctgct ccttgtccag gttggcctgg   1080
ttcctgaccc agcggtccca gaactggctg ggctctgagg cccagtataa gctgtcctgg   1140
aggttggctg catacaggtt gctccagata ccttctaaga agcagatgcg ggactcagga   1200
agcctcttca tcagctgccc cataaagaac tcggagccaa agagctcaga ggggatgaag   1260
gccccgtact tggggaagcc gacctcgtag ggagagaact cgcaccactc cccaaattca   1320
aaagtggtca ggctctgccc tttggtgttg agggcacagt agatgggcag agggttctgg   1380
ccatgactca gggcctcccg ttgatctgag agcttgtgat catgggctc atcatgcagc    1440 agcgcctcgt tgatgaggc ccacaggttg gtgaagcagc ttgggtagcc caagcgggca    1500
cgctcggcca gctcctgccg gtaccgctgc agctggctgg gggccagcac acccagcttg   1560
ttcttggtca cctgggtctt cagcaactca gtgggccctg ccaggtcctt ctgagaccac   1620
tctgggtcct yataaaggtt ggccaaggcc caggtggagc ccgaggcccc ggtgatgtag   1680
gagacgcaat ccaagaggcc ccagctcctt tcaggccagc cagctgccca tacagggaag   1740
tcattgcccg gatcccacca ccagtggcca taatagctac cactgggatc tcatcctcct   1800
gcaggtctcc atccagct                                                  1818
```

<210> SEQ ID NO 88
<211> LENGTH: 539
<212> TYPE: DNA
<213> ORGANISM: Homo sapiens
<220> FEATURE:
<221> NAME/KEY: SITE
<222> LOCATION: (395)
<223> OTHER INFORMATION: n equals a,t,g, or c
<220> FEATURE:
<221> NAME/KEY: SITE
<222> LOCATION: (396)
<223> OTHER INFORMATION: n equals a,t,g, or c

<400> SEQUENCE: 88

```
agggtaatta atatgaagtg caaaaagttg aatgttccag tctaaaaggc agtgggagaa     60
attacatagc atggaaataa taaatgaay tcttattaat gagaacgagg ytcttgcagt    120
ggcaagttct gctggtcacc cgatggggat gggagccttt caagcttttt tttgggtaat    180
actcacagtt tccaacgtct gtgtactttt caaaatgagc ttgttcttcc ttctgacact    240
catctcaaag ctccatggtg acgcagaggt ctgttgaagg tcacagggtc ctcgcttgca    300
ttggcatacg gtcctgtagc atcacttgtt agcccactgc tgcttgaagg aactaagagt    360
attcagggat agagagctga aaataggatt aattnnttcc ttttgactct ccctcaaga    420 tgtccttgct ttggtctgaa acctctcct gacaactttt gcccaaagca aaccatctgc     480
cttttctgaa ctctgagtga atatattagc atcttccctt ctgagccctc gtactgcca    539
```

<210> SEQ ID NO 89
<211> LENGTH: 855
<212> TYPE: DNA
<213> ORGANISM: Homo sapiens
<220> FEATURE:
<221> NAME/KEY: SITE

```
<222> LOCATION: (103)
<223> OTHER INFORMATION: n equals a,t,g, or c
<220> FEATURE:
<221> NAME/KEY: SITE
<222> LOCATION: (767)
<223> OTHER INFORMATION: n equals a,t,g, or c
<220> FEATURE:
<221> NAME/KEY: SITE
<222> LOCATION: (831)
<223> OTHER INFORMATION: n equals a,t,g, or c

<400> SEQUENCE: 89
cctctgccca ggccgcaccc gagctcaggc tcgtgcccac ccaccaagtt ccagtgccgc      60
accagtggct tatgcgtgcc cctcacctgg cgctgcgaca ggnacttgga ctgcagcgat     120
ggcagcgatg aggaggagtg caggattgag ccatgtaccc agaaagggca atgcccaccg     180 cccctggcc tccctgccc ctgcaccggc gtcagtgact gctctggggg aactgacaag      240
aaactgcgca actgcagccg cctggcctgc ctagcagcgg agctccgttg cacgctgagc     300
gatgactgca ttccactcac gtggcgctgc gacggccacc cagactgtcc cgactccagc     360
gacgagctcg gctgtggaac caatgagatc ctcccgaag gggatgccac aaccatgggg     420 cccctgtga ccctggagag tgtcacctct ctcaggaatg ccacaaccat ggggcccct      480 gtgaaccctg gagagtgtcc cctctgtcgg aatgccaca tcctcctctg ccggagacca     540
gtctggaagc ccaactgcct atggggttat tgcagctgct gcggtgctca gtgcaagcct     600
ggtcaccgcc accctcctcc ttttgtcctg gctccgagcc caggagcgcc tccgcccact     660
ggggttactg gtgccatga aggagtccct gctgctgtca gaacagaaga cctcgctgcc      720
ctgaggacaa gcacttgcca ccaccgtcac tcagccctgg gcgtacngsa caggaggaga     780
gcagtgatgc ggatgggtac cgggcacacc agcccttcag agacctgagc ncttctggcc     840
actggaactt cgaac                                                       855

<210> SEQ ID NO 90
<211> LENGTH: 628
<212> TYPE: DNA
<213> ORGANISM: Homo sapiens
<220> FEATURE:
<221> NAME/KEY: SITE
<222> LOCATION: (593)
<223> OTHER INFORMATION: n equals a,t,g, or c

<400> SEQUENCE: 90
aaggacgtgc cgtgccgctg ggttctgagc cggagtggtc ggtgggtggg atggaggcga      60
ccttggagca gcacttggaa gacacaatga agaatccctc cattgttgga gtcctgtgca     120
cagattcaca aggacttaat ctgggttgcc gcgggaccct gtcagatgag catgctggag     180
tgatatctgt tctagcccag caagcagcta agctaacctc tgaccccact gatattcctg     240
tggtgtgtct agaatcagat aatgggaaca ttatgatcca gaaacacgat ggcatcacgg     300
tggcagtgca caaatggcc tcttgatgct catatctgtt cttcagcagc ctgtcatagg      360
aactggatcc tacctatgtt aattaccttg tagaactact aaagttccag tagttaggcc     420
attcatttaa tgtgcattag gcacttttct gtttatttaa gagtcaattg ctttctaatg     480
ctctatggac cgactatcaa gatattagta agaaaggatc atgttttgaa gcagcaggtc     540
caggtcactt tgtatataga attttgctgt attcaataaa tctgtttgga ggnaaaaaaa     600
aaaaaaraaa aamtsgaggg ccgaagct                                         628

<210> SEQ ID NO 91
```

```
<211> LENGTH: 1053
<212> TYPE: DNA
<213> ORGANISM: Homo sapiens
<220> FEATURE:
<221> NAME/KEY: SITE
<222> LOCATION: (653)
<223> OTHER INFORMATION: n equals a,t,g, or c
<220> FEATURE:
<221> NAME/KEY: SITE
<222> LOCATION: (1044)
<223> OTHER INFORMATION: n equals a,t,g, or c

<400> SEQUENCE: 91
ctcttttctg cagttcaagg gaaagacgag atcttgcaca aggcactctg cttctgccct      60
tggctgggga agggtggcat ggarcctctc cggctgctca tcttactctt tgtcacagag    120
ctgtccggag cccacaacac cacagtgttc cagggcgtgg cgggccagtc cctgcaggtg    180
tcttgcccct atgactccat gaagcactgg gggaggcgca aggcctggtg ccgccagctg    240
ggagagaagg gcccatgcca gcgtgtggtc agcacgcaca acttgtggct gctgtccttc    300
ctgaggaggt ggaatgggag cacagccatc acagacgata ccctgggtgg cactctcacc    360
attacgctgc ggaatctaca accccatgat gcgggtctct accagtgcca gagcctccat    420
ggcagtgagg ctgacaccct caggaaggtc tggtggagg tgctggcaga ccccctggat    480
caccgggatg ctggagatct ctggttcccc ggggagtctg agagcttcga ggatgcccat    540
gtggagcaca gcatctccag gagcctcttg aaggagaaa tccccttccc acccacttcc    600
atccttctcc tcctggcctg catctttctc atcaagattc tagcagccag cgncctctgg    660
gctgcagcct ggcatggaca gaagccaggg acacatccac ccagtgaact ggactgtggc    720
catgaccag ggtatcagct ccaaactctg ccagggctga gagacacgtg aaggaagatg    780
atgggaggaa aagcccagga gaagtcccac cagggaccag cccagcctgc atacttgcca    840
cttggccacc aggactcctt gttctgctct ggcaagagac tactctgcct gaacactgct    900
tctcctggac cctggaagca gggactggtt gagggagtgg ggaggtggta agaacacctg    960
acaacttctg aatattggac attttaaaca cttacaaata aatccaagac tgtcatattt   1020
aaaaaaaaaa aaaaaaaaa aacncgaggg ggg                                 1053

<210> SEQ ID NO 92
<211> LENGTH: 1075
<212> TYPE: DNA
<213> ORGANISM: Homo sapiens
<220> FEATURE:
<221> NAME/KEY: SITE
<222> LOCATION: (1060)
<223> OTHER INFORMATION: n equals a,t,g, or c
<220> FEATURE:
<221> NAME/KEY: SITE
<222> LOCATION: (1070)
<223> OTHER INFORMATION: n equals a,t,g, or c

<400> SEQUENCE: 92
gcacgagcct gatcctctct tttctgcagt tcaagggaaa gacgagatct tgcacaaggc      60
actctgcttc tgcccttggc tggggaaggg tggcatggag cctctccggc tgctcatctt    120
actctttgtc acagagctgt ccggagccca caacaccaca gtgttccagg gcgtggcggg    180
ccagtccctg caggtgtctt gcccctatga ctccatgaag cactggggga ggcgcaaggc    240
ctggtgccgc cagctgggag agaagggccc atgccagcgt gtggtcagca cgcacaactt    300
gtggctgctg tccttcctga ggaggtggaa tgggagcaca gccatcacag acgataccct    360
gggtggcact ctcaccatta cgctgcggaa tctacaaccc catgatgcgg gtctctacca    420
```

```
gtgccagagc ctccatggca gtgaggctga caccctcagg aagtcctggt ggaggtgct    480 ggcagacccc ctggatcacc gggatgctgg agatctctgg ttccccgggg agtctgagag    540
cttcgaggat gcccatgtgg agcacagcat ctccaggagc ctcttggaag gagaaatccc    600
cttcccaccc acttccatcc ttctcctcct ggcctgcatc tttctcatca agattctagc    660
agccagcgcc ctctgggctg cagcctggca tggacagaag ccaggacaca atccacccag    720
tgaactggac tgtggccatg acccagggta tcagctccaa actctgccag ggctgagaga    780
cacgtgaagg aagatgatgg gaggaaaagc ccaggagaag tcccaccagg gaccagccca    840
gcctgcatac ttgccacttg gccaccagga ctccttgttc tgctctggca agagactact    900
ctgcctgaac actgcttctc ctggaccctg aagcaggga ctggttgagg gagtggggag    960
gtggtaagaa cacctgacaa cttctgaata ttggacatttt taaacactta caaataaatc   1020
caagactgtc atatttaaaa aaaaaaaaaa aaaaaaaacn cgagggggn cccgg          1075
```

<210> SEQ ID NO 93  
<211> LENGTH: 2492  
<212> TYPE: DNA  
<213> ORGANISM: Homo sapiens  
<220> FEATURE:  
<221> NAME/KEY: SITE  
<222> LOCATION: (1976)  
<223> OTHER INFORMATION: n equals a,t,g, or c

<400> SEQUENCE: 93

```
tcccgactca gcttcccacc ctgggctttc cgaggtgctk tcgccgctgt ccccaccact     60
gcagccatga tctccttaac ggacacgcag aaaattggaa tgggattaac aggatttgga    120 gtgttttttcc tgttctttgg aatgattctc ttttttgaca aagcactact ggctattgga    180
aatgttttat ttgtagccgg cttggctttt gtaattggtt tagaaagaac attcagattc    240
ttcttccaaa aacataaaat gaaagctaca ggttttttttc tgggtggtgt atttgtagtc    300
cttattggtt ggccttttgat aggcatgatc ttcgaaattt atggattttt tctcttgttc    360
aggggcttct ttcctgtcgt tgttggcttt attagaagag tgccagtcct tggatccctc    420
ctaaatttac ctggaattag atcatttgta gataaagttg gagaaagcaa caatatggta    480
taacaacaag tgaatttgaa gactcattta aaatattgtg ttatttataa agtcatttga    540
agaatattca gcacaaaatt aaattacatg aaatagcttg taatgttctt tacaggagtt    600
taaaacgtat agcctacaaa gtaccagcag caaattagca aagaagcagt gaaaacaggc    660
ttctactcaa gtgaactaag aagaagtcag caagcaaact gagagaggtg aaatccatgt    720
taatgatgct taagaaactc ttgaaggcta tttgtgttgt ttttccacaa tgtgcgaaac    780
tcagccatcc ttagagaact gtggtgcctg tttcttttct ttttattttg aaggctcagg    840
agcatccata ggcatttgct ttttagaaat gtccactgca atggcaaaaa tatttccagt    900
tgcactgtat ctctggaagt gatgcatgaa ttcgattgga ttgtgtcatt ttaaagtatt    960
aaaaccaagg aaaccccaat tttgatgtat ggattacttt tttttgtaaa catggttaaa   1020
ataaaacttc tgtggttctt ctgaatctta atatttcaaa gccaggtgaa atctgaact    1080 agatattctt tgttggaata tgcaaaggtc attctttact aacttttagt tactaaatta   1140
tagctaagtt ttgtcagcag catactccgg aaagtctcat acttcttggg agtctgccct   1200
cctaagtatc tgtctatatc attcattacg tgtaagtatt taacaaaaaa gcattcttga   1260
ccatgaatga agtagtttgt ttcatagctt gtctcattga atagtattat tgaagatact   1320
```

```
aaatgatgca aaccaaatgg attttttcca tgtcatgatg taatttttct ttcttctttc      1380 tttttttaa attttagcag tggcttatta tttgtttttc ataaattaaa ataacttttg       1440
ataatgttta ctttaagaca tgtaacatgt taaaaggtta aacttatggc tgttttaaa       1500 gggctattca tttaatctga gttttccctt attttcagct ttttcctagc atataatagt      1560
cattaagcat gacatatcct tcatgatc actcatcttg agttaattag aaaatacctg        1620
agttcacgtg ctaaagtcat ttcactgtaa taaactgact rtggtttctt aagaacatga      1680
cactaaaaaa aaagtgggttt ttttccaccg ttgctgatta ttagacagta ggaaatagct     1740
gttttcttta gttttacaag atgtgacagc tttagtggta gatgtaggga aacatttcaa      1800
cagccatagt actatttgtt ttaccactga ttgcactgtt ttgttttttt aacagttgca      1860
aagcttttta atgcataaaa gtataattga aatctgtggt atttatttac aaacatgtct      1920
acaaaaatag attacagctt atttattttt tagttaaatc tcttaataca cagagnaact      1980
cccaatcttg ctcatctaaa taaggaaaga cttggtgtat agtgtgatgg tttagtctta      2040
aggattaaga cattttttggt acttgcattt gacttacgat gtatctgtga aaatgggatg     2100
atattgacaa atggagactc ctacctcaat agttaatgga ataataagag gctactgttg      2160
tgtctaatgt tcttcaaaaa agtaatatcc tcacttggag agtgtcaaat acatactttg      2220
aggattgact ttatataagg tgccctgtag aamtctgtta cacatatttt tgacccatat      2280
tatttacaat gtcttgataa ttctacctttt ttagagcaag aatagtatct gctaatgtaa     2340
gggacatctg tatttaactc ctttgtagac atgaatttct atcaaaatgt tctttgcact      2400
gtaacagaga ttccttttttt caataatctt aattcaaagc attattaggm cttgaaaggg    2460
tttgrtaatc tccccgtcct tggtaaaggt tg                                    2492
```

<210> SEQ ID NO 94
<211> LENGTH: 3058
<212> TYPE: DNA
<213> ORGANISM: Homo sapiens
<220> FEATURE:
<221> NAME/KEY: SITE
<222> LOCATION: (3033)
<223> OTHER INFORMATION: n equals a,t,g, or c
<220> FEATURE:
<221> NAME/KEY: SITE
<222> LOCATION: (3048)
<223> OTHER INFORMATION: n equals a,t,g, or c
<220> FEATURE:
<221> NAME/KEY: SITE
<222> LOCATION: (3056)
<223> OTHER INFORMATION: n equals a,t,g, or c

<400> SEQUENCE: 94

```
accctaaatc aacagacaat ggcattgtcg aagagcaacc tgttaatgaa atcatgttaa       60
aaatcaaggt ttggcttcag tttaaatcac ttgaggtatg aagtttatcc tgttttccag      120
agataaacat aagttgatct tcccaaaata ccatcattag gacctatcac acaatatcac      180
tagttttttt tgtttgtttg tttttttgttt tttttcttgg taaagccatg caccacagac     240
ttctgggcag agctgagaga caatggtcct gacataataa ggatctttga ttaaccccca      300
taaggcatgt gtgtgtatac aaatatactt ctctttggct tttcgacata gaacctcagc      360
tgttaaccaa ggggaaatac atcagatctg caacacagaa atgctctgcc tgaaatttcc      420
accatgccta ggactcaccc catttatcca ggtctttctg gatctgttta atcaataagc      480
cctataatca cttgctaaac actgggcttc atcacccagg gataaaaaca gagatcattg      540
tcttggacct cctgcatcag cctattcaaa attatctctc tctctagctt tccacaaatc      600
```

```
ctaaaattcc tgtcccaagc cacccaaatt ctcagatctt ttctggaaca aggcagaata    660
taaaataaat atacatttag tggcttgggc tatggtctcc aaagatcctt caaaaataca    720
tcaagccagc ttcattcact cactttactt agaacagaga tataagggcc tgggatgcat    780
ttattttatc ataccaatt tttgtggcca tggcagacat tgctaatcaa tcacagcact    840
atttcctatt aagcccactg atttcttcac aatccttctc aaattacaat tccaaagagc    900
cgccactcaa cagtcagatg aacccaacag tcagatgaga gaaatgaacc ctacttgcta    960
tctctatctt agaaagcaaa aacaaacagg agtttccagg gagaatggga aagccagggg   1020
gcataaaagg tacagtcagg ggaaaataga tctaggcaga gtgccttagt cagggaccac   1080
gggcgctgaa tctgcagtgc caacaccaaa ctgacacatc tccaggtgta cctccaaccc   1140
tagccttctc ccacagctgc ctacaacaga gtctcccagc cttctcagag agctaaaacc   1200
agaaatttcc agactcatga aagcaacccc ccagcctctc cccaaccctg ccgcattgtc   1260
taattttag aacactaggc ttcttctttc atgtagttcc tcataagcag gggccagaat   1320
atctcagcca cctgcagtga cattgctgga cccctgaaaa ccattccata ggagaatggg   1380
ttccccaggc tcacagtgta gagacattga gcccatcaca actgttttga ctgctggcag   1440
tctaaaacag tccacccacc ccatggcact gccgcgtgat tcccgcgcca ttcagaagtt   1500
caagccgaga tgctgacgtt gctgagcaas agatggtgag catcagtgca aatgcaccat   1560
tcagcacatc agtcatatgc ccagtgcagt tacaagatgt tgtttcggca aagcattttg   1620
atggaatagg gaactgcaaa tgtatgatga ttttgaaaag gctcagcagg atttgttctt   1680
aaaccgactc agtgtgtcat ccccggttat ttagaattac agttaagaag agaaacttc    1740
tataagactg tatgaacaag gtgatatctt catagtgggc tattacaggc aggaaaatgt   1800
tttaactggt ttacaaaatc catcaatact tgtgtcattc cctgtaaaag gcaggagaca   1860
tgtgattatg atcaggaaac tgcacaaaat tattgttttc agccccgtg ttattgtcct   1920
tttgaactgt ttttttttta ttaaagccaa atttgtgttg tatatattcg tattccatgt   1980
gttagatgga agcatttcct atccagtgtg aataaaaaga acagttgtag taaattatta   2040
taaagccgat gatatttcat ggcaggttat tctaccaagc tgtgcttgtt ggttttccc    2100
atgactgtat tgctttatat aatgtacaaa tagttactga aatgacgaga cccttgtttg   2160
cacagcatta ataagaacct tgataagaac catattctgt tgacagccag ctcacagttt   2220
cttgcctgaa gcttggtgca ccctccagtg agacacaaga tctctctttt accaaagttg   2280
agaacagagc tggtggatta ttaatagtc ttcgatatct ggccatgggt aacctcattg    2340
taactatcat cagaatgggc agagatgatc ttgaagtgtc acatacacta aagtccaaac   2400
actatgtcag atgggggtaa aatccattaa agaacaggaa aaaataatta taagatgata   2460
agcaaatgtt tcagcccaat gtcaacccag ttaaaaaaaa aattaatgct gtgtaaaatg   2520
gttgaattag tttgcaaact atataaagac atatgcagta aaaagtctgt taatgcacat   2580
cctgtgggaa tggagtgttc taaccaattg ccttttcttg ttatctgagc tctcctatat   2640
tatcatactc agataaccaa attaaagaa ttagaatatg attttaata cacttaacat     2700
taaactcttc taactttctt ctttctgtga taattcagaa gatagttatg gatcttcaat   2760
gcctctgagt cattgttata aaaaatcagt tatcactata ccatgctata ggagactggg   2820
caaaacctgt acaatgacaa ccctggaagt tgctttttt aaaaaaataa taatttcttt   2880
aaatcaactc ttttttctgg ttgtctgttt gttataaagt gcaacgkatt caagtcctca   2940
```

```
                                                          -continued atatcctgat cataatacca tgctatagga gactgggcaa aacctgtaca atgacaaccc      3000
tggaagttgc ttttttaaaa aaataataat ttnttaatcc aaaaaaanaa aaaaantt       3058

<210> SEQ ID NO 95
<211> LENGTH: 1099
<212> TYPE: DNA
<213> ORGANISM: Homo sapiens
<220> FEATURE:
<221> NAME/KEY: SITE
<222> LOCATION: (64)
<223> OTHER INFORMATION: n equals a,t,g, or c

<400> SEQUENCE: 95
ggctttgtag ctgctccgca gcccagcccg ggcgcgctcg cagagtccta ggcggtgcgc      60
ggcntcctgc ctcctccctc ctcggcggtc gcggcccgcg cctccgcggt gcctgccttc     120
gctctcaggt tgaggagctc aagcttggga aaatggtgtg cattccttgt atcgtcattc     180
cagttctgct ctggatctac aaaaaattcc tggagccata tatataccct ctggtttccc    240
ccttcgttag tcgtatatgg cctaagaaag caatacaaga atccaatgat acaaacaaag     300
gcaaagtaaa ctttaagggt gcagacatga atggattacc aacaaaagga ccaacagaaa    360
tctgtgataa aaagaaagac taaagaaatt ttcctaaagg accccatcat ttaaaaaatg    420
gacctgataa tatgaagcat cttccttgta attgtctctg acctttttat ctgagaccgg    480
aattcaggat aggagtctag atatttacct gatactaatc aggaaatata tgatatccgt    540
atttaaaatg tagttagtta tatttaatga cctcattcct aagttccttt ttcgttaatg    600
tagctttcat ttctgttatt gctgtttgaa taatatgatt aaatagaagg tttgtgccag    660
tagacattat gttactaaat cagcacttta aaatctttgg ttctctaatt catatgaatt    720
tgctgtttgc tctaatttct ttgggctctt ctaatttgag tggagtacaa ttttgttgtg    780
aaacagtcca gtgaaactgt gcagggaaat gaaggtagaa ttttgggagg taataatgat    840
gtgaaacata aagatttaat aattactgtc caacacagtg gagcagcttg tccacaaata    900
tagtaattac tatttattgc tctaaggaag attaaaaaaa gatagggaaa agggggaaac    960
ttctttgaaa aatgaaacat ctgttacatt aatgtctaat tataaaattt taatccttac    1020
tgcatttctt ctgttcctac aaatgtatta aacattcagt ttaactggta aaaaaaaaa    1080 aaaaaaccc gggggggg                                                   1099

<210> SEQ ID NO 96
<211> LENGTH: 1580
<212> TYPE: DNA
<213> ORGANISM: Homo sapiens
<220> FEATURE:
<221> NAME/KEY: SITE
<222> LOCATION: (1443)
<223> OTHER INFORMATION: n equals a,t,g, or c
<220> FEATURE:
<221> NAME/KEY: SITE
<222> LOCATION: (1578)
<223> OTHER INFORMATION: n equals a,t,g, or c

<400> SEQUENCE: 96
ggcagagact ggaatctctc ttcatgaaaa aatgcagccc cttaacttca gttcgacara     60
gtgcagctcc ttctctccac ccaccacagt gattctcctt atcctgctgt gctttgaggg    120
cctgctcttc ctcatttcca catcagtgat gtttgggacc caggtgcact ccatctgcac    180
agatgagacg ggaatagaac aattgaaaaa ggaagagaga agatgggcta aaaaaacaaa    240
atggatgaac atgaaagccg ttttggcca ccccttctct ctaggctggg ccagcccctt     300
```

```
tgccacgcca gaccaaggga aggcagaccc gtaccagtat gtggtctgaa ggaccccgac      360
cggcatggcc actcagacac aagtccacac cacagcacta ccgtcccatc cgttctcatg      420
aatgtttaaa tcgaaaaagc aaaacaacta ctcttaaaac ttttttttatg tctcaagtaa     480 aatggctgag cattgcagag araaaaaaaa gtccccacat tttatttttt aaaaaccatc      540
ctttcgattt cttttggtga ccgawgctgc tctcttttcc ttttaaaatc acttctctgg      600
cctctggttt ctctctgctg tctgtctggc atgactaatg tagagggcgc tgtctcgcgc      660
tgtgcccatt ctactaactg agtgagacat gacgctgtgc tggatggaat agtctggaca      720
cctggtgggg gatgcatggg aaagccagga gggccctgac ctcccactgc ccaggaggca      780
gtggcgggct ccccgatggg acataaaacc tcaccgaaga tggatgctta ccccttgagg      840
cctgagaagg gcaggatcag aagggacctt ggcacagcga cctcatcccc caagtggaca      900
cggtttgcct gctaactcgc aaagcaattg cctgccttgt actttatggg cttggggtgt      960
gtagaatgat tttgcggggg agtggggaga aagatgaaag aggtcttatt tgtattctga     1020
atcagcaatt atattccctg tgattatttg gaagagtgtg taggaaagac gttttttccag   1080 ttcaaaatgc cttatacaat caagaggaaa aaaaattaca caatttcagg caagctacgt     1140
tttcctttgt ttcatctgct tcctctctca ccacccccatc tccctctctt ccccagcaag    1200
atgtcaatta agcagtgtga attctgactg caataggcac cagtgcccaa cacatacagc     1260
cccaccatca tccccttctc atttttataaa cctcaaagtg gattcacttt ctgatagtta    1320 accccccataa atgtgcacgt acctgtgtct tatctatatt ttaacckggg agactgttgt    1380
cctgggcatg ggagatgacc atgatgctgg ggttacctca cagtcccccac cctttcaaag   1440 ttngacatat gggccatccc attgggccag gaattccaca ggacacacct aaggctgtgg    1500 gmaytgggggg acaaatagat tttccatttt gaggagggca ctttccctgt tgttcagttc   1560
ttgttttgaa gggaggtngg                                                1580

<210> SEQ ID NO 97
<211> LENGTH: 678
<212> TYPE: DNA
<213> ORGANISM: Homo sapiens
<220> FEATURE:
<221> NAME/KEY: SITE
<222> LOCATION: (676)
<223> OTHER INFORMATION: n equals a,t,g, or c
<220> FEATURE:
<221> NAME/KEY: SITE
<222> LOCATION: (678)
<223> OTHER INFORMATION: n equals a,t,g, or c

<400> SEQUENCE: 97
atattttttt aggctaatgt ccaagataca gcattgagga ggcagctatg tctaatgagg      60
gctctcttgt ttgctagaga tgagagaaat gtatactaat cattttaatt tgtacttaaa    120
atacatttta ctaatcatat tgattttaaa tatgacaaat tcttctagta gatactaatc    180
tttcttgttt atcatattgt cctagagaag cctaggtaaa aatgggttcc acctagtctg    240
tttgtataac accttccccc gtccctctc catccctgcc aattgggctc tatgcatatt     300
gacaagcaaa taagaaaacc ttaggtttct tgtatttgaa tttccaaaac aataaaaggt    360
tttgactcaa gatttgcatt caagaagagg cagaaatttt gtcttatctt tttatcattt    420
tgtgaactag tgtttctctg tatgcttaga aaatttttaca cacaaggaat gtttgaaaaa  480
gtgagaattt tagagtgctt gggtggtttt tatttggtca gtgctgatgt gttargtgtt   540
```

| tagggaaata atgcttcagg accttttttga caacacagyt tcatgaatga cyggggata | 600 |
| ttwakgttgt gctgagaaaa gggagggagt gggcagttgg aatgggggac ccttaccatt | 660 |
| ggaaaacatg cattcngn | 678 |

<210> SEQ ID NO 98
<211> LENGTH: 1253
<212> TYPE: DNA
<213> ORGANISM: Homo sapiens
<220> FEATURE:
<221> NAME/KEY: SITE
<222> LOCATION: (158)
<223> OTHER INFORMATION: n equals a,t,g, or c
<220> FEATURE:
<221> NAME/KEY: SITE
<222> LOCATION: (181)
<223> OTHER INFORMATION: n equals a,t,g, or c
<220> FEATURE:
<221> NAME/KEY: SITE
<222> LOCATION: (663)
<223> OTHER INFORMATION: n equals a,t,g, or c

<400> SEQUENCE: 98

| acctccctcc ctctcagact ggtccgaatc cacgcctagc ccagccactg ccactggggc | 60 |
| catggccacc accactgggg cactgcctgc ccagccactt cccttgtctg ttcccagctc | 120 |
| ccttgctcag gcccagaccc agctgggggcc ccaccggnaa gttaccccca agaggcaagt | 180 |
| nttggcctga gacgctcgtc agttcttaga tcttggggggc ctaaagagac ccccgtcctg | 240 |
| cctccttttct ttctctgtct cttccttcct tttagtcttt ttcatcctct tctctttcca | 300 |
| ccaaccctcc tgcatccttg ccttgcagcg tgaccgagat aggtcatcag cccagggctt | 360 |
| cagtcttcct ttatttataa tgggtggggg ctaccaccca ccctgctgca gtcttgtgaa | 420 |
| gagtctggga cctccttctt ccccacttct ctcttccctc attcctttct ctctccttct | 480 |
| ggcctctcat ttccttacac tctgacatga atgaattatt attatttttc tttttctttt | 540 |
| tttttttaca ttttgtatag aaacaaattc atttaaacaa acttattatt attatttttt | 600 |
| acaaaatata tatatggaga tgctccctcc cctgtgaac cccccagtgc cccgtgggc | 660 |
| tgnagtctgt gggcccattc ggccaagctg gattctgtgt acctagtaca caggcatgac | 720 |
| tgggatcccg tgtaccgagt acacgaccca ggtatgtacc aagtaggcac ccttgggcgc | 780 |
| acccactggg gccaggggtc gggggagtgt tgggagcctc ctccccaccc cacctccctc | 840 |
| acttcactgc attccagatt ggacatgttc catagccttg ctggggaagg gcccactgcc | 900 |
| aactccctct gccccagccc cacccttggc catctccctt tgggaactag ggggctgctg | 960 |
| gtgggaaatg ggagccaggg cagatgtatg cattcctta tgtccctgta aatgtgggac | 1020 |
| tacaagaaga ggagctgcct gagtggtact ttctcttcct ggtaatcctc tggcccagcc | 1080 |
| ttatggcaga atagaggtat ttttaggcta tttttgtaat atggcttctg gtcaaaatcc | 1140 |
| ctgtgtagct gaattcccaa gcctgcatt gtacagcccc ccactcccct caccacctaa | 1200 |
| taaaggaata gttaacactc aaaaaaaaaa aaaaaaaaa acttgaggggg ggg | 1253 |

<210> SEQ ID NO 99
<211> LENGTH: 447
<212> TYPE: DNA
<213> ORGANISM: Homo sapiens

<400> SEQUENCE: 99

| caaagaatga aatttaccac tctcctcttc ttggcagctg tagcaggggc cctggtctat | 60 |
| gctgaagatg cctcctctga ctcgacgggt gctgatcctg cccaggaagc tgggacctct | 120 |

```
aagcctaatg aagagatctc aggtccagca gaaccagctt caccccaga gacaaccaca    180 acagcccagg agayttcggc ggcagcagtt caggggacag ccaaggtcac ctcaagcagg    240
caggaactaa accccctgaa atccatagtg gagaaaagta tcttactaac agaacaagcc    300
cttgcaaaag caggaaaagg aatgcacgga ggcgtgccag gtggaaaaca attcatcgaa    360
aatggaagtg aatttgcaca aaaattactg aagaaattca gtctattaaa accatgggca    420
tgagaagctg aaaagaatkg gatcatt                                        447

<210> SEQ ID NO 100
<211> LENGTH: 611
<212> TYPE: DNA
<213> ORGANISM: Homo sapiens

<400> SEQUENCE: 100
ggtctgggga ggtgacatgt tgggctgtgg gatcccagcg ctgggcctgc tcctgctgct     60
gcaggswtcg gcagacggaa atggaatcca gggattcttc tacccatgga gctgtgaggg    120
tgacatatgg gaccgggaga gctgtggggg ccaggcggcc attcgatagc ccaacytct    180 gcctgcgtct ccggtgctgc taccgcaatg gtctgctac caccagcgtc cagacgaaaa    240 cgtgcgagg aagcacatgt gggcgctggt ctggacgtgc agcggcctcc tcctcctgag    300
ctgcagcatc tgcttgttmt ggtgggccaa cgccgggac gtgctgcata tgcccggttt    360
cctggcgggt ccgtgtgaca tgtccaagtc cgtctcgctg ctctccaagc accgagggac    420
caagaagacg ccgtccacgg gcagcgtgcc agtcgccctg tccaaagagt ccaggggatgt    480 ggagggaggc accgagggg aagggacgga ggagggtgag gagacagagg gcgaggaaga    540
ggaggattag gggagtcccc ggggactgg tcaatacaga tacggtggac ggaaaaaaaa    600 aaaaaaaaa a                                                           611

<210> SEQ ID NO 101
<211> LENGTH: 609
<212> TYPE: DNA
<213> ORGANISM: Homo sapiens

<400> SEQUENCE: 101
gcattggtaa agctggcagt tgaaaccagt tggacggccc agcttgcgtc tcttctgcct     60
gagtgggcct ctcaggtcac tcgtgccctg ctggaggaca gaggggcacc tcagccgccc    120
ccaagcccag agcacagcaa taaggtcggc ctgcaggagc cgggtgggg gtgggggtgg    180 ggggrgcagg accctrarat gccaccagga cctgatgggc caggaagggc gtggacatgg    240
aggctgtttt tacagttttt tttttttgt tgttttgttt ttaaagaata cagaaggagc    300
caagcttttt tgcactttgt atccagctgc aagctcaggg cagagtcaag ggcctgggtt    360
ggaaaaacct gactcacagg aatgcataat tgacccttgc agctacccaa tagcccttgg    420
agctggcact gaaccaggct gcaagatttg actgccttaa aaacacaagg ccctctaggc    480
ctggcaggga tgtccctgtg cccagcactg ggggctcgaa gactggtttc tagcactacc    540
ggtcacggcc atgtcgtcct agaagggtcc agaagattat tttacgttga gtccattttt    600
aatgttctg                                                           609

<210> SEQ ID NO 102
<211> LENGTH: 1770
<212> TYPE: DNA
<213> ORGANISM: Homo sapiens
<220> FEATURE:
```

<221> NAME/KEY: SITE
<222> LOCATION: (524)
<223> OTHER INFORMATION: n equals a,t,g, or c

<400> SEQUENCE: 102

```
acggyccgga atcccgggtc gacccacgcg tccgggaaat tgaaactgag tggcccacga      60
tgggaagagg ggaaagccca ggggtacagg aggcctctgg gtgaaggcag aggctaacat     120
ggggttcgga gcgaccttgg ccgttggcct gaccatcttt gtgctgtctg tcgtcactat     180
catcatctgc ttcacctgct cctgctgctg cctttacaag acgtgccgcc gaccacgtcc     240
ggttgtcacc accaccacat ccaccactgt ggtgcatgcc ccttatcctc agcctccaag     300
tgtgccgccc agctaccctg gaccaagcta ccagggctac acaccatgc cgcctcagcc      360
agggatgcca gcagcaccct acccaatgca gtacccacca ccttacccag cccagcccat     420
gggcccaccg gcctaccacg agaccctggc tggaggagca gccgcgccct accccgccag     480
ccagcctcct tacaacccgg sctacatgga tgccccgaag sggncctctg agcattccct     540
ggcctctytg gctgccactt ggttatgttt tgtgtgtgcg tgartggtgt gcaggcgcgg     600
ttccttacgc cccatgtgtg ctgtgtgtgt cctgcctgta tatgtggctt cctctgatgc     660
tgacaaggtg gggaacaatc cttgccagag tgggctggga ccagactttg ttctcttcct     720
cacctgaaat tatgcttcct aaaatctcaa gccaaactaa agaatggggg tggtgggggg     780
caccctgtga ggtggcccct gagaggtggg ggcctctcca gggcacatct ggagttcttc     840
tccagcttac cctagggtga ccaagtaggg cctgtcacac caggtggcg cagctttctg      900
tgtgatgcag atgtgtcctg gtttcggcag cgtagccagc tgctgcttga ggccatggct     960
cgtccccgga gttgggggta cccgttgcag agccaggac atgatgcagg cgaagcttgg     1020
gatctggcca gttggactt tgatcctttg ggcagatgtc ccattgctcc ctggagcctg     1080
tcatgcctgt tggggatcag gcagcctcct gatgccagaa cacctcaggc agagccctac     1140
tcagctgtac ctgtctgcct ggactgtccc ctgtccccgc atctcccctg ggaccagctg     1200
gagggccaca tgcacacaca gcctagctgc ccccagggag ctctgctgcc cttgctggcc     1260
ctgcccttcc cacaggtgag cagggctcct gtccaccagc acactcagtt ctcttccctg     1320
cagtgttttc attttatttt agccaaacat tttgcctgtt ttctgtttca acatgatag      1380
ttgatatgag actgaaaccc ctgggttgtg gagggaaatt ggctcagaga tggacaacct     1440
ggcaactgtg agtccctgct tcccgacacc agcctcatgg aatatgcaac aactcctgta     1500
ccccagtcca cggtgttctg gcagcaggga cacctgggcc aatgggccat ctggaccaaa     1560
ggtggggtgt ggggccctgg atggcagctc tgcccagac atgaatacct cgtgttcctc      1620
ctccctctat tactgtttca ccagagctgt cttagctcaa atctgttgtg tttctgagtc     1680
tagggtctgt acacttgttt ataataaatg caatcgtttg gaaaaaaaaa aaaaaaaac      1740
tcgtaggggg ggcccgtacc caatsgccta                                      1770
```

<210> SEQ ID NO 103
<211> LENGTH: 1832
<212> TYPE: DNA
<213> ORGANISM: Homo sapiens
<220> FEATURE:
<221> NAME/KEY: SITE
<222> LOCATION: (1775)
<223> OTHER INFORMATION: n equals a,t,g, or c
<220> FEATURE:
<221> NAME/KEY: SITE
<222> LOCATION: (1786)
<223> OTHER INFORMATION: n equals a,t,g, or c
<220> FEATURE:
<221> NAME/KEY: SITE
<222> LOCATION: (1788)
<223> OTHER INFORMATION: n equals a,t,g, or c
<220> FEATURE:
<221> NAME/KEY: SITE
<222> LOCATION: (1820)
<223> OTHER INFORMATION: n equals a,t,g, or c
<220> FEATURE:
<221> NAME/KEY: SITE
<222> LOCATION: (1825)
<223> OTHER INFORMATION: n equals a,t,g, or c

<400> SEQUENCE: 103

| | | | | | |
|---|---|---|---|---|---|
| tgtggctgac | gtcatctgga | ggagatttgc | tttcttttc | tccaaaaggg | gaggaaattg | 60 |
| aaactgcagt | ggcccacgat | gggaagaggg | gaaagcccag | gggtacagga | ggcctctggg | 120 |
| tgaaggcaga | ggctaacatg | gggttcggag | cgaccttggc | cgttggctga | ccatctttgt | 180 |
| gctgtctgtc | gtcactatca | tcatctgctt | cacctgctcc | tgctgctgcc | tttacaagac | 240 |
| gtgccgccga | ccacgtccgg | ttgtcaccac | caccacatcc | accactgtgg | tgcatgcccc | 300 |
| ttatcctcag | cctccaagtg | tgccgcccag | ctaccctgga | ccaagctacc | agggctacca | 360 |
| caccatgccg | cctcagccag | ggatgccagc | agcaccctac | ccaatgcagt | acccaccacc | 420 |
| ttacccagcc | cagcccatgg | gcccaccggc | ctaccacgag | accctggctg | gaggagcagc | 480 |
| cgcgccctam | ccgscagcc | agcctcctta | caacccggcc | tacatggatg | cccgaagcgg | 540 |
| ccctctgagc | attccctggc | ctctytggct | gccacttggt | tatgttgtgt | gtgtgcgtra | 600 |
| gtggtgtgca | ggcgcggttc | cttacgcccc | atgtgtgctg | tgtgtgtcca | ggcacggttc | 660 |
| cttacgcccc | atgtgtgctg | tgtgtgtcct | gcctgtatat | gtggcttcct | ctgatgctga | 720 |
| caagtgggga | acaatccttg | ccagagtggg | ctgggaccag | actttgttct | cttcctcacc | 780 |
| tgaaattatg | cttcctaaaa | tctcaagcca | aactcaaaga | atggggtggt | gggggcacc | 840 |
| ctgtgaggtg | gcccctgaga | ggtggggcc | tctccagggc | acatctggag | ttcttctcca | 900 |
| gcttacccta | gggtgaccaa | gtagggcctg | tcacaccagg | gtggcgcast | ttctgtgtga | 960 |
| tgcagatgtg | tcctggtttc | ggcagcgtag | ccagctgctg | cttgaggcca | tggctcgtcc | 1020 |
| ccggagttgg | gggtacccgt | tgcagagcca | gggacatgat | gcaggcgaag | yttgggatct | 1080 |
| ggccaagttg | gactttgatc | ctttgggcag | atgtcccatt | gctccctgga | gcctgtcatg | 1140 |
| cctgttgggg | atcaggcagc | ctcctgatgc | cagaacacct | caggcagagc | cctactcagc | 1200 |
| tgtacctgtc | tgcctggact | gtcccctgtc | cccgcatctc | ccctgggacc | agctggaggg | 1260 |
| ccacatgcac | acacagccta | gctgccccca | gggagtctg | ctgcccttgc | tggccctgcc | 1320 |
| cttcccacag | gtgagcaggg | ctcctgtcca | ccagcacact | cagttctctt | ccctgcagtg | 1380 |
| ttttcatttt | attttagcca | aacattttgc | ctgttttctg | tttcaaacat | gatagttgat | 1440 |
| atgagactga | aaccctggg | ttgtggaggg | aaattggctc | agagatggac | aacctggcaa | 1500 |
| ctgtgagtcc | ctgcttcccg | acaccagcct | catggaatat | gcaacaactc | ctgtaccca | 1560 |
| gtccacggtg | ttctggcagc | agggacacct | gggccaatgg | gccatctgga | ccaaaggtgg | 1620 |
| ggtgtgggc | cctggatggc | agctctggcc | cagacatgaa | tacctcgtgt | tcctcctccc | 1680 |
| tctattactg | tttcaccaga | gctgtcttag | ctcaaatctg | ttgtgtttct | gagtctaggg | 1740 |
| tctgtacact | tgtttataat | aaatgcaatc | gtttnggaaa | aaaananaa | aaaaaaagg | 1800 |
| ggsggcgctc | taaaaggatn | cccnaaggg | gg | | | 1832 |

<210> SEQ ID NO 104

<211> LENGTH: 2237
<212> TYPE: DNA
<213> ORGANISM: Homo sapiens
<220> FEATURE:
<221> NAME/KEY: SITE
<222> LOCATION: (605)
<223> OTHER INFORMATION: n equals a,t,g, or c
<220> FEATURE:
<221> NAME/KEY: SITE
<222> LOCATION: (2215)
<223> OTHER INFORMATION: n equals a,t,g, or c

<400> SEQUENCE: 104

```
agttcccggt actttattac caaggttgcc atcggaacca ggaatgacat tactcactat      60
cagaattgag aaaattggtt tgaaagatgc tgggcagtgc atcgatccct atattacagt     120
tagtgtaaag gatctgaatg gcatagactt aactcctgtg caagatactc ctgtggcttc     180
aagaaaagaa gatacatatg ttcattttaa tgtggacatt gagctccaga agcatgttga     240
aaaattaacc aaaggtgcag ctatcttctt tgaattcaaa cactacaagc ctaaaaaaag     300
gtttaccagc accaagtgtt ttgctttcat ggagatggat gaaattaaac ctgggccaat     360
tgtaatagaa ctatacaaga aacccactga ctttaaaaga aagaaattgc aattattgac     420
caagaaacca ctttatcttc atctacatca aactttgcac aaggaatgat cctgacatga     480
tgaacctgga acttctgtga attttaccac tcagtagaaa ccatcatagc tctgtgtagc     540
atattcaccc ttcaacaggc aggaagcaag ccgtacccag accagtaggc cggacggagt     600
caatngcaaa gctgtaccac agaattcaga gtccagcaca tcacactgac gtataggact     660
ccttgggata caggtttatt gtagattttg aaacatgttt ttactttttct attaattgtg     720
caattaatag tctattttct aatttaccac tactcctacc ctgcttcctg gaacaatact     780
gttgtgggta ggatgtgctc atcttcagac ttaatacagc aataagaatg tgctagagtt     840
tacacatctg ttcacttttg ctccaatatg ctctttttgac ttaacgtcaa gctttgggtt     900
gatgtgggta gggtagtgtc aaactgcttt gagaggaatg ggaccagttc tgctgcctaa     960
gaaggtctgt ctggatgttt ataggcagca cctctgaagt ggcctaaatt cacccctgatc    1020
tgatagtttt cctgcttaga aagtgtgcct tggccagatc agtatcccac atgggagtgt    1080
tccctaggtt gtagctgtga ttgtttccag atgaccagat tgttttttctg aaaatgagca    1140
tattttttagt catgtcgatt agctgttctt ctacatcaca ttgttactct ttctgatgat    1200
gattctaggg ttaacattgg aaccatctca aaataattac aaagttttag atgggtttac    1260
aatgtcttct aaacaatgta atctaaaaat aattgagtca gatgctaacg agatactgca    1320
ggcataactg ctgttttttct gacaactgat tgtgaaacct aaaacctgc atacctcttc    1380
ttacagtgag gagtatgcaa aatctggaaa gatattctat tttttttata taggtagata    1440
ggatcgccat ttatttccta tttagatata ctgacattca tccatatgaa aatatgcagg    1500
tcattagctt actataattt acttttgact taatgggca taaataaaac tttcatagta    1560
cacatgaggt ggatatttga tacacagaac atttgcggtg ggctttctgt gggttagatg    1620
taaagcccac atattttaat attcactatt ttaaatgagc aatgcatgag gggaatgcag    1680
tgtcagtacc tggcctattt ttaaactagt gtaatcaccc tagtcatacc attcagtatg    1740
tttgctttt aaaataagta accacaatta agttgttgta gcccttgcac ttcaagagat    1800
ctagtcttta ctttcagttg tctgttaggt ccattctgtt tactagacgg atgttaataa    1860
aaactatgcg agcctgaatg aattctcagc caaatttagt cttgtctctc atcttgattg    1920
gattaattcc aaattctaaa atgattcagt ccacaatagc tctaggggat gaagaatttg    1980
```

```
ccttactttg cccagttcct aagactgtga gttgtcaaat ccctagactg taagctcttc    2040
aaggagcaag aggcgcattt tctccgtgtc atgtaatttt tctaaggtgt ttggcagcac    2100
tctgtaccct gtggagtact cagtaccttt tgtttgatgt tgctgacaag acctgaaaaa    2160
aaatccctta aaaaaaaaac ccattaaagt gtagcaaaac cgaaaaaaaa aaaanaaaaa    2220
actcgagacg ggcccgg                                                   2237

<210> SEQ ID NO 105
<211> LENGTH: 1822
<212> TYPE: DNA
<213> ORGANISM: Homo sapiens

<400> SEQUENCE: 105
ggtcgaccca cgcgtccgga attttcgtag caataagttt gtgcatgtat agtaatttgc      60
attagcaagt tgtaacctc tgcctcttgg gttcaagtga ttctcgtgcc ccagcctccc     120
gagtagctgg gactacaggc acgtgccacc acgcccagct aattttttata ttttttagtag   180 agacggggtt ttgctgtgtt ggccaggctg gtctcaaact cctgacctca gtaatccac    240 ctggcctgct cttttcatgt cttaacatgg catgtctttt agtttcatta ttttcctact    300
ccttgtatgt caagaaatta cattttgcat gtcttatgga gatgctgtta attgcttcag    360
tgagtgcttt tctaatctgc agaccattta catttcctgt ttgcagcatg ctgtgtgcaa    420
acactcagta atttggagta ttcaattatt tgttagggct cttcctattt ccaaatgtgc    480
tgaattgtct attgatggga ttttcagatc tttttcatgag aactggaaat gtagctgggt    540
ggcacctacc taggttgcta cgtagtgagt agactttctc ttgggtatag taagcctcag    600
acagctttca cttttatcta ctttacttgt ggaaataaaa cagtcatttt gttctgaaag    660
aataagatag cttctgtag agaaggaatt cctacctcta aaagctgcct tgagaactca    720
gaactggcag ttttctgagg tgatttttaa atttcagtat tagggagagt ccagcatttg    780
ctgacacaga ttctacataa ctaatgtatg atagcaaatg caaaactatt ataatgtggt    840
gtatcttgcg catacacagg ttagaacaag tagactctgg cagcagatct ccagagaccc    900
aagtttaggt tctcatagtg tatttgaagt agttatactc ctggcttaag tagtttagtg    960
cctgggagaa tccattactg aaaagcattt aacttaaaaa aaaaaaaaaa aaaaaaaaa    1020 aaacctcgtg ccgaattcgg cacgagctaa cccagaaaca tccaattctc aaactgaagc   1080
tcgcactctc gcctccagca tgaaagtctc tgccgcccctt ctgtgcctgc tgctcatagc    1140
agccaccttc attccccaag ggctcgctca gccagatgca atcaatgccc cagtcacctg    1200
ctgytataac ttcaccaata ggaagatctc agtgcagagg ctcgcgagct atagaagaat    1260
caccagcagc aagtgtccca agaagctgt gatcttcaag accattgtgg ccaaggagat    1320
ctgtgctgac cccaagcaga agtgggttca ggattccatg gaccacctgg acaagcaaac    1380
ccaaactccg aagacttgaa cactcactcc acaacccaag aatctgcagc taacttattt    1440
tcccctagct ttccccagac accctgtttt atttattatt aatgaatttt gtttgttgat    1500
gtgaaacatt atgccttaag taatgttaat tcttatttaa gttattgatg ttttaagttt    1560
atctttcatg gtactagtgt tttttagata cagagacttg gggaaattgc ttttcctctt    1620
gaaccacagt tctacccctg ggatgtttg agggtctttg caagaatcat taatacaaag    1680 aattttttt aacattccaa tgcattgcta aaatattatt gtgaaatga atattttgta    1740 actattacac caaataaata tattttgta caaaaaaaaa aaaaaaaaa aaaaaaaaa    1800
```

```
aagsggccgc tcgaattaag cc                                              1822

<210> SEQ ID NO 106
<211> LENGTH: 1712
<212> TYPE: DNA
<213> ORGANISM: Homo sapiens

<400> SEQUENCE: 106
cgtgccccag cctcccgagt agctggract acaggcacgt sccaccacgc ccagctaatt      60
ttwatatttt wagtagagac ggggttttsc tgtkttggcc aggctggtct caaactcctg     120
acctcaagta atccacctgg cctgctcttt tcatgtctta acatggcatg tcttttagtt    180
tcattatttt cctactcctt gtatgtcaag aaattacatt ttgcatgtct tatggagatg    240
ctgttaattg cttcagtgag tgcttttcta atctgcagac catttacatt tcctgtttgc    300
agcatgctgt gtgcaaacac tcagtaattt ggagtattca attatttgtt agggctcttc    360
ctatttccaa atgtgctgaa ttgtctattg atgggatttt cagatctttt catgagaact    420
ggaaatgtag ctgggtggca cctacctagg ttgctacgta gtgagtagac tttctcttgg    480
gtatagtaag cctcagacag ctttcacttt tatctacttt acttgtggaa ataaaacagt    540
cattttgttc tgaaagaata agatagcttt ctgtagagaa ggaattccta cctctaaaag    600
ctgccttgag aactcagaac tggcagtttt ctgaggtgat ttttaaattt cagtattagg    660
gagagtccag catttgctga cacagattct acataactaa tgtatgatag caatgcaaa    720 actattataa tgtggtgtat cttgcgcata cacaggttag aacaagtaga ctctggcagc    780
agatctccag agacccaagt ttaggttctc atagtgtatt tgaagtagtt atactcctgg    840
cttaagtagt ttagtgcctg ggagaatcca ttactgaaaa gcatttaact taaaaaaaaa    900
aaaaaaaaaa aaaaaaaaac ctcgtgccga attcggcacg agcagaaaca tccaattctc    960
aaactgaagc tcgcactctc gcctccagca tgaaagtctc tgccgccctt ctgtgcctgc   1020
tgctcatagc agccaccttc attccccaag ggctcgctca gccagatgca atcaatgccc   1080
cagtcaccct ctgytataac ttcaccaata ggaagatctc agtgcagagg ctcgcgagct   1140
atagaagaat caccagcagc aagtgtccca agaagctgt gatcttcaag accattgtgg   1200
ccaaggagat ctgtgctgac cccaagcaga agtgggttca ggattccatg gaccacctgg   1260
acaagcaaac ccaaactccg aagacttgaa cactcactcc acaacccaag aatctgcagc   1320
taacttattt tcccctagct ttccccagac accctgtttt attttattat aatgaatttt   1380
gtttgttgat gtgaaacatt atgccttaag taatgttaat tcttatttaa gttattgatg   1440
ttttaagttt atctttcatg gtactagtgt tttttagata cagagacttg gggaaattgc   1500
ttttcctctt gaaccacagt tctacccctg ggatgttttg agggtctttg caagaatcat   1560
taatacaaag aattttttt aacattccaa tgcattgcta aaatattatt gtggaaatga   1620
atattttgta actattacac caaataaata tattttgta caaaaaaaa aaaaaaaaa    1680 aaaaaaaaaa aagsggccgc tcgaattaag cc                                  1712

<210> SEQ ID NO 107
<211> LENGTH: 1969
<212> TYPE: DNA
<213> ORGANISM: Homo sapiens
<220> FEATURE:
<221> NAME/KEY: SITE
<222> LOCATION: (890)
<223> OTHER INFORMATION: n equals a,t,g, or c

<400> SEQUENCE: 107
```

```
cccctccttc ccctygccac ctactgaacc ctcctccgag gtgcccgagc agccgtctgc    60
ccagccactc cctgggagtc cccccagaag agcctattac atctactccg ggggcgagaa   120
gatcccsctg gtgttgagcc ggcccctctc ctccaacgtg ccactcttc agcatctctg    180
tcggaagacc gtcaacggcc acctggactc tatgagaaa gtcacccagc tgccggggcc    240
cattcggrag ttcctggacc agtacgatgc cccgmtttaa ggggtaaagg gcgcaaaggg   300
catgggtcgg gagaggggac gcaggcccct ctcctccgtg gcacatggca caagcacaag   360
aagccaacca ggagagagtc ctgtagctct gggggggaaa agggcggaca ggcccctccc   420
tctgccctct ccctgcagaa tgtggcaggc ggacctggaa tgtgttggag gaaggggga    480
gtaccacctg agtctccagc ttctccggag acccagctgt cctggtggga cgatagcaac   540
cacaagtgga ttctccttca attcctcagc ttcccctctg cctccaaaca ggggacactt   600
cgggaatgct gaaytaatga gaactgccag ggaatcttca aactttccaa cggaacttgt   660
ttgctctttg atttggttta aacctgagct ggttgtggag cctgggaaag gtggaagaga   720
gagaggtcct gagggcccca gggstgcggg ctggcgaagg aaatggtcac accccccgcc   780
caccccaggc gaggatcctg gtgacatgct cctctccctg gctccgggga aagggcttg    840
gggtgacctg aagggaacca tcctggtgcc ccacatcctc cctccgggn acagtcaccg    900
aaaacacagg ttccaaagtc tacctggtgc ctgagagccc agggcccttc ctccgtttta   960
aggggggaagc aacatttgga ggggacggat ggctggtca gctggtctcc ttttcctact  1020
catactatac cttcctgtac ctgggtggat ggagcgggag gatggaggag acgggacatc  1080
tttcacctca ggctcctggt agagaagaca ggggattcta ctctgtgcct cctgactatg   1140
tctggctaag agattcgcct taaatgctcc ctgtcccatg gagagggacc cagcatagga   1200
aagccacata ctcagcctgg atgggtggag aggctgaggg actcactgga gggcaccaag   1260
ccagcccaca gccagggaag tggggagggg gggcggaaac ccatgcctcc cagctgagca   1320
ctgggaatgt cagcccagta agtattggcc agtcaggcgc ctcgtggtca gagcagagcc   1380
accaggtccc actgccccga gccctgcaca gccctccctc ctgcctgggt ggggaggct    1440
ggaggtcatt ggagaggctg gactgctgcc acccgggtg ctcccgctct gccatagcac    1500
tgatcagtga caatttacag gaatgtagca gcgatggaat tacctggaac attttttgtt   1560
tttgttttg tttttgtttt tgtgggggg ggcaactaaa caaacacaaa gtattctgtg    1620
tcaggtattg ggctggacag ggcagttgtg tgttgggtg gtttttttct ctattttttt    1680
gtttgtttct tgttttttaa taatgtttac aatctgcctc aatcactctg tcttttataa  1740
agattccacc tccagtcctc tctcctcccc cctactcagg cccttgaggc tattaggaga   1800
tgcttgaaga actcaacaaa atcccaatcc aagtcaaact ttgcacatat ttatatttat   1860
attcagaaaa gaaacatttc agtaatttat aataaagagc actatttttt aatgaaaaaa   1920
aaaaaaaaaa aaaaaaaaa cgacgctggt gaccggaaty cgacgtacg                1969
```

<210> SEQ ID NO 108
<211> LENGTH: 1734
<212> TYPE: DNA
<213> ORGANISM: Homo sapiens
<220> FEATURE:
<221> NAME/KEY: SITE
<222> LOCATION: (189)
<223> OTHER INFORMATION: n equals a,t,g, or c
<220> FEATURE:
<221> NAME/KEY: SITE
<222> LOCATION: (761)

<223> OTHER INFORMATION: n equals a,t,g, or c

<400> SEQUENCE: 108

| | | | | | |
|---|---|---|---|---|---|
| cgggtcccaa | gcctgtgcct | gagcctgagc | ctgagcctga | gcccgagccg | ggagccggtc | 60 |
| gcgggggctc | cgggctgtgg | gaccgctggg | cccccagcga | tggcgaccct | gtggggaggc | 120 |
| cttcttcggc | ttggctcctt | gctcagcctg | tcgtgcctgg | cgctttccgt | gctgctgctg | 180 |
| gcgcatgtnc | agacgccgcc | aagaatttcg | aggatgtcag | atgtaaatgt | atctgccctc | 240 |
| cctataaaga | aaattctggg | catatttata | ataagaacat | atctcagaaa | gattgtgatt | 300 |
| gccttcatgt | tgtggagccc | atgcctgtgc | ggggcctga | tgtagaagca | tactgtctac | 360 |
| gctgtgaatg | caaatatgaa | gaaagaagct | ctgtcacaat | caaggttacc | attataattt | 420 |
| atctctccat | tttgggcctt | ctacttctgt | acatggtata | tcttactctg | gttgagccca | 480 |
| tactgaagag | gcgcctcttt | ggacatgcac | agttgataca | gagtgatgat | gatattgggg | 540 |
| atcaccagcc | ttttgcaaat | gcacacgatg | tgctagcccg | ctcccgcagt | cgagccaacg | 600 |
| tgctgaacaa | ggtagaatat | gcacagcagc | gctggaagct | tcaagtccaa | gagcagcgaa | 660 |
| agtctgtctt | tgaccggcat | gttgtcctca | gctaattggg | gaattgaatt | caaggtgact | 720 |
| agaaagaaac | aggcagacaa | ctgggaaaga | actgactggg | nttttgctgg | gtttcatttt | 780 |
| aataccttgt | tgatttcacc | aactgttgct | ggaagattca | aaactggaag | caaaaacttg | 840 |
| cttgattttt | ttttcttgtt | aacgtaataa | tagagacatt | tttaaaagca | cacagctcaa | 900 |
| agtcagccaa | taagtctttt | cctatttgtg | acttttacta | ataaaaataa | atctgcctgt | 960 |
| aaattatctt | gaagtccttt | acctggaaca | agcactctct | ttttcaccac | atagttttaa | 1020 |
| cttgactttc | aagataattt | tcagggtttt | tgttgttgtt | gttttttgtt | tgtttgtttt | 1080 |
| ggtgggagag | gggagggatg | cctgggaagt | ggttaacaac | tttttttcaag | tcactttact | 1140 |
| aaacaaactt | ttgtaaatag | accttacctt | ctatttttcga | gtttcattta | tattttgcag | 1200 |
| tgtagccagc | tcatcaaag | agctgactta | ctcatttgac | ttttgcactg | actgtattat | 1260 |
| ctgggtatct | gctgtgtctg | cacttcatgg | taaacgggat | ctaaaatgcc | tggtggcttt | 1320 |
| tcacaaaaag | cagattttct | tcatgtactg | tgatgtctga | tgcaatgcat | cctagaacaa | 1380 |
| actggccatt | tgctagttta | ctctaaagac | taaacatagt | cttggtgtgt | gtggtcttac | 1440 |
| tcatcttcta | gtacctttaa | ggacaaatcc | taaggacttg | gacacttgca | ataaagaaat | 1500 |
| tttattttaa | acccaagcct | ccctggattg | ataatatata | cacatttgtc | agcatttccg | 1560 |
| gtcgtggtga | gaggcagctg | tttgagctcc | aatgtgtgca | gctttgaact | agggctgggg | 1620 |
| ttgtgggtgc | ctcttctgaa | aggtctaacc | attattggat | aactggcttt | tttcttcctc | 1680 |
| tttggaatgt | aacaataaaa | ataattttg | aaacatcaaa | aaaaaaaaaa | aaaa | 1734 |

<210> SEQ ID NO 109
<211> LENGTH: 2003
<212> TYPE: DNA
<213> ORGANISM: Homo sapiens
<220> FEATURE:
<221> NAME/KEY: SITE
<222> LOCATION: (211)
<223> OTHER INFORMATION: n equals a,t,g, or c
<220> FEATURE:
<221> NAME/KEY: SITE
<222> LOCATION: (768)
<223> OTHER INFORMATION: n equals a,t,g, or c
<220> FEATURE:
<221> NAME/KEY: SITE
<222> LOCATION: (1025)
<223> OTHER INFORMATION: n equals a,t,g, or c

```
<220> FEATURE:
<221> NAME/KEY: SITE
<222> LOCATION: (2003)
<223> OTHER INFORMATION: n equals a,t,g, or c

<400> SEQUENCE: 109 cgcaggggc gcgcggcccg gggactcgca ttccccggtt ccccctccac cccacgcggc      60
ctggaccatg gacgccagat ggtgggcagt ggtggtgctg gctgcgttcc cctccctagg    120
ggcaggtggg gagactcccg aagcccctcc ggagtcatgg acccagctat ggttcttccg    180
atttgtggtg aatgctgctg ctatgccag nttatggta cctggctacc tcctggtgca     240
gtacttcagg cggaagaact acctggagac cggtaggggc ctctgctttc ccctggtgaa    300
agcttgtgtg tttggcaatg agcccaaggc tctgatgag gttccctgg cgccccgaac      360
agaggcggca gagaccaccc cgatgtggca ggccctgaag ctgctcttct gtgccacagg    420
gctccaggtg tcttatctga cttggggtgt gctgcaggaa agagtgatga cccgcagcta    480
tggggccaca gccacatcac cgggtgagcg ctttacggac tcgcagttcc tggtgctaat    540
gaaccgagtg ctggcactga ttgtggctgg cctctcctgt gttctctgca agcagccccg    600
gcatggggca cccatgtacc ggtactcctt tgccagcctg tccaatgtgc ttagcagctg    660
gtgccaatac gaagctctta agttcgtcag cttccccacc caggtgctgg ccaaggcctc    720
taaggtgatc cctgtcatgc tgatgggaaa gcttgtgtct cggcgcanta acgaacactg    780
ggagtacctg acagccaccc tcatctccat tggggtcagc atgtttctgc tatccagcgg    840
accagagccc cgcagctccc cagccaccac actctcaggc ctcatcttac tggcaggtta    900
tattgctttt gacagcttca cctcaaactg gcaggatgcc tgtttgccta aagatgtca    960
tcggtgcaga tgatgtttgg ggtcaatttc ttctcctgcc tcttcacagt gggstcactg   1020
ctagnaacag ggggmccta ctggagggaa cccgcttcat ggggcgacac agtgagtttg   1080
ctgcccatgc cctgctactc tccatctgct ccgcatgtgg ccagctcttc atcttttaca   1140
ccattgggca gtttggggct gccgtcttca ccatcatcat gaccctccgc caggcctttg   1200
ccatccttct ttcctgcctt ctctatggcc acactgtcac tgtggtggga gggctggggg   1260
tggctgtggt ctttgctgcc ctcctgctca gagtctacgc gcggggccgt ctaaagcaac   1320
ggggaaagaa ggctgtgcct gttgagtctc ctgtgcagaa ggtttgaggg tggaaagggc   1380
ctgaggggtg aagtgaaata ggaccctccc accatcccct tctgctgtaa cctctgaggg   1440
agctggctga aagggcaaaa tgcaggtgtt ttctcagtat cacagaccag ctctgcagca   1500
ggggattggg gagcccagga ggcagccttc cctttttgcct taagtcaccc atcttccagt   1560
aagcagttta ttctgagccc cgggggtaga cagtcctcag tgagggtttt tggggagttt   1620
ggggtcaaga gagcataggt aggttccaca gttactcttc ccacaagttc ccttaagtct   1680
tgccctagct gtgctctgcc accttccaga ctcactcccc tctgcaaata cctgcatttc   1740
ttaccctggt gagaaaagca caagcggtgt aggctccaat gctgctttcc caggagggtg   1800
aagatggtgc tgtgctgagg aaaggggatg cagagccctg cccagcacca ccacctccta   1860
tgctcctgga tccctaggct ctgttccatg agcctgttgc aggttttggt actttagaaa   1920
tgtaactttt tgctcttata attttatttt attaaattaa attactgcaa aaaaaaaaa    1980
aaaaaaatcg gggggggcc cgn                                           2003

<210> SEQ ID NO 110
<211> LENGTH: 1320
<212> TYPE: DNA
```

<213> ORGANISM: Homo sapiens
<220> FEATURE:
<221> NAME/KEY: SITE
<222> LOCATION: (1208)
<223> OTHER INFORMATION: n equals a,t,g, or c

<400> SEQUENCE: 110

| | | | | | |
|---|---|---|---|---|---|
| gctgagctgc | cttgaggtgc | agtgttgggg | atccagagcc | atgtcggacc | tgctactact | 60 |
| gggcctgatt | gggggcctga | ctctcttact | gctgctgacg | ctgctggcct | ttgccgggta | 120 |
| ctcagggcta | ctggctgggg | tggaagtgag | tgctgggtca | cccccatcc | gcaacgtcac | 180 |
| tgtggcctac | aagttccaca | tggggctcta | tggtgagact | gggcggcttt | tcactgagag | 240 |
| ctgcagcatc | tctcccaagc | tccgctccat | cgctgtctac | tatgacaacc | cccacatggt | 300 |
| gccccctgat | aagtgccgat | gtgccgtggg | cagcatcctg | agtgaaggtg | aggaatcgcc | 360 |
| ctcccctgag | ctcatcgacc | tctaccagaa | atttggcttc | aaggtgttct | ccttcccggc | 420 |
| acccagccat | gtggtgacag | ccaccttccc | ctacaccacc | attctgtcca | tctggctggc | 480 |
| tacccgccgt | gtccatcctg | ccttggacac | ctacatcaag | gagcggaagc | tgtgtgccta | 540 |
| tcctcggctg | gagatctacc | aggaagacca | gatccatttc | atgtgcccac | tggcasggca | 600 |
| gggagacttc | tatgtgcctg | agatgaagga | gacagagtgg | aaatggcggg | ggcttgtgga | 660 |
| ggccattgac | acccaggtgg | atggcacagg | agctgacaca | atgagtgaca | cgagttctgt | 720 |
| aagcttggaa | gtgagccctg | gcagccggga | gacttcagct | gccacactgt | cacctggggc | 780 |
| gagcagccgt | ggctgggatg | acggtgacac | ccgcagcgag | cacagctaca | gcgagtcagg | 840 |
| tgccagcggc | tcctcttttg | aggagctgga | yttggagggc | gagggcccct | tagggagtc | 900 |
| acggctggac | cctgggactk | agcccctggg | gactaccaag | tggctctggg | agcccactgc | 960 |
| ccctgagaag | ggcaaggagt | aacccatggc | ctgcaccctc | cctgcagtgc | agttgctgag | 1020 |
| gaactgagca | gactctccag | cagactctcc | agccctcttc | ctccttcctc | tgggggagga | 1080 |
| ggggttcctg | agggacctga | cttcccctgc | tccaggcctc | ttgctaagcc | ttctcctcac | 1140 |
| tgcccttag | gctcccaggg | ccagaggagc | caggactat | tttctgcaac | cagccccag | 1200 |
| ggctgccncc | cctgttgtgt | cttttttca | gactcacagt | ggagcttcca | ggacccagaa | 1260 |
| taaagccaat | gatttacttg | tttcaaaaaa | aaawaaaaa | aaaaaaaaaa | aaaaaaaaa | 1320 |

<210> SEQ ID NO 111
<211> LENGTH: 1962
<212> TYPE: DNA
<213> ORGANISM: Homo sapiens
<220> FEATURE:
<221> NAME/KEY: SITE
<222> LOCATION: (21)
<223> OTHER INFORMATION: n equals a,t,g, or c
<220> FEATURE:
<221> NAME/KEY: SITE
<222> LOCATION: (56)
<223> OTHER INFORMATION: n equals a,t,g, or c
<220> FEATURE:
<221> NAME/KEY: SITE
<222> LOCATION: (1006)
<223> OTHER INFORMATION: n equals a,t,g, or c
<220> FEATURE:
<221> NAME/KEY: SITE
<222> LOCATION: (1077)
<223> OTHER INFORMATION: n equals a,t,g, or c
<220> FEATURE:
<221> NAME/KEY: SITE
<222> LOCATION: (1921)
<223> OTHER INFORMATION: n equals a,t,g, or c

<400> SEQUENCE: 111

```
cggacccctt cctcctcctc naagcatgtc ccaccattgt ggcagggget ggggana cag     60 tcacctgatg cggggaccac ggccactcca cctcgstggc gctgtcagtg ggcagcactg    120
gctgggcctg cactgaggtc cctgctgggg cagttcttcc agaattatct tcagaggggg    180
cctccagctc cctggtaccc tcaggggccc gtgtggctgg aagcagggaa ggggcaccct    240
cggagcttcc tgtctcctcg ctctctcctc gagggacccc agatagctca ggaccaccag    300
ttgcctcccc cacctctctt gcctcaacca gagtggaagg tgatgggat gctaggttcc    360 tctccctggg agtgggcaga gtctcagtag gtggtccatg gacccttgga ggcctggaag    420
cttctgactc tccatcagga agtggtgatg caccaggctg caggactgcc cttgctggcg    480
cctgggagag tgactcctcc tgggctgctg gctcagtggg gagagaggcc tcagggcccg    540
ggctgctgag ctcgctgggc catgcccaca gagcctcatc ctccacctcc tcctcttctt    600
cttcctcctc tttctcttct tcatcttcat atttctcttc ttcctccaat gccttacctt    660
cctcttytgr aaacccgtg ggcggtacca tggattgtgt ttcaaattct aggagcgtcc    720 tagggcccte tgctgggtct tctggagtgg agcttccacc tcctccgtcc tccatgatgg    780
ggatggagta ratgccccca cgggattcac tctctgtggc ttcctgaggc agctgcagtt    840
cctccagggt ctctgtcact gtgacratag cctctagtcc atcaaaagct gggttggagg    900
ctgggttgga ggcctcaggg atggcagaag gctgggccga gtctcggaag cagtaracgt    960 tgaagcgget gtgcttattg gggaagccag tctggttggg gaagangaag agagtcttga   1020
caccaggcaa gcccccacca cagcgctggc tgggtgtgac gatgggtag cgcacantgc   1080 catcagctag ccacctgggc tgcagtggtc caggccacca tcccaggctg catacagttg   1140
gcccgtggtg gcaatctctg cacccgctc ctggcagtac gcccgtgctt cctccaatgt   1200
cagcttctct ggagggtcac ccaggaacag ttctccattt aggtcttcag cataacagta   1260
cacatcatag aggtcatccg ggtccaccac accatagttc cggacccegg ggaagccatc   1320 catgtctccg taacaggcct ctcgtggggt ctggatggga tacctttgac cttgamctcc   1380
acagcgtcgc tgctgtcatc gatgccgtgc tggacctcac agcgatagat acctgagtcg   1440
ttggggcgca gctcgctcag cgccagggga gacgtcggtg agcgacgctg ggtacgcagg   1500
cagtgccacg cggaaccggt aggcctcgtt caccttgacg cgcactcccc gcgccaccag   1560
cacytctgcc tcccggcccc gggacaggaa agtccacttg acccgcggag agcccagcac   1620
agcccggcgg ctcggcggtg sccgcaggta gtggacgtgg caagggatgk tgagggcscc   1680
gccgagcaac gccytgcagt ggcgcgtcgc ccgcgatgcg cacgcgaaaa gcgcgktcct   1740
ctgagctgtc tccttccaga acatctgcta aagctgcagg agcctgggcc aggaccaggg   1800
ctgccagcag gggcaggaac agctgggcca tgctgcaggc tacccagggc tggggttggg   1860
tcgcggcact gcgaagtttg tcgcctcctc cggggggtctc ctccgggtkc acggctcagt   1920
ncctgcagct gcagctgaga ctgcggcgga gactgcgcga gc                      1962
```

<210> SEQ ID NO 112
<211> LENGTH: 1785
<212> TYPE: DNA
<213> ORGANISM: Homo sapiens
<220> FEATURE:
<221> NAME/KEY: SITE
<222> LOCATION: (924)
<223> OTHER INFORMATION: n equals a,t,g, or c
<220> FEATURE:
<221> NAME/KEY: SITE
<222> LOCATION: (1749)

<223> OTHER INFORMATION: n equals a,t,g, or c
<220> FEATURE:
<221> NAME/KEY: SITE
<222> LOCATION: (1761)
<223> OTHER INFORMATION: n equals a,t,g, or c

<400> SEQUENCE: 112

| | | | | | |
|---|---|---|---|---|---|
| aagtttcagc | caaacttcgg | gcggctgagg | cggcggccga | ggagcggcgg | actcsgggcg | 60 |
| cggggagtcg | aggcatttgc | gcctgggctt | cggagcgtac | cgcagggcct | gagcctttga | 120 |
| agcaggagga | gggggaggaga | gagtgggggct | cctctatcgg | gaccccctcc | ccatgtggat | 180 |
| ctgcccaggc | ggcggcggcg | gccgaggagg | cgaccgagaa | gatrcccgcc | ctgcgccccg | 240 |
| ctctgctgtg | ggcgctgctg | gcgctctggc | tgtgctgcgc | gaccccgcgc | atgcattgca | 300 |
| gtgtcgagat | ggctatgaac | cctgtgtaaa | tgaaggaatg | tgtgttacct | accacaatgg | 360 |
| cacaggatac | tgcaaatgtc | cagaaggctt | cttgggggaa | tattgtcaac | atcgagaccc | 420 |
| ctgtgagaag | aaccgctgcc | agaatggtgg | gacttgtgtg | gcccaggcca | tgctggggaa | 480 |
| agccacgtgc | cgatgtgcct | cagggtttac | aggagaggac | tgccagtact | cgacatctca | 540 |
| tccatgcttt | gtgtctcgac | cttgcctgaa | tggcggcaca | tgccatatgc | tcagccggga | 600 |
| tacctatgag | tgcacctgtc | aagtcgggtt | tacaggtaag | gagtgccaat | ggaccgatgc | 660 |
| ctgcctgtct | catccctgtg | caaatggaag | tacctgtacc | actgtggcca | accagttctc | 720 |
| ctgcaaatgc | ctcacaggct | tcacagggca | gaagtgtgag | actgatgtca | atgagtgtga | 780 |
| cattccagga | cactgccagc | atggtggcac | ctgcctcaac | ctgcctggtt | cctaccagtg | 840 |
| ccagtgcctt | cagggcttca | caggccagta | ctgtgacagc | ctgtatgtgc | cctgtgcacc | 900 |
| ctcgccttgt | gtcaatggag | gcanctgtcg | gcagactggt | gacttcactt | ttgagtgcaa | 960 |
| ctgccttcca | gaaacagtga | aagaggaac | agagctctgg | gaaagagaca | gggaagtctg | 1020 |
| gaatggaaaa | gaacacgatg | agaattagac | actggaaaat | atgtatgtgt | ggttaataaa | 1080 |
| gtgctttaaa | ctgaattgac | attaacagtr | ggtgatcaac | tttmctatgt | gcttgtgctt | 1140 |
| ttgcttttga | tggagtaatt | cattgttttc | ttatccacct | aaatgcaccc | agctgccctt | 1200 |
| gattttctct | gggctactgg | ccttcacaac | cctctcccat | gtaccctctc | tgactttggg | 1260 |
| gtaaccctcc | cctaacttaa | agctagagaa | ttctgaaact | gaggagggga | tcctctgtta | 1320 |
| atcagtgagc | acttttgat | gagctgatag | atgatatatg | agagactatg | cgtggcacaa | 1380 |
| tactttgtta | cactcttcac | tgatacaagt | gttctagagt | gyacacacaa | cccaaagata | 1440 |
| gaaataaaaa | gaggagcagt | gtcgggagc | ttggggcctg | gtgttccatg | gagagggaga | 1500 |
| aaggaacaag | cttgrccaat | tcattcaact | ccttataaaa | atgatgagga | ggctgaaaac | 1560 |
| caagaatttt | gattgggaac | agaatacaag | cagctgaakc | agatgawtta | ctaagcaaca | 1620 |
| aagatcctgt | ttttatacaa | atatccttag | tacaaaaaca | aaaraaggaa | aactgtaggg | 1680 |
| gggagtaatg | tgctaagtaa | gcagaattgc | ctccaaaaga | agttgtttct | agttactctt | 1740 |
| ttccgggtng | ggatctttag | nttccggtat | tgtgggtatg | gttcc | 1785 |

<210> SEQ ID NO 113
<211> LENGTH: 1842
<212> TYPE: DNA
<213> ORGANISM: Homo sapiens

<400> SEQUENCE: 113

| | | | | | |
|---|---|---|---|---|---|
| ggagcctctc | ttgcaacttc | tgccaccgcg | ggccaccgcg | gccgcctgat | cccgcagagg | 60 |
| aagtcgcggc | cgtggagcga | tgacccgcgg | cggtccgggc | gggcgcccgg | ggctgccaca | 120 |

```
gccgccgccg cttctgctgc tgctgctgct gcmgctgttg ttagtcaccg cggagccgcc      180
gaaacctgca ggagtctact atgcaactgc atactggatg cctgctgaaa agacagtaca      240
agtcaaaaat gtaatggaca agaatgggga cgcctatggc ttttacaata actctgtgaa      300
aaccacaggc tggggcatcc tggagatcag agctggctat ggctctcaaa ccctgagcaa      360
tgagatcatc atgtttgtgg ctggcttttt ggaggggtac ctcactgccc cacacatgaa      420
tgaccactac acaaacctct acccacagct gatcacgaaa ccttccatca tggataaagt      480
gcaggatttt atggagaagc aagataagtg acccgaaa aatatcaaag aatacaagac      540
tgattcattt tggagacata caggctatgt gatggcacaa atagatggcc tctatgtagg      600
agcaaagaag agggctatat tagaagggac aaagccaatg accctgttcc agattcagtt      660
cctgaatagt gttggagatc tattggatct gattccctca ctctctccca caaaaaacgg      720
cagcctaaag gtttttaaga gatgggacat gggacattgc tccgctctta tcaaggttct      780
tcctggattt gagaacatcc ttttgctca ctcaagctgg tacacgtatg cagccatgct      840
caggatatat aaacactggg acttcaacrt catagataaa gataccagca gtagtcgcct      900
ctctttcagc agttacccag ggttttgga gtctctggat gattttaca ttcttagcag      960 tggattgata ttgctgcaga ccacaaacag tgtgtttaat aaaaccctgc taaagcagta     1020 ataccccgaga ctctcctgtc ctggcaaaga gtccgtgtgg ccaatatgat ggcagatagt     1080
ggcaagaggt gggcagacat cttttcaaaa tacaactctg gcacctataa caatcaatac     1140
atggttctgg acctgaagaa agtaaagctg aaccacagtc ttgacaaagg cactctgtac     1200
attgtggagc aaattcctac atatgtagaa tattctgaac aaactgatgt tctacggaaa     1260
ggatattggc cctcctacaa tgttcctttc catgaaaaaa tctacaactg gagtggctat     1320
ccactgttag ttcagaagct gggcttggac tactcttatg atttagctcc acgagccaaa     1380
attttccggc gtgaccaagg gaaagtgact gatacggcat ccatgaaata tatcatgcga     1440
tacaacaatt ataagaagga tccttacagt agaggtgacc cctgtaatac catctgctgc     1500
cgtgaggacc tgaactcacc taacccaagt cctggaggtt gttatgacac aaaggtggca     1560
gatatctacc tagcatctca gtacacatcc tatgccataa gtggtcccac agtacaaggt     1620
ggcctccctg tttttcgctg ggaccgtttc aacaaaactc tacatcaggg catgscagag     1680
gtctacaact tgatttat taccatgaaa ccaatttga aacttgatat aaaatgaagg     1740
agggagatga cggactagaa gactgtaaat aagataccaa aggcactatt ttagctatgt     1800
ttttcccatc agaattatgc aataaaatat attaatttgt ca                        1842
```

<210> SEQ ID NO 114
<211> LENGTH: 1960
<212> TYPE: DNA
<213> ORGANISM: Homo sapiens
<220> FEATURE:
<221> NAME/KEY: SITE
<222> LOCATION: (563)
<223> OTHER INFORMATION: n equals a,t,g, or c

<400> SEQUENCE: 114

```
gaattcggca cgagcttctc cgcgcccag ccgccggctg ccagcttttc ggggccccga        60
gtcgcaccca gcgaagagag cgggcccggg acaagctcga actccggccg cctcgccctt      120
ccccggctcc gctccctctg cccctcgggg gtcgcgcgcc cacgatgctg cagggccctg      180
gctcgctgct gctgctcttc ctcgcctcgc actgctgcct gggctcggcg cgcgggctct      240
```

-continued

```
tcctctttgg ccagcccgac ttctcctaca agcgcagmaa ttgcaagccc atcccggtca      300
acctgcagct gtgccacggc atcgaatacc agaacatgcg gctgcccaac ctgctgggcc      360
acgagaccat gaaggaggtg ctggagcagg ccggcgcttg gatcccgctg gtcatgaagc      420
agtgccaccc ggacaccaag aagttcctgt gctcgctctt cgccccgtc tgcctcgatg       480 acctagacga gaccatccag ccatgccact cgctctgcgt gcaggtgaag gaccgctgcg      540
ccccggtcat gtccgccttc ggnttcccct ggcccgacat gcttgagtgc gaccgtttcc      600
cccaggacaa cgacctttgc atcccccctcg ctagcagcga ccacctcctg ccagccaccg     660
aggaagctcc aaaggtatgt gaagcctgca aaataaaaa tgatgatgac aacgacataa       720
tggaaacgct ttgtaaaaat gattttgcac tgaaaataaa agtgaaggag ataacctaca     780
tcaaccgaga taccaaaatc atcctggaga ccaagagcaa gaccatttac aagctgaacg      840
gtgtgtccga aagggacctg aagaaatcgg tgctgtggct caaagacagc ttgcagtgca      900
cctgtgagga gatgaacgac atcaacgcgc cctatctggt catgggacag aaacagggtg      960
gggagctggt gatcacctcg gtgaagcggt ggcagaaggg gcagagagag ttcaagcgca      1020
tctcccgcag catccgcaag ctgcagtgct agtcccggca tcctgatggc tccgacaggc      1080
ctgctccaga gcacggctga ccatttctgc tccgggatct cagctcccgt tccccaagca      1140
cactcctagc tgctccagtc tcagcctggg cagcttcccc ctgccttttg cacgtttgca      1200
tccccagcat ttcctgagtt ataaggccac aggagtggat agctgttttc acctaaagga      1260
aaagcccacc cgaatcttgt agaaatattc aaactaataa aatcatgaat attttatga      1320 agtttaaaaa tagctcactt taaagctagt tttgaatagg tgcaactgtg acttgggtct      1380
ggttggttgt tgtttgttgt tttgagtcag ctgattttca cttcccactg aggttgtcat      1440
aacatgcaaa ttgcttcaat tttctctgtg gcccaaactt gtgggtcaca aaccctgttg      1500
agataaagct ggctgttatc tcaacatctt catcagctcc agactgagac tcagtgtcta      1560
agtcttacaa caattcatca ttttatacct tcaatgggaa cttaaactgt tacatgtatc      1620
acattccagc tacaatactt ccatttatta gaagcacatt aaccatttct atagcatgat      1680
ttcttcaagt aaaaggcaaa agatataaat tttataattg acttgagtac tttaagcctt      1740
gtttaaaaca tttcttactt aacttttgca aattaaaccc attgtagctt acctgtaata      1800
tacatagtag tttacctttta aaagttgtaa aaatattgct ttaaccaaca ctgtaaatat      1860
ttcagataaa cattatattc ttgtatataa actttacatc ctgttttacc taaaaaaaaa      1920
aaaaaaaaaa aaaaaactcg aggggggccc ggtacccaat                            1960
```

<210> SEQ ID NO 115
<211> LENGTH: 536
<212> TYPE: DNA
<213> ORGANISM: Homo sapiens
<220> FEATURE:
<221> NAME/KEY: SITE
<222> LOCATION: (344)
<223> OTHER INFORMATION: n equals a,t,g, or c

<400> SEQUENCE: 115

```
gtgctcagcc cccggggcac agyaggacgt ttgggggcct tctttcagca ggggacagcc       60
cgattgggga caatggcgtc tcttggccac atcttggttt tctgtgtggg tctcctcacc      120
atggccaagg cagaaagtcc aaaggaacac gacccgttca cttacgacta ccagtccctg      180
cagatcggag gcctcgtcat cgccgggatc ctcttcatcc tgggcatcct catcgtgctg      240
agcagaagat gccggtgcaa gttcaaccag cagcagagga ctggggaacc cgatgaagag      300
```

```
gagggaactt tccgcagctc catccgccgt ctgtccamcc gcangcggta gaaacacctg    360
gagcgatgga atccggccag gactcccctg gcacctgaca tctcccacgc tccacctgcg    420
cgcccaccgc cccctccgcc gcccttccc  cagccctgcc cccgcagact ccccctgccg    480
ccaagacttc aataaaacg  tgcgttcctc tcgamaaaaa aaaaaataaa aaaact        536
```

```
<210> SEQ ID NO 116
<211> LENGTH: 790
<212> TYPE: DNA
<213> ORGANISM: Homo sapiens
<220> FEATURE:
<221> NAME/KEY: SITE
<222> LOCATION: (360)
<223> OTHER INFORMATION: n equals a,t,g, or c
<220> FEATURE:
<221> NAME/KEY: SITE
<222> LOCATION: (750)
<223> OTHER INFORMATION: n equals a,t,g, or c
<220> FEATURE:
<221> NAME/KEY: SITE
<222> LOCATION: (753)
<223> OTHER INFORMATION: n equals a,t,g, or c

<400> SEQUENCE: 116
gtggggaggg ggcggagcaa agccgcgcct ctgggtgggc gggtcgggcc gtccaggtcc    60
ctgacttgaa ccttcccggt ccccagccct caacaggagg cgcagaaaat cttcaaagcc    120
aaccacccca tggacgcaga agttactaag gccaagcttc tggggtttgg ctctgctctc    180
ctggacaatg tggaccccaa ccctgagaac ttcgtggggg cggggatcat ccagactaaa    240
gccctgcagg tgggctgtct gcttcggctg gagcccaatg cccaggccca gatgtaccgg    300
ctgaccctgc gcaccagcaa ggagcccgtc tcccgtcacc tgtgtgagct gctggcacan    360
agttctgagc cctggactct gccccggggg atgtggccgg cactgggcag ccccttggac    420
tgaggcagtt ttggtggatg ggggacctcc actggtgaca gagaagacac cagggtttgg    480
gggatgcctg ggactttcct ccggcctttt gtattttat  ttttgttcat ctgctgctgt    540
ttacattctg gggggttagg gggagtcccc ctccctccct ttccccccca agcacagagg    600
ggagaggggc cagggaagtg gatgtctcct ccctcccac  cccaccctgt tgtagcccct    660
cctaccccct cccatccag  gggctgtgta ttattgtgag cgaataaaca gagagacgtt    720
aacagcccca tgtctgtgtc catcacccan tgntaggtag tcaaagaagt ggggtgaggg    780
catgcagagt                                                           790
```

```
<210> SEQ ID NO 117
<211> LENGTH: 776
<212> TYPE: DNA
<213> ORGANISM: Homo sapiens
<220> FEATURE:
<221> NAME/KEY: SITE
<222> LOCATION: (750)
<223> OTHER INFORMATION: n equals a,t,g, or c

<400> SEQUENCE: 117
cagcgctgga agcagctgag cctgtgaggg gtggggaggg ggcggagcaa agccgcgcct    60
ctgggtgggc gggtcgggcc gtccaggtcc ctgacttgaa ccttcccggt ccccagccct    120
caacaggagg cgcagaaaat cttcaaagcc aaccacccca tggacgcaga agttactaag    180
gccaagcttc tggggtttgg ctctgctctc ctggacaatg tggaccccaa ccctgagaac    240
ttcgtggggg cggggatcat ccagactaaa gccctgcagg tgggctgtct gcttcggctg    300
```

-continued

```
gagcccaatg cccaggccca gatgtaccgg ctgaccctgc gcaccagcaa ggagcccgtc    360
tcccgtcacc tgtgtgagct gctggcacag agttctgagc cctggactct gccccggggg    420
atgtggccgg cactgggcag ccccttggac tgaggcagtt ttggtggatg ggggacctcc    480
actggtgaca gagaagacac cagggtttgg gggatgcctg gactttcct ccggccttt     540 gtatttttat ttttgttcat ctgctgctgt ttacattctg gggggttagg gggagtcccc    600
ctccctccct ttcccccca agcacagagg ggagaggggc cagggaagtg gatgtctcct    660
cccctcccac cccaccctgt tgtagcccct cctacccct cccatccag gggctgtgta      720 ttattgtgag cgaataaaca gagagacgcn taaaaaaaaa aaaaaaaat tgaggg         776
```

<210> SEQ ID NO 118
<211> LENGTH: 453
<212> TYPE: DNA
<213> ORGANISM: Homo sapiens

<400> SEQUENCE: 118

```
ggttctgaca ccagatgttc tctgctcctg gttaatgtca gtgagggctg gaagttgaat     60
aaatgagaac aggagtggtc tgggcccatg taaatgatcc tcccttgaaa ggaggaacag    120 cttttcatcat ttgttccagc taagccttgc atgcattata gatctggtgc taagcagtgg   180
gaaagatctc ataagtaatg ttttatgttc tttckgtctc tcytcttckg ttgttcttgg   240
cttgtgggtt gtgtttgkgg ttgttaactg gaaaattgct ataagccagt tgtcyckaak   300
tttwaaaaac gaattagaaa aaccataaaa tcytctggcc yatgcacatk gtcccygttt   360
tgtgaaaaca ttaaagggta aataaaaagg aaggagaaca gtcaataatg tgcatcaaat   420
atattctgag ttctagagaa attaatgacc aag                                 453
```

<210> SEQ ID NO 119
<211> LENGTH: 2016
<212> TYPE: DNA
<213> ORGANISM: Homo sapiens
<220> FEATURE:
<221> NAME/KEY: SITE
<222> LOCATION: (152)
<223> OTHER INFORMATION: n equals a,t,g, or c
<220> FEATURE:
<221> NAME/KEY: SITE
<222> LOCATION: (441)
<223> OTHER INFORMATION: n equals a,t,g, or c
<220> FEATURE:
<221> NAME/KEY: SITE
<222> LOCATION: (697)
<223> OTHER INFORMATION: n equals a,t,g, or c
<220> FEATURE:
<221> NAME/KEY: SITE
<222> LOCATION: (1998)
<223> OTHER INFORMATION: n equals a,t,g, or c

<400> SEQUENCE: 119

```
aggctgttca caggcacccc gagacagcgt cccccctctg ggcgcactgg atttgacgtt     60
gcaggacgcg cggctggaac ccccaggccc cgctgctcac agaccgggac tccgcctccg    120
gttcccgagg gcgtggcgag gcgctgcggg ancccaacag gatgccttcc gtgccttcca    180
tcaagatctc aattttgtgc gcaattccta cagcccctgt tgattggaga gctggctccg    240
gaagaaccca gccakgatgg acccctgaat gcgcatggtc gaggacttcc gagccctgca    300
ccaggcagcc gaggacatga agctgtttga tgccagtccc accttctttg ctttcctact    360
gggccacatc ctgccatgg aggtgctggc ctggctcctt atctacctcc tgggtcctgg    420
ctgggtgccc agtgccctgg nccgccttca tcctggccat ctctcaggct cagtcctggt   480
```

```
gtctgcagca tgacctgggc catgctccat cttcaagaag tcctggtgga accacgtggc    540
ccagaagttc gtgatgggc agctaaaggg cttctccgcc cactggtgga acttccgcca    600
cttccagcac cacgccaagc ccaacatctt ccacaaagac ccagacgtga cggtggcgcc    660
cgtyttcctc ctgggggagt catccgtcga gtatggncaa gaagaaacgc agataccctac   720
cctacaacca gcagcacctg tacttcttcc tgatcggccc gccgctgctc accctggtga    780
actttgaagt ggaaaatctg gcgtacatgc tggtgtgcat gcagtgggcg gatttgctct    840
gggccgccag cttctatgcc cgcttcttct tatcctacct ccccttctac ggcgtccctg    900
gggtgctgct cttctttgtt gctgtcaggt atggcaggga gtggcgaggt cacacacagg    960
cgacaggtga cccccactgc agcccccac cagagcttcc cttttcccgt ctgcagaatg    1020
gggccagtgg tactgcctcc ctggcttgct ggtggaatca cataaacaca agyttcagga   1080
gcccagggtc ggtgggttta gggagcgtgg cctggcttgt aagtggcccg gtgggtgtcg   1140
gagctgctct ggactcagcc tcacagtgga cactgctcca ttcagattct ttaaacactg   1200
gcaaggggc gatggccaca atcctattgt acagataagg aagtcaaggc cayttgggga   1260
cagytgctct tccagcctcc actcagggtg ccttaagtgg tgagctggac ctagggcagt   1320
gccgagcytc cccacagggt cctggaaagc cactggttcg tgtggatcac acagatgaac   1380
cacatcccca aggagatcgg ccacgagaag caccgggact gggtcagctc tcagctggca   1440
gccacctgca acgtggagcc ctcacttttc accaactggt tcagcgggca cctcaacttc   1500
cagatcgagc accacctctt ccccaggatg ccgagacaca actacagccg ggtggccccg   1560
ctggtcaagt cgctgtgtgc caagcacggc ctcagctacg aatgaagccc ttcctcaccg   1620
cgctggtgga catcgtcagg tccctgaaga agtctggtga catctggctg gacgcctacc   1680
tccatcagtg aaggcaacac ccaggcgggc agagaagggc tcagggcacc agcaaccaag   1740
ccagccccg gcgggatcga tacccccamc cctccactgg ccagcctggg ggtgccctgc    1800
ctgccctcct ggtactgttg tcttcccctc ggcccctca catgtgtatt cagcagccct    1860
atggccttgg ctctgggcct gatgggacag gggtagaggg aaggtgagca tagcacattt    1920
tcctagagcg agaattgggg gaaagctgtt atttttatat taaatacat tcagatgtaa    1980
aaaaaaaaaa aaaaaaanct cgaggggggg ccccgg                              2016

<210> SEQ ID NO 120
<211> LENGTH: 2136
<212> TYPE: DNA
<213> ORGANISM: Homo sapiens

<400> SEQUENCE: 120
ggggacggag ccgctgtcaa ctctccaact cagctcagct gatcggttgc cgccgccgcc     60
gccgccagat tctggaggcg aagaacgcaa agctgagaac atggacgtta atatcgcccc    120
actccgcgcc tgggacgatt tcttcccggg ttccgatcgc tttgcccggc cggacttcag    180
ggacatttcc aaatggaaca accgcgtagt gagcaacctg ctctattacc agaccaacta    240
cctggtggtg gctgccatga tgatttccat tgtgggtttt ctgagtccct tcaacatgat    300
cctgggagga atcgtggtgg tgctggtgtt cacagggttt gtgtgggcag cccacaataa    360
agacgtcctt cgccggatga agaagcgcta ccccacgacg ttcgttatgg tggtcatgtt    420
ggcgagctat ttccttatct ccatgtttgg aggagtcatg gtctttgtgt ttggcattac    480
ttttcctttg ctgttgatgt ttatccatgc atcgttgaga cttcggaacc tcaagaacaa    540
```

```
actggagaat aaaatggaag gaataggttt gaagaggaca ccgatgggca ttgtcctgga      600
tgccctagaa cagcaggaag aaggcatcaa cagactcact gactatatca gcaaagtgaa      660
ggaataaaca taacttacct gagctagggt tgcagcagaa attgagttgc agcttgccct      720
tgtccagacc tatkttctgc ttgcgttttt gaaacaggag gtgcacgtac cacccaatta      780
tctatggcag catgcatgta taggccgaac tattatcagc tctgatgttt cagagagaag      840
acctcagaaa ccgaaagaaa accaccaccc tcctattgtg tctgaagttt cacgtgtgtt      900
tatgaaatct aatgggaaat ggatcacacg atttctttaa gggaattaaa aaaataaaa       960 gaattacggc ttttacagca acaatacgat tatcttatag gaaaaaaaaa atcattgtaa     1020
agtatcaaga caatacgagt aaatgaaaag gctgttaaag tagatgacat catgtgttag     1080
cctgttccta atcccctaga attgtaatgt gtgggatata aattagtttt tattattctc     1140
ttaaaaatca aagatgatct ctatcacttt gccacctgtt tgatgtgcag tggaaactgg     1200
ttaagccagt tgttcatact tcstttacaa atataaagat agctgtttag gatattttgt     1260 tacattttttg taaattttttg aaatgctagt aatgtgtttt caccagcaag tatttgttgc     1320
aaacttaatg tcatttttcct taagatggtt acagctatgt aacctgtatt attctggacg     1380
gacttattaa aatacaaaca gacaaaaaat aaaacaaaac ttgagttcta tttaccttgc     1440 acatttttttg ttgttacagt gaaaaaaatg gtccaagaaa atgtttgcca ttttttgcatt     1500 gtttcgttttt taactggaac atttagaaag aaggaaatga atgtgcattt tattaattcc     1560
ttaggggcac aaggaggaca ataatagctg atcttttgaa atttgaaaaa cgtctttaga     1620
tgaccaagca aaaagacttt aaaaaatggt aatgaaaatg gaatgcagct actgcagcta     1680
ataaaaaatt ttagatagca attgttacaa ccatatgcct ttatagctag acattagaat     1740
tatgatagca tgagtttata cattctatta ttttcctcc ctttctcatg tttttataaa      1800
taggtaataa aaaatgttttt gcctgccaat tgaatgattt cgtagctgaa gtagaaacat     1860
ttaggttcct gtagcattaa attgtgaaga caactggagt ggtacttact gaagaaactc     1920
tctgtatgtc ctagaataag aagcaatgat gtgctgcttc tgattttct tgcattttaa      1980 attctcagcc aacctacagc catgatcttt agcacagtga tatcaccatg acttcacaga     2040
catggtctag aatctgtacc cttacccaca tatgaagaat aaaattgatt aaaggttaaa     2100
aaaaaaawaa aaaaamwagg ggggcccggt wcccag                               2136
```

<210> SEQ ID NO 121
<211> LENGTH: 219
<212> TYPE: DNA
<213> ORGANISM: Homo sapiens

<400> SEQUENCE: 121

```
gccctagtat ctgggcagct gtgcatggag atagccagag gaaacatttt ttttcttaat       60
grattggtga ccacattttg ttgttcttgc ctcctattat ccgtgcscta tttgcatsct      120
ggtttcttct acagtagttt atgtaaatgt tgttttgtcc ttgtcgttct cagtagaatt      180
ggttctgtaa acgaaacctg gtcctgtaat ttcagtata                             219
```

<210> SEQ ID NO 122
<211> LENGTH: 1686
<212> TYPE: DNA
<213> ORGANISM: Homo sapiens
<220> FEATURE:
<221> NAME/KEY: SITE
<222> LOCATION: (622)
<223> OTHER INFORMATION: n equals a,t,g, or c

<400> SEQUENCE: 122

```
gctggagatt cacattttac ctgattgcct tcattgccgg catggccgtc attgtggata      60
aaccctggtt ctatgacatg aagaaagttt gggagggata tcccatacag agcactatcc     120
cttcccagta ttggtactac atgattgaac tttccttcta ctggtccctg ctcttcagca     180
ttgcctctga tgtcaagcga aaggatttca aggaacagat catccaccat gtgrccacca     240
tcattctcat cagcttttcc tggtttgcca attacatccg agctgggact ctaatcatgg     300
ctctgcatga ctcttccgat tacctgctgg agtcagccaa gatgtttaac tacgcgggat     360
ggaagaacac ctgcaacaac atcttcatcg tcttcgccat tgtttttatc atcacccgac     420
tggtcatcct gcccttctgg atcctgcatt gcacctggt gtacccactg gagctctatc      480
ctgccttctt tggstattac ttcttcaatt ccatgatggg agttctacag ctgctgcata     540
tcttctgggc ctacctcatt ttgcgcatgg cccacaagtt cataactggg aaagctggta     600
aagatgaac gcawgcrcgg gnaagaaaca gagagctcag aggggagga ggctgcagct       660
gggggaggag caaagagccg gcccctagcc aatggccacc ccatcctcaa taacaaccat     720
cgtaagaatg actgaaccat tattccagct gcctcccaga ttaatgcata aagccaagga    780
actacccygc tccctgcgct ataggggtcac tttaagctct ggggaaaaag agaaagtga    840
gaggagagtt ctctgcatcc tccctccttg cttgtcaccc agttgccttt aaaccaaatt    900
ctaaccagcc tatccccagg taggggacg ttggttatat tctgttagag ggggacggtc     960
gtattttcct ccctacccgc caagtcatcc tttctactgc ttttgaggcc ctccctcagc   1020
tctctgtggg taggggttac aattcacatt ccttattctg agaatttggc cccagctgtt   1080
tgcctttgac tccctgacct ccagagccag ggttgtgcct tattgtccca tctgtgggcc   1140
tcattctgcc aaagctggac caaggctaac ctttctaagc tccctaactt gggccagaaa   1200
ccaaagctga gcttttaact ttctccctct atgacacaaa tgaattgagg gtaggaggag   1260
ggtgcacata acccttaccc tacctctgcc aaaaagtggg ggctgtactg gggactgctc   1320
ggatgatctt tcttagtgct acttctttca gctgtccctg tagcgacagg tctaagatct   1380
gactgcctcc tcctttctct ggcctcttcc cccttccctc ttctcttcag ctaggctagc   1440
tggtttggag tagaatggca actaattcta attttattt attaaatatt tggggttttg    1500
gttttaaagc cagaattacg gctagcacct agcatttcag cagagggacc attttagacc   1560
aaaatgtact gttaatgggt ttttttttaa aattaaaaga ttaaataaaa aatattaaat   1620
aaaacatggc aataagtgtc agactattag gaattgagaa ggggatcaa ctaaataaac    1680
gaagag                                                              1686
```

<210> SEQ ID NO 123
<211> LENGTH: 1211
<212> TYPE: DNA
<213> ORGANISM: Homo sapiens

<400> SEQUENCE: 123

```
cagcctgtgc cagacgagga ggtgattgag ctgtatgggg gtacccagca catcccacta      60
taccagatga gtggcttcta tggcaagggt ccctccatta agcagttcat ggacatcttc     120
tcgctaccgg agatggctct gctgtcctgt gtggtggact actttctggg ccacagcctg     180
gagtttgacc aaacatctct acaaggacgt gacggacgcc atccgagacg tgcatgtgaa     240
gggcctcatg taccagtgga tcgagcagga catggagaag tacatcctga gagggatga     300
```

```
gacgtttgct gtcctgagcc gcctggtggc ccatgggaaa cagctgttcc tcatcaccaa    360
cagtcctttc agcttcgtag acaaggggat gcggcacatg gtgggtcccg attggcgcca    420
ctcttcgatg tggtcattgt ccaggcagac aagcccagct tcttcactga ccggcgcaac    480
tttcagaaaa ctcgatgaga agggctcact tcagtgggac cggatcaccc gcttggaaaa    540
gggcaagatc tatcggcagg gaaacctgtt tgacttctta cgcttgacgg aatggcgtgg    600
cccccgcgtg ctctacttcg ggaccacct ctatagtgat ctggcggatc tcatgctgcg    660
gcacggctgg cgcacaggcg ccatcatccc gagctggag cgtgagatcc gcatcatcaa    720
cacggagcag tacatgcact cgctgacgtg gcagcaggcg ctcacggggc tgctggagcg    780
catgcagacc tatcaggacg cggagtcgag gcaggtgctg gctgcctgga tgaaagagcg    840
gcaggagctg aggtgcatca ccaaggccct gttcaatgcg cagttcggca gcatcttccg    900
caccttccac aaccccacct acttctcaag gcgcctcgtg cgcttctctg acctctacat    960
ggcctccctc agctgcctgc tcaactaccg cgtggacttc accttctacc cacgccgtac   1020
gccgctgcag cacgaggcac ccctctggat ggaccagctt ctgcaccggc tgcatgaaga   1080
cccccttcct tggtgacatg gcccacatcc gctgagggca cctttattgt ctgggacagg   1140
ccctcagccc ctcctgcccc atccacccag acaagcaata aaagtggtct cctccctgaa   1200
aaaaaaaaaa a                                                       1211
```

<210> SEQ ID NO 124
<211> LENGTH: 1804
<212> TYPE: DNA
<213> ORGANISM: Homo sapiens
<220> FEATURE:
<221> NAME/KEY: SITE
<222> LOCATION: (550)
<223> OTHER INFORMATION: n equals a,t,g, or c

<400> SEQUENCE: 124

```
cgcacctatg ggctcgctac caggacatgc ggagactggt gcacgacctc ctgcccccg     60 aggtctgcag tctcctgaac ccagcagcca tctacgccaa caacgagatc agcctgcgtg    120
acgttgaggt ctacggcttt gactacgact acaccctggc ccagtatgca gacgcactgc    180
accccgagat cttcagtacc gcccgtgaca tcctgatcga gcactacaag tacccagaag    240
ggattcggaa gtatgactac aaccccagct ttgccatccg tggcctccac tatgacattc    300
agaagagcct tctgatgaag attgacgcct ccactacgt gcagctgggg acagcctaca    360
ggggcctcca gcctgtgcca cgaggagg tgattgagct gtatgggggt acccagcaca    420
tcccactata ccagatgagt ggcttctatg caagggtcc ctccattaag cagttcatgg    480
acatcttctc gctaccggag atggctctgc tgtcctgtgt ggtggactac tttctgggcc    540
acagcctggn agtttgacca agcacatctc tacaaggacg tgacgacgc catccgagac    600 gtgcatgtga agggcctcat gtaccagtgg atcgagcagg acatggagaa gtacatcctg    660 agagggatg agacgtttgc tgtcctgagc cgcctggtgg cccatgggaa acagctgttc    720
ctcatcacca cagtcctttt cagcttcgta gacaagggga tgcggcacat ggtgggtccc    780
gattggcgcc actcttcgat gtggtcattg tccaggcaga caagcccagc ttcttcactg    840
accggcgcaa gcttttcaga aaactcgatg agaagggctc acttcagtgg gaccggatca    900
cccgcttgga aagggcaag atctatcggc agggaaacct gtttgacttc ttacgcttga    960
cggaatggcg tggcccccgc gtgctctact tcggggacca cctctatagt gatctggcgg   1020
atctcatgct gcggcacggc tggcgcacag gcgccatcat ccccgagctg gagcgtgaga   1080
```

```
tccgcatcat caacacggag cagtacatgc actcgctgac gtggcagcag gcgctcacgg      1140
ggctgctgga gcgcatgcag acctatcagg acgcggagtc gaggcaggtg ctggctgcct      1200
ggatgaaaga gcggcaggag ctgaggtgca tcaccaaggc cctgttcaat gcgcagttcg      1260
gcagcatctt ccgcaccttc cacaacccca cctacttctc aaaggcgcct cgtgcgcttc      1320
tctgacctct acatggcctc cctcagctgc ctgctcaact accgcgtgga cttcaccttc      1380
tacccacgcc gtacgccgct gcagcacgag gcacccctct ggatggacca gctctgcacc      1440
ggctgcatga agaccccctt ccttggtgac atggcccaca tccgctgagg gcaccttttat     1500 tgtctgggac aggccctcag cccctcctgc ccatccacc cagacaagca ataaaagtgg       1560
tctcctccct gtgcatgctt ctgctttcag ccccagcctc gtcacttgac tgtgaggatc      1620
ctctgggtgt cagggaagtc ctcctccagc agtgagtcat cgaagggttc acaaaaggtg     1680
tcgctgccaa agacagggtt ggggacagag accagggtgg ggttggtccc ttcttgccac     1740
ggtgagaagt cgtcgtcagc cggacgcgtg ggtcgacccg ggaattccgg accggtacct     1800
gcag                                                                   1804

<210> SEQ ID NO 125
<211> LENGTH: 1282
<212> TYPE: DNA
<213> ORGANISM: Homo sapiens
<220> FEATURE:
<221> NAME/KEY: SITE
<222> LOCATION: (8)
<223> OTHER INFORMATION: n equals a,t,g, or c
<220> FEATURE:
<221> NAME/KEY: SITE
<222> LOCATION: (1276)
<223> OTHER INFORMATION: n equals a,t,g, or c
<220> FEATURE:
<221> NAME/KEY: SITE
<222> LOCATION: (1277)
<223> OTHER INFORMATION: n equals a,t,g, or c
<220> FEATURE:
<221> NAME/KEY: SITE
<222> LOCATION: (1282)
<223> OTHER INFORMATION: n equals a,t,g, or c

<400> SEQUENCE: 125
ccgcaggnca gcgacgcgac tctggtgcgg gccgtcttct tcccccgag ctgggcgtgc       60 gcggccgcaa tgaactggga gctgctgctg tggctgctgg tgctgtgcgc gctgctcctg     120
ctcttggtgc agctgctgcg cttcctgagg gctgacggcg acctgacgct actatgggcc    180
gagtggcagg gacgacgccc agaatgggag ctgactgata tggtggtgtg ggtgactgga     240
gcctcgagtg gaattggtga ggagctggct taccagttgt ctaaactagg agtttctctt    300
gtgctgtcag ccagaagagt gcatgagctg gaaagggtga aagaagatg cctagagaat     360 ggcaatttaa aagaaaaaga tatacttgtt ttgccccttg acctgaccga cactggttcc    420
catgaagcgg ctaccaaagc tgttctccag gagtttggta gaatcgacat tctggtcaac    480
aatggtggaa tgtcccagcg ttctctgtgc atggatacca gcttggatgt ctacagaaag    540
ctaatagagc ttaactactt agggacggtg tccttgacaa atgtgttct gcctcacatg     600 atcgagagga agcaaggaaa gattgttact gtgaatagca tcctgggtat catatctgta    660
cctctttcca ttggatactg tgctagcaag catgctctcc ggggtttttt taatggcctt    720
cgaacagaac ttgccacata cccaggtata atagtttcta catttgccc aggacctgtg     780 caatcaaata ttgtggagaa ttccctagct ggagaagtca caaagactat aggcaataat    840
```

-continued

```
ggagaccagt cccacaagat gacaaccagt cgttgtgtgc ggctgatgtt aatcagcatg     900
gccaatgatt tgaaagaagt ttggatctca gaacaacctt tcttgttagt aacatatttg     960
tggcaataca tgccaacctg ggcctggtgg ataaccaaca agatgggaa gaaaaggatt     1020 gagaacttta agagtggtgt ggatgcagac tcttcttatt ttaaaatctt taagacaaaa    1080
catgactgaa aagagcayct gtacttttca agccactgga gggaraaatg gaaaacatga    1140
aaacagcaat cttcttatgc ttctgaataa tcaaagacta atttgtgrtt ttacttttta    1200
atagatatga ctttgcttcc aacatggaat gaaataaaaa ataaataata aagattgcc     1260 atggaaaaaa aaaagnnggg an                                             1282
```

<210> SEQ ID NO 126
<211> LENGTH: 1296
<212> TYPE: DNA
<213> ORGANISM: Homo sapiens
<220> FEATURE:
<221> NAME/KEY: SITE
<222> LOCATION: (803)
<223> OTHER INFORMATION: n equals a,t,g, or c

<400> SEQUENCE: 126

```
ggcagagctt agagtgtgga aaaggcaacc aggttggccg taagtgcctg ctggaatgcg      60
tgtgcctcca casggrtctg ggcatccgga ctgataacca gccggccaga ctgagggatg     120
gaaggcactg agatggggc ccgtccaggc ggacacccgc agaaatggag ctttctgtgg     180
tctcttgcac tctggctgcc tcttgccctc tctgtgtctc tctttcttgg tctctccctc     240
tctcctcctc agcctggtct ttctctttgg tgcacactta gttattgttg tgagcaatgg     300
aagttcaaag gaactccctc tccagctctt ctgaatcttg ggacacagcc taaaaaggac    360
aaaaagttag aagacagcat agcaactcag ctcagggrgc taccagagaa aaatagcaac    420
tgatgtgggt gcttttttt tttttttaat ttgaataaaa agaattagaa gtgatgtcct     480
tttataaaat gccttctccc ccttcccgcc tacagtctct tcctctcccc ttagagggg     540 gaaagtgtat aaacctacag ggttgtgagt ctgaaaagag gatcccctc accccaccc     600 tgggcagagc agtgggggtt ggggggtggg agagggggac acagatcctg gcacactgtg     660
gatatttctt gcagattgca gtctcttgtg gcccaaacag gttaggtaga ctatcgcctc     720
tggcaggtgc cacctttgg taccaacatg ttctgaggtg ttaggatttg ggttgggttt     780
tttttgtttg tttttttttt ccntttggtc tttttttttt tcyccttkta aagaaaagct    840
aaaggccgct gtgagtcctg gtggcaggct ctccatggat gtagcatatc gaagataatt     900
tttatactgc atttttatgg attatttttgt aatgtgtgat tccgtctgct gaggaggtgg    960 gagggctcc agggaaagcc acccacccttc agtgaggttg ctccccagct gagcgcaccg    1020
ggcatgggat gtggaggctg gcgacacacc ctgtgcctct ccaaggctgg gcgcgtgggg    1080
cgtccagagt ctctctgggt tcagatgtc catctgccac ctcttgttaa ggctctagcc     1140
agaagggagg gtgagggtag aagaaagtta ttcccgaaga aaaaaagaat gaaaagtcat    1200
tgtactgaac tgtttttata tttttaaaag ttactattta aagcggacgt cgtgggtcga    1260
cccgggaatt cccggaccgg tactgtcagg tctaac                              1296
```

<210> SEQ ID NO 127
<211> LENGTH: 737
<212> TYPE: DNA
<213> ORGANISM: Homo sapiens
<220> FEATURE:
<221> NAME/KEY: SITE

```
<222> LOCATION: (5)
<223> OTHER INFORMATION: n equals a,t,g, or c
<220> FEATURE:
<221> NAME/KEY: SITE
<222> LOCATION: (111)
<223> OTHER INFORMATION: n equals a,t,g, or c
<220> FEATURE:
<221> NAME/KEY: SITE
<222> LOCATION: (471)
<223> OTHER INFORMATION: n equals a,t,g, or c
<220> FEATURE:
<221> NAME/KEY: SITE
<222> LOCATION: (491)
<223> OTHER INFORMATION: n equals a,t,g, or c
<220> FEATURE:
<221> NAME/KEY: SITE
<222> LOCATION: (716)
<223> OTHER INFORMATION: n equals a,t,g, or c
<220> FEATURE:
<221> NAME/KEY: SITE
<222> LOCATION: (735)
<223> OTHER INFORMATION: n equals a,t,g, or c

<400> SEQUENCE: 127
ggcanagtgg aggcaatgcc agctccagga cagaggctca ggtgcccaac gggcaaggca      60
gcccagggggg ctgtgtctgt tcaagtcagg cttccccggc ccytcgcgca ncagcgcttc    120
cacgggcagc ccggggcccc accccacgca ctgaagaggc cgcctgggct gccatggccc    180
tgaccttcct gctggtgctg ctcaccctgg ccacgctctg cacacggctg cacagaaact    240
tccgacgcgg ggagagcatc tactgggggc ccacagcgga cagccaggac acagtggctg    300
ctgtgctgaa gcggaggctg ctgcagccct cgcgccgggt caagcgctcg cgccggagac    360
ccytcytccc gcccacgccg dacagcgccc cggaaggcga gagctcggag tgacggcctg    420
ggacctgcca ctgtggcgtg cggtctcccc gcgccgcgag gccgcgamct ntgccacgtg    480
gaccgcgcgc ngggcgctmc cctggtggcg atggcgcggc actggcgagc actgcgkggg    540
ctttcctcct tgttggttgc tgagtgggcg gccaagggga gaaaggagc cgcttytgcc    600
tcccttgcca aaactccgtt tctaattaaa ttattttttag tagaaaaaaa aaaaaaaaa    660
aaaaaaaaaa aaaaaaaaaa aaaaaaaaac tcgagggggg gcccggtacc caattngcca    720
aatagcgatc gtatnaa                                                    737

<210> SEQ ID NO 128
<211> LENGTH: 1925
<212> TYPE: DNA
<213> ORGANISM: Homo sapiens

<400> SEQUENCE: 128
ccccgcctcc aaagctaacc ctcgggcttg aggggaagar gctgactgta cgttccttct     60
actctggcac cactctccag gctgccatgg ggcccagcac ccctctcctc atcttgttcc    120
ttttgtcatg gtcgggaccc ctccaaggac agcagcacca ccttgtggag tacatggaac    180
gccgactagc tgctttagag gaacggctgg cccagtgcca ggaccagagt agtcggcatg    240
ctgctgagct gcgggacttc aagaacaaga tgctgccact gctggaggtg gcagagaagg    300
agcgggaggc actcagaact gaggccgaca ccatctccgg gagagtggat cgtctggagc    360
gggaggtaga ctatctggag acccagaacc cagctctgcc ctgtgtagag tttgatgaga    420
aggtgactgg aggccctggg accaaaggca agggaagaag gaatgagaag tacgatatgg    480
tgacagactg tggctacaca atctctcaag tgagatcaat gaagattctg aagcgatttg    540
gtggcccagc tggtctatgg accaaggatc cactgggggca aacagagaag atctacgtgt    600
```

```
tagatgggac acagaatgac acagcctttg tcttcccaag gctgcgtgac ttcacccttg    660
ccatggctgc ccggaaagct tcccgagtcc gggtgcccct ccctgggta ggcacagggc    720 agctggtata tggtggcttt ctttatttg ctcggaggcc tcctggaaga cctggtggag    780
gtggtgagat ggagaacact ttgcagctaa tcaaattcca cctggcaaac cgaacagtgg    840
tggacagctc agtattccca gcagaggggc tgatccccc ctacggcttg acagcagaca    900
cctacatcga cctggcagct gatgaggaag gtctttgggc tgtctatgcc acccgggagg    960
atgacaggca cttgtgtctg gccaagttag atccacagac actggacaca gagcagcagt   1020
gggacacacc atgtcccaga gagaatgctg aggctgcctt tktcatctgt gggaccctct   1080
atgtcgtcta taacacccgt cctgccagtc gggcccgcat ccagtgctcc tttgatgcca   1140
gcggaccctg acccctgaac gggcagcact cccttatttt ccccgcagat atggtgccca   1200
tgccagcctc cgctataacc cccgagaacg ccagctctat gcctgggatg atggctacca   1260
gattgtctat aagctggaga tgaggaagaa agaggaggag gtttgaggag ctagccttgt   1320
tttttgcatc tttctcactc ccatacattt atattatatc cccactaaat ttcttgttcc   1380
tcattcttca aatgtgggcc agttgtggct caaatcctct atatttttag ccaatggcaa   1440
tcaaattctt tcagctcctt tgtttcatac ggaactccag atcctgagta atccttttag   1500
agcccgaaga gtcaaaaccc tcaatgttcc ctcctgctct cctgccccat gtcaacaaat   1560
ttcaggctaa ggatgcccca gacccagggc tctaaccttg tatgcgggca ggcccaggga   1620
gcaggcagca gtgttcttcc cctcagagtg acttggggag ggagaaatag gaggagacgt   1680
ccagctctgt cctctcttcc tcactcctcc cttcagtgtc ctgaggaaca ggactttctc   1740
cacattgttt tgtattgcaa cattttgcat taaaaggaaa atccamaaaa aaaaaaaaa   1800 aaaaaaaaa aaaaaaaaa aaaaaaaaa aaaaaaaaa aaaaaaaaa aaaaaaaaa   1860 actgcggccg ctgtcccttc tgtcgtcttc tcgcagccgt acccttctgt cgtcttctcg   1920
cagcc                                                               1925
```

<210> SEQ ID NO 129
<211> LENGTH: 2713
<212> TYPE: DNA
<213> ORGANISM: Homo sapiens
<220> FEATURE:
<221> NAME/KEY: SITE
<222> LOCATION: (424)
<223> OTHER INFORMATION: n equals a,t,g, or c
<220> FEATURE:
<221> NAME/KEY: SITE
<222> LOCATION: (444)
<223> OTHER INFORMATION: n equals a,t,g, or c
<220> FEATURE:
<221> NAME/KEY: SITE
<222> LOCATION: (572)
<223> OTHER INFORMATION: n equals a,t,g, or c
<220> FEATURE:
<221> NAME/KEY: SITE
<222> LOCATION: (577)
<223> OTHER INFORMATION: n equals a,t,g, or c

<400> SEQUENCE: 129

```
tcctaccttc caaccctct ggcatcccca gcactgatgg tcctggcatc cacggctgag     60
gccagccgtg actgcttcca tcccttgtca gcagccacga ccctttggtg tacctgtytc   120
agttgacaag gacgtgcata ttcctttcac caacggttcc tataccttg cctctatgta    180 ccatcggcaa ggtgggtgc caggcacttt tgccaatcgt gatttccccc cttctctact    240
acacctccac cctcaatttg ctcccccaaa tctagattgc accccaatca gtatgctgaa    300
```

```
tcataagtgg tgtgggggtt tccggccttt gsctccaccc grggaccggg rgagytatca    360
gtcagcttta cgccggccaa gcgacttaag aactgccatg acacagagtc tccccacttg    420
cgcntctcag atgcagatgg gaangaatat gactttggga cacagctgcm atctagctcc    480
cccggttcac taaaggttga tgacactggg aagaagattt ttgctgtctc tggcctcatt    540
tctgatcggg aagcctcatc tagcccagag gntcggnaat gacagatgta agaagaaagc    600
agcggcattg ttcgacagcc aggcccaat ttgccccatc tgccaggtcc tgctgaggcc     660
cagtgagctg caggagcata tggagcagga actggagcag ctagcccaac tgccctcgag    720
caagaattcc cttctgaagg atgccatggc tccaggcacc ccaaagtccc tcctgttgtc    780
tgcttccatc aagagggaag gagagtctcc aacggcatca ccccactcat ctgccaccga    840
tgacctccac cattcagaca gataccagac ctttctgcga gtacgagcca accggcagac    900
ccgaytgaat gytcggattg ggaaaatgaa acggaggaag caagatgaag ggcaggtatg    960
tccctgtgc aaccgccccc tggcaggatc ggagcaggag atgagtaggc atgtggagca    1020
ttgccttct aagagggaag gctcctgcat ggctgaggat gatgctgtgg acatcgagca    1080
tgagaacaac aaccgctttg aggagtatga gtggtgtgga cagaagcgga tacgggccac    1140
cactctcctg gaaggtggct tccgaggctc tggcttcatc atgtgcagcg gcaaagagaa    1200
cccggacagt gatgctgact tggatgtgga tgggatgac actctggagt atgggaagcc     1260
acaatacaca gaggctgatg tcatcccctg cacaggcgag gagcctggtg aagccaagga    1320
gagagaggca cttcggggcg cagtcctaaa tggcggccct cccagcacgc gcatcacacc    1380
tgagttctct aaatgggcca gtgatgagat gccatccacc agcaatggtg aaagcagcaa    1440
gcaggaggcc atgcagaaga cctgcaagaa cagcgacatc gagaaaatca ccgaagattc    1500
agctgtgacc acgtttgagg ctctgaaggc tcgggtcaga gaacttgaac ggcagctatc    1560
tcgtggggac cgttacaaat gcctcatctg catggactcg tactcgatgc ccctaacgtc    1620
catccagtgt tggcacgtgc actgcgagga gtgctggctg cggaccctgg gtgccaagaa    1680
gctctgcccct cagtgcaaca cgatcacagc gcccggagac ctgcggagga tctacttgtg    1740
agctatctgc cccaggcagg cctcgcctcc agcagcccca cctgccccca gcctctgtga    1800
cagtgaccgt ytcccttgt acatacttgc acacaggttc cccatgtaca tacatgcaca    1860
tactcaaaca tgcgtacaca cacacacatt tacacacgca ggactctgga gccagagtag    1920
aggctgtggc ccaggcacta cctgctggct cccacctatg gtttgggggc catacctgtt    1980
ccagctctgt tcccagggtg gggcaggag gtgggggttg ggggagtagt ggggcacggc     2040
tcctaagatc cagcccccat actgacagac ggacagacag acatgcaaac accagactga    2100
agcacatgta atatagaccg tgtatgtttta caatgttgtg tataaatggg acaactcctc    2160
gccctctacc tgtcccctcc ccctttggtt gtatgatttt cttctttttt aagaacccct    2220
ggaagcagcg cctccttcag ggttggctgg gagctcggcc catccacctc ttggggtayc    2280
tgcctctctc tctcctgtgg tgtcccttcc ctctcccatg tgctcggtgt tcagtggtgt    2340
atatttcttc tcccagacat ggggcacacg ccccaaggga catgatcctc tccttagtct    2400
tagctcatgg ggctctttat aaggagttgg ggggtagagg caggaaatgg gaaccgagct    2460
gaagcagagg ctgagttagg gggctagagg acagtgctcc tggccaccca gcctctgctg    2520
agaaccattc ctgggattag agctgccttt cccagggaaa aagtgtcgtc tccccgaccc    2580
tcccgtgggc cctgtggtgt gatgctgtgt ctgtatattc tatacaaagg tacttgtcct    2640
```
ttccctttgt aaactacatt tgacatggat taaaccagta taaacagtta aaaaaaaaaa    2700
aaaaaaaact cga    2713

<210> SEQ ID NO 130
<211> LENGTH: 1011
<212> TYPE: DNA
<213> ORGANISM: Homo sapiens
<220> FEATURE:
<221> NAME/KEY: SITE
<222> LOCATION: (357)
<223> OTHER INFORMATION: n equals a,t,g, or c
<220> FEATURE:
<221> NAME/KEY: SITE
<222> LOCATION: (516)
<223> OTHER INFORMATION: n equals a,t,g, or c
<220> FEATURE:
<221> NAME/KEY: SITE
<222> LOCATION: (985)
<223> OTHER INFORMATION: n equals a,t,g, or c

<400> SEQUENCE: 130
agaggacggt gtgacccggg aggaagtaga gcctgaggag gctgaagaag gcatctctga    60
gcaaccctgc ccagctgaca cagaggtggt ggaagactcc ttgaggcagc gtaaaagtca    120
gcatgctgac aagggactgt agatttaatg atgcgttttc aagaatacac accaaaacaa    180
tatgtcagct tcccttttggc ctgcagtttg taccaaatcc ttaatttttty ytgaatgagc    240 aagcttctct taaagatgc tctctagtca tttggtctca tggcagtaag cctcatgtat    300
actaaggaga gtcttccagg tgtgacaatc aggatataga aaaacaaacg tagtgtntgg    360
gatctgtttg gagactggga tgggaacaag ttcatttact taggggtcag agagtctcga    420
ccagaggagg ccattcccag tcctaatcag caccttccag agacaaggct gcaggccctg    480
tgaaatgaaa gccaagcagg agccttggct ctgagncatc cccaaagtgt aacgtagaag    540
ccttgcatcc ttttcttgtg taaagtattt attttttgtca aattgcagga acatcaggc    600 accacagtgc atgaaaaatc tttcacagct agaaattgaa agggccttgg gtatagagag    660
cagctcagaa gtcatcccag ccctctgaat ctcctgtgct atgttttatt tcttaccttt    720
aatttttcca gcatttccac catgggcatt caggctctcc acactcttca ctattatctc    780
ttggtcagag gactccaata acagccaggt ttacatgaac tgtgtttgtt cattctgacc    840 taagggttt agataatcag taaccataac ccctgaagct gtgactgcca aacatctcaa    900
atgaaatgtt gtrgccatca gagactcaaa aggaagtaag gatttttacaa gacagattaa    960 aaaaaaattg ttttgtccaa aaanaaaaa aaaaaaactc gaaggggggg c    1011

<210> SEQ ID NO 131
<211> LENGTH: 2278
<212> TYPE: DNA
<213> ORGANISM: Homo sapiens
<220> FEATURE:
<221> NAME/KEY: SITE
<222> LOCATION: (956)
<223> OTHER INFORMATION: n equals a,t,g, or c
<220> FEATURE:
<221> NAME/KEY: SITE
<222> LOCATION: (1062)
<223> OTHER INFORMATION: n equals a,t,g, or c
<220> FEATURE:
<221> NAME/KEY: SITE
<222> LOCATION: (1290)
<223> OTHER INFORMATION: n equals a,t,g, or c
<220> FEATURE:
<221> NAME/KEY: SITE
<222> LOCATION: (1911)
<223> OTHER INFORMATION: n equals a,t,g, or c

<400> SEQUENCE: 131

```
gtaattcggc acgaggcgcc caacatggcg ggtgggcgct gcggcccgca sctaacggcg        60
ctcctggccg cctggatcgc ggctgtggcg gcgacggcag gccccgagga ggccgcgctg       120
ccgccggagc agagccgggt ccagcccatg accgcctcca actggacgct ggtgatggag       180
ggcgagtgga tgctgaaatt ttacgcccca tggtgtccat cctgccagca gactgattca       240
gaatgggagg cttttgcaaa gaatggtgaa atacttcaga tcagtgtggg gaaggtagat       300
gtcattcaag aaccaggttt gagtggccgc ttctttgtca ccactctccc agcatttttt       360
catgcaaagg atgggatatt ccgccgttat cgtgcccag gaatcttcga agacctgcag        420
aattatatct tagagaagaa atggcaatca gtcgagcctc tgactggctg gaaatccccg       480
gcttctctaa cgatgtctgg aatggctggt cttttagca tctctggcaa gatatggcat       540
cttcacaact atttcacagt gactcttgga attcctgctt ggtgttctta tgtctttttc       600
gtcatagcca ccttggtttt tggccttttt atgggtctgg tcttggtggt aatatcagaa       660
tgtttctatg tgccacttcc aaggcattta tctgagcgtt ctgagcagaa tcggagatca       720
gaggaggctc atagagctga acagttgcag gatgcggagg aggaaaaaga tgattcaaat       780
gaagaagaaa acaaagacag ccttgtagat gatgaagaag agaaagaaga tcttggcgat       840
gaggatgaag cagaggaaga agaggaggag gacaacttgg ctgctggtgt ggatgaggag       900
agaagtgagg ccaatgatca ggggccccca ggagaggacg tgtgacccg ggaggnaagt        960
agagcctgag gaggctgaag aaggcatctc tgagcaaccc tgcccagctg acacagaggt      1020
ggtggaagac tccttgaggc agcgtaaaag tcagcatgct gncaagggac tgtagattta      1080
atgatgcgtt ttcaagaata cacaccaaaa caatatgtca gcttcccttt ggcctgcagt      1140
ttgtaccaaa tccttaattt ttcctgaatg agcaagcttc tcttaaaaga tgctctctag      1200
tcatttggtc tcatggcagt aagcctcatg tatactaagg agagtcttcc aggtgtgaca      1260
atcaggatat agaaaaacaa acgtagtgtn tgggatctgt ttggagactg ggatgggaac      1320
aagttcattt acttaggggt cagagagtct cgaccagagg aggccattcc cagtcctaat      1380
cagcaccttc cagagacaag gctgcaggcc tgtgaaatga agccaagca ggagccttgg       1440
ctctgaggca tccccaaagt gtaacgtaga agccttgcat ccttttcttg tgtaaagtat      1500
ttattttgt caaattgcag gaaacatcag gcaccacagt gcatgaaaaa tctttcacag       1560
ctagaaattg aaagggcctt gggtatagag agcagctcag aagtcatccc agccctctga      1620
atctcctgtg ctatgtttta tttcttacct ttaattttc cagcatttcc accatgggca       1680
ttcaggctct ccacactctt cactattatc tcttggtcag aggactccaa taacagccag      1740
gtttacatga actgtgtttg ttcattctga cctaaggggt ttagataatc agtaaccata      1800
accctgaag ctgtgactgc caaacatctc aaatgaaatg ttgtrgccat cagagactca       1860
aaaggaagta aggattttac aagacagatt aaaaaaaaat tgttttgtcc naaatatag       1920
ttgttgttga ttttttttta agttttctaa gcaatatttt tcaagccaga agtcctctaa      1980
gtcttgccag tacaaggtag tcttgtgaag aaaagttgaa tactgttttg ttttcatctc      2040
aagggttcc ctggtcttg aactacttta ataatacta aaaaaccact tctgattttc         2100
cttcagtgat gtgcttttgg tgaaagaatt aatgaactcc agtacctgaa agtgaaagat      2160
ttgattttgt ttccatcttc tgtaatcttc caaagaatta tatctttgta aatctctcaa      2220
tactcaatct actgtaagta cccagggrgg staatttcyt taaaaaaaaa aaaaaaaa       2278
```

<210> SEQ ID NO 132
<211> LENGTH: 1088
<212> TYPE: DNA
<213> ORGANISM: Homo sapiens
<220> FEATURE:
<221> NAME/KEY: SITE
<222> LOCATION: (193)
<223> OTHER INFORMATION: n equals a,t,g, or c
<220> FEATURE:
<221> NAME/KEY: SITE
<222> LOCATION: (998)
<223> OTHER INFORMATION: n equals a,t,g, or c
<220> FEATURE:
<221> NAME/KEY: SITE
<222> LOCATION: (1049)
<223> OTHER INFORMATION: n equals a,t,g, or c
<220> FEATURE:
<221> NAME/KEY: SITE
<222> LOCATION: (1050)
<223> OTHER INFORMATION: n equals a,t,g, or c
<220> FEATURE:
<221> NAME/KEY: SITE
<222> LOCATION: (1056)
<223> OTHER INFORMATION: n equals a,t,g, or c

<400> SEQUENCE: 132

| | | | | | |
|---|---|---|---|---|---|
| ggcaggggcg | gcgtgaaccc | gtcgggcact | gtgtccctga | caatgggaac | agccgacagt | 60 |
| gatgagatgg | ccccggagcc | ccacagcaca | cccacatcga | tgtgcacatc | caccaggagt | 120 |
| ctgccctggc | caagctcctg | ctcacctgct | gctctgcgct | gcggccccgg | gccacccagg | 180 |
| ccaggggcag | canccggctg | ctggtggcct | cgtgggtgat | gcagatcgtg | ctggggatct | 240 |
| tgagtgcagt | cctaggagga | tttttctaca | tccgcgacta | caccctcctc | gtcacctcgg | 300 |
| gagctgccat | ctggacaggg | gctgtggctg | tgctggctgg | agctgctgcc | ttcatttayg | 360 |
| agaaacgggg | tggtacatac | tgggccctgc | tgaggactct | gctarcgctg | gcagctttct | 420 |
| ccacagccat | cgctgccctc | aaactttgga | atgaagattt | ccgatatggc | tactcttatt | 480 |
| acaacagtgc | ctgccgcatc | tccagctcga | gtgactggaa | cactccagcc | ccactcaga | 540 |
| gtccagaaga | agtcagaagg | ctacacctat | gtacctcctt | catggacatg | ctgaaggcct | 600 |
| tgttcagaac | ccttcaggcc | atgctcttgg | gtgtctggat | tctgctgctt | ctggcatctc | 660 |
| tggcccctct | gtggctgtac | tgctggagaa | tgttcccaac | caaagggaaa | agagaccaga | 720 |
| aggaaatgtt | ggaagtgagt | ggaatctagc | catgcctctc | ctgattatta | gtgcctggtg | 780 |
| cttctgcacc | gggcgtccct | gcatctgact | gctggaagaa | gaaccagact | gaggaaaaga | 840 |
| ggctcttcaa | cagccccagt | tatcctggcc | ccatgaccgt | ggccacagcc | ctgctccagc | 900 |
| agcacttgcc | cattccttac | acccctttccc | catcctgctc | cgcttcatgt | ccctcctga | 960 |
| gtagtcatgt | gataataaac | tctcatgtta | ttgttccnaa | aaaaaaaaa | aaaaaaaat | 1020 |
| tggggggggg | ccggtaccca | ttgggcctnn | ggggngggtt | taaaattaat | ggggggggtt | 1080 |
| taaaaggg | | | | | | 1088 |

<210> SEQ ID NO 133
<211> LENGTH: 553
<212> TYPE: DNA
<213> ORGANISM: Homo sapiens

<400> SEQUENCE: 133

| | | | | | |
|---|---|---|---|---|---|
| ggcagagagc | agatggcctt | gacaccagca | gggtgacatc | cgctattgct | acttctctgc | 60 |
| tcccccacag | ttcctctgga | cttctctgga | ccacagtcct | ctgccagacc | cctgccagac | 120 |
| cccagtccac | catgatccat | ctgggtcaca | tcctcttcct | gcttttgctc | ccagtggctg | 180 |

```
cagctcagac gactccagga gagagatcat cactccctgc cttttaccct ggcacttcag    240
gctcttgttc cggatgtggg tccctctctc tgccgctcct ggcaggcctc gtggctgctg    300
atgcggtggc atcgctgctc atcgtggggg cggtgttcct gtgcgcacgc ccacgccgca    360
gccccgccca agatggcaaa gtctacatca acatgccagg cagggctga ccctcctgca     420 gcttggacct ttgacttctg accctctcat cctggatggt gtgtggtggc acaggaaccc    480
ccgccccaac ttttggattg taataaaaca attgaaacac caaaaaaaaa aaaaaaaaa    540 aaaaaaaaaa aaa                                                       553
```

<210> SEQ ID NO 134
<211> LENGTH: 467
<212> TYPE: PRT
<213> ORGANISM: Homo sapiens
<220> FEATURE:
<221> NAME/KEY: SITE
<222> LOCATION: (97)
<223> OTHER INFORMATION: Xaa equals any of the naturally occurring L-amino acids
<220> FEATURE:
<221> NAME/KEY: SITE
<222> LOCATION: (119)
<223> OTHER INFORMATION: Xaa equals any of the naturally occurring L-amino acids
<220> FEATURE:
<221> NAME/KEY: SITE
<222> LOCATION: (240)
<223> OTHER INFORMATION: Xaa equals any of the naturally occurring L-amino acids

<400> SEQUENCE: 134

```
Met Arg Pro Gln Glu Leu Pro Arg Leu Ala Phe Pro Leu Leu L Leu
 1               5                  10                  15

Leu Leu Leu Leu Pro Pro Pro Cys Pro Ala His Ser A Thr
                20                  25                  30

Arg Phe Asp Pro Thr Trp Glu Ser Leu Asp Ala Arg Gln Leu Pro Ala
            35                  40                  45

Trp Phe Asp Gln Ala Lys Phe Gly Ile Phe Ile His Trp Gly Val Phe
        50                  55                  60

Ser Val Pro Ser Phe Gly Ser Glu Trp Phe Trp Trp Tyr Trp Gln Lys
 65                  70                  75                  80

Glu Lys Ile Pro Lys Tyr Val Glu Phe Met Lys Asp Asn Tyr Pro Pro
                85                  90                  95

Xaa Phe Lys Tyr Glu Asp Phe Gly Pro Leu Phe Thr Ala Lys Phe Phe
                100                 105                 110

Asn Ala Asn Gln Trp Ala Xaa Ile Phe Gln Ala Ser Gly Ala Lys Tyr
            115                 120                 125

Ile Val Leu Thr Ser Lys His His Glu Gly Phe Thr Leu Trp Gly Ser
        130                 135                 140

Glu Tyr Ser Trp Asn Trp Asn Ala Ile Asp Glu Gly Pro Lys Arg Asp
145                 150                 155                 160

Ile Val Lys Glu Leu Glu Val Ala Ile Arg Asn Arg Thr Asp Leu Arg
                165                 170                 175

Phe Gly Leu Tyr Tyr Ser Leu Phe Glu Trp Phe His Pro Leu Phe Leu
            180                 185                 190

Glu Asp Glu Ser Ser Ser Phe His Lys Arg Gln Phe Pro Val Ser Lys
        195                 200                 205

Thr Leu Pro Glu Leu Tyr Glu Leu Val Asn Asn Tyr Gln Pro Glu Val
        210                 215                 220
```

-continued

```
Leu Trp Ser Asp Gly Asp Gly Gly Ala Pro Asp Gln Tyr Trp Asn Xaa
225                 230                 235                 240

Thr Gly Phe Leu Ala Trp Leu Tyr Asn Glu Ser Pro Val Arg Gly Thr
            245                 250                 255

Val Val Thr Asn Asp Arg Trp Ala Gly Ser Ile Cys Lys His Gly
        260                 265                 270

Gly Phe Tyr Thr Cys Ser Asp Arg Tyr Asn Pro Gly His Leu Leu Pro
        275                 280                 285

His Lys Trp Glu Asn Cys Met Thr Ile Asp Lys Leu Ser Trp Gly Tyr
    290                 295                 300

Arg Arg Glu Ala Gly Ile Ser Asp Tyr Leu Thr Ile Glu Glu Leu Val
305                 310                 315                 320

Lys Gln Leu Val Glu Thr Val Ser Cys Gly Gly Asn Leu Leu Met Asn
                325                 330                 335

Ile Gly Pro Thr Leu Asp Gly Thr Ile Ser Val Val Phe Glu Glu Arg
            340                 345                 350

Leu Arg Gln Met Gly Ser Trp Leu Lys Val Asn Gly Glu Ala Ile Tyr
        355                 360                 365

Glu Thr His Thr Trp Arg Ser Gln Asn Asp Thr Val Thr Pro Asp Val
    370                 375                 380

Trp Tyr Thr Ser Lys Pro Lys Glu Lys Leu Val Tyr Ala Ile Phe Leu
385                 390                 395                 400

Lys Trp Pro Thr Ser Gly Gln Leu Phe Leu Gly His Pro Lys Ala Ile
                405                 410                 415

Leu Gly Ala Thr Glu Val Lys Leu Leu Gly His Gly Gln Pro Leu Asn
            420                 425                 430

Trp Ile Ser Leu Glu Gln Asn Gly Ile Met Val Glu Leu Pro Gln Leu
        435                 440                 445

Thr Ile His Gln Met Pro Cys Lys Trp Gly Trp Ala Leu Ala Leu Thr
    450                 455                 460

Asn Val Ile
465

<210> SEQ ID NO 135
<211> LENGTH: 222
<212> TYPE: PRT
<213> ORGANISM: Homo sapiens
<220> FEATURE:
<221> NAME/KEY: SITE
<222> LOCATION: (222)
<223> OTHER INFORMATION: Xaa equals stop translation

<400> SEQUENCE: 135

Met Trp Ser Ala Gly Arg Gly Gly Ala Ala Trp Pro Val Leu Leu Gly
1               5                   10                  15

Leu Leu Leu Ala Leu Leu Val Pro Gly Gly Ala Ala Lys Thr Gly
            20                  25                  30

Ala Glu Leu Val Thr Cys Gly Ser Val Leu Lys Leu Leu Asn Thr His
        35                  40                  45

His Arg Val Arg Leu His Ser His Asp Ile Lys Tyr Gly Ser Gly Ser
    50                  55                  60

Gly Gln Gln Ser Val Thr Gly Val Glu Ala Ser Asp Ala Asn Ser
65                  70                  75                  80

Tyr Trp Arg Ile Arg Gly Gly Ser Glu Gly Gly Cys Arg Arg Gly Ser
                85                  90                  95
```

-continued

```
Pro Val Arg Cys Gly Gln Ala Val Arg Leu Thr His Val Leu Thr Gly
            100                 105                 110

Lys Asn Leu His Thr His His Phe Pro Ser Pro Leu Ser Asn Asn Gln
        115                 120                 125

Glu Val Ser Ala Phe Gly Asp Gly Glu Gly Asp Asp Leu Asp Leu
    130                 135                 140

Trp Thr Val Arg Cys Ser Gly Gln His Trp Glu Arg Glu Ala Ala Val
145                 150                 155                 160

Arg Phe Gln His Val Gly Thr Ser Val Phe Leu Ser Val Thr Gly Glu
                165                 170                 175

Gln Tyr Gly Ser Pro Ile Arg Gly Gln His Glu Val His Gly Met Pro
            180                 185                 190

Ser Ala Asn Thr His Asn Thr Trp Lys Ala Met Glu Gly Ile Phe Ile
                195                 200                 205

Lys Pro Ser Val Glu Pro Ser Ala Gly His Asp Glu Leu Xaa
            210                 215                 220

<210> SEQ ID NO 136
<211> LENGTH: 156
<212> TYPE: PRT
<213> ORGANISM: Homo sapiens

<400> SEQUENCE: 136

Met Val Ile Glu Ile Ser Asn Lys Thr Ser Ser Ser Thr Cys Ile
1               5                   10                  15

Leu Val Leu Leu Val Ser Phe Cys Leu Leu Val Pro Ala Met Tyr
                20                  25                  30

Ser Ser Asp Thr Arg Gly Ser Leu Pro Ala Glu His Gly Val Leu Ser
            35                  40                  45

Arg Gln Leu Arg Ala Leu Pro Ser Glu Asp Pro Tyr Gln Leu Glu Leu
    50                  55                  60

Pro Ala Leu Gln Ser Glu Val Pro Lys Asp Ser Thr His Gln Trp Leu
65                  70                  75                  80

Asp Gly Ser Asp Cys Val Leu Gln Ala Pro Gly Asn Thr Ser Cys Leu
                85                  90                  95

Leu His Tyr Met Pro Gln Ala Pro Ser Ala Glu Pro Pro Leu Glu Trp
                100                 105                 110

Pro Phe Pro Asp Leu Phe Ser Glu Pro Leu Cys Arg Gly Pro Ile Leu
            115                 120                 125

Pro Leu Gln Ala Asn Leu Thr Arg Lys Gly Gly Trp Leu Pro Thr Gly
    130                 135                 140

Ser Pro Ser Val Ile Leu Gln Asp Arg Tyr Ser Gly
145                 150                 155

<210> SEQ ID NO 137
<211> LENGTH: 233
<212> TYPE: PRT
<213> ORGANISM: Homo sapiens
<220> FEATURE:
<221> NAME/KEY: SITE
<222> LOCATION: (233)
<223> OTHER INFORMATION: Xaa equals stop translation

<400> SEQUENCE: 137

Met Met Ile Leu Phe Asn Leu Leu Ile Phe Leu Cys Gly Ala Ala Leu
1               5                   10                  15
```

-continued

```
Leu Ala Val Gly Ile Trp Val Ser Ile Asp Gly Ala Ser Phe Leu Lys
            20                  25                  30

Ile Phe Gly Pro Leu Ser Ser Ser Ala Met Gln Phe Val Asn Val Gly
        35                  40                  45

Tyr Phe Leu Ile Ala Ala Gly Val Val Phe Ala Leu Gly Phe Leu
    50                  55                  60

Gly Cys Tyr Gly Ala Lys Thr Glu Ser Lys Cys Ala Leu Val Thr Phe
65                  70                  75                  80

Phe Phe Ile Leu Leu Leu Ile Phe Ile Ala Glu Val Ala Ala Val
                85                  90                  95

Val Ala Leu Val Tyr Thr Thr Met Ala Glu His Phe Leu Thr Leu Leu
                100                 105                 110

Val Val Pro Ala Ile Lys Lys Asp Tyr Gly Ser Gln Glu Asp Phe Thr
            115                 120                 125

Gln Val Trp Asn Thr Thr Met Lys Gly Leu Lys Cys Cys Gly Phe Thr
        130                 135                 140

Asn Tyr Thr Asp Phe Glu Asp Ser Pro Tyr Phe Lys Glu Asn Ser Ala
145                 150                 155                 160

Phe Pro Pro Phe Cys Cys Asn Asp Asn Val Thr Asn Thr Ala Asn Glu
                165                 170                 175

Thr Cys Thr Lys Gln Lys Ala His Asp Gln Lys Val Glu Gly Cys Phe
            180                 185                 190

Asn Gln Leu Leu Tyr Asp Ile Arg Thr Asn Ala Val Thr Val Gly Gly
        195                 200                 205

Val Ala Ala Gly Ile Gly Gly Leu Glu Leu Ala Ala Met Ile Val Ser
    210                 215                 220

Met Tyr Leu Tyr Cys Asn Leu Gln Xaa
225                 230

<210> SEQ ID NO 138
<211> LENGTH: 61
<212> TYPE: PRT
<213> ORGANISM: Homo sapiens
<220> FEATURE:
<221> NAME/KEY: SITE
<222> LOCATION: (38)
<223> OTHER INFORMATION: Xaa equals any of the naturally occurring
      L-amino acids
<220> FEATURE:
<221> NAME/KEY: SITE
<222> LOCATION: (43)
<223> OTHER INFORMATION: Xaa equals any of the naturally occurring
      L-amino acids
<220> FEATURE:
<221> NAME/KEY: SITE
<222> LOCATION: (50)
<223> OTHER INFORMATION: Xaa equals any of the naturally occurring
      L-amino acids
<220> FEATURE:
<221> NAME/KEY: SITE
<222> LOCATION: (54)
<223> OTHER INFORMATION: Xaa equals any of the naturally occurring
      L-amino acids
<220> FEATURE:
<221> NAME/KEY: SITE
<222> LOCATION: (56)
<223> OTHER INFORMATION: Xaa equals any of the naturally occurring
      L-amino acids

<400> SEQUENCE: 138

Met Gly Ser Ser Arg Trp Ser Val Ala Cys Pro Thr Gly Leu Gly Val
1               5                   10                  15

Leu Met Leu Gly Leu Gly Gly Asp His Pro Pro Gly Ser Gln Val Asp
```

-continued

```
                    20                  25                  30
Pro Leu Leu Met Gly Xaa Cys Val Arg Pro Xaa Leu Pro Glu Leu Thr
                35                  40                  45

Ala Xaa Trp Arg Glu Xaa Gln Xaa Arg Ser Ala Ser Ala
    50                  55                  60

<210> SEQ ID NO 139
<211> LENGTH: 73
<212> TYPE: PRT
<213> ORGANISM: Homo sapiens
<220> FEATURE:
<221> NAME/KEY: SITE
<222> LOCATION: (73)
<223> OTHER INFORMATION: Xaa equals any of the naturally occurring
      L-amino acids

<400> SEQUENCE: 139

Met Gly Trp Leu Phe Leu Lys Val Leu Leu Ala Gly Val Ser Phe Ser
 1               5                  10                  15

Gly Phe Leu Tyr Pro Leu Val Asp Phe Cys Ile Ser Gly Lys Thr Arg
                20                  25                  30

Gly Gln Lys Pro Asn Phe Val Ile Ile Leu Ala Asp Asp Met Gly Trp
            35                  40                  45

Gly Asp Trp Gly Ala Asn Trp Ala Glu Thr Lys Asp Thr Ala Asn Leu
        50                  55                  60

Asp Lys Met Ala Ser Glu Gly Met Xaa
65                  70

<210> SEQ ID NO 140
<211> LENGTH: 377
<212> TYPE: PRT
<213> ORGANISM: Homo sapiens
<220> FEATURE:
<221> NAME/KEY: SITE
<222> LOCATION: (377)
<223> OTHER INFORMATION: Xaa equals stop translation

<400> SEQUENCE: 140

Met His Gly Asn Glu Ala Leu Gly Arg Glu Leu Leu Leu Leu Leu Met
 1               5                  10                  15

Gln Phe Leu Cys His Glu Phe Leu Arg Gly Asn Pro Arg Val Thr Arg
                20                  25                  30

Leu Leu Ser Glu Met Arg Ile His Leu Leu Pro Ser Met Asn Pro Asp
            35                  40                  45

Gly Tyr Glu Ile Ala Tyr His Arg Gly Ser Glu Leu Val Gly Trp Ala
        50                  55                  60

Glu Gly Arg Trp Asn Asn Gln Ser Ile Asp Leu Asn His Asn Phe Ala
65                  70                  75                  80

Asp Leu Asn Thr Pro Leu Trp Glu Ala Gln Asp Asp Gly Lys Val Pro
                85                  90                  95

His Ile Val Pro Asn His His Leu Pro Leu Pro Thr Tyr Tyr Thr Leu
                100                 105                 110

Pro Asn Ala Thr Val Ala Pro Glu Thr Arg Ala Val Ile Lys Trp Met
            115                 120                 125

Lys Arg Ile Pro Phe Val Leu Ser Ala Asn Leu His Gly Gly Glu Leu
        130                 135                 140

Val Val Ser Tyr Pro Phe Asp Met Thr Arg Thr Pro Trp Ala Ala Arg
145                 150                 155                 160

Glu Leu Thr Pro Thr Pro Asp Asp Ala Val Phe Arg Trp Leu Ser Thr
```

-continued

```
                165                 170                 175

Val Tyr Ala Gly Ser Asn Leu Ala Met Gln Asp Thr Ser Arg Arg Pro
            180                 185                 190

Cys His Ser Gln Asp Phe Ser Val His Gly Asn Ile Ile Asn Gly Ala
        195                 200                 205

Asp Trp His Thr Val Pro Gly Ser Met Asn Asp Phe Ser Tyr Leu His
    210                 215                 220

Thr Asn Cys Phe Glu Val Thr Val Glu Leu Ser Cys Asp Lys Phe Pro
225                 230                 235                 240

His Glu Asn Glu Leu Pro Gln Glu Trp Glu Asn Asn Lys Asp Ala Leu
                245                 250                 255

Leu Thr Tyr Leu Glu Gln Val Arg Met Gly Ile Ala Gly Val Val Arg
            260                 265                 270

Asp Lys Asp Thr Glu Leu Gly Ile Ala Asp Ala Val Ile Ala Val Asp
        275                 280                 285

Gly Ile Asn His Asp Val Thr Thr Ala Trp Gly Gly Asp Tyr Trp Arg
    290                 295                 300

Leu Leu Thr Pro Gly Asp Tyr Met Val Thr Ala Ser Ala Glu Gly Tyr
305                 310                 315                 320

His Ser Val Thr Arg Asn Cys Arg Val Thr Phe Glu Glu Gly Pro Phe
                325                 330                 335

Pro Cys Asn Phe Val Leu Thr Lys Thr Pro Lys Gln Arg Leu Arg Glu
            340                 345                 350

Leu Leu Ala Ala Gly Ala Lys Val Pro Pro Asp Leu Arg Arg Arg Leu
        355                 360                 365

Glu Arg Leu Arg Gly Gln Lys Asp Xaa
    370                 375

<210> SEQ ID NO 141
<211> LENGTH: 43
<212> TYPE: PRT
<213> ORGANISM: Homo sapiens

<400> SEQUENCE: 141

Met Ile Cys Leu Ile Leu Leu Gln Ala Val Val Phe Leu Arg Ser
1               5                   10                  15

Leu His Val Val His Asn Phe Gln Ile Leu Asp Leu Ser Gly Thr Ser
            20                  25                  30

Tyr Pro Lys Phe Tyr Gln Thr Leu His Arg Gln
        35                  40

<210> SEQ ID NO 142
<211> LENGTH: 41
<212> TYPE: PRT
<213> ORGANISM: Homo sapiens

<400> SEQUENCE: 142

Met Val His Val Leu Glu Ile Leu Leu Phe Ile Thr Met Gln Ala Val
1               5                   10                  15

Ser Phe Pro Phe Gln Thr Gln Ile Asp Thr Cys Asn Thr Gln Asp Pro
            20                  25                  30

Ala Glu Arg Gln Pro Ala Ser Ile Val
        35                  40

<210> SEQ ID NO 143
<211> LENGTH: 70
<212> TYPE: PRT
```

```
<213> ORGANISM: Homo sapiens

<400> SEQUENCE: 143

Met Gly Ser Cys Ser Lys Asn Arg Ser Phe Phe Trp Met Thr Gly Leu
 1               5                  10                  15

Leu Val Phe Ile Ser Leu Leu Leu Ser Glu Trp Gln Gly Pro Trp Glu
                20                  25                  30

Gly Arg Ala Ile Gly Glu Gly Trp Ala Ser Trp Ala Leu Thr Asn Gly
            35                  40                  45

Trp Ala Val Gln Leu Leu Met Ser Leu Gly Asn Asn Thr Glu Lys His
        50                  55                  60

Ser Val Met Ile Tyr Glu
65                  70

<210> SEQ ID NO 144
<211> LENGTH: 483
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids
<220> FEATURE:
<221> NAME/KEY: SITE
<222> LOCATION: (483)
<223> OTHER INFORMATION: Xaa equals stop translation

<400> SEQUENCE: 144

Met Ala Thr Gly Gly Gly Ile Arg Ala Met Thr Ser Leu Tyr Gly Gln
 1               5                  10                  15

Leu Ala Gly Leu Lys Glu Leu Gly Leu Leu Asp Cys Xaa Ser Tyr Ile
                20                  25                  30

Thr Gly Ala Ser Gly Ser Thr Trp Ala Leu Ala Asn Leu Tyr Lys Asp
            35                  40                  45

Pro Glu Trp Ser Gln Lys Asp Leu Ala Gly Pro Thr Glu Leu Leu Lys
        50                  55                  60

Thr Gln Val Thr Lys Asn Lys Leu Gly Val Leu Ala Pro Ser Gln Leu
65                  70                  75                  80

Gln Arg Tyr Arg Gln Glu Leu Ala Glu Arg Ala Arg Leu Gly Tyr Pro
                85                  90                  95

Ser Cys Phe Thr Asn Leu Trp Ala Leu Ile Asn Glu Ala Leu Leu His
               100                 105                 110

Asp Glu Pro His Asp His Lys Leu Ser Asp Gln Arg Glu Ala Leu Ser
            115                 120                 125

His Gly Gln Asn Pro Leu Pro Ile Tyr Cys Ala Leu Asn Thr Lys Gly
        130                 135                 140

Gln Ser Leu Thr Thr Phe Glu Phe Gly Leu Trp Cys Glu Phe Ser Pro
145                 150                 155                 160

Tyr Glu Val Gly Phe Pro Lys Tyr Gly Ala Phe Ile Pro Ser Glu Leu
                165                 170                 175

Phe Gly Ser Glu Phe Phe Met Gly Gln Leu Met Lys Arg Leu Pro Glu
            180                 185                 190

Ser Arg Ile Cys Phe Leu Glu Gly Ile Trp Ser Asn Leu Tyr Ala Ala
        195                 200                 205

Asn Leu Gln Asp Ser Leu Tyr Trp Ala Ser Glu Pro Ser Gln Phe Trp
210                 215                 220

Asp Arg Trp Val Arg Asn Gln Ala Asn Leu Asp Lys Glu Gln Val Pro
```

-continued

```
            225                 230                 235                 240
Leu Leu Lys Ile Glu Glu Pro Pro Ser Thr Ala Gly Arg Ile Ala Glu
                245                 250                 255

Phe Phe Thr Asp Leu Leu Thr Trp Arg Pro Leu Ala Gln Ala Thr His
                260                 265                 270

Asn Phe Leu Arg Gly Leu His Phe His Lys Asp Tyr Phe Gln His Pro
                275                 280                 285

His Phe Ser Thr Trp Lys Ala Thr Thr Leu Asp Gly Leu Pro Asn Gln
                290                 295                 300

Leu Thr Pro Ser Glu Pro His Leu Cys Leu Leu Asp Val Gly Tyr Leu
305                 310                 315                 320

Ile Asn Thr Ser Cys Leu Pro Leu Leu Gln Pro Thr Arg Asp Val Asp
                325                 330                 335

Leu Ile Leu Ser Leu Asp Tyr Asn Leu His Gly Ala Phe Gln Gln Leu
                340                 345                 350

Gln Leu Leu Gly Arg Phe Cys Gln Glu Gln Gly Ile Pro Phe Pro Pro
                355                 360                 365

Ile Ser Pro Ser Pro Glu Glu Gln Leu Gln Pro Arg Glu Cys His Thr
                370                 375                 380

Phe Ser Asp Pro Thr Cys Pro Gly Ala Pro Ala Val Leu His Phe Pro
385                 390                 395                 400

Leu Val Ser Asp Ser Phe Arg Glu Tyr Ser Ala Pro Gly Val Arg Arg
                405                 410                 415

Thr Pro Glu Glu Ala Ala Ala Gly Glu Val Asn Leu Ser Ser Ser Asp
                420                 425                 430

Ser Pro Tyr His Tyr Thr Lys Val Thr Tyr Ser Gln Glu Asp Val Asp
                435                 440                 445

Lys Leu Leu His Leu Thr His Tyr Asn Val Cys Asn Asn Gln Glu Gln
                450                 455                 460

Leu Leu Glu Ala Leu Arg Gln Ala Val Gln Arg Arg Gln Arg Arg
465                 470                 475                 480

Pro His Xaa

<210> SEQ ID NO 145
<211> LENGTH: 226
<212> TYPE: PRT
<213> ORGANISM: Homo sapiens

<400> SEQUENCE: 145

Met Glu Gly Ala Pro Pro Gly Ser Leu Ala Leu Arg Leu Leu Leu Phe
  1               5                  10                  15

Val Ala Leu Pro Ala Ser Gly Trp Leu Thr Gly Ala Pro Glu Pro
                 20                  25                  30

Pro Pro Leu Ser Gly Ala Pro Gln Asp Gly Ile Arg Ile Asn Val Thr
                 35                  40                  45

Thr Leu Lys Asp Asp Gly Asp Ile Ser Lys Gln Gln Val Val Leu Asn
                 50                  55                  60

Ile Thr Tyr Glu Ser Gly Gln Val Tyr Val Asn Asp Leu Pro Val Asn
 65                  70                  75                  80

Ser Gly Val Thr Arg Ile Ser Cys Gln Thr Leu Ile Val Lys Asn Glu
                 85                  90                  95

Asn Leu Glu Asn Leu Glu Glu Lys Glu Tyr Phe Gly Ile Val Ser Val
                100                 105                 110

Arg Ile Leu Val His Glu Trp Pro Met Thr Ser Gly Ser Ser Leu Gln
```

```
                115                 120                     125
Leu Ile Val Ile Gln Glu Val Glu Ile Asp Gly Lys Gln Val
        130                 135                 140

Gln Gln Lys Asp Val Thr Glu Ile Asp Ile Leu Val Lys Asn Arg Gly
145                 150                 155                 160

Val Leu Arg His Ser Asn Tyr Thr Leu Pro Leu Glu Glu Ser Met Leu
                165                 170                 175

Tyr Ser Ile Ser Arg Asp Ser Asp Ile Leu Phe Thr Leu Pro Asn Leu
            180                 185                 190

Ser Lys Lys Glu Ser Val Ser Ser Leu Gln Thr Thr Ser Gln Tyr Leu
        195                 200                 205

Ile Arg Asn Val Glu Thr Thr Val Asp Glu Asp Val Leu Pro Gly Gln
    210                 215                 220

Val Thr
225

<210> SEQ ID NO 146
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 146

Met Gly Met Gly Ala Phe Gln Ala Phe Phe Trp Val Ile Leu Thr Val
1               5                   10                  15

Ser Asn Val Cys Val Leu Phe Lys Met Ser Leu Phe Phe Leu Leu Thr
            20                  25                  30

Leu Ile Ser Lys Leu His Gly Asp Ala Glu Val Cys Xaa
        35                  40                  45

<210> SEQ ID NO 147
<211> LENGTH: 132
<212> TYPE: PRT
<213> ORGANISM: Homo sapiens
<220> FEATURE:
<221> NAME/KEY: SITE
<222> LOCATION: (132)
<223> OTHER INFORMATION: Xaa equals stop translation

<400> SEQUENCE: 147

Met Ser Gly Gly Trp Met Ala Gln Val Gly Ala Trp Arg Thr Gly Ala
1               5                   10                  15

Leu Gly Leu Ala Leu Leu Leu Leu Gly Leu Gly Leu Glu
            20                  25                  30

Ala Pro Arg Ala Arg Phe Pro Pro Arg Pro Leu Pro Arg Pro His Pro
        35                  40                  45

Ser Ser Gly Ser Cys Pro Pro Thr Lys Phe Gln Cys Arg Thr Ser Gly
    50                  55                  60

Leu Cys Val Pro Leu Thr Trp Arg Cys Asp Arg Thr Trp Thr Ala Ala
65                  70                  75                  80

Met Ala Ala Met Arg Arg Ser Ala Gly Leu Ser His Val Pro Arg Lys
                85                  90                  95

Gly Asn Ala His Arg Pro Leu Ala Ser Pro Ala Pro Ala Pro Ala Ser
            100                 105                 110

Val Thr Ala Leu Gly Glu Leu Thr Arg Asn Cys Ala Thr Ala Ala Ala
        115                 120                 125
```

Trp Pro Ala Xaa
    130

<210> SEQ ID NO 148
<211> LENGTH: 92
<212> TYPE: PRT
<213> ORGANISM: Homo sapiens
<220> FEATURE:
<221> NAME/KEY: SITE
<222> LOCATION: (92)
<223> OTHER INFORMATION: Xaa equals stop translation

<400> SEQUENCE: 148

Met Glu Ala Thr Leu Glu Gln His Leu Glu Asp Thr Met Lys Asn Pro
1               5                   10               15

Ser Ile Val Gly Val Leu Cys Thr Asp Ser Gln Gly Leu Asn Leu Gly
             20                  25               30

Cys Arg Gly Thr Leu Ser Asp Glu His Ala Gly Val Ile Ser Val Leu
             35                  40               45

Ala Gln Gln Ala Ala Lys Leu Thr Ser Asp Pro Thr Asp Ile Pro Val
      50               55                 60

Val Cys Leu Glu Ser Asp Asn Gly Asn Ile Met Ile Gln Lys His Asp
65              70                 75               80

Gly Ile Thr Val Ala Val His Lys Met Ala Ser Xaa
             85                  90

<210> SEQ ID NO 149
<211> LENGTH: 165
<212> TYPE: PRT
<213> ORGANISM: Homo sapiens
<220> FEATURE:
<221> NAME/KEY: SITE
<222> LOCATION: (165)
<223> OTHER INFORMATION: Xaa equals stop translation

<400> SEQUENCE: 149

Met Glu Pro Leu Arg Leu Leu Ile Leu Leu Phe Val Thr Glu Leu Ser
1               5                   10               15

Gly Ala His Asn Thr Thr Val Phe Gln Gly Val Ala Gly Gln Ser Leu
             20                  25               30

Gln Val Ser Cys Pro Tyr Asp Ser Met Lys His Trp Gly Arg Arg Lys
             35                  40               45

Ala Trp Cys Arg Gln Leu Gly Glu Lys Gly Pro Cys Gln Arg Val Val
      50               55                 60

Ser Thr His Asn Leu Trp Leu Leu Ser Phe Leu Arg Arg Trp Asn Gly
65              70                 75               80

Ser Thr Ala Ile Thr Asp Asp Thr Leu Gly Gly Thr Leu Thr Ile Thr
             85                  90               95

Leu Arg Asn Leu Gln Pro His Asp Ala Gly Leu Tyr Gln Cys Gln Ser
             100                105              110

Leu His Gly Ser Glu Ala Asp Thr Leu Arg Lys Val Leu Val Glu Val
            115                120              125

Leu Ala Asp Pro Leu Asp His Arg Asp Ala Gly Asp Leu Trp Phe Pro
      130               135                140

Gly Glu Ser Glu Ser Phe Glu Asp Ala His Val Glu His Ser Ile Ser
145            150                155              160

Arg Ser Ser Ser Xaa
             165

```
<210> SEQ ID NO 150
<211> LENGTH: 139
<212> TYPE: PRT
<213> ORGANISM: Homo sapiens
<220> FEATURE:
<221> NAME/KEY: SITE
<222> LOCATION: (139)
<223> OTHER INFORMATION: Xaa equals stop translation

<400> SEQUENCE: 150

Met Ile Ser Leu Thr Asp Thr Gln Lys Ile Gly Met Gly Leu Thr Gly
 1               5                  10                  15

Phe Gly Val Phe Phe Leu Phe Phe Gly Met Ile Leu Phe Asp Lys
            20                  25                  30

Ala Leu Leu Ala Ile Gly Asn Val Leu Phe Val Ala Gly Leu Ala Phe
            35                  40                  45

Val Ile Gly Leu Glu Arg Thr Phe Arg Phe Phe Gln Lys His Lys
         50                  55                  60

Met Lys Ala Thr Gly Phe Phe Leu Gly Gly Val Phe Val Val Leu Ile
 65                  70                  75                  80

Gly Trp Pro Leu Ile Gly Met Ile Phe Glu Ile Tyr Gly Phe Leu
                 85                  90                  95

Leu Phe Arg Gly Phe Phe Pro Val Val Val Gly Phe Ile Arg Arg Val
            100                 105                 110

Pro Val Leu Gly Ser Leu Leu Asn Leu Pro Gly Ile Arg Ser Phe Val
            115                 120                 125

Asp Lys Val Gly Glu Ser Asn Asn Met Val Xaa
        130                 135

<210> SEQ ID NO 151
<211> LENGTH: 58
<212> TYPE: PRT
<213> ORGANISM: Homo sapiens
<220> FEATURE:
<221> NAME/KEY: SITE
<222> LOCATION: (38)
<223> OTHER INFORMATION: Xaa equals any of the naturally occurring
      L-amino acids

<400> SEQUENCE: 151

Met Ser Ala Pro Gln Thr Arg Ile Ser Arg Ala Leu Val Leu Leu Phe
 1               5                  10                  15

Leu Ala Pro Thr Leu Leu Ser Leu Gly His Gly Ile His Pro Ile Asn
            20                  25                  30

Thr Ala Thr Pro Tyr Xaa Thr Asp Gln Ala Lys Leu Ala Pro Gly Thr
            35                  40                  45

Lys Glu Leu Asn His Asp Gln Ser Val Thr
        50                  55

<210> SEQ ID NO 152
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 152

Met Ile Arg Lys Leu His Lys Ile Ile Val Phe Ser Pro Arg Val Ile
 1               5                  10                  15
```

-continued

```
Val Leu Leu Asn Cys Phe Phe Phe Ile Lys Ala Lys Phe Val Leu Tyr
             20                  25                  30

Ile Phe Val Phe His Val Leu Asp Gly Ser Ile Ser Tyr Pro Val Xaa
             35                  40                  45
```

<210> SEQ ID NO 153
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

<400> SEQUENCE: 153

```
Met Leu Leu Asn Gln His Phe Lys Ile Phe Gly Ser Leu Ile His Met
 1               5                  10                  15

Asn Leu Leu Phe Ala Leu Ile Ser Leu Gly Ser Ser Asn Leu Ser Gly
             20                  25                  30

Val Gln Phe Cys Cys Glu Thr Val Gln Xaa
             35                  40
```

<210> SEQ ID NO 154
<211> LENGTH: 72
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids
<220> FEATURE:
<221> NAME/KEY: SITE
<222> LOCATION: (40)
<223> OTHER INFORMATION: Xaa equals any of the naturally occurring
      L-amino acids

<400> SEQUENCE: 154

```
Met Leu Ser Leu Ser Phe Leu Leu Arg Arg Val Leu Phe Leu Gly Phe
 1               5                  10                  15

Leu Gln Ala Ser Val Gly Glu Lys Lys Ser Leu Arg Xaa Leu Asn Tyr
             20                  25                  30

Ser Val Pro His Pro Met Leu Xaa His Pro Pro Asp Thr Ala Gln
             35                  40                  45

Val Pro Pro Arg Leu Glu Arg Ser Leu Leu Gln Gln Glu Leu Trp Thr
     50                  55                  60

Pro Gly Pro His His Ser Asn Ile
 65                  70
```

<210> SEQ ID NO 155
<211> LENGTH: 106
<212> TYPE: PRT
<213> ORGANISM: Homo sapiens
<220> FEATURE:
<221> NAME/KEY: SITE
<222> LOCATION: (106)
<223> OTHER INFORMATION: Xaa equals stop translation

<400> SEQUENCE: 155

```
Met Gln Pro Leu Asn Phe Ser Ser Thr Glu Cys Ser Ser Phe Ser Pro
 1               5                  10                  15

Pro Thr Thr Val Ile Leu Leu Ile Leu Leu Cys Phe Glu Gly Leu Leu
             20                  25                  30

Phe Leu Ile Phe Thr Ser Val Met Phe Gly Thr Gln Val His Ser Ile
```

-continued

```
                35                  40                  45
Cys Thr Asp Glu Thr Gly Ile Glu Gln Leu Lys Lys Glu Arg Arg
        50                  55                  60
Trp Ala Lys Lys Thr Lys Trp Met Asn Met Lys Ala Val Phe Gly His
65                  70                  75                  80
Pro Phe Ser Leu Gly Trp Ala Ser Pro Phe Ala Thr Pro Asp Gln Gly
                85                  90                  95
Lys Ala Asp Pro Tyr Gln Tyr Val Val Xaa
                100                 105

<210> SEQ ID NO 156
<211> LENGTH: 29
<212> TYPE: PRT
<213> ORGANISM: Homo sapiens

<400> SEQUENCE: 156

Met Tyr Thr Asn His Phe Asn Leu Tyr Leu Lys Tyr Ile Leu Leu Ile
1               5                   10                  15
Ile Leu Ile Leu Asn Met Thr Asn Ser Ser Ser Arg Tyr
                20                  25

<210> SEQ ID NO 157
<211> LENGTH: 53
<212> TYPE: PRT
<213> ORGANISM: Homo sapiens
<220> FEATURE:
<221> NAME/KEY: SITE
<222> LOCATION: (53)
<223> OTHER INFORMATION: Xaa equals stop translation

<400> SEQUENCE: 157

Met Asn Glu Leu Leu Leu Phe Phe Phe Phe Phe Phe Phe Thr Phe
1               5                   10                  15
Cys Ile Glu Thr Asn Ser Phe Lys Gln Thr Tyr Tyr Tyr Phe Leu
                20                  25                  30
Gln Asn Ile Tyr Met Glu Met Leu Pro Pro Val Asn Pro Pro Val
            35                  40                  45
Pro Pro Trp Gly Xaa
        50

<210> SEQ ID NO 158
<211> LENGTH: 75
<212> TYPE: PRT
<213> ORGANISM: Homo sapiens

<400> SEQUENCE: 158

Met Tyr Ala Val Tyr Gln Gln Leu Ala Gln Leu Thr Leu Met Val Thr
1               5                   10                  15
Leu Leu Ala Pro Ile Leu Pro Asp Glu Gln Ser Glu Val Phe Glu Ala
                20                  25                  30
Leu Ser Asn Leu Pro Lys Val Thr Trp Leu Gly Ser Asn Ser Pro Ser
            35                  40                  45
Ser Glu Met Pro Glu Pro Gly Arg Phe Val Ile Val His His Gln Leu
        50                  55                  60
Ser Ala Ala Ser His Ser Ser Ser Gln Leu Ala
65                  70                  75

<210> SEQ ID NO 159
<211> LENGTH: 81
<212> TYPE: PRT
```

<213> ORGANISM: Homo sapiens

<400> SEQUENCE: 159

```
Met Trp Pro Pro Leu Leu Leu Leu Leu Leu Pro Ala Ala Pro
 1               5                  10                  15

Val Pro Thr Ala Lys Ala Ala Pro His Pro Asp Ala Asn Thr Gln Glu
                20                  25                  30

Gly Leu Gln Asn Leu Leu Gln Gly Val Gly Ala Gly Gly Asp Gly Glu
                35                  40                  45

Leu Arg Ala Asp Ser His Leu Ala Pro Gly Ser Gly Cys Ile Asp Gly
                50                  55                  60

Ala Val Val Ala Thr Arg Pro Glu Ser Arg Gly Gly Arg Pro Ala Val
 65                  70                  75                  80

Pro
```

<210> SEQ ID NO 161
<211> LENGTH: 139
<212> TYPE: PRT
<213> ORGANISM: Homo sapiens
<220> FEATURE:
<221> NAME/KEY: SITE
<222> LOCATION: (139)
<223> OTHER INFORMATION: Xaa equals stop translation

<400> SEQUENCE: 160

```
Met Lys Phe Thr Thr Leu Leu Phe Leu Ala Ala Val Ala Gly Ala Leu
 1               5                  10                  15

Val Tyr Ala Glu Asp Ala Ser Ser Asp Ser Thr Gly Ala Asp Pro Ala
                20                  25                  30

Gln Glu Ala Gly Thr Ser Lys Pro Asn Glu Glu Ile Ser Gly Pro Ala
                35                  40                  45

Glu Pro Ala Ser Pro Glu Thr Thr Thr Ala Gln Glu Thr Ser
 50                  55                  60

Ala Ala Ala Val Gln Gly Thr Ala Lys Val Thr Ser Ser Arg Gln Glu
 65                  70                  75                  80

Leu Asn Pro Leu Lys Ser Ile Val Glu Lys Ser Ile Leu Thr Glu
                85                  90                  95

Gln Ala Leu Ala Lys Ala Gly Lys Gly Met His Gly Gly Val Pro Gly
                100                 105                 110

Gly Lys Gln Phe Ile Glu Asn Gly Ser Glu Phe Ala Gln Lys Leu Leu
                115                 120                 125

Lys Lys Phe Ser Leu Leu Lys Pro Trp Ala Xaa
                130             135
```

<210> SEQ ID NO 161
<211> LENGTH: 178
<212> TYPE: PRT
<213> ORGANISM: Homo sapiens
<220> FEATURE:
<221> NAME/KEY: SITE
<222> LOCATION: (178)
<223> OTHER INFORMATION: Xaa equals stop translation

<400> SEQUENCE: 161

```
Met Leu Gly Cys Gly Ile Pro Ala Leu Gly Leu Leu Leu Leu Leu Gln
 1               5                  10                  15

Gly Ser Ala Asp Gly Asn Gly Ile Gln Gly Phe Phe Tyr Pro Trp Ser
                20                  25                  30

Cys Glu Gly Asp Ile Trp Asp Arg Glu Ser Cys Gly Gly Gln Ala Ala
```

```
                35                  40                  45
Ile Asp Ser Pro Asn Leu Cys Leu Arg Leu Arg Cys Cys Tyr Arg Asn
     50                  55                  60
Gly Val Cys Tyr His Gln Arg Pro Asp Glu Asn Val Arg Arg Lys His
 65                  70                  75                  80
Met Trp Ala Leu Val Trp Thr Cys Ser Gly Leu Leu Leu Ser Cys
                 85                  90                  95
Ser Ile Cys Leu Phe Trp Trp Ala Lys Arg Arg Asp Val Leu His Met
                100                 105                 110
Pro Gly Phe Leu Ala Gly Pro Cys Asp Met Ser Lys Ser Val Ser Leu
            115                 120                 125
Leu Ser Lys His Arg Gly Thr Lys Lys Thr Pro Ser Thr Gly Ser Val
    130                 135                 140
Pro Val Ala Leu Ser Lys Glu Ser Arg Asp Val Glu Gly Thr Glu
145                 150                 155                 160
Gly Glu Gly Thr Glu Glu Gly Glu Glu Thr Glu Gly Glu Glu Glu Glu
                165                 170                 175
Asp Xaa

<210> SEQ ID NO 162
<211> LENGTH: 72
<212> TYPE: PRT
<213> ORGANISM: Homo sapiens
<220> FEATURE:
<221> NAME/KEY: SITE
<222> LOCATION: (72)
<223> OTHER INFORMATION: Xaa equals stop translation

<400> SEQUENCE: 162

Met Glu Ala Val Phe Thr Val Phe Phe Val Val Leu Phe Leu
 1               5                  10                  15
Lys Asn Thr Glu Gly Ala Lys Leu Phe Cys Thr Leu Tyr Pro Ala Ala
                20                  25                  30
Ser Ser Gly Gln Ser Gln Gly Pro Gly Leu Glu Lys Pro Asp Ser Gln
            35                  40                  45
Glu Cys Ile Ile Asp Pro Cys Ser Tyr Pro Ile Ala Leu Gly Ala Gly
     50                  55                  60
Thr Glu Pro Gly Cys Lys Ile Xaa
 65                  70

<210> SEQ ID NO 163
<211> LENGTH: 67
<212> TYPE: PRT
<213> ORGANISM: Homo sapiens
<220> FEATURE:
<221> NAME/KEY: SITE
<222> LOCATION: (16)
<223> OTHER INFORMATION: Xaa equals any of the naturally occurring
       L-amino acids
<220> FEATURE:
<221> NAME/KEY: SITE
<222> LOCATION: (19)
<223> OTHER INFORMATION: Xaa equals any of the naturally occurring
       L-amino acids
<220> FEATURE:
<221> NAME/KEY: SITE
<222> LOCATION: (35)
<223> OTHER INFORMATION: Xaa equals any of the naturally occurring
       L-amino acids
<220> FEATURE:
<221> NAME/KEY: SITE
<222> LOCATION: (50)
<223> OTHER INFORMATION: Xaa equals any of the naturally occurring
```

L-amino acids

<400> SEQUENCE: 163

Met Trp Phe Tyr Phe Leu Ser Val Ser Phe Pro Leu Leu Pro Val Xaa
1               5                   10                  15

Ala Pro Xaa Pro Pro Ala Pro Thr Thr Leu Cys Leu Leu Leu Phe
            20                  25                  30

Leu Gly Xaa Leu Tyr Asn Ser Thr Cys Ile His Cys Val His Thr Thr
            35                  40                  45

Ser Xaa Thr Gln Asn Pro Thr Ala Asn Thr Leu Lys Lys Lys Lys
    50                  55                  60

Asn Trp Gly
65

<210> SEQ ID NO 164
<211> LENGTH: 155
<212> TYPE: PRT
<213> ORGANISM: Homo sapiens
<220> FEATURE:
<221> NAME/KEY: SITE
<222> LOCATION: (155)
<223> OTHER INFORMATION: Xaa equals stop translation

<400> SEQUENCE: 164

Met Gly Phe Gly Ala Thr Leu Ala Val Gly Leu Thr Ile Phe Val Leu
1               5                   10                  15

Ser Val Val Thr Ile Ile Cys Phe Thr Cys Ser Cys Cys Leu
            20                  25                  30

Tyr Lys Thr Cys Arg Arg Pro Arg Pro Val Val Thr Thr Thr Thr Ser
            35                  40                  45

Thr Thr Val Val His Ala Pro Tyr Pro Gln Pro Pro Ser Val Pro Pro
    50                  55                  60

Ser Tyr Pro Gly Pro Ser Tyr Gln Gly Tyr His Thr Met Pro Pro Gln
65                  70                  75                  80

Pro Gly Met Pro Ala Ala Pro Tyr Pro Met Gln Tyr Pro Pro Tyr
            85                  90                  95

Pro Ala Gln Pro Met Gly Pro Ala Tyr His Glu Thr Leu Ala Gly
            100                 105                 110

Glu Gln Pro Arg Pro Thr Pro Pro Ala Ser Leu Leu Thr Thr Arg Pro
        115                 120                 125

Thr Trp Met Pro Arg Arg Arg Pro Ser Glu His Ser Leu Ala Ser Leu
    130                 135                 140

Ala Ala Thr Trp Leu Cys Cys Val Cys Ala Xaa
145                 150                 155

<210> SEQ ID NO 165
<211> LENGTH: 104
<212> TYPE: PRT
<213> ORGANISM: Homo sapiens
<220> FEATURE:
<221> NAME/KEY: SITE
<222> LOCATION: (104)
<223> OTHER INFORMATION: Xaa equals stop translation

<400> SEQUENCE: 165

Met Ile Ile Leu Val Phe Ile Ala Phe Phe Ile Pro Leu Gln Lys Thr
1               5                   10                  15

Ile Gly Lys Ile Ala Thr Cys Leu Glu Leu Arg Ser Ala Ala Leu Gln
            20                  25                  30

```
Ser Thr Gln Ser Gln Glu Glu Phe Lys Leu Glu Asp Leu Lys Lys Leu
            35                  40                  45

Glu Pro Ile Leu Lys Asn Ile Leu Thr Tyr Asn Lys Glu Phe Pro Phe
        50                  55                  60

Asp Val Gln Pro Val Pro Leu Arg Arg Ile Leu Ala Pro Gly Glu Glu
65                  70                  75                  80

Glu Asn Leu Glu Phe Glu Asp Glu Glu Gly Gly Ala Gly Ala
                85                  90                  95

Gly Leu Leu Ile Leu Ser Cys Xaa
            100
```

<210> SEQ ID NO 166
<211> LENGTH: 81
<212> TYPE: PRT
<213> ORGANISM: Homo sapiens

<400> SEQUENCE: 166

```
Met Ala Gly Thr Met Val Ile Val Val Val Val Gly Glu Val
 1               5                  10                  15

Val Val Glu Ala Glu Val Val Gln Ala Arg Glu Glu Ala Gly Glu
            20                  25                  30

Glu Glu Gly Ala Arg Ile Ile Thr Lys Gly Val Asn Leu Asn Ser Ile
        35                  40                  45

Ser Ser Met Glu Val Ile Ser Ile Ile Leu Asp Leu Asp Arg Glu
    50                  55                  60

Asp Ile Thr Leu Val Glu Ala Thr Glu Pro Tyr Ile Leu Leu Glu Leu
65                  70                  75                  80

Lys
```

<210> SEQ ID NO 167
<211> LENGTH: 93
<212> TYPE: PRT
<213> ORGANISM: Homo sapiens

<400> SEQUENCE: 167

```
Met Ser Phe Ser Phe Ile Ile Phe Leu Leu Leu Val Cys Gln Glu Ile
 1               5                  10                  15

Thr Phe Cys Met Ser Tyr Gly Asp Ala Val Asn Cys Phe Ser Glu Cys
            20                  25                  30

Phe Ser Asn Leu Gln Thr Ile Tyr Ile Ser Cys Leu Gln His Ala Val
        35                  40                  45

Cys Lys His Ser Val Ile Trp Ser Ile Gln Leu Phe Val Arg Ala Leu
    50                  55                  60

Pro Ile Ser Lys Cys Ala Glu Leu Ser Ile Asp Gly Ile Phe Arg Ser
65                  70                  75                  80

Phe His Glu Asn Trp Lys Cys Ser Trp Val Ala Pro Thr
                85                  90
```

<210> SEQ ID NO 168
<211> LENGTH: 58
<212> TYPE: PRT
<213> ORGANISM: Homo sapiens
<220> FEATURE:
<221> NAME/KEY: SITE
<222> LOCATION: (58)
<223> OTHER INFORMATION: Xaa equals stop translation

<400> SEQUENCE: 168

Met Gly Trp Ser Ala Gly Leu Leu Phe Leu Leu Ile Leu Tyr Leu Pro

```
               1               5                  10                 15
        Val Pro Gly Trp Met Glu Arg Glu Asp Gly Glu Thr Gly His Leu Ser
                       20                  25                 30

Pro Gln Ala Pro Gly Arg Glu Tyr Arg Gly Phe Tyr Ser Val Pro Pro
                   35                  40                 45

Asp Tyr Val Trp Leu Arg Asp Ser Pro Xaa
               50                  55

<210> SEQ ID NO 169
<211> LENGTH: 232
<212> TYPE: PRT
<213> ORGANISM: Homo sapiens
<220> FEATURE:
<221> NAME/KEY: SITE
<222> LOCATION: (232)
<223> OTHER INFORMATION: Xaa equals stop translation

<400> SEQUENCE: 169

Met Ala Thr Leu Trp Gly Gly Leu Leu Arg Leu Gly Ser Leu Leu Ser
 1               5                  10                 15

Leu Ser Cys Leu Ala Leu Ser Val Leu Leu Ala His Cys Gln Thr
             20                  25                 30

Pro Pro Arg Ile Ser Arg Met Ser Asp Val Asn Val Ser Ala Leu Pro
         35                  40                 45

Ile Lys Lys Asn Ser Gly His Ile Tyr Asn Lys Asn Ile Ser Gln Lys
     50                  55                 60

Asp Cys Asp Cys Leu His Val Val Glu Pro Met Pro Val Arg Gly Pro
 65                 70                  75                 80

Asp Val Glu Ala Tyr Cys Leu Arg Cys Glu Cys Lys Tyr Glu Glu Arg
             85                  90                 95

Ser Ser Val Thr Ile Lys Val Thr Ile Ile Tyr Leu Ser Ile Leu
                100                 105                110

Gly Leu Leu Leu Tyr Met Val Tyr Leu Thr Leu Val Glu Pro Ile
         115                 120                 125

Leu Lys Arg Arg Leu Phe Gly His Ala Gln Leu Ile Gln Ser Asp Asp
     130                 135                 140

Asp Ile Gly Asp His Gln Pro Phe Ala Asn Ala His Asp Val Leu Ala
145                 150                 155                 160

Arg Ser Arg Ser Arg Ala Asn Val Leu Asn Lys Val Glu Tyr Gly Thr
                165                 170                 175

Ala Ala Leu Glu Ala Ser Ser Pro Arg Ala Ala Lys Ser Leu Ser Leu
         180                 185                 190

Thr Gly Met Leu Ser Ser Ala Asn Trp Gly Ile Glu Phe Lys Val Thr
     195                 200                 205

Arg Lys Lys Gln Ala Asp Asn Trp Lys Gly Thr Asp Trp Val Leu Leu
     210                 215                 220

Gly Phe Ile Leu Ile Pro Cys Xaa
225                 230

<210> SEQ ID NO 170
<211> LENGTH: 72
<212> TYPE: PRT
<213> ORGANISM: Homo sapiens

<400> SEQUENCE: 170

Met Ser Ala Ile Phe Asn Phe Gln Ser Leu Leu Thr Val Ile Leu Leu
 1               5                  10                 15
```

```
Leu Ile Cys Thr Cys Ala Tyr Ile Arg Ser Leu Ala Pro Ser Leu Leu
             20                  25                  30

Asp Arg Asn Lys Thr Gly Leu Leu Gly Ile Phe Trp Lys Cys Ala Arg
         35                  40                  45

Ile Gly Glu Arg Lys Ser Pro Tyr Val Ala Val Cys Cys Ile Val Met
     50                  55                  60

Ala Phe Ser Ile Leu Phe Ile Gln
 65                  70
```

<210> SEQ ID NO 171
<211> LENGTH: 65
<212> TYPE: PRT
<213> ORGANISM: Homo sapiens

<400> SEQUENCE: 171

```
Met Gly Thr Phe Ser Leu Ser Leu Phe Gly Leu Met Gly Val Ala Phe
 1               5                  10                  15

Gly Met Asn Leu Glu Ser Ser Leu Glu Glu Asp His Arg Ile Phe Trp
             20                  25                  30

Leu Ile Thr Gly Ile Met Phe Met Gly Ser Gly Leu Ile Trp Arg Arg
         35                  40                  45

Leu Leu Ser Phe Leu Gly Arg Gln Leu Glu Ala Pro Leu Pro Pro Met
     50                  55                  60

Val
 65
```

<210> SEQ ID NO 172
<211> LENGTH: 75
<212> TYPE: PRT
<213> ORGANISM: Homo sapiens

<400> SEQUENCE: 172

```
Met Tyr Lys Gly Lys Leu Val Ile Val Leu Ile Leu Leu Leu Leu Pro
 1               5                  10                  15

Ser His Phe Met Phe Leu Thr Gln Cys Lys Glu Ile Lys His Asn Leu
             20                  25                  30

Lys Lys Asn Met Ser Leu Leu Leu Phe Thr Ile Lys Ser Trp Leu Tyr
         35                  40                  45

Ser Ala Ser Leu Gly Ile Leu Tyr Asn Trp Gln His Leu Thr Ala Gln
     50                  55                  60

Val Asp Gln Cys Thr Ser Leu Ile Leu Ile His
 65                  70                  75
```

<210> SEQ ID NO 173
<211> LENGTH: 334
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring
      L-amino acids

<400> SEQUENCE: 173

```
Met Val Gly His Glu Met Ala Ser Xaa Ser Ser Asn Thr Ser Leu Pro
 1               5                  10                  15

Phe Ser Asn Met Gly Asn Pro Met Asn Thr Thr Gln Leu Gly Lys Ser
             20                  25                  30

Leu Phe Gln Trp Gln Val Glu Gln Glu Ser Lys Leu Ala Asn Ile
         35                  40                  45
```

Ser Gln Asp Gln Phe Leu Ser Lys Asp Ala Asp Gly Asp Thr Phe Leu
            50                  55                  60

His Ile Ala Val Ala Gln Gly Arg Arg Ala Leu Ser Tyr Val Leu Ala
 65                  70                  75                  80

Arg Lys Met Asn Ala Leu His Met Leu Asp Ile Lys Glu His Asn Gly
                 85                  90                  95

Gln Ser Ala Phe Gln Val Ala Val Ala Ala Asn Gln His Leu Ile Val
                100                 105                 110

Gln Asp Leu Val Asn Ile Gly Ala Gln Val Asn Thr Thr Asp Cys Trp
            115                 120                 125

Gly Arg Thr Pro Leu His Val Cys Ala Glu Lys Gly His Ser Gln Val
130                 135                 140

Leu Gln Ala Ile Gln Lys Gly Ala Val Gly Ser Asn Gln Phe Val Asp
145                 150                 155                 160

Leu Glu Ala Thr Asn Tyr Asp Gly Leu Thr Pro Leu His Cys Ala Val
                165                 170                 175

Ile Ala His Asn Ala Val Val His Glu Leu Gln Arg Asn Gln Gln Pro
                180                 185                 190

His Ser Pro Glu Val Gln Glu Leu Leu Leu Lys Asn Lys Ser Leu Val
            195                 200                 205

Asp Thr Ile Lys Cys Leu Ile Gln Met Gly Ala Ala Val Glu Ala Lys
210                 215                 220

Asp Arg Lys Ser Gly Arg Thr Ala Leu His Leu Ala Ala Glu Glu Ala
225                 230                 235                 240

Asn Leu Glu Leu Ile Arg Leu Phe Leu Glu Leu Pro Ser Cys Leu Ser
                245                 250                 255

Phe Val Asn Ala Lys Ala Tyr Asn Gly Asn Thr Ala Leu His Val Ala
                260                 265                 270

Ala Ser Leu Gln Tyr Arg Leu Thr Gln Leu Asp Ala Val Arg Leu Leu
            275                 280                 285

Met Arg Lys Gly Ala Asp Pro Ser Thr Arg Asn Leu Glu Asn Glu Gln
    290                 295                 300

Pro Val His Leu Val Pro Asp Gly Pro Val Gly Glu Gln Ile Arg Arg
305                 310                 315                 320

Ile Leu Lys Gly Lys Ser Ile Gln Gln Arg Ala Pro Pro Tyr
                325                 330

<210> SEQ ID NO 174
<211> LENGTH: 196
<212> TYPE: PRT
<213> ORGANISM: Homo sapiens
<220> FEATURE:
<221> NAME/KEY: SITE
<222> LOCATION: (196)
<223> OTHER INFORMATION: Xaa equals stop translation

<400> SEQUENCE: 174

Met Asp Ala Arg Trp Trp Ala Val Val Leu Ala Ala Phe Pro Ser
  1               5                  10                  15

Leu Gly Ala Gly Gly Glu Thr Pro Glu Ala Pro Pro Glu Ser Trp Thr
                 20                  25                  30

Gln Leu Trp Phe Phe Arg Phe Val Asn Ala Ala Gly Tyr Ala Ser
             35                  40                  45

Phe Met Val Pro Gly Tyr Leu Val Gln Tyr Phe Arg Arg Lys Asn
 50                  55                  60

-continued

Tyr Leu Glu Thr Gly Arg Gly Leu Cys Phe Pro Leu Val Lys Ala Cys
 65                  70                  75                  80

Val Phe Gly Asn Glu Pro Lys Ala Ser Asp Glu Val Pro Leu Ala Pro
                 85                  90                  95

Arg Thr Glu Ala Ala Glu Thr Thr Pro Met Trp Gln Ala Leu Lys Leu
            100                 105                 110

Leu Phe Cys Ala Thr Gly Leu Gln Val Ser Tyr Leu Thr Trp Gly Val
        115                 120                 125

Leu Gln Glu Arg Val Met Thr Arg Ser Tyr Gly Ala Thr Ala Thr Ser
130                 135                 140

Pro Gly Glu Arg Phe Thr Asp Ser Gln Phe Leu Val Leu Met Asn Arg
145                 150                 155                 160

Val Leu Ala Leu Ile Val Ala Gly Leu Ser Cys Val Leu Cys Lys Gln
                165                 170                 175

Pro Arg His Gly Ala Pro Met Tyr Arg Tyr Ser Phe Cys Gln Pro Val
            180                 185                 190

Gln Cys Ala Xaa
        195

<210> SEQ ID NO 175
<211> LENGTH: 265
<212> TYPE: PRT
<213> ORGANISM: Homo sapiens
<220> FEATURE:
<221> NAME/KEY: SITE
<222> LOCATION: (265)
<223> OTHER INFORMATION: Xaa equals stop translation

<400> SEQUENCE: 175

Met Ser Asp Leu Leu Leu Gly Leu Ile Gly Leu Thr Leu Leu
 1               5                  10                  15

Leu Leu Leu Thr Leu Leu Ala Phe Ala Gly Tyr Ser Gly Leu Leu Ala
                20                  25                  30

Gly Val Glu Val Ser Ala Gly Ser Pro Pro Ile Arg Asn Val Thr Val
            35                  40                  45

Ala Tyr Lys Phe His Met Gly Leu Tyr Gly Glu Thr Gly Arg Leu Phe
        50                  55                  60

Thr Glu Ser Cys Ser Ile Ser Pro Lys Leu Arg Ser Ile Ala Val Tyr
 65                  70                  75                  80

Tyr Asp Asn Pro His Met Val Pro Pro Asp Lys Cys Arg Cys Ala Val
                 85                  90                  95

Gly Ser Ile Leu Ser Glu Gly Glu Ser Pro Ser Pro Glu Leu Ile
            100                 105                 110

Asp Leu Tyr Gln Lys Phe Gly Phe Lys Val Phe Ser Phe Pro Glu Pro
        115                 120                 125

Ser His Val Val Thr Ala Thr Phe Pro Leu Thr Pro Phe Cys Pro
130                 135                 140

Ile Trp Leu Gly Tyr Pro Pro Cys Pro Ser Cys Leu Gly His Leu His
145                 150                 155                 160

Gln Gly Ala Glu Ala Val Cys Leu Ser Ser Ala Gly Asp Leu Pro Gly
                165                 170                 175

Arg Pro Glu Ser Ile Ser Cys Ala His Trp His Gly Gln Gly Asp Phe
            180                 185                 190

Tyr Val Pro Glu Met Lys Glu Thr Glu Trp Lys Trp Arg Gly Leu Val
        195                 200                 205

Glu Ala Ile Asp Thr Gln Val Asp Gly Thr Gly Ala Asp Thr Met Ser

```
                     210                 215                 220
Asp Thr Ser Ser Val Ser Leu Glu Val Ser Pro Gly Ser Arg Glu Thr
225                 230                 235                 240

Ser Ala Ala Thr Leu Ser Pro Gly Ala Ser Ser Arg Gly Trp Asp Asp
                245                 250                 255

Gly Asp Thr Arg Ser Glu His Ser Xaa
            260                 265

<210> SEQ ID NO 176
<211> LENGTH: 138
<212> TYPE: PRT
<213> ORGANISM: Homo sapiens
<220> FEATURE:
<221> NAME/KEY: SITE
<222> LOCATION: (138)
<223> OTHER INFORMATION: Xaa equals stop translation

<400> SEQUENCE: 176

Met Ala Gln Leu Phe Leu Pro Leu Leu Ala Ala Leu Val Leu Ala Gln
  1               5                  10                  15

Ala Pro Ala Ala Leu Ala Asp Val Leu Glu Gly Asp Ser Ser Glu Asp
                 20                  25                  30

Arg Ala Phe Arg Val Arg Ile Ala Gly Asp Ala Pro Leu Gln Gly Val
             35                  40                  45

Leu Gly Gly Ala Leu Thr Ile Pro Cys His Val His Tyr Leu Arg Pro
         50                  55                  60

Pro Pro Ser Arg Arg Ala Val Leu Gly Ser Pro Arg Val Lys Trp Thr
     65                  70                  75                  80

Phe Leu Ser Arg Gly Arg Glu Ala Glu Val Leu Val Ala Arg Gly Val
                 85                  90                  95

Arg Val Lys Val Asn Glu Ala Tyr Arg Phe Arg Val Ala Leu Pro Ala
                100                 105                 110

Tyr Pro Ala Ser Leu Thr Asp Val Ser Pro Gly Ala Glu Arg Ala Ala
            115                 120                 125

Pro Gln Arg Leu Arg Tyr Leu Ser Leu Xaa
        130                 135

<210> SEQ ID NO 177
<211> LENGTH: 179
<212> TYPE: PRT
<213> ORGANISM: Homo sapiens
<220> FEATURE:
<221> NAME/KEY: SITE
<222> LOCATION: (179)
<223> OTHER INFORMATION: Xaa equals stop translation

<400> SEQUENCE: 177

Met Pro Ala Leu Arg Pro Ala Leu Leu Trp Ala Leu Leu Ala Leu Trp
  1               5                  10                  15

Leu Cys Cys Ala Thr Pro Ala His Ala Leu Gln Cys Arg Asp Gly Tyr
                 20                  25                  30

Glu Pro Cys Val Asn Glu Gly Met Cys Val Thr Tyr His Asn Gly Thr
             35                  40                  45

Gly Tyr Cys Lys Gly Pro Glu Gly Phe Leu Gly Glu Tyr Cys Gln His
         50                  55                  60

Arg Asp Pro Cys Glu Lys Asn Arg Cys Gln Asn Gly Gly Thr Cys Val
     65                  70                  75                  80

Ala Gln Ala Met Leu Gly Lys Ala Thr Cys Arg Cys Ala Ser Gly Phe
                 85                  90                  95
```

```
Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
            115                 120                 125

Tyr Glu Cys Thr Cys Gln Val Gly Phe Thr Gly Lys Glu Cys Gln Trp
            130                 135                 140

Thr Asp Ala Cys Leu Ser His Pro Cys Ala Asn Gly Ser Thr Cys Thr
145                 150                 155                 160

Thr Val Ala Asn His Phe Leu Gln Met Pro Arg Leu His Arg Ala
                165                 170                 175

Glu Val Xaa

<210> SEQ ID NO 178
<211> LENGTH: 155
<212> TYPE: PRT
<213> ORGANISM: Homo sapiens
<220> FEATURE:
<221> NAME/KEY: SITE
<222> LOCATION: (155)
<223> OTHER INFORMATION: Xaa equals stop translation

<400> SEQUENCE: 178

Met Thr Arg Gly Gly Pro Gly Gly Arg Pro Gly Leu Pro Gln Pro Pro
1               5                   10                  15

Pro Leu Leu Leu Leu Leu Leu Pro Leu Leu Leu Val Thr Ala Glu
                20                  25                  30

Pro Pro Lys Pro Ala Gly Val Tyr Tyr Ala Thr Ala Tyr Trp Met Pro
            35                  40                  45

Ala Glu Lys Thr Val Gln Val Lys Asn Val Met Asp Lys Asn Gly Asp
        50                  55                  60

Ala Tyr Gly Phe Tyr Asn Asn Ser Val Lys Thr Thr Gly Trp Gly Ile
65                  70                  75                  80

Leu Glu Ile Arg Ala Gly Tyr Gly Ser Gln Thr Leu Ser Asn Glu Ile
                85                  90                  95

Ile Met Phe Val Ala Gly Phe Leu Glu Gly Tyr Leu Ile Ala Pro His
                100                 105                 110

Met Asn Asp His Tyr Thr Asn Leu Tyr Pro Gln Leu Ile Thr Lys Pro
            115                 120                 125

Ser Ile Met Asp Lys Val Gln Asp Phe Met Glu Lys Gln Asp Lys Val
        130                 135                 140

Asp Pro Glu Lys Tyr Gln Arg Ile Gln Asp Xaa
145                 150                 155

<210> SEQ ID NO 179
<211> LENGTH: 295
<212> TYPE: PRT
<213> ORGANISM: Homo sapiens
<220> FEATURE:
<221> NAME/KEY: SITE
<222> LOCATION: (38)
<223> OTHER INFORMATION: Xaa equals any of the naturally occurring
      L-amino acids

<400> SEQUENCE: 179

Met Leu Gln Gly Pro Gly Ser Leu Leu Leu Phe Leu Ala Ser His
1               5                   10                  15

Cys Cys Leu Gly Ser Ala Arg Gly Leu Phe Leu Phe Gly Gln Pro Asp
                20                  25                  30
```

-continued

```
Phe Ser Tyr Lys Arg Xaa Asn Cys Lys Pro Ile Pro Val Asn Leu Gln
             35                  40                  45

Leu Cys His Gly Ile Glu Tyr Gln Asn Met Arg Leu Pro Asn Leu Leu
 50                  55                  60

Gly His Glu Thr Met Lys Glu Val Leu Glu Gln Ala Gly Ala Trp Ile
 65                  70                  75                  80

Pro Leu Val Met Lys Gln Cys His Pro Asp Thr Lys Lys Phe Leu Cys
                 85                  90                  95

Ser Leu Phe Ala Pro Val Cys Leu Asp Asp Leu Asp Glu Thr Ile Gln
                100                 105                 110

Pro Cys His Ser Leu Cys Val Gln Val Lys Asp Arg Cys Ala Pro Val
                115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asp Asn Asp Ile Met Glu Thr Leu Cys Lys Asn
                180                 185                 190

Asp Phe Ala Leu Lys Ile Lys Val Lys Glu Ile Thr Tyr Ile Asn Arg
            195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Gly Glu Leu Val Ile Thr Ser
                260                 265                 270

Val Lys Arg Trp Gln Lys Gly Gln Arg Glu Phe Lys Arg Ile Ser Arg
            275                 280                 285

Ser Ile Arg Lys Leu Gln Cys
    290                 295
```

<210> SEQ ID NO 180
<211> LENGTH: 256
<212> TYPE: PRT
<213> ORGANISM: Homo sapiens

<400> SEQUENCE: 180

```
Met Arg Pro Ala Ala Leu Arg Gly Ala Leu Leu Gly Cys Leu Cys Leu
  1               5                  10                  15

Ala Leu Leu Cys Leu Gly Gly Ala Asp Lys Arg Leu Arg Asp Asn His
                 20                  25                  30

Glu Trp Lys Lys Leu Ile Met Val Gln His Trp Pro Glu Thr Val Cys
             35                  40                  45

Glu Lys Ile Gln Asn Asp Cys Arg Asp Pro Pro Asp Tyr Trp Thr Ile
 50                  55                  60

His Gly Leu Trp Pro Asp Lys Ser Glu Gly Cys Asn Arg Ser Trp Pro
 65                  70                  75                  80

Phe Asn Leu Glu Glu Ile Lys Asp Leu Leu Pro Glu Met Arg Ala Tyr
                 85                  90                  95

Trp Pro Asp Val Ile His Ser Phe Pro Asn Arg Ser Arg Phe Trp Lys
                100                 105                 110
```

```
His Glu Trp Glu Lys His Gly Thr Cys Ala Ala Gln Val Asp Ala Leu
        115                 120                 125
Asn Ser Gln Lys Lys Tyr Phe Gly Arg Ser Leu Glu Leu Tyr Arg Glu
130                 135                 140
Leu Asp Leu Asn Ser Val Leu Leu Lys Leu Gly Ile Lys Pro Ser Ile
145                 150                 155                 160
Asn Tyr Tyr Gln Val Ala Asp Phe Lys Asp Ala Leu Ala Arg Val Tyr
                165                 170                 175
Gly Val Ile Pro Lys Ile Gln Cys Leu Pro Pro Ser Gln Asp Glu Glu
            180                 185                 190
Val Gln Thr Ile Gly Gln Ile Glu Leu Cys Leu Thr Lys Gln Asp Gln
        195                 200                 205
Gln Leu Gln Asn Cys Thr Glu Pro Gly Glu Gln Pro Ser Pro Lys Gln
    210                 215                 220
Glu Val Trp Leu Ala Asn Gly Ala Ala Glu Ser Arg Gly Leu Arg Val
225                 230                 235                 240
Cys Glu Asp Gly Pro Val Phe Tyr Pro Pro Lys Lys Thr Lys His
                245                 250                 255

<210> SEQ ID NO 181
<211> LENGTH: 324
<212> TYPE: PRT
<213> ORGANISM: Homo sapiens

<400> SEQUENCE: 181

Met Ala Pro Leu Leu Gln Leu Ala Val Leu Gly Ala Ala Leu Ala
1               5                   10                  15
Ala Ala Ala Leu Val Leu Ile Ser Ile Val Ala Phe Thr Thr Ala Thr
                20                  25                  30
Lys Met Pro Ala Leu His Arg His Glu Glu Glu Lys Phe Phe Leu Asn
            35                  40                  45
Ala Lys Gly Gln Lys Glu Thr Leu Pro Ser Ile Trp Asp Ser Pro Thr
        50                  55                  60
Lys Gln Leu Ser Val Val Val Pro Ser Tyr Asn Glu Glu Lys Arg Leu
65                  70                  75                  80
Pro Val Met Met Asp Glu Ala Leu Ser Tyr Leu Glu Lys Arg Gln Lys
                85                  90                  95
Arg Asp Pro Ala Phe Thr Tyr Glu Val Ile Val Asp Asp Gly Ser
            100                 105                 110
Lys Asp Gln Thr Ser Lys Val Ala Phe Lys Tyr Cys Gln Lys Tyr Gly
        115                 120                 125
Ser Asp Lys Val Arg Val Ile Thr Leu Val Lys Asn Arg Gly Lys Gly
    130                 135                 140
Gly Ala Ile Arg Met Gly Ile Phe Ser Ser Arg Gly Glu Lys Ile Leu
145                 150                 155                 160
Met Ala Asp Ala Asp Gly Ala Thr Lys Phe Pro Asp Val Glu Lys Leu
                165                 170                 175
Glu Lys Gly Leu Asn Asp Leu Gln Pro Trp Pro Asn Gln Met Ala Ile
            180                 185                 190
Ala Cys Gly Ser Arg Ala His Leu Glu Lys Glu Ser Ile Ala Gln Arg
        195                 200                 205
Ser Tyr Phe Arg Thr Leu Leu Met Tyr Gly Phe His Phe Leu Val Trp
    210                 215                 220
Phe Leu Cys Val Lys Gly Ile Arg Asp Thr Gln Cys Gly Phe Lys Leu
```

```
                225                 230                 235                 240
Phe Thr Arg Glu Ala Ala Ser Arg Thr Phe Ser Ser Leu His Val Glu
                    245                 250                 255
Arg Trp Ala Phe Asp Val Glu Leu Leu Tyr Ile Ala Gln Phe Phe Lys
                260                 265                 270
Ile Pro Ile Ala Glu Ile Ala Val Asn Trp Thr Glu Ile Glu Gly Ser
            275                 280                 285
Lys Leu Val Pro Phe Trp Ser Trp Leu Gln Met Gly Lys Asp Leu Leu
        290                 295                 300
Phe Ile Arg Leu Arg Tyr Leu Thr Gly Ala Trp Arg Leu Glu Gln Thr
305                 310                 315                 320
Arg Lys Met Asn

<210> SEQ ID NO 182
<211> LENGTH: 47
<212> TYPE: PRT
<213> ORGANISM: Homo sapiens

<400> SEQUENCE: 182

Met Asp Ile Cys Phe Phe His Tyr Val Leu Leu Phe Leu Val Arg
 1               5                  10                  15
Cys Ala Leu Val Val Leu Ile Leu Leu Cys Gln Gly Trp Gly Asn Gly
                20                  25                  30
Gly Gly Cys Val Gly Arg Val Leu Ile Ile Val Phe Ser Ser Val
            35                  40                  45

<210> SEQ ID NO 183
<211> LENGTH: 93
<212> TYPE: PRT
<213> ORGANISM: Homo sapiens
<220> FEATURE:
<221> NAME/KEY: SITE
<222> LOCATION: (93)
<223> OTHER INFORMATION: Xaa equals stop translation

<400> SEQUENCE: 183

Met Ala Ser Leu Gly His Ile Leu Val Phe Cys Val Gly Leu Leu Thr
 1               5                  10                  15
Met Ala Lys Ala Glu Ser Pro Lys Glu His Asp Pro Phe Thr Tyr Asp
                20                  25                  30
Tyr Gln Ser Leu Gln Ile Gly Gly Leu Val Ile Ala Gly Ile Leu Phe
            35                  40                  45
Ile Leu Gly Ile Leu Ile Val Leu Ser Arg Arg Cys Arg Cys Lys Phe
        50                  55                  60
Asn Gln Gln Gln Arg Thr Gly Glu Pro Asp Glu Glu Gly Thr Phe
 65                 70                  75                  80
Arg Ser Ser Ile Arg Arg Leu Ser Thr Arg Arg Xaa
                85                  90

<210> SEQ ID NO 184
<211> LENGTH: 168
<212> TYPE: PRT
<213> ORGANISM: Homo sapiens
<220> FEATURE:
<221> NAME/KEY: SITE
<222> LOCATION: (2)
<223> OTHER INFORMATION: Xaa equals any of the naturally
      occurring L-amino acids
<220> FEATURE:
<221> NAME/KEY: SITE
<222> LOCATION: (8)
```

```
<223> OTHER INFORMATION: Xaa equals any of the naturally
      occurring L-amino acids
<220> FEATURE:
<221> NAME/KEY: SITE
<222> LOCATION: (51)
<223> OTHER INFORMATION: Xaa equals any of the naturally
      occurring L-amino acids
<220> FEATURE:
<221> NAME/KEY: SITE
<222> LOCATION: (168)
<223> OTHER INFORMATION: Xaa equals stop translation

<400> SEQUENCE: 184

Met Xaa Thr Lys Glu Phe Gly Xaa Gly Arg Ala Val Gln Gln Val Leu
 1               5                  10                  15

Asn Ile Glu Cys Leu Arg Asp Phe Leu Thr Pro Pro Leu Leu Ser Val
            20                  25                  30

Arg Phe Arg Tyr Val Gly Ala Pro Gln Ala Leu Thr Leu Lys Leu Pro
        35                  40                  45

Val Thr Xaa Asn Lys Phe Phe Gln Pro Thr Glu Met Ala Ala Gln Asp
    50                  55                  60

Phe Phe Gln Arg Trp Lys Gln Leu Ser Leu Pro Gln Gln Glu Ala Gln
65                  70                  75                  80

Lys Ile Phe Lys Ala Asn His Pro Met Asp Ala Glu Val Thr Lys Ala
                85                  90                  95

Lys Leu Leu Gly Phe Gly Ser Ala Leu Leu Asp Asn Val Asp Pro Asn
            100                 105                 110

Pro Glu Asn Phe Val Gly Ala Gly Ile Ile Gln Thr Lys Ala Leu Gln
        115                 120                 125

Val Gly Cys Leu Leu Arg Leu Glu Pro Asn Ala Gln Ala Gln Met Tyr
    130                 135                 140

Arg Leu Thr Leu Arg Thr Ser Lys Glu Pro Val Ser Arg His Leu Cys
145                 150                 155                 160

Glu Leu Leu Ala Gln Gln Phe Xaa
                165

<210> SEQ ID NO 185
<211> LENGTH: 43
<212> TYPE: PRT
<213> ORGANISM: Homo sapiens
<220> FEATURE:
<221> NAME/KEY: SITE
<222> LOCATION: (12)
<223> OTHER INFORMATION: Xaa equals any of the naturally occurring
      L-amino acids
<220> FEATURE:
<221> NAME/KEY: SITE
<222> LOCATION: (43)
<223> OTHER INFORMATION: Xaa equals stop translation

<400> SEQUENCE: 185

Met Phe Tyr Val Leu Ser Val Ser Pro Leu Leu Xaa Phe Leu Ala Cys
 1               5                  10                  15

Gly Leu Cys Leu Cys Val Asn Trp Lys Ile Ala Ile Ser Gln Leu Ser
            20                  25                  30

Leu Ser Phe Lys Asn Glu Leu Glu Lys Pro Xaa
        35                  40

<210> SEQ ID NO 186
<211> LENGTH: 59
<212> TYPE: PRT
<213> ORGANISM: Homo sapiens
<220> FEATURE:
```

```
<221> NAME/KEY: SITE
<222> LOCATION: (42)
<223> OTHER INFORMATION: Xaa equals any of the naturally
      occurring L-amino acids
<220> FEATURE:
<221> NAME/KEY: SITE
<222> LOCATION: (59)
<223> OTHER INFORMATION: Xaa equals stop translation

<400> SEQUENCE: 186

Met Lys Leu Phe Asp Ala Ser Pro Thr Phe Ala Phe Leu Leu Gly
  1               5                  10                  15

His Ile Leu Ala Met Glu Val Leu Ala Trp Leu Leu Ile Tyr Leu Leu
                 20                  25                  30

Gly Pro Gly Trp Val Pro Ser Ala Leu Xaa Arg Leu His Pro Gly His
             35                  40                  45

Leu Ser Gly Ser Val Leu Val Ser Ala Ala Xaa
         50                  55

<210> SEQ ID NO 187
<211> LENGTH: 123
<212> TYPE: PRT
<213> ORGANISM: Homo sapiens

<400> SEQUENCE: 187

Met Ile Leu Gly Gly Ile Val Val Leu Val Phe Thr Gly Phe Val
  1               5                  10                  15

Trp Ala Ala His Asn Lys Asp Val Leu Arg Arg Met Lys Lys Arg Tyr
                 20                  25                  30

Pro Thr Thr Phe Val Met Val Val Met Leu Ala Ser Tyr Phe Leu Ile
             35                  40                  45

Ser Met Phe Gly Gly Val Met Val Phe Val Phe Gly Ile Thr Phe Pro
         50                  55                  60

Leu Leu Leu Met Phe Ile His Ala Ser Leu Arg Leu Arg Asn Leu Lys
 65                  70                  75                  80

Asn Lys Leu Glu Asn Lys Met Glu Gly Ile Gly Leu Lys Arg Thr Pro
                 85                  90                  95

Met Gly Ile Val Leu Asp Ala Leu Glu Gln Gln Glu Glu Gly Ile Asn
            100                 105                 110

Arg Leu Thr Asp Tyr Ile Ser Lys Val Lys Glu
            115                 120

<210> SEQ ID NO 188
<211> LENGTH: 146
<212> TYPE: PRT
<213> ORGANISM: Homo sapiens

<400> SEQUENCE: 188

Met Phe Leu Thr Arg Ile Leu Cys Pro Thr Tyr Ile Ala Leu Thr Phe
  1               5                  10                  15

Leu Val Tyr Ile Val Ala Leu Val Ser Gly Gln Leu Cys Met Glu Ile
                 20                  25                  30

Ala Arg Gly Asn Ile Phe Phe Leu Asn Glu Leu Val Thr Thr Phe Cys
             35                  40                  45

Cys Ser Cys Leu Leu Leu Ser Val Pro Tyr Leu His Pro Gly Phe Phe
         50                  55                  60

Tyr Ser Ser Leu Cys Lys Cys Cys Phe Val Leu Val Val Leu Ser Arg
 65                  70                  75                  80

Ile Gly Ser Val Asn Glu Thr Trp Ser Cys Asn Phe Ser Ile Cys Ser
```

```
                        85                  90                  95
Tyr Leu Ile Phe Gly Ser Pro Ile Phe Thr Ala Val Ile Pro Lys Arg
                100                 105                 110
Cys Ala Leu Glu Asp Ile Gln Asn Asn Pro Ile Gly Cys Leu Leu Arg
            115                 120                 125
Cys Thr Pro Ala Trp Glu Thr Glu Gly Asp Ser Ile Ser Lys Lys Ile
    130                 135                 140

Lys Lys
145

<210> SEQ ID NO 189
<211> LENGTH: 84
<212> TYPE: PRT
<213> ORGANISM: Homo sapiens

<400> SEQUENCE: 189

Met Gly Ser Arg Ala Glu Leu Cys Thr Leu Leu Gly Gly Phe Ser Phe
  1               5                  10                  15
Leu Leu Leu Leu Ile Pro Gly Glu Gly Ala Lys Gly Gly Ser Leu Arg
                20                  25                  30
Glu Ser Gln Gly Val Cys Ser Lys Gln Thr Leu Val Val Pro Leu His
            35                  40                  45
Tyr Asn Glu Ser Tyr Ser Gln Pro Val Tyr Lys Pro Tyr Leu Thr Leu
    50                  55                  60
Cys Ala Gly Ser Ala Ser Ala Leu Thr Gly Pro Cys Thr Ala Leu
 65                  70                  75                  80

Cys Gly Gly Arg

<210> SEQ ID NO 190
<211> LENGTH: 58
<212> TYPE: PRT
<213> ORGANISM: Homo sapiens
<220> FEATURE:
<221> NAME/KEY: SITE
<222> LOCATION: (58)
<223> OTHER INFORMATION: Xaa equals stop translation

<400> SEQUENCE: 190

Met Met Gly Val Leu Gln Leu His Ile Phe Trp Ala Tyr Leu Ile
  1               5                  10                  15
Leu Arg Met Ala His Lys Phe Ile Thr Gly Lys Leu Val Glu Asp Glu
                20                  25                  30
Arg Ser Thr Gly Lys Lys Gln Arg Ala Gln Arg Gly Arg Arg Leu Gln
            35                  40                  45
Leu Gly Glu Glu Gln Arg Ala Gly Pro Xaa
    50                  55

<210> SEQ ID NO 191
<211> LENGTH: 311
<212> TYPE: PRT
<213> ORGANISM: Homo sapiens
<220> FEATURE:
<221> NAME/KEY: SITE
<222> LOCATION: (277)
<223> OTHER INFORMATION: Xaa equals any of the naturally
      occurring L-amino acids
<220> FEATURE:
<221> NAME/KEY: SITE
<222> LOCATION: (311)
<223> OTHER INFORMATION: Xaa equals stop translation

<400> SEQUENCE: 191
```

```
Met Arg Arg Leu Val His Asp Leu Leu Pro Pro Glu Val Cys Ser Leu
 1               5                  10                  15

Leu Asn Pro Ala Ala Ile Tyr Ala Asn Asn Glu Ile Ser Leu Arg Asp
             20                  25                  30

Val Glu Val Tyr Gly Phe Asp Tyr Asp Tyr Thr Leu Ala Gln Tyr Ala
         35                  40                  45

Asp Ala Leu His Pro Glu Ile Phe Ser Thr Ala Arg Asp Ile Leu Ile
     50                  55                  60

Glu His Tyr Lys Tyr Pro Glu Gly Ile Arg Lys Tyr Asp Tyr Asn Pro
 65                  70                  75                  80

Ser Phe Ala Ile Arg Gly Leu His Tyr Asp Ile Gln Lys Ser Leu Leu
                 85                  90                  95

Met Lys Ile Asp Ala Phe His Tyr Val Gln Leu Gly Thr Ala Tyr Arg
             100                 105                 110

Gly Leu Gln Pro Val Pro Asp Glu Val Ile Glu Leu Tyr Gly Gly
         115                 120                 125

Thr Gln His Ile Pro Leu Tyr Gln Met Ser Gly Phe Tyr Gly Lys Gly
     130                 135                 140

Pro Ser Ile Lys Gln Phe Met Asp Ile Phe Ser Leu Pro Glu Met Ala
145                 150                 155                 160

Leu Leu Ser Cys Val Val Asp Tyr Phe Leu Gly His Ser Leu Glu Phe
                 165                 170                 175

Asp Gln Ala His Leu Tyr Lys Asp Val Thr Asp Ala Ile Arg Asp Val
             180                 185                 190

His Val Lys Gly Leu Met Tyr Gln Trp Ile Glu Gln Asp Met Glu Lys
         195                 200                 205

Tyr Ile Leu Arg Gly Asp Glu Thr Phe Ala Val Leu Ser Arg Leu Val
     210                 215                 220

Ala His Gly Lys Gln Leu Phe Leu Ile Thr Asn Ser Pro Phe Ser Phe
225                 230                 235                 240

Val Asp Lys Gly Met Arg His Met Val Gly Pro Asp Trp Arg His Ser
                 245                 250                 255

Ser Met Trp Ser Leu Ser Arg Gln Thr Ser Pro Ala Ser Ser Leu Thr
             260                 265                 270

Gly Ala Ser Phe Xaa Glu Asn Ser Met Arg Arg Ala His Phe Ser Gly
         275                 280                 285

Thr Gly Ser Pro Ala Trp Lys Arg Ala Arg Ser Ile Gly Arg Glu Thr
     290                 295                 300

Cys Leu Thr Ser Tyr Ala Xaa
305                 310

<210> SEQ ID NO 192
<211> LENGTH: 318
<212> TYPE: PRT
<213> ORGANISM: Homo sapiens
<220> FEATURE:
<221> NAME/KEY: SITE
<222> LOCATION: (318)
<223> OTHER INFORMATION: Xaa equals stop translation

<400> SEQUENCE: 192

Met Asn Trp Glu Leu Leu Leu Trp Leu Leu Val Leu Cys Ala Leu Leu
 1               5                  10                  15

Leu Leu Leu Val Gln Leu Leu Arg Phe Leu Arg Ala Asp Gly Asp Leu
             20                  25                  30
```

-continued

Thr Leu Leu Trp Ala Glu Trp Gln Gly Arg Arg Pro Glu Trp Glu Leu
            35                  40                  45

Thr Asp Met Val Val Trp Val Thr Gly Ala Ser Ser Gly Ile Gly Glu
         50                  55                  60

Glu Leu Ala Tyr Gln Leu Ser Lys Leu Gly Val Ser Leu Val Leu Ser
 65                  70                  75                  80

Ala Arg Arg Val His Glu Leu Glu Arg Val Lys Arg Cys Leu Glu
                 85                  90                  95

Asn Gly Asn Leu Lys Glu Lys Asp Ile Leu Val Leu Pro Leu Asp Leu
             100                 105                 110

Thr Asp Thr Gly Ser His Glu Ala Ala Thr Lys Ala Val Leu Gln Glu
         115                 120                 125

Phe Gly Arg Ile Asp Ile Leu Val Asn Asn Gly Met Ser Gln Arg
130                 135                 140

Ser Leu Cys Met Asp Thr Ser Leu Asp Val Tyr Arg Lys Leu Ile Glu
145                 150                 155                 160

Leu Asn Tyr Leu Gly Thr Val Ser Leu Thr Lys Cys Val Leu Pro His
                 165                 170                 175

Met Ile Glu Arg Lys Gln Gly Lys Ile Val Thr Val Asn Ser Ile Leu
             180                 185                 190

Gly Ile Ile Ser Val Pro Leu Ser Ile Gly Tyr Cys Ala Ser Lys His
         195                 200                 205

Ala Leu Arg Gly Phe Phe Asn Gly Leu Arg Thr Glu Leu Ala Thr Tyr
210                 215                 220

Pro Gly Ile Ile Val Ser Asn Ile Cys Pro Gly Pro Val Gln Ser Asn
225                 230                 235                 240

Ile Val Glu Asn Ser Leu Ala Gly Val Thr Lys Thr Ile Gly Asn
                 245                 250                 255

Asn Gly Asp Gln Ser His Lys Met Thr Thr Ser Arg Cys Val Arg Leu
             260                 265                 270

Met Leu Ile Ser Met Ala Asn Asp Leu Lys Glu Val Trp Ile Ser Glu
         275                 280                 285

Gln Pro Phe Leu Phe Ser Asn Ile Phe Val Ala Ile His Ala Asn Leu
290                 295                 300

Gly Leu Val Asp Asn Gln Gln Asp Gly Glu Lys Asp Xaa
305                 310                 315

<210> SEQ ID NO 193
<211> LENGTH: 53
<212> TYPE: PRT
<213> ORGANISM: Homo sapiens

<400> SEQUENCE: 193

Met Trp Pro Ser Phe Pro Gln Val Arg Val Gly Ser Phe Leu Phe Gly
 1               5                  10                  15

Ile Leu Phe Phe Ser Phe Gly Ser Ser Ser Leu Pro Pro Gly Leu Pro
             20                  25                  30

Pro Pro Ala Ser Leu Leu Cys Cys Ala Val Gln Trp Gly Ala Arg Ala
         35                  40                  45

Leu Phe Leu Pro Ala
     50

<210> SEQ ID NO 194
<211> LENGTH: 42
<212> TYPE: PRT
<213> ORGANISM: Homo sapiens -continued

<400> SEQUENCE: 194

Met Leu Val Thr Cys Ser Val Cys Cys Tyr Leu Phe Trp Leu Ile Ala
 1               5                  10                  15

Ile Leu Ala Gln Leu Asn Pro Leu Phe Gly Pro Gln Leu Lys Asn Glu
            20                  25                  30

Thr Ile Trp Tyr Leu Lys Tyr His Trp Pro
        35                  40

<210> SEQ ID NO 195
<211> LENGTH: 96
<212> TYPE: PRT
<213> ORGANISM: Homo sapiens

<400> SEQUENCE: 195

Met Gly Ala Arg Pro Gly Gly His Pro Gln Lys Trp Ser Phe Leu Trp
 1               5                  10                  15

Ser Leu Ala Leu Trp Leu Pro Leu Ala Leu Ser Val Ser Leu Phe Leu
            20                  25                  30

Gly Leu Ser Leu Ser Pro Pro Gln Pro Gly Leu Ser Leu Trp Cys Thr
        35                  40                  45

Leu Ser Tyr Cys Cys Glu Gln Trp Lys Phe Lys Gly Thr Pro Ser Pro
    50                  55                  60

Ala Leu Leu Asn Leu Gly Thr Gln Pro Lys Lys Asp Lys Lys Leu Glu
65                  70                  75                  80

Asp Ser Ile Ala Thr Gln Leu Arg Glu Leu Pro Glu Lys Asn Ser Asn
                85                  90                  95

<210> SEQ ID NO 196
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 196

Met Ala Leu Thr Phe Leu Leu Val Leu Leu Thr Leu Ala Thr Ser Ala
 1               5                  10                  15

His Gly Cys Thr Glu Thr Ser Asp Ala Gly Arg Ala Ser Thr Gly Gly
            20                  25                  30

Pro Gln Arg Thr Ala Arg Thr Gln Trp Leu Leu Cys Xaa
        35                  40                  45

<210> SEQ ID NO 197
<211> LENGTH: 355
<212> TYPE: PRT
<213> ORGANISM: Homo sapiens
<220> FEATURE:
<221> NAME/KEY: SITE
<222> LOCATION: (355)
<223> OTHER INFORMATION: Xaa equals stop translation

<400> SEQUENCE: 197

Met Gly Pro Ser Thr Pro Leu Leu Ile Leu Phe Leu Leu Ser Trp Ser
 1               5                  10                  15

Gly Pro Leu Gln Gly Gln Gln His His Leu Val Glu Tyr Met Glu Arg
            20                  25                  30

Arg Leu Ala Ala Leu Glu Glu Arg Leu Ala Gln Cys Gln Asp Gln Ser
        35                  40                  45

```
Ser Arg His Ala Ala Glu Leu Arg Asp Phe Lys Asn Lys Met Leu Pro
     50                  55                  60

Leu Leu Glu Val Ala Glu Lys Glu Arg Glu Ala Leu Arg Thr Glu Ala
 65                  70                  75                  80

Asp Thr Ile Ser Gly Arg Val Asp Arg Leu Glu Arg Glu Val Asp Tyr
                 85                  90                  95

Leu Glu Thr Gln Asn Pro Ala Leu Pro Cys Val Glu Phe Asp Glu Lys
            100                 105                 110

Val Thr Gly Gly Pro Gly Thr Lys Gly Lys Gly Arg Arg Asn Glu Lys
        115                 120                 125

Tyr Asp Met Val Thr Asp Cys Gly Tyr Thr Ile Ser Gln Val Arg Ser
    130                 135                 140

Met Lys Ile Leu Lys Arg Phe Gly Pro Ala Gly Leu Trp Thr Lys
145                 150                 155                 160

Asp Pro Leu Gly Gln Thr Glu Lys Ile Tyr Val Leu Asp Gly Thr Gln
                165                 170                 175

Asn Asp Thr Ala Phe Val Phe Pro Arg Leu Arg Asp Phe Thr Leu Ala
            180                 185                 190

Met Ala Ala Arg Lys Ala Ser Arg Val Arg Val Pro Phe Pro Trp Val
    195                 200                 205

Gly Thr Gly Gln Leu Val Tyr Gly Gly Phe Leu Tyr Phe Ala Arg Arg
    210                 215                 220

Pro Pro Gly Arg Pro Gly Gly Gly Glu Met Glu Asn Thr Leu Gln
225                 230                 235                 240

Leu Ile Lys Phe His Leu Ala Asn Arg Thr Val Val Asp Ser Ser Val
                245                 250                 255

Phe Pro Ala Glu Gly Leu Ile Pro Pro Tyr Gly Leu Thr Ala Asp Thr
            260                 265                 270

Tyr Ile Asp Leu Ala Ala Asp Glu Gly Leu Trp Ala Val Tyr Ala
    275                 280                 285

Thr Arg Glu Asp Asp Arg His Leu Cys Leu Ala Lys Leu Asp Pro Gln
    290                 295                 300

Thr Leu Asp Thr Glu Gln Gln Trp Asp Thr Pro Cys Pro Arg Glu Asn
305                 310                 315                 320

Ala Glu Ala Ala Phe Val Ile Cys Gly Thr Leu Tyr Val Val Tyr Asn
            325                 330                 335

Thr Arg Pro Ala Ser Arg Ala Arg Ile Gln Cys Ser Phe Asp Ala Ser
            340                 345                 350

Gly Pro Xaa
        355

<210> SEQ ID NO 198
<211> LENGTH: 74
<212> TYPE: PRT
<213> ORGANISM: Homo sapiens

<400> SEQUENCE: 198

Met Val Leu Pro Leu Leu Ile Phe Val Leu Leu Pro Lys Val Val Asn
  1               5                  10                  15

Thr Ser Asp Pro Asp Met Arg Arg Glu Met Gln Ser Met Asn Met
            20                  25                  30

Leu Asn Ser Asn His Glu Leu Pro Asp Val Ser Glu Phe Met Thr Arg
        35                  40                  45

Leu Phe Ser Ser Lys Ser Ser Gly Lys Ser Ser Ser Gly Ser Ser Lys
```

-continued

```
                 50                  55                  60
Thr Gly Lys Ser Gly Ala Gly Lys Arg Arg
 65                  70
```

<210> SEQ ID NO 199
<211> LENGTH: 113
<212> TYPE: PRT
<213> ORGANISM: Homo sapiens
<220> FEATURE:
<221> NAME/KEY: SITE
<222> LOCATION: (113)
<223> OTHER INFORMATION: Xaa equals stop translation

<400> SEQUENCE: 199

```
Met Phe Thr Met Leu Cys Ile Asn Gly Thr Thr Pro Arg Pro Leu Pro
 1               5                  10                  15

Val Pro Ser Pro Phe Gly Cys Met Ile Phe Phe Phe Lys Asn Pro
             20                  25                  30

Trp Lys Gln Arg Leu Leu Gln Gly Trp Leu Gly Ala Arg Pro Ile His
             35                  40                  45

Leu Leu Gly Tyr Leu Pro Leu Ser Leu Leu Trp Cys Pro Phe Pro Leu
     50                  55                  60

Pro Cys Ala Arg Cys Ser Val Val Tyr Ile Ser Ser Pro Arg His Gly
 65                  70                  75                  80

Ala His Ala Pro Arg Asp Met Ile Leu Ser Leu Val Leu Ala His Gly
                 85                  90                  95

Ala Leu Tyr Lys Glu Leu Gly Gly Arg Gly Arg Lys Trp Glu Pro Ser
             100                 105                 110

Xaa
```

<210> SEQ ID NO 200
<211> LENGTH: 123
<212> TYPE: PRT
<213> ORGANISM: Homo sapiens

<400> SEQUENCE: 200

```
Met Ala Cys Arg Cys Leu Ser Phe Leu Leu Met Gly Thr Phe Leu Ser
 1               5                  10                  15

Val Ser Gln Thr Val Leu Ala Gln Leu Asp Ala Leu Leu Val Phe Pro
             20                  25                  30

Gly Gln Val Ala Gln Leu Ser Cys Thr Leu Ser Pro Gln His Val Thr
             35                  40                  45

Ile Arg Asp Tyr Gly Val Ser Trp Tyr Gln Gln Arg Ala Gly Ser Ala
     50                  55                  60

Pro Arg Tyr Leu Leu Tyr Tyr Arg Ser Glu Glu Asp His Arg Arg Pro
 65                  70                  75                  80

Ala Asp Ile Pro Asp Arg Phe Ser Ala Ala Lys Asp Glu Ala His Asn
                 85                  90                  95

Ala Cys Val Leu Thr Ile Ser Pro Val Gln Pro Glu Asp Asp Ala Asp
             100                 105                 110

Tyr Tyr Cys Ser Val Gly Tyr Gly Phe Ser Pro
             115                 120
```

<210> SEQ ID NO 201
<211> LENGTH: 315
<212> TYPE: PRT
<213> ORGANISM: Homo sapiens
<220> FEATURE:
<221> NAME/KEY: SITE -continued

```
<222> LOCATION: (9)
<223> OTHER INFORMATION: Xaa equals any of the naturally occurring
      L-amino acids
<220> FEATURE:
<221> NAME/KEY: SITE
<222> LOCATION: (311)
<223> OTHER INFORMATION: Xaa equals any of the naturally occurring
      L-amino acids
<220> FEATURE:
<221> NAME/KEY: SITE
<222> LOCATION: (315)
<223> OTHER INFORMATION: Xaa equals stop translation

<400> SEQUENCE: 201

Met Ala Gly Gly Arg Cys Gly Pro Xaa Leu Thr Ala Leu Leu Ala Ala
  1               5                  10                  15

Trp Ile Ala Ala Val Ala Ala Thr Ala Gly Pro Glu Glu Ala Ala Leu
             20                  25                  30

Pro Pro Glu Gln Ser Arg Val Gln Pro Met Thr Ala Ser Asn Trp Thr
         35                  40                  45

Leu Val Met Glu Gly Glu Trp Met Leu Lys Phe Tyr Ala Pro Trp Cys
     50                  55                  60

Pro Ser Cys Gln Gln Thr Asp Ser Glu Trp Glu Ala Phe Ala Lys Asn
 65                  70                  75                  80

Gly Glu Ile Leu Gln Ile Ser Val Gly Lys Val Asp Val Ile Gln Glu
                 85                  90                  95

Pro Gly Leu Ser Gly Arg Phe Phe Val Thr Thr Leu Pro Ala Phe Phe
            100                 105                 110

His Ala Lys Asp Gly Ile Phe Arg Arg Tyr Arg Gly Pro Gly Ile Phe
        115                 120                 125

Glu Asp Leu Gln Asn Tyr Ile Leu Glu Lys Lys Trp Gln Ser Val Glu
130                 135                 140

Pro Leu Thr Gly Trp Lys Ser Pro Ala Ser Leu Thr Met Ser Gly Met
145                 150                 155                 160

Ala Gly Leu Phe Ser Ile Ser Gly Lys Ile Trp His Leu His Asn Tyr
                165                 170                 175

Phe Thr Val Thr Leu Gly Ile Pro Ala Trp Cys Ser Tyr Val Phe Phe
            180                 185                 190

Val Ile Ala Thr Leu Val Phe Gly Leu Phe Met Gly Leu Val Leu Val
        195                 200                 205

Val Ile Ser Glu Cys Phe Tyr Val Pro Leu Pro Arg His Leu Ser Glu
210                 215                 220

Arg Ser Glu Gln Asn Arg Arg Ser Glu Glu Ala His Arg Ala Glu Gln
225                 230                 235                 240

Leu Gln Asp Ala Glu Glu Lys Asp Asp Ser Asn Glu Glu Glu Glu Asn
                245                 250                 255

Lys Asp Ser Leu Val Asp Asp Glu Glu Lys Glu Asp Leu Gly Asp
            260                 265                 270

Glu Asp Glu Ala Glu Glu Glu Glu Glu Asp Asn Leu Ala Ala Gly
        275                 280                 285

Val Asp Glu Glu Arg Ser Glu Ala Asn Asp Gln Gly Pro Pro Gly Glu
    290                 295                 300

Asp Gly Val Thr Arg Glu Xaa Ser Arg Ala Xaa
305                 310                 315

<210> SEQ ID NO 202
<211> LENGTH: 236
<212> TYPE: PRT
```

```
<213> ORGANISM: Homo sapiens
<220> FEATURE:
<221> NAME/KEY: SITE
<222> LOCATION: (236)
<223> OTHER INFORMATION: Xaa equals stop translation

<400> SEQUENCE: 202

Met Gly Thr Ala Asp Ser Asp Glu Met Ala Pro Glu Ala Pro Gln His
 1               5                  10                  15

Thr His Ile Asp Val His Ile His Gln Glu Ser Ala Leu Ala Lys Leu
                20                  25                  30

Leu Leu Thr Cys Cys Ser Ala Leu Arg Pro Arg Ala Thr Gln Ala Arg
            35                  40                  45

Gly Ser Ser Arg Leu Leu Val Ala Ser Trp Val Met Gln Ile Val Leu
 50                  55                  60

Gly Ile Leu Ser Ala Val Leu Gly Gly Phe Phe Tyr Ile Arg Asp Tyr
 65                  70                  75                  80

Thr Leu Val Thr Ser Gly Ala Ala Ile Trp Thr Gly Ala Val Ala
                85                  90                  95

Val Leu Ala Gly Ala Ala Ala Phe Ile Tyr Glu Lys Arg Gly Gly Thr
                100                 105                 110

Tyr Trp Ala Leu Leu Arg Thr Leu Leu Ala Leu Ala Ala Phe Ser Thr
            115                 120                 125

Ala Ile Ala Ala Leu Lys Leu Trp Asn Glu Asp Phe Arg Tyr Gly Tyr
130                 135                 140

Ser Tyr Tyr Asn Ser Ala Cys Arg Ile Ser Ser Ser Ser Asp Trp Asn
145                 150                 155                 160

Thr Pro Ala Pro Thr Gln Ser Pro Glu Glu Val Arg Arg Leu His Leu
                165                 170                 175

Cys Thr Ser Phe Met Asp Met Leu Lys Ala Leu Phe Arg Thr Leu Gln
            180                 185                 190

Ala Met Leu Leu Gly Val Trp Ile Leu Leu Leu Ala Ser Leu Ala
                195                 200                 205

Pro Leu Trp Leu Tyr Cys Trp Arg Met Phe Pro Thr Lys Gly Lys Arg
    210                 215                 220

Asp Gln Lys Glu Met Leu Glu Val Ser Gly Ile Xaa
225                 230                 235

<210> SEQ ID NO 203
<211> LENGTH: 93
<212> TYPE: PRT
<213> ORGANISM: Homo sapiens

<400> SEQUENCE: 203

Met Ile His Leu Gly His Ile Leu Phe Leu Leu Leu Pro Val Ala
 1               5                  10                  15

Ala Ala Gln Thr Thr Pro Gly Glu Arg Ser Ser Leu Pro Ala Phe Tyr
                20                  25                  30

Pro Gly Thr Ser Gly Ser Cys Ser Gly Cys Gly Ser Leu Ser Leu Pro
            35                  40                  45

Leu Leu Ala Gly Leu Val Ala Ala Asp Ala Val Ala Ser Leu Leu Ile
 50                  55                  60

Val Gly Ala Val Phe Leu Cys Ala Arg Pro Arg Arg Ser Pro Ala Gln
 65                  70                  75                  80

Glu Asp Gly Lys Val Tyr Ile Asn Met Pro Gly Arg Gly
                85                  90
```

<210> SEQ ID NO 204
<211> LENGTH: 35
<212> TYPE: PRT
<213> ORGANISM: Homo sapiens

<400> SEQUENCE: 204

Met Trp Ser Ala Gly Arg Gly Gly Ala Ala Trp Pro Val Leu Leu Gly
1               5                   10                  15

Leu Leu Leu Ala Leu Leu Val Pro Gly Gly Ala Ala Lys Thr Gly
            20                  25                  30

Ala Asp Ser
        35

<210> SEQ ID NO 205
<211> LENGTH: 43
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the naturally occurring
      L-amino acids

<400> SEQUENCE: 205

Asp Cys Xaa His Val Ser Val Leu Gln Ser Thr Ile Ser Pro Leu Leu
1               5                   10                  15

Pro Leu Pro Leu Leu Leu Pro His Gly Asn Cys Glu Glu Ala Pro Trp
            20                  25                  30

Gln Ala Ala Val Ile Gly Gly Gly Asp Arg Ile
        35                  40

<210> SEQ ID NO 206
<211> LENGTH: 85
<212> TYPE: PRT
<213> ORGANISM: Homo sapiens
<220> FEATURE:
<221> NAME/KEY: SITE
<222> LOCATION: (85)
<223> OTHER INFORMATION: Xaa equals stop translation

<400> SEQUENCE: 206

Met Arg Asp Cys Leu Ser Leu Lys Pro Arg Pro Leu Phe Pro Thr Gln
1               5                   10                  15

Phe Phe Phe Ile Leu Leu Leu Ile Phe Ile Ala Glu Val Ala Ala Ala
            20                  25                  30

Val Val Ala Leu Val Tyr Thr Thr Met Val Arg His Trp Asp Gly Gly
        35                  40                  45

Arg Glu Glu Asp Trp Ala Lys Pro Trp Glu Trp Ala Val Ala Cys Glu
    50                  55                  60

Trp Pro Pro Ser Val Pro Ala Pro Lys His Trp Pro Ala Ser Pro Arg
65                  70                  75                  80

Leu Ser Thr Ser Xaa
                85

<210> SEQ ID NO 207
<211> LENGTH: 208
<212> TYPE: PRT
<213> ORGANISM: Homo sapiens
<220> FEATURE:
<221> NAME/KEY: SITE
<222> LOCATION: (26)
<223> OTHER INFORMATION: Xaa equals any of the naturally occurring
      L-amino acids

```
<220> FEATURE:
<221> NAME/KEY: SITE
<222> LOCATION: (81)
<223> OTHER INFORMATION: Xaa equals any of the naturally occurring
      L-amino acids

<400> SEQUENCE: 207

Met His Gly Asn Glu Ala Leu Gly Arg Glu Leu Leu Leu Leu Leu Met
 1               5                  10                  15

Gln Phe Leu Cys His Glu Phe Leu Arg Xaa Asn Pro Arg Val Thr Arg
            20                  25                  30

Leu Leu Ser Glu Met Arg Ile His Leu Leu Pro Ser Met Asn Pro Asp
        35                  40                  45

Gly Tyr Glu Ile Ala Tyr His Arg Gly Ser Glu Leu Val Gly Trp Ala
    50                  55                  60

Glu Gly Arg Trp Asn Asn Gln Ser Ile Asp Leu Asn His Asn Phe Ala
65                  70                  75                  80

Xaa Leu Asn Thr Pro Leu Trp Glu Ala Gln Asp Asp Gly Lys Val Pro
                85                  90                  95

His Ile Val Pro Asn His His Leu Pro Leu Pro Thr Tyr Tyr Thr Leu
            100                 105                 110

Pro Asn Ala Thr Val Ala Pro Glu Thr Arg Ala Val Ile Lys Trp Met
        115                 120                 125

Lys Arg Ile Pro Phe Val Leu Ser Ala Asn Leu His Gly Gly Glu Leu
    130                 135                 140

Val Val Ser Tyr Pro Phe Asp Met Thr Arg Thr Pro Trp Ala Ala Arg
145                 150                 155                 160

Glu Leu Thr Pro Thr Pro Asp Asp Ala Val Phe Arg Trp Leu Ser Thr
                165                 170                 175

Val Tyr Ala Gly Ser Asn Leu Ala Met Gln Asp Thr Ser Arg Arg Pro
            180                 185                 190

Cys His Ser Gln Asp Phe Ser Val His Gly Asn Ile Ile Asn Gly Ala
        195                 200                 205

<210> SEQ ID NO 208
<211> LENGTH: 24
<212> TYPE: PRT
<213> ORGANISM: Homo sapiens

<400> SEQUENCE: 208

Met Glu Ile Ser Cys Leu Leu Leu Leu Ile Gln Asp Ser Asp Glu Met
 1               5                  10                  15

Glu Asp Gly Pro Gly Val Gln Asp
            20

<210> SEQ ID NO 209
<211> LENGTH: 483
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids
<220> FEATURE:
<221> NAME/KEY: SITE
<222> LOCATION: (483)
<223> OTHER INFORMATION: Xaa equals stop translation

<400> SEQUENCE: 209

Met Ala Thr Gly Gly Gly Ile Arg Ala Met Thr Ser Leu Tyr Gly Gln
```

-continued

```
  1               5              10              15
Leu Ala Gly Leu Lys Glu Leu Gly Leu Leu Asp Cys Xaa Ser Tyr Ile
             20              25              30

Thr Gly Ala Ser Gly Ser Thr Trp Ala Leu Ala Asn Leu Tyr Lys Asp
             35              40              45

Pro Glu Trp Ser Gln Lys Asp Leu Ala Gly Pro Thr Glu Leu Leu Lys
 50              55              60

Thr Gln Val Thr Lys Asn Lys Leu Gly Val Leu Ala Pro Ser Gln Leu
 65              70              75              80

Gln Arg Tyr Arg Gln Glu Leu Ala Glu Ala Arg Leu Gly Tyr Pro
             85              90              95

Ser Cys Phe Thr Asn Leu Trp Ala Leu Ile Asn Glu Ala Leu Leu His
            100             105             110

Asp Glu Pro His Asp His Lys Leu Ser Asp Gln Arg Glu Ala Leu Ser
            115             120             125

His Gly Gln Asn Pro Leu Pro Ile Tyr Cys Ala Leu Asn Thr Lys Gly
            130             135             140

Gln Ser Leu Thr Thr Phe Glu Phe Gly Glu Trp Cys Glu Phe Ser Pro
145             150             155             160

Tyr Glu Val Gly Phe Pro Lys Tyr Gly Ala Phe Ile Pro Ser Glu Leu
                165             170             175

Phe Gly Ser Glu Phe Phe Met Gly Gln Leu Met Lys Arg Leu Pro Glu
            180             185             190

Ser Arg Ile Cys Phe Leu Glu Gly Ile Trp Ser Asn Leu Tyr Ala Ala
            195             200             205

Asn Leu Gln Asp Ser Leu Tyr Trp Ala Ser Glu Pro Ser Gln Phe Trp
210             215             220

Asp Arg Trp Val Arg Asn Gln Ala Asn Leu Asp Lys Glu Gln Val Pro
225             230             235             240

Leu Leu Lys Ile Glu Glu Pro Pro Ser Thr Ala Gly Arg Ile Ala Glu
            245             250             255

Phe Phe Thr Asp Leu Leu Thr Trp Arg Pro Leu Ala Gln Ala Thr His
            260             265             270

Asn Phe Leu Arg Gly Leu His Phe His Lys Asp Tyr Phe Gln His Pro
            275             280             285

His Phe Ser Thr Trp Lys Ala Thr Thr Leu Asp Gly Leu Pro Asn Gln
            290             295             300

Leu Thr Pro Ser Glu Pro His Leu Cys Leu Leu Asp Val Gly Tyr Leu
305             310             315             320

Ile Asn Thr Ser Cys Leu Pro Leu Leu Gln Pro Thr Arg Asp Val Asp
                325             330             335

Leu Ile Leu Ser Leu Asp Tyr Asn Leu His Gly Ala Phe Gln Gln Leu
            340             345             350

Gln Leu Leu Gly Arg Phe Cys Gln Glu Gln Gly Ile Pro Phe Pro Pro
            355             360             365

Ile Ser Pro Ser Pro Glu Glu Gln Leu Gln Pro Arg Glu Cys His Thr
            370             375             380

Phe Ser Asp Pro Thr Cys Pro Gly Ala Pro Ala Val Leu His Phe Pro
385             390             395             400

Leu Val Ser Asp Ser Phe Arg Glu Tyr Ser Ala Pro Gly Val Arg Arg
            405             410             415

Thr Pro Glu Glu Ala Ala Ala Gly Glu Val Asn Leu Ser Ser Ser Asp
            420             425             430
```

-continued

```
Ser Pro Tyr His Tyr Thr Lys Val Thr Tyr Ser Gln Glu Asp Val Asp
        435                 440                 445

Lys Leu Leu His Leu Thr His Tyr Asn Val Cys Asn Asn Gln Glu Gln
    450                 455                 460

Leu Leu Glu Ala Leu Arg Gln Ala Val Gln Arg Arg Gln Arg Arg
465                 470                 475                 480

Pro His Xaa

<210> SEQ ID NO 210
<211> LENGTH: 13
<212> TYPE: PRT
<213> ORGANISM: Homo sapiens

<400> SEQUENCE: 210

Leu Glu Val Gly Cys Ile Gln Val Ala Pro Asp Thr Phe
  1               5                  10

<210> SEQ ID NO 211
<211> LENGTH: 20
<212> TYPE: PRT
<213> ORGANISM: Homo sapiens

<400> SEQUENCE: 211

Met Ser Leu Phe Phe Leu Leu Thr Leu Ile Ser Lys Leu His Gly Asp
  1               5                  10                  15

Ala Glu Val Cys
             20

<210> SEQ ID NO 212
<211> LENGTH: 55
<212> TYPE: PRT
<213> ORGANISM: Homo sapiens

<400> SEQUENCE: 212

Met Pro His Pro Pro Leu Pro Glu Thr Ser Leu Glu Ala Gln Leu Pro
  1               5                  10                  15

Met Gly Leu Leu Gln Leu Leu Arg Cys Ser Val Gln Ala Trp Ser Pro
                 20                  25                  30

Pro Pro Ser Ser Phe Cys Pro Gly Ser Glu Pro Arg Ser Ala Ser Ala
             35                  40                  45

His Trp Gly Tyr Trp Trp Pro
         50                  55

<210> SEQ ID NO 213
<211> LENGTH: 35
<212> TYPE: PRT
<213> ORGANISM: Homo sapiens

<400> SEQUENCE: 213

Asp Pro Glu Thr Arg Trp His His Gly Gly Ser Ala Gln Asn Gly Leu
  1               5                  10                  15

Leu Met Leu Ile Ser Val Leu Gln Gln Pro Val Ile Gly Thr Gly Ser
                 20                  25                  30

Tyr Leu Cys
         35

<210> SEQ ID NO 214
<211> LENGTH: 230
<212> TYPE: PRT
<213> ORGANISM: Homo sapiens
```

```
<220> FEATURE:
<221> NAME/KEY: SITE
<222> LOCATION: (192)
<223> OTHER INFORMATION: Xaa equals any of the naturally
      occurring L-amino acids

<400> SEQUENCE: 214

Met Glu Pro Leu Arg Leu Leu Ile Leu Leu Phe Val Thr Glu Leu Ser
 1               5                  10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Xaa
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230

<210> SEQ ID NO 215
<211> LENGTH: 231
<212> TYPE: PRT
<213> ORGANISM: Homo sapiens
<220> FEATURE:
<221> NAME/KEY: SITE
<222> LOCATION: (231)
<223> OTHER INFORMATION: Xaa equals stop translation

<400> SEQUENCE: 215

Met Glu Pro Leu Arg Leu Leu Ile Leu Leu Phe Val Thr Glu Leu Ser
 1               5                  10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80
```

```
Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr Xaa
225                 230

<210> SEQ ID NO 216
<211> LENGTH: 127
<212> TYPE: PRT
<213> ORGANISM: Homo sapiens

<400> SEQUENCE: 216

Met Gly Leu Thr Gly Phe Gly Val Phe Phe Leu Phe Gly Met Ile
  1               5                  10                  15

Leu Phe Phe Asp Lys Ala Leu Leu Ala Ile Gly Asn Val Leu Phe Val
            20                  25                  30

Ala Gly Leu Ala Phe Val Ile Gly Leu Glu Arg Thr Phe Arg Phe Phe
        35                  40                  45

Phe Gln Lys His Lys Met Lys Ala Thr Gly Phe Phe Leu Gly Gly Val
    50                  55                  60

Phe Val Val Leu Ile Gly Trp Pro Leu Ile Gly Met Ile Phe Glu Ile
 65                  70                  75                  80

Tyr Gly Phe Phe Leu Leu Phe Arg Gly Phe Phe Pro Val Val Val Gly
                85                  90                  95

Phe Ile Arg Arg Val Pro Val Leu Gly Ser Leu Leu Asn Leu Pro Gly
            100                 105                 110

Ile Arg Ser Phe Val Asp Lys Val Gly Glu Ser Asn Met Val
        115                 120                 125

<210> SEQ ID NO 217
<211> LENGTH: 47
<212> TYPE: PRT
<213> ORGANISM: Homo sapiens

<400> SEQUENCE: 217

Met Ile Arg Lys Leu His Lys Ile Ile Val Phe Ser Pro Arg Val Ile
  1               5                  10                  15

Val Leu Leu Asn Cys Phe Phe Ile Lys Ala Lys Phe Val Leu Tyr
            20                  25                  30

Ile Phe Val Phe His Val Leu Asp Gly Ser Ile Ser Tyr Pro Val
        35                  40                  45
```

-continued

<210> SEQ ID NO 218
<211> LENGTH: 41
<212> TYPE: PRT
<213> ORGANISM: Homo sapiens

<400> SEQUENCE: 218

Met Leu Leu Asn Gln His Phe Lys Ile Phe Gly Ser Leu Ile His Met
1               5                   10                  15

Asn Leu Leu Phe Ala Leu Ile Ser Leu Gly Ser Ser Asn Leu Ser Gly
            20                  25                  30

Val Gln Phe Cys Cys Glu Thr Val Gln
        35                  40

<210> SEQ ID NO 219
<211> LENGTH: 105
<212> TYPE: PRT
<213> ORGANISM: Homo sapiens
<220> FEATURE:
<221> NAME/KEY: SITE
<222> LOCATION: (10)
<223> OTHER INFORMATION: Xaa equals any of the naturally
      occurring L-amino acids

<400> SEQUENCE: 219

Met Gln Pro Leu Asn Phe Ser Ser Thr Xaa Cys Ser Ser Phe Ser Pro
1               5                   10                  15

Pro Thr Thr Val Ile Leu Leu Ile Leu Leu Cys Phe Glu Gly Leu Leu
            20                  25                  30

Phe Leu Ile Phe Thr Ser Val Met Phe Gly Thr Gln Val His Ser Ile
        35                  40                  45

Cys Thr Asp Glu Thr Gly Ile Glu Gln Leu Lys Lys Glu Glu Arg Arg
    50                  55                  60

Trp Ala Lys Lys Thr Lys Trp Met Asn Met Lys Ala Val Phe Gly His
65                  70                  75                  80

Pro Phe Ser Leu Gly Trp Ala Ser Pro Phe Ala Thr Pro Asp Gln Gly
                85                  90                  95

Lys Ala Asp Pro Tyr Gln Tyr Val Val
            100                 105

<210> SEQ ID NO 220
<211> LENGTH: 29
<212> TYPE: PRT
<213> ORGANISM: Homo sapiens

<400> SEQUENCE: 220

Met Tyr Thr Asn His Phe Asn Leu Tyr Leu Lys Tyr Ile Leu Leu Ile
1               5                   10                  15

Ile Leu Ile Leu Asn Met Thr Asn Ser Ser Ser Arg Tyr
            20                  25

<210> SEQ ID NO 221
<211> LENGTH: 17
<212> TYPE: PRT
<213> ORGANISM: Homo sapiens

<400> SEQUENCE: 221

Met Asn Glu Leu Leu Leu Phe Phe Phe Phe Phe Phe Phe Leu His Phe
1               5                   10                  15

Val

```
<210> SEQ ID NO 222
<211> LENGTH: 138
<212> TYPE: PRT
<213> ORGANISM: Homo sapiens
<220> FEATURE:
<221> NAME/KEY: SITE
<222> LOCATION: (63)
<223> OTHER INFORMATION: Xaa equals any of the naturally
      occurring L-amino acids

<400> SEQUENCE: 222

Met Lys Phe Thr Thr Leu Leu Phe Leu Ala Ala Val Ala Gly Ala Leu
  1               5                  10                  15

Val Tyr Ala Glu Asp Ala Ser Ser Asp Ser Thr Gly Ala Asp Pro Ala
                 20                  25                  30

Gln Glu Ala Gly Thr Ser Lys Pro Asn Glu Glu Ile Ser Gly Pro Ala
             35                  40                  45

Glu Pro Ala Ser Pro Pro Glu Thr Thr Thr Thr Ala Gln Glu Xaa Ser
 50                  55                  60

Ala Ala Ala Val Gln Gly Thr Ala Lys Val Thr Ser Ser Arg Gln Glu
 65                  70                  75                  80

Leu Asn Pro Leu Lys Ser Ile Val Glu Lys Ser Ile Leu Leu Thr Glu
                 85                  90                  95

Gln Ala Leu Ala Lys Ala Gly Lys Gly Met His Gly Val Pro Gly
            100                 105                 110

Gly Lys Gln Phe Ile Glu Asn Gly Ser Glu Phe Ala Gln Lys Leu Leu
            115                 120                 125

Lys Lys Phe Ser Leu Leu Lys Pro Trp Ala
        130                 135

<210> SEQ ID NO 223
<211> LENGTH: 50
<212> TYPE: PRT
<213> ORGANISM: Homo sapiens
<220> FEATURE:
<221> NAME/KEY: SITE
<222> LOCATION: (17)
<223> OTHER INFORMATION: Xaa equals any of the naturally
      occurring L-amino acids

<400> SEQUENCE: 223

Met Leu Gly Cys Gly Ile Pro Ala Leu Gly Leu Leu Leu Leu Leu Gln
  1               5                  10                  15

Xaa Ser Ala Asp Gly Asn Gly Ile Gln Gly Phe Phe Tyr Pro Trp Ser
                 20                  25                  30

Cys Glu Gly Asp Ile Trp Asp Arg Glu Ser Cys Gly Gly Gln Ala Ala
             35                  40                  45

Ile Arg
 50

<210> SEQ ID NO 224
<211> LENGTH: 15
<212> TYPE: PRT
<213> ORGANISM: Homo sapiens

<400> SEQUENCE: 224

Met Glu Ala Val Phe Thr Val Phe Phe Phe Leu Leu Phe Cys Phe
  1               5                  10                  15

<210> SEQ ID NO 225
<211> LENGTH: 155
```

```
<212> TYPE: PRT
<213> ORGANISM: Homo sapiens
<220> FEATURE:
<221> NAME/KEY: SITE
<222> LOCATION: (128)
<223> OTHER INFORMATION: Xaa equals any of the naturally occurring
      L-amino acids
<220> FEATURE:
<221> NAME/KEY: SITE
<222> LOCATION: (135)
<223> OTHER INFORMATION: Xaa equals any of the naturally occurring
      L-amino acids
<220> FEATURE:
<221> NAME/KEY: SITE
<222> LOCATION: (136)
<223> OTHER INFORMATION: Xaa equals any of the naturally occurring
      L-amino acids
<220> FEATURE:
<221> NAME/KEY: SITE
<222> LOCATION: (155)
<223> OTHER INFORMATION: Xaa equals stop translation

<400> SEQUENCE: 225

Met Gly Phe Gly Ala Thr Leu Ala Val Gly Leu Thr Ile Phe Val Leu
  1               5                  10                  15

Ser Val Val Thr Ile Ile Cys Phe Thr Cys Ser Cys Cys Cys Leu
             20                  25                  30

Tyr Lys Thr Cys Arg Arg Pro Arg Pro Val Val Thr Thr Thr Thr Ser
         35                  40                  45

Thr Thr Val Val His Ala Pro Tyr Pro Gln Pro Ser Val Pro Pro
     50                  55                  60

Ser Tyr Pro Gly Pro Ser Tyr Gln Gly Tyr His Thr Met Pro Pro Gln
 65                  70                  75                  80

Pro Gly Met Pro Ala Ala Pro Tyr Pro Met Gln Tyr Pro Pro Tyr
                 85                  90                  95

Pro Ala Gln Pro Met Gly Pro Pro Ala Tyr His Glu Thr Leu Ala Gly
                100                 105                 110

Gly Ala Ala Ala Pro Tyr Pro Ala Ser Gln Pro Pro Tyr Asn Pro Xaa
                115                 120                 125

Tyr Met Asp Ala Pro Lys Xaa Xaa Ser Glu His Ser Leu Ala Ser Leu
    130                 135                 140

Ala Ala Thr Trp Leu Cys Cys Val Cys Ala Xaa
145                 150                 155

<210> SEQ ID NO 226
<211> LENGTH: 10
<212> TYPE: PRT
<213> ORGANISM: Homo sapiens

<400> SEQUENCE: 226

Met Gly Phe Gly Ala Thr Leu Ala Val Gly
  1               5                  10

<210> SEQ ID NO 227
<211> LENGTH: 20
<212> TYPE: PRT
<213> ORGANISM: Homo sapiens

<400> SEQUENCE: 227

Met Ser Ile Phe Leu Val Met Ser Ile Ser Cys Ser Ser Thr Ser His
  1               5                  10                  15

Cys Tyr Ser Phe
             20
```

```
<210> SEQ ID NO 228
<211> LENGTH: 94
<212> TYPE: PRT
<213> ORGANISM: Homo sapiens
<220> FEATURE:
<221> NAME/KEY: SITE
<222> LOCATION: (94)
<223> OTHER INFORMATION: Xaa equals stop translation

<400> SEQUENCE: 228

Met Ser Phe Ser Phe Ile Ile Phe Leu Leu Leu Val Cys Gln Glu Ile
 1               5                  10                  15

Thr Phe Cys Met Ser Tyr Gly Asp Ala Val Asn Cys Phe Ser Glu Cys
             20                  25                  30

Phe Ser Asn Leu Gln Thr Ile Tyr Ile Ser Cys Leu Gln His Ala Val
         35                  40                  45

Cys Lys His Ser Val Ile Trp Ser Ile Gln Leu Phe Val Arg Ala Leu
     50                  55                  60

Pro Ile Ser Lys Cys Ala Glu Leu Ser Ile Asp Gly Ile Phe Arg Ser
 65                  70                  75                  80

Phe His Glu Asn Trp Lys Cys Ser Trp Val Ala Pro Thr Xaa
                 85                  90

<210> SEQ ID NO 229
<211> LENGTH: 94
<212> TYPE: PRT
<213> ORGANISM: Homo sapiens
<220> FEATURE:
<221> NAME/KEY: SITE
<222> LOCATION: (94)
<223> OTHER INFORMATION: Xaa equals stop translation

<400> SEQUENCE: 229

Met Ser Phe Ser Phe Ile Ile Phe Leu Leu Leu Val Cys Gln Glu Ile
 1               5                  10                  15

Thr Phe Cys Met Ser Tyr Gly Asp Ala Val Asn Cys Phe Ser Glu Cys
             20                  25                  30

Phe Ser Asn Leu Gln Thr Ile Tyr Ile Ser Cys Leu Gln His Ala Val
         35                  40                  45

Cys Lys His Ser Val Ile Trp Ser Ile Gln Leu Phe Val Arg Ala Leu
     50                  55                  60

Pro Ile Ser Lys Cys Ala Glu Leu Ser Ile Asp Gly Ile Phe Arg Ser
 65                  70                  75                  80

Phe His Glu Asn Trp Lys Cys Ser Trp Val Ala Pro Thr Xaa
                 85                  90

<210> SEQ ID NO 230
<211> LENGTH: 37
<212> TYPE: PRT
<213> ORGANISM: Homo sapiens

<400> SEQUENCE: 230

Met Gly Trp Ser Ala Gly Leu Leu Phe Leu Leu Ile Leu Tyr Leu Pro
 1               5                  10                  15

Val Pro Gly Trp Met Glu Arg Glu Asp Gly Gly Asp Gly Thr Ser Phe
             20                  25                  30

Thr Ser Gly Ser Trp
         35

<210> SEQ ID NO 231
```

```
<211> LENGTH: 81
<212> TYPE: PRT
<213> ORGANISM: Homo sapiens

<400> SEQUENCE: 231

Met Ala Thr Leu Trp Gly Gly Leu Leu Arg Leu Gly Ser Leu Leu Ser
  1               5                  10                  15
Leu Ser Cys Leu Ala Leu Ser Val Leu Leu Ala His Val Gln Thr
             20                  25                  30
Pro Pro Arg Ile Ser Arg Met Ser Asp Val Asn Val Ser Ala Leu Pro
             35                  40                  45
Ile Lys Lys Ile Leu Gly Ile Phe Ile Ile Arg Thr Tyr Leu Arg Lys
 50                  55                  60
Ile Val Ile Ala Phe Met Leu Trp Ser Pro Cys Leu Cys Gly Gly Leu
 65                  70                  75                  80
Met

<210> SEQ ID NO 232
<211> LENGTH: 301
<212> TYPE: PRT
<213> ORGANISM: Homo sapiens
<220> FEATURE:
<221> NAME/KEY: SITE
<222> LOCATION: (48)
<223> OTHER INFORMATION: Xaa equals any of the naturally
      occurring L-amino acids
<220> FEATURE:
<221> NAME/KEY: SITE
<222> LOCATION: (234)
<223> OTHER INFORMATION: Xaa equals any of the naturally
      occurring L-amino acids

<400> SEQUENCE: 232

Met Asp Ala Arg Trp Trp Ala Val Val Leu Ala Ala Phe Pro Ser
  1               5                  10                  15
Leu Gly Ala Gly Gly Glu Thr Pro Glu Ala Pro Pro Glu Ser Trp Thr
             20                  25                  30
Gln Leu Trp Phe Arg Phe Val Val Asn Ala Ala Gly Tyr Ala Xaa
             35                  40                  45
Phe Met Val Pro Gly Tyr Leu Leu Val Gln Tyr Phe Arg Arg Lys Asn
 50                  55                  60
Tyr Leu Glu Thr Gly Arg Gly Leu Cys Phe Pro Leu Val Lys Ala Cys
 65                  70                  75                  80
Val Phe Gly Asn Glu Pro Lys Ala Ser Asp Glu Val Pro Leu Ala Pro
             85                  90                  95
Arg Thr Glu Ala Ala Glu Thr Thr Pro Met Trp Gln Ala Leu Lys Leu
            100                 105                 110
Leu Phe Cys Ala Thr Gly Leu Gln Val Ser Tyr Leu Thr Trp Gly Val
            115                 120                 125
Leu Gln Glu Arg Val Met Thr Arg Ser Tyr Gly Ala Thr Ala Thr Ser
        130                 135                 140
Pro Gly Glu Arg Phe Thr Asp Ser Gln Phe Leu Val Leu Met Asn Arg
145                 150                 155                 160
Val Leu Ala Leu Ile Val Ala Gly Leu Ser Cys Val Leu Cys Lys Gln
                165                 170                 175
Pro Arg His Gly Ala Pro Met Tyr Arg Tyr Ser Phe Ala Ser Leu Ser
            180                 185                 190
Asn Val Leu Ser Ser Trp Cys Gln Tyr Glu Ala Leu Lys Phe Val Ser
            195                 200                 205
```

```
Phe Pro Thr Gln Val Leu Ala Lys Ala Ser Lys Val Ile Pro Val Met
    210                 215                 220

Leu Met Gly Lys Leu Val Ser Arg Arg Xaa Asn Glu His Trp Glu Tyr
225                 230                 235                 240

Leu Thr Ala Thr Leu Ile Ser Ile Gly Val Ser Met Phe Leu Leu Ser
                245                 250                 255

Ser Gly Pro Glu Pro Arg Ser Ser Pro Ala Thr Thr Leu Ser Gly Leu
                260                 265                 270

Ile Leu Leu Ala Gly Tyr Ile Ala Phe Asp Ser Phe Thr Ser Asn Trp
                275                 280                 285

Gln Asp Ala Cys Leu Pro Ile Arg Cys His Arg Cys Arg
    290                 295                 300

<210> SEQ ID NO 233
<211> LENGTH: 313
<212> TYPE: PRT
<213> ORGANISM: Homo sapiens
<220> FEATURE:
<221> NAME/KEY: SITE
<222> LOCATION: (186)
<223> OTHER INFORMATION: Xaa equals any of the naturally occurring
      L-amino acids
<220> FEATURE:
<221> NAME/KEY: SITE
<222> LOCATION: (294)
<223> OTHER INFORMATION: Xaa equals any of the naturally occurring
      L-amino acids

<400> SEQUENCE: 233

Met Ser Asp Leu Leu Leu Gly Leu Ile Gly Gly Leu Thr Leu Leu
  1               5                  10                  15

Leu Leu Leu Thr Leu Ala Phe Ala Gly Tyr Ser Gly Leu Leu Ala
                 20                  25                  30

Gly Val Glu Val Ser Ala Gly Ser Pro Pro Ile Arg Asn Val Thr Val
                35                  40                  45

Ala Tyr Lys Phe His Met Gly Leu Tyr Gly Glu Thr Gly Arg Leu Phe
    50                  55                  60

Thr Glu Ser Cys Ser Ile Ser Pro Lys Leu Arg Ser Ile Ala Val Tyr
65                  70                  75                  80

Tyr Asp Asn Pro His Met Val Pro Pro Asp Lys Cys Arg Cys Ala Val
                85                  90                  95

Gly Ser Ile Leu Ser Glu Gly Glu Ser Pro Ser Pro Glu Leu Ile
                100                 105                 110

Asp Leu Tyr Gln Lys Phe Gly Phe Lys Val Phe Ser Phe Pro Ala Pro
    115                 120                 125

Ser His Val Val Thr Ala Thr Phe Pro Tyr Thr Thr Ile Leu Ser Ile
    130                 135                 140

Trp Leu Ala Thr Arg Arg Val His Pro Ala Leu Asp Thr Tyr Ile Lys
145                 150                 155                 160

Glu Arg Lys Leu Cys Ala Tyr Pro Arg Leu Glu Ile Tyr Gln Glu Asp
                165                 170                 175

Gln Ile His Phe Met Cys Pro Leu Ala Xaa Gln Gly Asp Phe Tyr Val
                180                 185                 190

Pro Glu Met Lys Glu Thr Glu Trp Lys Trp Arg Gly Leu Val Glu Ala
                195                 200                 205

Ile Asp Thr Gln Val Asp Gly Thr Gly Ala Asp Thr Met Ser Asp Thr
    210                 215                 220
```

```
Ser Ser Val Ser Leu Glu Val Ser Pro Gly Ser Arg Glu Thr Ser Ala
225                 230                 235                 240

Ala Thr Leu Ser Pro Gly Ala Ser Ser Arg Gly Trp Asp Asp Gly Asp
            245                 250                 255

Thr Arg Ser Glu His Ser Tyr Ser Glu Ser Gly Ala Ser Gly Ser Ser
        260                 265                 270

Phe Glu Glu Leu Asp Leu Glu Gly Glu Gly Pro Leu Gly Glu Ser Arg
        275                 280                 285

Leu Asp Pro Gly Thr Xaa Pro Leu Gly Thr Thr Lys Trp Leu Trp Glu
    290                 295                 300

Pro Thr Ala Pro Glu Lys Gly Lys Glu
305                 310

<210> SEQ ID NO 234
<211> LENGTH: 48
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally
      occurring L-amino acids

<400> SEQUENCE: 234

Pro Gln Ser Leu Ile Leu His Leu Leu Phe Phe Leu Leu Phe
1               5                   10                  15

Leu Phe Phe Ile Phe Ile Phe Leu Phe Leu Gln Cys Leu Thr Phe
            20                  25                  30

Leu Phe Xaa Lys Pro Arg Gly Arg Tyr His Gly Leu Cys Phe Lys Phe
        35                  40                  45

<210> SEQ ID NO 235
<211> LENGTH: 34
<212> TYPE: PRT
<213> ORGANISM: Homo sapiens

<400> SEQUENCE: 235

Pro Ala Leu Arg Pro Ala Leu Leu Trp Ala Leu Leu Ala Leu Trp Leu
1               5                   10                  15

Cys Cys Ala Thr Pro Arg Met His Cys Ser Val Glu Met Ala Met Asn
            20                  25                  30

Pro Val

<210> SEQ ID NO 236
<211> LENGTH: 313
<212> TYPE: PRT
<213> ORGANISM: Homo sapiens
<220> FEATURE:
<221> NAME/KEY: SITE
<222> LOCATION: (25)
<223> OTHER INFORMATION: Xaa equals any of the naturally occurring
      L-amino acids
<220> FEATURE:
<221> NAME/KEY: SITE
<222> LOCATION: (264)
<223> OTHER INFORMATION: Xaa equals any of the naturally occurring
      L-amino acids

<400> SEQUENCE: 236

Met Thr Arg Gly Gly Pro Gly Gly Arg Pro Gly Leu Pro Gln Pro Pro
1               5                   10                  15

Pro Leu Leu Leu Leu Leu Leu Leu Xaa Leu Leu Val Thr Ala Glu
            20                  25                  30
```

```
Pro Pro Lys Pro Ala Gly Val Tyr Tyr Ala Thr Ala Tyr Trp Met Pro
            35                  40                  45

Ala Glu Lys Thr Val Gln Val Lys Asn Val Met Asp Lys Asn Gly Asp
    50                  55                  60

Ala Tyr Gly Phe Tyr Asn Asn Ser Val Lys Thr Thr Gly Trp Gly Ile
65                  70                  75                  80

Leu Glu Ile Arg Ala Gly Tyr Gly Ser Gln Thr Leu Ser Asn Glu Ile
                85                  90                  95

Ile Met Phe Val Ala Gly Phe Leu Glu Gly Tyr Leu Thr Ala Pro His
            100                 105                 110

Met Asn Asp His Tyr Thr Asn Leu Tyr Pro Gln Leu Ile Thr Lys Pro
            115                 120                 125

Ser Ile Met Asp Lys Val Gln Asp Phe Met Glu Lys Gln Asp Lys Trp
    130                 135                 140

Thr Arg Lys Asn Ile Lys Glu Tyr Lys Thr Asp Ser Phe Trp Arg His
145                 150                 155                 160

Thr Gly Tyr Val Met Ala Gln Ile Asp Gly Leu Tyr Val Gly Ala Lys
                165                 170                 175

Lys Arg Ala Ile Leu Glu Gly Thr Lys Pro Met Thr Leu Phe Gln Ile
            180                 185                 190

Gln Phe Leu Asn Ser Val Gly Asp Leu Leu Asp Leu Ile Pro Ser Leu
            195                 200                 205

Ser Pro Thr Lys Asn Gly Ser Leu Lys Val Phe Lys Arg Trp Asp Met
    210                 215                 220

Gly His Cys Ser Ala Leu Ile Lys Val Leu Pro Gly Phe Glu Asn Ile
225                 230                 235                 240

Leu Phe Ala His Ser Ser Trp Tyr Thr Tyr Ala Ala Met Leu Arg Ile
                245                 250                 255

Tyr Lys His Trp Asp Phe Asn Xaa Ile Asp Lys Asp Thr Ser Ser Ser
            260                 265                 270

Arg Leu Ser Phe Ser Ser Tyr Pro Gly Phe Leu Glu Ser Leu Asp Asp
            275                 280                 285

Phe Tyr Ile Leu Ser Ser Gly Leu Ile Leu Gln Thr Thr Asn Ser
    290                 295                 300

Val Phe Asn Lys Thr Leu Leu Lys Gln
305                 310
```

<210> SEQ ID NO 237
<211> LENGTH: 296
<212> TYPE: PRT
<213> ORGANISM: Homo sapiens
<220> FEATURE:
<221> NAME/KEY: SITE
<222> LOCATION: (38)
<223> OTHER INFORMATION: Xaa equals any of the naturally occurring
      L-amino acids
<220> FEATURE:
<221> NAME/KEY: SITE
<222> LOCATION: (296)
<223> OTHER INFORMATION: Xaa equals stop translation

<400> SEQUENCE: 237

```
Met Leu Gln Gly Pro Gly Ser Leu Leu Leu Phe Leu Ala Ser His
 1               5                  10                  15

Cys Cys Leu Gly Ser Ala Arg Gly Leu Phe Leu Phe Gly Gln Pro Asp
                20                  25                  30

Phe Ser Tyr Lys Arg Xaa Asn Cys Lys Pro Ile Pro Val Asn Leu Gln
```

```
                35                  40                  45
Leu Cys His Gly Ile Glu Tyr Gln Asn Met Arg Leu Pro Asn Leu Leu
     50                  55                  60

Gly His Glu Thr Met Lys Glu Val Leu Glu Gln Ala Gly Ala Trp Ile
 65                  70                  75                  80

Pro Leu Val Met Lys Gln Cys His Pro Asp Thr Lys Lys Phe Leu Cys
                 85                  90                  95

Ser Leu Phe Ala Pro Val Cys Leu Asp Asp Leu Asp Glu Thr Ile Gln
                100                 105                 110

Pro Cys His Ser Leu Cys Val Gln Val Lys Asp Arg Cys Ala Pro Val
            115                 120                 125

Met Ser Ala Phe Gly Phe Pro Trp Pro Asp Met Leu Glu Cys Asp Arg
    130                 135                 140

Phe Pro Gln Asp Asn Asp Leu Cys Ile Pro Leu Ala Ser Ser Asp His
145                 150                 155                 160

Leu Leu Pro Ala Thr Glu Ala Pro Lys Val Cys Glu Ala Cys Lys
                165                 170                 175

Asn Lys Asn Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Gly Glu Leu Val Ile Thr Ser
                260                 265                 270

Val Lys Arg Trp Gln Lys Gly Gln Arg Glu Phe Lys Arg Ile Ser Arg
            275                 280                 285

Ser Ile Arg Lys Leu Gln Cys Xaa
        290                 295

<210> SEQ ID NO 238
<211> LENGTH: 92
<212> TYPE: PRT
<213> ORGANISM: Homo sapiens
<220> FEATURE:
<221> NAME/KEY: SITE
<222> LOCATION: (89)
<223> OTHER INFORMATION: Xaa equals any of the naturally occurring
      L-amino acids
<220> FEATURE:
<221> NAME/KEY: SITE
<222> LOCATION: (91)
<223> OTHER INFORMATION: Xaa equals any of the naturally occurring
      L-amino acids

<400> SEQUENCE: 238

Met Ala Ser Leu Gly His Ile Leu Val Phe Cys Val Gly Leu Leu Thr
 1               5                  10                  15

Met Ala Lys Ala Glu Ser Pro Lys Glu His Asp Pro Phe Thr Tyr Asp
                20                  25                  30

Tyr Gln Ser Leu Gln Ile Gly Gly Leu Val Ile Ala Gly Ile Leu Phe
            35                  40                  45

Ile Leu Gly Ile Leu Ile Val Leu Ser Arg Arg Cys Arg Cys Lys Phe
        50                  55                  60
```

```
Asn Gln Gln Gln Arg Thr Gly Glu Pro Asp Glu Glu Gly Thr Phe
 65                  70                  75                  80

Arg Ser Ser Ile Arg Arg Leu Ser Xaa Arg Xaa Arg
                 85                  90
```

<210> SEQ ID NO 239
<211> LENGTH: 71
<212> TYPE: PRT
<213> ORGANISM: Homo sapiens

<400> SEQUENCE: 239

```
Met Pro Gly Thr Phe Leu Arg Pro Phe Val Phe Leu Phe Leu Phe Ile
 1               5                  10                  15

Cys Cys Cys Leu His Ser Gly Gly Leu Gly Gly Val Pro Leu Pro Pro
                 20                  25                  30

Phe Pro Pro Gln Ala Gln Arg Gly Glu Gly Pro Gly Lys Trp Met Ser
             35                  40                  45

Pro Pro Leu Pro Pro His Pro Val Val Ala Pro Pro Thr Pro Ser Pro
         50                  55                  60

Ser Arg Gly Cys Val Leu Leu
 65                  70
```

<210> SEQ ID NO 240
<211> LENGTH: 71
<212> TYPE: PRT
<213> ORGANISM: Homo sapiens

<400> SEQUENCE: 240

```
Met Pro Gly Thr Phe Leu Arg Pro Phe Val Phe Leu Phe Leu Phe Ile
 1               5                  10                  15

Cys Cys Cys Leu His Ser Gly Gly Leu Gly Gly Val Pro Leu Pro Pro
                 20                  25                  30

Phe Pro Pro Gln Ala Gln Arg Gly Glu Gly Pro Gly Lys Trp Met Ser
             35                  40                  45

Pro Pro Leu Pro Pro His Pro Val Val Ala Pro Pro Thr Pro Ser Pro
         50                  55                  60

Ser Arg Gly Cys Val Leu Leu
 65                  70
```

<210> SEQ ID NO 241
<211> LENGTH: 28
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring
      L-amino acids
<220> FEATURE:
<221> NAME/KEY: SITE
<222> LOCATION: (11)
<223> OTHER INFORMATION: Xaa equals any of the naturally occurring
      L-amino acids
<220> FEATURE:
<221> NAME/KEY: SITE
<222> LOCATION: (21)
<223> OTHER INFORMATION: Xaa equals any of the naturally occurring
      L-amino acids

<400> SEQUENCE: 241

```
Met Phe Tyr Val Leu Ser Val Ser Xaa Leu Xaa Leu Phe Leu Ala Cys
 1               5                  10                  15
```

```
Gly Leu Cys Leu Xaa Leu Leu Thr Gly Lys Leu Leu
            20              25
```

<210> SEQ ID NO 242
<211> LENGTH: 58
<212> TYPE: PRT
<213> ORGANISM: Homo sapiens
<220> FEATURE:
<221> NAME/KEY: SITE
<222> LOCATION: (42)
<223> OTHER INFORMATION: Xaa equals any of the naturally occurring
      L-amino acids

<400> SEQUENCE: 242

```
Met Lys Leu Phe Asp Ala Ser Pro Thr Phe Phe Ala Phe Leu Leu Gly
 1               5                  10                  15

His Ile Leu Ala Met Glu Val Leu Ala Trp Leu Leu Ile Tyr Leu Leu
            20                  25                  30

Gly Pro Gly Trp Val Pro Ser Ala Leu Xaa Arg Leu His Pro Gly His
            35                  40                  45

Leu Ser Gly Ser Val Leu Val Ser Ala Ala
            50                  55
```

<210> SEQ ID NO 243
<211> LENGTH: 123
<212> TYPE: PRT
<213> ORGANISM: Homo sapiens

<400> SEQUENCE: 243

```
Met Ile Leu Gly Gly Ile Val Val Leu Val Phe Thr Gly Phe Val
 1               5                  10                  15

Trp Ala Ala His Asn Lys Asp Val Leu Arg Arg Met Lys Lys Arg Tyr
            20                  25                  30

Pro Thr Thr Phe Val Met Val Met Leu Ala Ser Tyr Phe Leu Ile
            35                  40                  45

Ser Met Phe Gly Gly Val Met Val Phe Val Phe Gly Ile Thr Phe Pro
 50                  55                  60

Leu Leu Leu Met Phe Ile His Ala Ser Leu Arg Leu Arg Asn Leu Lys
 65                  70                  75                  80

Asn Lys Leu Glu Asn Lys Met Glu Gly Ile Gly Leu Lys Arg Thr Pro
            85                  90                  95

Met Gly Ile Val Leu Asp Ala Leu Glu Gln Gln Glu Glu Gly Ile Asn
            100                 105                 110

Arg Leu Thr Asp Tyr Ile Ser Lys Val Lys Glu
            115                 120
```

<210> SEQ ID NO 244
<211> LENGTH: 73
<212> TYPE: PRT
<213> ORGANISM: Homo sapiens
<220> FEATURE:
<221> NAME/KEY: SITE
<222> LOCATION: (21)
<223> OTHER INFORMATION: Xaa equals any of the naturally occurring
      L-amino acids
<220> FEATURE:
<221> NAME/KEY: SITE
<222> LOCATION: (36)
<223> OTHER INFORMATION: Xaa equals any of the naturally occurring
      L-amino acids
<220> FEATURE:
<221> NAME/KEY: SITE
<222> LOCATION: (40)
<223> OTHER INFORMATION: Xaa equals any of the naturally occurring L-amino acids

<400> SEQUENCE: 244

Ala Leu Val Ser Gly Gln Leu Cys Met Glu Ile Ala Arg Gly Asn Ile
1               5                   10                  15

Phe Phe Leu Asn Xaa Leu Val Thr Thr Phe Cys Cys Ser Cys Leu Leu
            20                  25                  30

Leu Ser Val Xaa Tyr Leu His Xaa Gly Phe Phe Tyr Ser Ser Leu Cys
        35                  40                  45

Lys Cys Cys Phe Val Leu Val Val Leu Ser Arg Ile Gly Ser Val Asn
    50                  55                  60

Glu Thr Trp Ser Cys Asn Phe Ser Ile
65                  70

<210> SEQ ID NO 245
<211> LENGTH: 49
<212> TYPE: PRT
<213> ORGANISM: Homo sapiens
<220> FEATURE:
<221> NAME/KEY: SITE
<222> LOCATION: (43)
<223> OTHER INFORMATION: Xaa equals any of the naturally occurring
      L-amino acids

<400> SEQUENCE: 245

Thr Pro Ala Thr Thr Ser Ser Ser Ser Pro Leu Phe Leu Ser Ser
1               5                   10                  15

Pro Asp Trp Ser Ser Cys Pro Ser Gly Ser Cys Ile Ala Pro Trp Cys
            20                  25                  30

Thr His Trp Ser Ser Ile Leu Pro Ser Leu Xaa Ile Thr Ser Ser Ile
        35                  40                  45

Pro

<210> SEQ ID NO 246
<211> LENGTH: 339
<212> TYPE: PRT
<213> ORGANISM: Homo sapiens
<220> FEATURE:
<221> NAME/KEY: SITE
<222> LOCATION: (339)
<223> OTHER INFORMATION: Xaa equals stop translation

<400> SEQUENCE: 246

Met Ala Arg Val Pro Pro Leu Ser Ser Trp Thr Ser Ser Arg Tyr
1               5                   10                  15

Arg Arg Trp Leu Cys Cys Pro Val Trp Trp Thr Thr Phe Trp Ala Thr
            20                  25                  30

Ala Trp Ser Leu Thr Lys His Leu Tyr Lys Asp Val Thr Asp Ala Ile
        35                  40                  45

Arg Asp Val His Val Lys Gly Leu Met Tyr Gln Trp Ile Glu Gln Asp
    50                  55                  60

Met Glu Lys Tyr Ile Leu Arg Gly Asp Glu Thr Phe Ala Val Leu Ser
65                  70                  75                  80

Arg Leu Val Ala His Gly Lys Gln Leu Phe Leu Ile Thr Asn Ser Pro
                85                  90                  95

Phe Ser Phe Val Asp Lys Gly Met Arg His Met Val Gly Pro Asp Trp
            100                 105                 110

Arg His Ser Ser Met Trp Ser Leu Ser Arg Gln Thr Ser Pro Ala Ser
        115                 120                 125

```
Ser Leu Thr Gly Ala Thr Phe Arg Lys Leu Asp Glu Lys Gly Ser Leu
    130                 135                 140

Gln Trp Asp Arg Ile Thr Arg Leu Glu Lys Gly Lys Ile Tyr Arg Gln
145                 150                 155                 160

Gly Asn Leu Phe Asp Phe Leu Arg Leu Thr Glu Trp Arg Gly Pro Arg
                165                 170                 175

Val Leu Tyr Phe Gly Asp His Leu Tyr Ser Asp Leu Ala Asp Leu Met
            180                 185                 190

Leu Arg His Gly Trp Arg Thr Gly Ala Ile Ile Pro Glu Leu Glu Arg
        195                 200                 205

Glu Ile Arg Ile Ile Asn Thr Glu Gln Tyr Met His Ser Leu Thr Trp
210                 215                 220

Gln Gln Ala Leu Thr Gly Leu Leu Glu Arg Met Gln Thr Tyr Gln Asp
225                 230                 235                 240

Ala Glu Ser Arg Gln Val Leu Ala Ala Trp Met Lys Glu Arg Gln Glu
                245                 250                 255

Leu Arg Cys Ile Thr Lys Ala Leu Phe Asn Ala Gln Phe Gly Ser Ile
            260                 265                 270

Phe Arg Thr Phe His Asn Pro Thr Tyr Phe Ser Arg Arg Leu Val Arg
        275                 280                 285

Phe Ser Asp Leu Tyr Met Ala Ser Leu Ser Cys Leu Leu Asn Tyr Arg
    290                 295                 300

Val Asp Phe Thr Phe Tyr Pro Arg Arg Thr Pro Leu Gln His Glu Ala
305                 310                 315                 320

Pro Leu Trp Met Asp Gln Leu Leu His Arg Leu His Glu Asp Pro Leu
                325                 330                 335

Pro Trp Xaa

<210> SEQ ID NO 247
<211> LENGTH: 18
<212> TYPE: PRT
<213> ORGANISM: Homo sapiens
<220> FEATURE:
<221> NAME/KEY: SITE
<222> LOCATION: (17)
<223> OTHER INFORMATION: Xaa equals any of the naturally occurring
      L-amino acids

<400> SEQUENCE: 247

Met Ala Leu Leu Ser Cys Val Val Asp Tyr Phe Leu Gly His Ser Leu
  1               5                  10                  15

Xaa Val

<210> SEQ ID NO 248
<211> LENGTH: 339
<212> TYPE: PRT
<213> ORGANISM: Homo sapiens

<400> SEQUENCE: 248

Met Asn Trp Glu Leu Leu Leu Trp Leu Leu Val Leu Cys Ala Leu Leu
  1               5                  10                  15

Leu Leu Leu Val Gln Leu Leu Arg Phe Leu Arg Ala Asp Gly Asp Leu
                20                  25                  30

Thr Leu Leu Trp Ala Glu Trp Gln Gly Arg Arg Pro Glu Trp Glu Leu
            35                  40                  45

Thr Asp Met Val Val Trp Val Thr Gly Ala Ser Ser Gly Ile Gly Glu
        50                  55                  60
```

```
Glu Leu Ala Tyr Gln Leu Ser Lys Leu Gly Val Ser Leu Val Leu Ser
 65                  70                  75                  80

Ala Arg Arg Val His Glu Leu Glu Arg Val Lys Arg Arg Cys Leu Glu
                 85                  90                  95

Asn Gly Asn Leu Lys Glu Lys Asp Ile Leu Val Leu Pro Leu Asp Leu
            100                 105                 110

Thr Asp Thr Gly Ser His Glu Ala Ala Thr Lys Ala Val Leu Gln Glu
        115                 120                 125

Phe Gly Arg Ile Asp Ile Leu Val Asn Asn Gly Gly Met Ser Gln Arg
    130                 135                 140

Ser Leu Cys Met Asp Thr Ser Leu Asp Val Tyr Arg Lys Leu Ile Glu
145                 150                 155                 160

Leu Asn Tyr Leu Gly Thr Val Ser Leu Thr Lys Cys Val Leu Pro His
                165                 170                 175

Met Ile Glu Arg Lys Gln Gly Lys Ile Val Thr Val Asn Ser Ile Leu
            180                 185                 190

Gly Ile Ile Ser Val Pro Leu Ser Ile Gly Tyr Cys Ala Ser Lys His
        195                 200                 205

Ala Leu Arg Gly Phe Phe Asn Gly Leu Arg Thr Glu Leu Ala Thr Tyr
    210                 215                 220

Pro Gly Ile Ile Val Ser Asn Ile Cys Pro Gly Pro Val Gln Ser Asn
225                 230                 235                 240

Ile Val Glu Asn Ser Leu Ala Gly Glu Val Thr Lys Thr Ile Gly Asn
                245                 250                 255

Asn Gly Asp Gln Ser His Lys Met Thr Thr Ser Arg Cys Val Arg Leu
            260                 265                 270

Met Leu Ile Ser Met Ala Asn Asp Leu Lys Glu Val Trp Ile Ser Glu
        275                 280                 285

Gln Pro Phe Leu Leu Val Thr Tyr Leu Trp Gln Tyr Met Pro Thr Trp
    290                 295                 300

Ala Trp Trp Ile Thr Asn Lys Met Gly Lys Lys Arg Ile Glu Asn Phe
305                 310                 315                 320

Lys Ser Gly Val Asp Ala Asp Ser Ser Tyr Phe Lys Ile Phe Lys Thr
                325                 330                 335

Lys His Asp

<210> SEQ ID NO 249
<211> LENGTH: 96
<212> TYPE: PRT
<213> ORGANISM: Homo sapiens
<220> FEATURE:
<221> NAME/KEY: SITE
<222> LOCATION: (89)
<223> OTHER INFORMATION: Xaa equals any of the naturally occurring
      L-amino acids

<400> SEQUENCE: 249

Met Gly Ala Arg Pro Gly Gly His Pro Gln Lys Trp Ser Phe Leu Trp
  1               5                  10                  15

Ser Leu Ala Leu Trp Leu Pro Leu Ala Leu Ser Val Ser Leu Phe Leu
             20                  25                  30

Gly Leu Ser Leu Ser Pro Pro Gln Pro Gly Leu Ser Leu Trp Cys Thr
         35                  40                  45

Leu Ser Tyr Cys Cys Glu Gln Trp Lys Phe Lys Gly Thr Pro Ser Pro
     50                  55                  60

Ala Leu Leu Asn Leu Gly Thr Gln Pro Lys Lys Asp Lys Lys Leu Glu
```

```
                    65                  70                  75                  80
Asp Ser Ile Ala Thr Gln Leu Arg Xaa Leu Pro Glu Lys Asn Ser Asn
                            85                  90                  95

<210> SEQ ID NO 250
<211> LENGTH: 79
<212> TYPE: PRT
<213> ORGANISM: Homo sapiens
<220> FEATURE:
<221> NAME/KEY: SITE
<222> LOCATION: (64)
<223> OTHER INFORMATION: Xaa equals any of the naturally occurring
      L-amino acids
<220> FEATURE:
<221> NAME/KEY: SITE
<222> LOCATION: (65)
<223> OTHER INFORMATION: Xaa equals any of the naturally occurring
      L-amino acids

<400> SEQUENCE: 250

Met Ala Leu Thr Phe Leu Leu Val Leu Leu Thr Leu Ala Thr Leu Cys
  1               5                  10                  15

Thr Arg Leu His Arg Asn Phe Arg Arg Gly Glu Ser Ile Tyr Trp Gly
                 20                  25                  30

Pro Thr Ala Asp Ser Gln Asp Thr Val Ala Ala Val Leu Lys Arg Arg
             35                  40                  45

Leu Leu Gln Pro Ser Arg Arg Val Lys Arg Ser Arg Arg Pro Xaa
 50                  55                  60

Xaa Pro Pro Thr Pro Asp Ser Gly Pro Glu Gly Glu Ser Ser Glu
 65                  70                  75

<210> SEQ ID NO 251
<211> LENGTH: 354
<212> TYPE: PRT
<213> ORGANISM: Homo sapiens
<220> FEATURE:
<221> NAME/KEY: SITE
<222> LOCATION: (326)
<223> OTHER INFORMATION: Xaa equals any of the naturally occurring
      L-amino acids

<400> SEQUENCE: 251

Met Gly Pro Ser Thr Pro Leu Leu Ile Leu Phe Leu Leu Ser Trp Ser
  1               5                  10                  15

Gly Pro Leu Gln Gly Gln Gln His His Leu Val Glu Tyr Met Glu Arg
                 20                  25                  30

Arg Leu Ala Ala Leu Glu Glu Arg Leu Ala Gln Cys Gln Asp Gln Ser
             35                  40                  45

Ser Arg His Ala Ala Glu Leu Arg Asp Phe Lys Asn Lys Met Leu Pro
 50                  55                  60

Leu Leu Glu Val Ala Glu Lys Glu Arg Glu Ala Leu Arg Thr Glu Ala
 65                  70                  75                  80

Asp Thr Ile Ser Gly Arg Val Asp Arg Leu Glu Arg Glu Val Asp Tyr
                 85                  90                  95

Leu Glu Thr Gln Asn Pro Ala Leu Pro Cys Val Glu Phe Asp Glu Lys
                100                 105                 110

Val Thr Gly Gly Pro Gly Thr Lys Gly Lys Gly Arg Arg Asn Glu Lys
            115                 120                 125

Tyr Asp Met Val Thr Asp Cys Gly Tyr Thr Ile Ser Gln Val Arg Ser
        130                 135                 140

Met Lys Ile Leu Lys Arg Phe Gly Gly Pro Ala Gly Leu Trp Thr Lys
```

```
               145                 150                 155                 160

Asp Pro Leu Gly Gln Thr Glu Lys Ile Tyr Val Leu Asp Gly Thr Gln
                165                 170                 175

Asn Asp Thr Ala Phe Val Phe Pro Arg Leu Arg Asp Phe Thr Leu Ala
            180                 185                 190

Met Ala Ala Arg Lys Ala Ser Arg Val Arg Val Pro Phe Pro Trp Val
        195                 200                 205

Gly Thr Gly Gln Leu Val Tyr Gly Gly Phe Leu Tyr Phe Ala Arg Arg
    210                 215                 220

Pro Pro Gly Arg Pro Gly Gly Gly Glu Met Glu Asn Thr Leu Gln
225                 230                 235                 240

Leu Ile Lys Phe His Leu Ala Asn Arg Thr Val Val Asp Ser Ser Val
                245                 250                 255

Phe Pro Ala Glu Gly Leu Ile Pro Pro Tyr Gly Leu Thr Ala Asp Thr
            260                 265                 270

Tyr Ile Asp Leu Ala Ala Asp Glu Glu Gly Leu Trp Ala Val Tyr Ala
        275                 280                 285

Thr Arg Glu Asp Asp Arg His Leu Cys Leu Ala Lys Leu Asp Pro Gln
    290                 295                 300

Thr Leu Asp Thr Glu Gln Gln Trp Asp Thr Pro Cys Pro Arg Glu Asn
305                 310                 315                 320

Ala Glu Ala Ala Phe Xaa Ile Cys Gly Thr Leu Tyr Val Val Tyr Asn
                325                 330                 335

Thr Arg Pro Ala Ser Arg Ala Arg Ile Gln Cys Ser Phe Asp Ala Ser
            340                 345                 350

Gly Pro

<210> SEQ ID NO 252
<211> LENGTH: 109
<212> TYPE: PRT
<213> ORGANISM: Homo sapiens

<400> SEQUENCE: 252

Met Leu Cys Ile Asn Gly Thr Thr Pro Arg Pro Leu Pro Val Pro Ser
  1               5                  10                  15

Pro Phe Gly Cys Met Ile Phe Phe Phe Lys Asn Pro Trp Lys Gln
            20                  25                  30

Arg Leu Leu Gln Gly Trp Leu Gly Ala Arg Pro Ile His Leu Leu Gly
        35                  40                  45

Tyr Leu Pro Leu Ser Leu Leu Trp Cys Pro Phe Pro Leu Pro Cys Ala
    50                  55                  60

Arg Cys Ser Val Val Tyr Ile Ser Ser Pro Arg His Gly Ala His Ala
65                  70                  75                  80

Pro Arg Asp Met Ile Leu Ser Leu Val Leu Ala His Gly Ala Leu Tyr
                85                  90                  95

Lys Glu Leu Gly Gly Arg Gly Arg Lys Trp Glu Pro Ser
            100                 105

<210> SEQ ID NO 253
<211> LENGTH: 45
<212> TYPE: PRT
<213> ORGANISM: Homo sapiens

<400> SEQUENCE: 253

Met Phe Tyr Phe Leu Pro Leu Ile Phe Pro Ala Phe Pro Pro Trp Ala
  1               5                  10                  15
```

```
Phe Arg Leu Ser Thr Leu Phe Thr Ile Ile Ser Trp Ser Glu Asp Ser
                20                  25                  30

Asn Asn Ser Gln Val Tyr Met Asn Cys Val Cys Ser Phe
        35                  40                  45

<210> SEQ ID NO 254
<211> LENGTH: 315
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring
      L-amino acids
<220> FEATURE:
<221> NAME/KEY: SITE
<222> LOCATION: (311)
<223> OTHER INFORMATION: Xaa equals any of the naturally occurring
      L-amino acids
<220> FEATURE:
<221> NAME/KEY: SITE
<222> LOCATION: (315)
<223> OTHER INFORMATION: Xaa equals stop translation

<400> SEQUENCE: 254

Met Ala Gly Gly Arg Cys Gly Pro Xaa Leu Thr Ala Leu Leu Ala Ala
  1               5                  10                  15

Trp Ile Ala Ala Val Ala Ala Thr Ala Gly Pro Glu Glu Ala Ala Leu
                20                  25                  30

Pro Pro Glu Gln Ser Arg Val Gln Pro Met Thr Ala Ser Asn Trp Thr
            35                  40                  45

Leu Val Met Glu Gly Glu Trp Met Leu Lys Phe Tyr Ala Pro Trp Cys
 50                  55                  60

Pro Ser Cys Gln Gln Thr Asp Ser Glu Trp Glu Ala Phe Ala Lys Asn
 65                  70                  75                  80

Gly Glu Ile Leu Gln Ile Ser Val Gly Lys Val Asp Val Ile Gln Glu
                85                  90                  95

Pro Gly Leu Ser Gly Arg Phe Phe Val Thr Thr Leu Pro Ala Phe Phe
            100                 105                 110

His Ala Lys Asp Gly Ile Phe Arg Arg Tyr Arg Gly Pro Gly Ile Phe
        115                 120                 125

Glu Asp Leu Gln Asn Tyr Ile Leu Glu Lys Lys Trp Gln Ser Val Glu
130                 135                 140

Pro Leu Thr Gly Trp Lys Ser Pro Ala Ser Leu Thr Met Ser Gly Met
145                 150                 155                 160

Ala Gly Leu Phe Ser Ile Ser Gly Lys Ile Trp His Leu His Asn Tyr
                165                 170                 175

Phe Thr Val Thr Leu Gly Ile Pro Ala Trp Cys Ser Tyr Val Phe Phe
            180                 185                 190

Val Ile Ala Thr Leu Val Phe Gly Leu Phe Met Gly Leu Val Leu Val
        195                 200                 205

Val Ile Ser Glu Cys Phe Tyr Val Pro Leu Pro Arg His Leu Ser Glu
210                 215                 220

Arg Ser Glu Gln Asn Arg Arg Ser Glu Glu Ala His Arg Ala Glu Gln
225                 230                 235                 240

Leu Gln Asp Ala Glu Glu Glu Lys Asp Asp Ser Asn Glu Glu Glu Asn
                245                 250                 255

Lys Asp Ser Leu Val Asp Asp Glu Glu Glu Lys Glu Asp Leu Gly Asp
            260                 265                 270
```

```
Glu Asp Glu Ala Glu Glu Glu Glu Asp Asn Leu Ala Ala Gly
        275                 280                 285

Val Asp Glu Glu Arg Ser Glu Ala Asn Asp Gln Gly Pro Pro Gly Glu
    290                 295                 300

Asp Gly Val Thr Arg Glu Xaa Ser Arg Ala Xaa
305                 310                 315

<210> SEQ ID NO 255
<211> LENGTH: 53
<212> TYPE: PRT
<213> ORGANISM: Homo sapiens

<400> SEQUENCE: 255

Met Leu Lys Ala Leu Phe Arg Thr Leu Gln Ala Met Leu Leu Gly Val
1               5                   10                  15

Trp Ile Leu Leu Leu Ala Ser Leu Ala Pro Leu Trp Leu Tyr Cys
            20                  25                  30

Trp Arg Met Phe Pro Thr Lys Gly Lys Arg Asp Gln Lys Glu Met Leu
        35                  40                  45

Glu Val Ser Gly Ile
    50

<210> SEQ ID NO 256
<211> LENGTH: 93
<212> TYPE: PRT
<213> ORGANISM: Homo sapiens
<220> FEATURE:
<221> NAME/KEY: SITE
<222> LOCATION: (93)
<223> OTHER INFORMATION: Xaa equals stop translation

<400> SEQUENCE: 256

Met Ile His Leu Gly His Ile Leu Phe Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Arg Ser Pro Ala Gln
65                  70                  75                  80

Asp Gly Lys Val Tyr Ile Asn Met Pro Gly Arg Gly Xaa
                85                  90

<210> SEQ ID NO 257
<211> LENGTH: 12
<212> TYPE: PRT
<213> ORGANISM: Homo sapiens

<400> SEQUENCE: 257

Pro Gly His Leu Leu Pro His Lys Trp Glu Asn Cys
1               5                   10

<210> SEQ ID NO 258
<211> LENGTH: 1852
<212> TYPE: DNA
<213> ORGANISM: Homo sapiens

<400> SEQUENCE: 258
```

-continued

```
tggcatctgt gagcagctgc caggctccgg ccaggatccc ttccttctcc tcattggctg      60
atggatccca agggctcct ctccttgacc ttcgtgctgt ttctctccct ggcttttggg     120
gcaagctacg aacaggtgg gcgcatgatg aactgcccaa agattctccg gcagttggga     180
agcaaagtgc tgctgcccct gacatatgaa aggataaata gagcatgaa caaaagcatc     240 cacattgtcg tcacaatggc aaaatcactg gagaacagtg tcgagaacaa aatagtgtct     300
cttgatccat ccgaagcagg ccctccacgt tatctaggag atcgctacaa gttttatctg     360
gagaatctca ccctggggat acgggaaagc aggaaggagg atgagggatg gtaccttatg     420
accctggaga aaatgtttc agttcagcgc ttttgcctgc agttgaggct ttatgagcag     480
gtctccactc cagaaattaa agttttaaac aagacccagg agaacgggac ctgcaccttg     540
atactgggct gcacagtgga aagggggac catgtggctt acagctggag tgaaaaggcg     600
ggcacccacc cactgaaccc agccaacagc tcccacctcc tgtccctcac cctcggcccc     660
cagcatgctg acaatatcta catctgcacc gtgagcaacc ctatcagcaa caattcccag     720
accttcagcc cgtggcccgg atgcaggaca gaccccctcag aaacaaaacc atgggcagtg     780
tatgctgggc tgttagggg tgtcatcatg attctcatca tggtggtaat actacagttg     840
agaagaagag gtaaaacgaa ccattaccag acaacagtgg aaaaaaaaag ccttacgatc     900
tatgcccaag tccagaaacc aggtgacact catcatcaga cttcggactt attctaatcc     960
aggatgacct tattttgaaa tccttatctt gacatctgtg aagacctta ttcaaataaa    1020 gtcacatttt gacattctgc gagggctgg agccggccg gggcgatgtg gagcgcgggc    1080
cgcggcgggg ctgcctggcc ggtgctgttg gggctgctgc tggcgctgtt agtgccgggc    1140
ggtggtgccg ccaagaccgg tgcggagctc gtgactgcgg tcggtgctg aagctgctca    1200 atacgcacca ccggtgcggc tgcactcgca cgacatcaaa tacggatccg gcagcggcca    1260
gcaatcggtg accggcgtag aggtcggagc gacgaatagc tactggcgga tccgcggcgg    1320
ctcggagggg ggtgcccgcg cgggtccccg gtgcgctgcg ggcaggcggt gaggtcacac    1380
atgtgcttac gggcaagaac ctgcacacgc accacttccc gtcgccgctg tccaacaacc    1440
aggaagtgag tgccaaaggg gaagacggcg agggcgacga cctggaccta tggacagtgc    1500
gctgctctgc tctggacagc actggagcgc tgaggctgct gtggcgcctt ccagcatgtg    1560
gcacctctgt ggttcctgtc agtcacggta gcagtatgga agccccatcc gtgggcagca    1620
tgaggtccac gcatgcccag tgccaacacg cacaatacgt ggaaggccat ggaaggcatc    1680
ttcatcaagc ctagtgtgga gccctctgca ggtcacgatg aactctgagt gtgtggatgg    1740
atgggtggat ggagggtggc aggtggggcg tctgcagggc cactcttggc agagactttg    1800
ggtttgtagg ggtcctcaag tgcctttgtg attaaagaat gttggtctat ga           1852
```

<210> SEQ ID NO 259
<211> LENGTH: 371
<212> TYPE: PRT
<213> ORGANISM: Homo sapiens

<400> SEQUENCE: 259

```
Met Glu Leu Glu Leu Asp Ala Gly Asp Gln Asp Leu Leu Ala Phe Leu
  1               5                  10                  15

Leu Glu Glu Ser Gly Asp Leu Gly Thr Ala Pro Asp Glu Ala Val Arg
             20                  25                  30

Ala Pro Leu Asp Trp Ala Leu Pro Leu Ser Glu Val Pro Ser Asp Trp
         35                  40                  45
```

```
Glu Val Asp Asp Leu Leu Cys Ser Leu Leu Ser Pro Ala Ser Leu
 50                  55                  60

Asn Ile Leu Ser Ser Ser Asn Pro Cys Leu Val His His Asp His Thr
 65                  70                  75                  80

Tyr Ser Leu Pro Arg Glu Thr Val Ser Met Asp Leu Glu Ser Glu Ser
                 85                  90                  95

Cys Arg Lys Glu Gly Thr Gln Met Thr Pro Gln His Met Glu Glu Leu
                100                 105                 110

Ala Glu Gln Glu Ile Ala Arg Leu Val Leu Thr Asp Glu Lys Ser
            115                 120                 125

Leu Leu Glu Lys Glu Gly Leu Ile Leu Pro Glu Thr Leu Pro Leu Thr
        130                 135                 140

Lys Thr Glu Glu Gln Ile Leu Lys Arg Val Arg Lys Ile Arg Asn
145                 150                 155                 160

Lys Arg Ser Ala Gln Glu Ser Arg Arg Lys Lys Lys Val Tyr Val Gly
                165                 170                 175

Gly Leu Glu Ser Arg Val Leu Lys Tyr Thr Ala Gln Asn Met Glu Leu
            180                 185                 190

Gln Asn Lys Val Gln Leu Leu Glu Glu Gln Asn Leu Ser Leu Leu Asp
        195                 200                 205

Gln Leu Arg Lys Leu Gln Ala Met Val Ile Glu Ile Ser Asn Lys Thr
    210                 215                 220

Ser Ser Ser Ser Thr Cys Ile Leu Val Leu Leu Val Ser Phe Cys Leu
225                 230                 235                 240

Leu Leu Val Pro Ala Met Tyr Ser Ser Asp Thr Arg Gly Ser Leu Pro
                245                 250                 255

Ala Glu His Gly Val Leu Ser Arg Gln Leu Arg Ala Leu Pro Ser Glu
            260                 265                 270

Asp Pro Tyr Gln Leu Glu Leu Pro Ala Leu Gln Ser Glu Val Pro Lys
        275                 280                 285

Asp Ser Thr His Gln Trp Leu Asp Gly Ser Asp Cys Val Leu Gln Ala
    290                 295                 300

Pro Gly Asn Thr Ser Cys Leu Leu His Tyr Met Pro Gln Ala Pro Ser
305                 310                 315                 320

Ala Glu Pro Pro Leu Glu Trp Pro Phe Pro Asp Leu Ser Ser Glu Pro
                325                 330                 335

Leu Cys Arg Gly Pro Ile Leu Pro Leu Gln Ala Asn Leu Thr Arg Lys
            340                 345                 350

Gly Gly Trp Leu Pro Thr Gly Ser Pro Ser Val Ile Leu Gln Asp Arg
        355                 360                 365

Tyr Ser Gly
    370

<210> SEQ ID NO 260
<211> LENGTH: 98
<212> TYPE: PRT
<213> ORGANISM: Homo sapiens

<400> SEQUENCE: 260

Asn Lys Arg Pro Thr Phe Leu Lys Ile Lys Lys Pro Leu Ser Tyr Arg
  1               5                  10                  15

Lys Pro Met Asp Thr Asp Leu Val Tyr Ile Glu Lys Ser Pro Asn Tyr
                 20                  25                  30

Cys Glu Glu Asp Pro Val Thr Gly Ser Val Gly Thr Gln Gly Arg Ala
             35                  40                  45
```

```
Cys Asn Lys Thr Ala Pro Gln Ala Ser Gly Cys Asp Leu Met Cys Cys
         50                  55                  60

Gly Arg Gly Tyr Asn Thr His Gln Tyr Ala Arg Val Trp Gln Cys Asn
 65                  70                  75                  80

Cys Lys Phe His Trp Cys Cys Tyr Val Lys Cys Asn Thr Cys Ser Glu
                 85                  90                  95

Arg Thr
```

<210> SEQ ID NO 261
<211> LENGTH: 165
<212> TYPE: PRT
<213> ORGANISM: Homo sapiens

<400> SEQUENCE: 261

```
Ser Ala Glu Pro Ala Gly Thr Phe Leu Ile Arg Asp Ser Ser Asp Gln
  1               5                  10                  15

Arg His Phe Phe Thr Leu Ser Val Lys Thr Gln Ser Gly Thr Lys Asn
                 20                  25                  30

Leu Arg Ile Gln Cys Glu Gly Gly Ser Phe Ser Leu Gln Ser Asp Pro
             35                  40                  45

Arg Ser Thr Gln Pro Val Pro Arg Phe Asp Cys Val Leu Lys Leu Val
         50                  55                  60

His His Tyr Met Pro Pro Pro Gly Ala Pro Ser Phe Pro Ser Pro Pro
 65                  70                  75                  80

Thr Glu Pro Ser Ser Glu Val Pro Glu Gln Pro Ser Ala Gln Pro Leu
                 85                  90                  95

Pro Gly Ser Pro Pro Arg Arg Ala Tyr Tyr Ile Tyr Ser Gly Gly Glu
                100                 105                 110

Lys Ile Pro Leu Val Leu Ser Arg Pro Leu Ser Ser Asn Val Ala Thr
            115                 120                 125

Leu Gln His Leu Cys Arg Lys Thr Val Asn Gly His Leu Asp Ser Tyr
        130                 135                 140

Glu Lys Val Thr Gln Leu Pro Gly Pro Ile Arg Glu Phe Leu Asp Gln
145                 150                 155                 160

Tyr Asp Ala Pro Leu
                165
```

<210> SEQ ID NO 262
<211> LENGTH: 40
<212> TYPE: PRT
<213> ORGANISM: Homo sapiens

<400> SEQUENCE: 262

```
Met Val Thr His Ser Lys Phe Pro Ala Ala Gly Met Ser Arg Pro Leu
  1               5                  10                  15

Asp Thr Ser Leu Arg Leu Lys Thr Phe Ser Ser Lys Ser Glu Tyr Gln
                 20                  25                  30

Leu Val Val Asn Ala Val Arg Lys
             35                  40
```

<210> SEQ ID NO 263
<211> LENGTH: 33
<212> TYPE: PRT
<213> ORGANISM: Homo sapiens

<400> SEQUENCE: 263

```
Gln Glu Ser Gly Phe Tyr Trp Ser Ala Val Thr Gly Gly Glu Ala Asn
```

-continued

```
                1               5                  10                  15
Leu Leu Leu Ser Ala Glu Pro Ala Gly Thr Phe Leu Ile Arg Asp Ser
                    20                  25                  30
Ser
```

<210> SEQ ID NO 264
<211> LENGTH: 12
<212> TYPE: PRT
<213> ORGANISM: Homo sapiens

<400> SEQUENCE: 264

```
Cys Arg Cys Ala Ser Gly Phe Thr Gly Glu Asp Cys
 1               5                  10
```

<210> SEQ ID NO 265
<211> LENGTH: 12
<212> TYPE: PRT
<213> ORGANISM: Homo sapiens

<400> SEQUENCE: 265

```
Cys Thr Cys Gln Val Gly Phe Thr Gly Lys Glu Cys
 1               5                  10
```

<210> SEQ ID NO 266
<211> LENGTH: 12
<212> TYPE: PRT
<213> ORGANISM: Homo sapiens

<400> SEQUENCE: 266

```
Cys Leu Asn Leu Pro Gly Ser Tyr Gln Cys Gln Cys
 1               5                  10
```

<210> SEQ ID NO 267
<211> LENGTH: 12
<212> TYPE: PRT
<213> ORGANISM: Homo sapiens

<400> SEQUENCE: 267

```
Cys Lys Cys Leu Thr Gly Phe Thr Gly Gln Lys Cys
 1               5                  10
```

<210> SEQ ID NO 268
<211> LENGTH: 12
<212> TYPE: PRT
<213> ORGANISM: Homo sapiens

<400> SEQUENCE: 268

```
Cys Gln Cys Leu Gln Gly Phe Thr Gly Gln Tyr Cys
 1               5                  10
```

<210> SEQ ID NO 269
<211> LENGTH: 70
<212> TYPE: PRT
<213> ORGANISM: Homo sapiens

<400> SEQUENCE: 269

```
Pro Lys Glu His Asp Pro Phe Thr Tyr Asp Tyr Gln Ser Leu Gln Ile
 1               5                  10                  15
Gly Gly Leu Val Ile Ala Gly Ile Leu Phe Ile Leu Gly Ile Leu Ile
                    20                  25                  30
Val Leu Ser Arg Arg Cys Arg Cys Lys Phe Asn Gln Gln Gln Arg Thr
                35                  40                  45
```

```
Gly Glu Pro Asp Glu Glu Gly Thr Phe Arg Ser Ser Ile Arg Arg
        50                  55                  60

Leu Ser Thr Arg Arg Arg
 65                  70

<210> SEQ ID NO 270
<211> LENGTH: 65
<212> TYPE: PRT
<213> ORGANISM: Homo sapiens

<400> SEQUENCE: 270

Met Asp Val Asn Ile Ala Pro Leu Arg Ala Trp Asp Phe Phe Pro
  1               5                  10                  15

Gly Ser Asp Arg Phe Ala Arg Pro Asp Phe Arg Asp Ile Ser Lys Trp
             20                  25                  30

Asn Asn Arg Val Val Ser Asn Leu Leu Tyr Tyr Gln Thr Asn Tyr Leu
         35                  40                  45

Val Val Ala Ala Met Met Ile Ser Ile Val Gly Phe Leu Ser Pro Phe
        50                  55                  60

Asn
 65

<210> SEQ ID NO 271
<211> LENGTH: 127
<212> TYPE: PRT
<213> ORGANISM: Homo sapiens
<220> FEATURE:
<221> NAME/KEY: SITE
<222> LOCATION: (37)
<223> OTHER INFORMATION: Xaa equals any of the naturally occurring
      L-amino acids

<400> SEQUENCE: 271

Gly Leu Ala Cys Trp Leu Ala Gly Val Ile Phe Ile Asp Arg Lys Arg
  1               5                  10                  15

Thr Gly Asp Ala Ile Ser Val Met Ser Glu Val Ala Gln Thr Leu Leu
             20                  25                  30

Thr Gln Asp Val Xaa Val Trp Val Phe Pro Glu Gly Thr Arg Asn His
         35                  40                  45

Asn Gly Ser Met Leu Pro Phe Lys Arg Gly Ala Phe His Leu Ala Val
     50                  55                  60

Gln Ala Gln Val Pro Ile Val Pro Ile Val Met Ser Ser Tyr Gln Asp
 65                  70                  75                  80

Phe Tyr Cys Lys Lys Glu Arg Arg Phe Thr Ser Gly Gln Cys Gln Val
                 85                  90                  95

Arg Val Leu Pro Pro Val Pro Thr Glu Gly Leu Thr Pro Asp Asp Val
            100                 105                 110

Pro Ala Leu Ala Asp Arg Val Arg His Ser Met Leu His Cys Phe
            115                 120                 125

<210> SEQ ID NO 272
<211> LENGTH: 98
<212> TYPE: PRT
<213> ORGANISM: Homo sapiens

<400> SEQUENCE: 272

Pro Ser Ala Lys Tyr Phe Phe Lys Met Ala Phe Tyr Asn Gly Trp Ile
  1               5                  10                  15

Leu Phe Leu Ala Val Leu Ala Ile Pro Val Cys Ala Val Arg Gly Arg
             20                  25                  30
```

```
Asn Val Glu Asn Met Lys Ile Leu Arg Leu Met Leu His Ile Lys
            35                  40                  45

Tyr Leu Tyr Gly Ile Arg Val Glu Val Arg Gly Ala His His Phe Pro
    50                  55                  60

Pro Ser Gln Pro Tyr Val Val Ser Asn His Gln Ser Ser Leu Asp
65                  70                  75                  80

Leu Leu Gly Met Met Glu Val Leu Pro Gly Arg Cys Val Pro Ile Ala
                85                  90                  95

Lys Arg

<210> SEQ ID NO 273
<211> LENGTH: 9
<212> TYPE: PRT
<213> ORGANISM: Homo sapiens

<400> SEQUENCE: 273

Thr Val Phe Arg Glu Ile Ser Thr Asp
1               5

<210> SEQ ID NO 274
<211> LENGTH: 11
<212> TYPE: PRT
<213> ORGANISM: Homo sapiens

<400> SEQUENCE: 274

Leu Trp Ala Gly Ser Ala Gly Trp Pro Ala Gly
1               5                   10

<210> SEQ ID NO 275
<211> LENGTH: 29
<212> TYPE: PRT
<213> ORGANISM: Homo sapiens

<400> SEQUENCE: 275

Ser Ile Leu Gly Ile Ile Ser Val Pro Leu Ser Ile Gly Tyr Cys Ala
1               5                   10                  15

Ser Lys His Ala Leu Arg Gly Phe Phe Asn Gly Leu Arg
            20                  25

<210> SEQ ID NO 276
<211> LENGTH: 8
<212> TYPE: PRT
<213> ORGANISM: Homo sapiens

<400> SEQUENCE: 276

Met Ala Tyr His Gly Leu Thr Val
1               5

<210> SEQ ID NO 277
<211> LENGTH: 6
<212> TYPE: PRT
<213> ORGANISM: Homo sapiens

<400> SEQUENCE: 277

Ile Ser Ala Ala Arg Val
1               5

<210> SEQ ID NO 278
<211> LENGTH: 11
<212> TYPE: PRT
<213> ORGANISM: Homo sapiens
```

-continued

```
<400> SEQUENCE: 278

Pro Asp Val Ser Glu Phe Met Thr Arg Leu Phe
 1               5                  10

<210> SEQ ID NO 279
<211> LENGTH: 17
<212> TYPE: PRT
<213> ORGANISM: Homo sapiens

<400> SEQUENCE: 279

Phe Asp Pro Val Arg Val Asp Ile Thr Ser Lys Gly Lys Met Arg Ala
 1               5                  10                  15

Arg

<210> SEQ ID NO 280
<211> LENGTH: 168
<212> TYPE: PRT
<213> ORGANISM: Homo sapiens

<400> SEQUENCE: 280

Met Ala Ala Ala Leu Trp Gly Phe Phe Pro Val Leu Leu Leu Leu Leu
 1               5                  10                  15

Leu Ser Gly Asp Val Gln Ser Ser Glu Val Pro Gly Ala Ala Ala Glu
                20                  25                  30

Gly Ser Gly Gly Ser Gly Val Gly Ile Gly Asp Arg Phe Lys Ile Glu
                35                  40                  45

Gly Arg Ala Val Val Pro Gly Val Lys Pro Gln Asp Trp Ile Ser Ala
        50                  55                  60

Ala Arg Val Leu Val Asp Gly Glu His Val Gly Phe Leu Lys Thr
65                  70                  75                  80

Asp Gly Ser Phe Val Val His Asp Ile Pro Ser Gly Ser Tyr Val Val
                85                  90                  95

Glu Val Val Ser Pro Ala Tyr Arg Phe Asp Pro Val Arg Val Asp Ile
                100                 105                 110

Thr Ser Lys Gly Lys Met Arg Ala Arg Tyr Val Asn Tyr Ile Lys Thr
            115                 120                 125

Ser Glu Val Val Arg Leu Pro Tyr Pro Leu Gln Met Lys Ser Ser Gly
        130                 135                 140

Pro Pro Ser Tyr Phe Ile Lys Arg Glu Ser Trp Gly Trp Thr Asp Phe
145                 150                 155                 160

Leu Met Asn Pro Met Val Met Met
                165
```